US006825170B2

(12) United States Patent
Henninger et al.

(10) Patent No.: US 6,825,170 B2
(45) Date of Patent: Nov. 30, 2004

(54) 6-O-ACYL KETOLIDE ANTIBACTERIALS

(75) Inventors: Todd C. Henninger, High Bridge, NJ (US); Mark J. Macielag, Branchburg, NJ (US); Manomi A. Tennakoon, Bridgewater, NJ (US); Xiaodong Xu, Bridgewater, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/301,412

(22) Filed: Nov. 21, 2002

(65) Prior Publication Data

US 2003/0220272 A1 Nov. 27, 2003

Related U.S. Application Data

(60) Provisional application No. 60/392,513, filed on Jun. 28, 2002, and provisional application No. 60/338,566, filed on Dec. 5, 2001.

(51) Int. Cl.[7] .......................... A61K 31/70; C07H 1/00; C07H 17/08
(52) U.S. Cl. .......................... 514/29; 536/7.4; 536/18.5
(58) Field of Search ............................ 514/29; 536/7.4, 536/18.5

(56) References Cited

U.S. PATENT DOCUMENTS

| 4,826,820 | A | 5/1989 | Brain |
| 5,444,051 | A | 8/1995 | Agouridas et al. |
| 5,559,256 | A | 9/1996 | Gordon et al. |
| 5,561,118 | A | 10/1996 | Agouridas et al. |
| 5,770,579 | A | 6/1998 | Agouridas et al. |
| 5,780,473 | A | 7/1998 | Murugesan et al. |
| 5,866,549 | A | 2/1999 | Or et al. |
| 5,992,683 | A | 11/1999 | Sigl |
| 6,034,069 | A | 3/2000 | Or et al. |
| 6,355,620 | B1 | 3/2002 | Ma et al. |
| 6,613,747 | B2 * | 9/2003 | Henninger et al. ........... 514/29 |

FOREIGN PATENT DOCUMENTS

| EP | 0216169 A2 | 4/1987 |
| EP | 1114826 A2 | 7/2001 |
| EP | 1146051 A2 | 10/2001 |
| EP | 1146051 A2 * | 10/2001 |
| WO | WO 97/17356 A1 | 5/1997 |
| WO | WO 97/24124 A1 | 7/1997 |
| WO | WO 98/03476 A1 | 1/1998 |
| WO | WO 98/09978 A1 | 3/1998 |
| WO | WO 98/21188 A1 | 5/1998 |
| WO | WO 98/28264 A1 | 7/1998 |
| WO | WO 99/21864 A1 | 5/1999 |
| WO | WO 99/21871 A1 | 5/1999 |
| WO | WO 99/35157 A1 | 7/1999 |
| WO | WO 00/62783 A2 | 10/2000 |
| WO | WO 00/63224 A2 | 10/2000 |
| WO | WO 00/63225 A2 | 10/2000 |
| WO | WO 00/71557 A1 | 11/2000 |
| WO | WO 00/75156 A1 | 12/2000 |
| WO | WO 01/40241 A2 | 6/2001 |
| WO | WO 02/32918 A2 | 4/2002 |
| WO | WO 02/32919 A2 | 4/2002 |
| WO | WO 03/090760 A1 | 11/2003 |
| WO | WO 03/093289 A1 | 11/2003 |

OTHER PUBLICATIONS

Albert, P. et al.: "Tetrabutylammonium and Polymer–supported Dihydrogentriflouride: New Hydrofluorinating Reagents for Electrophilic Alkynes"; J. Chem. Soc., Chem. Commun., 1985, pp. 961–962.

Amishiro, N. et al.: "Synthesis and Antitumor Activity of Duocarmycin Derivatives: A–Ring Pyrrole Compounds Bearing 5–Membered Heteroarylacryloyl Groups"; Chem. Pharm. Bull. 47(10) 1999, pp. 1393–1403.

Bianchi, G. et al.: "5–Isoxazoleboronic Acids"; J. Organometal. Chem., 6 (1966), pp. 598–602.

Blake, A.J. et al.: "Thermolysis of Polyazapentadienes, Part 11.[1] Concerted and Free Radical Mechanisms in 2–Aza Enone and 2–Aza Enthione Pyrolyses: Crystal and Molecular Structures of 3–Dimethylamino–1–p–tolyl–2–azaprop–2–en–1–one and 3–Dimethylamino–1–phenyl–2–azaprop–2–ene–1–thione"; J. Chem. Soc. Perkin Trans. 1 1989, pp. 589–595.

Boutros, A. et al.: "4–Quinolylmethyl and 1–Naphthylmethyl as Benzyl–type Protecting Groups of Carboxylic Acids Removable by Homogeneous Palladium–Catalyzed Hydrogenolysis"; Tetrahedron 56 (2000), pp. 2239–2246.

Clerici, A, et al.: "Efficient Acetalisation of Aldehydes Catalyzed by Titanium Tetrachloride in a Basic Medium"; Tetrahedron 54 (1998), pp. 15679–15690.

Daubresse, N. et al.: "Phase Transfer Wittig Reaction with 1,3–Dioxolan–2–yl–methyltriphenyl phosphonium Salts: an Efficient Method for Vinylogation of Aromatic Aldehydes"; Tetrahedron 54 (1998), pp. 10761–10770.

(List continued on next page.)

Primary Examiner—Elli Peselev

(57) ABSTRACT

6-O-Acyl ketolide antibacterials of the formula:

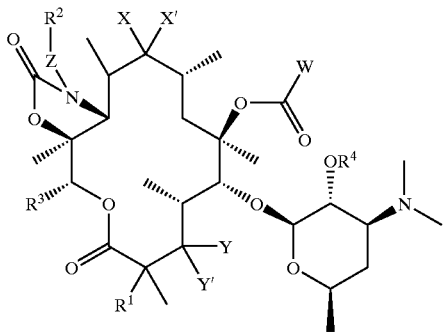

wherein $R^1$, $R_2$, $R_3$, $R^4$, W, X, X', Y, and Y' are as described herein and in which the substituents have the meaning indicated in the description. These compounds are useful as antibacterial agents.

56 Claims, No Drawings

OTHER PUBLICATIONS

Dunaiskis, A. et al.: "Large Scale Synthesis of 2–Chloro–5–Fluoropyrimidine"; Org. Prep. Proc. Int., vol. 27., No. 5, 1995, pp. 600–602.

Elguero, J. et al.: No 475.—"Recherches dans la serie des azoles. VIII. ——Nitrophenyl–1, dinitro–2,4 phenyl–1 et picryl–1 pyrazoles(*)."; Bull. Soc. Chim. Fr., 1996, pp. 2832–2845. (Note: not in English; see drawings and tables).

Glase, S.A. et al.: "Aryl 1 But–3–ynyl–4–phenyl–1,2,3, 6–tetrahydropyridines as Potential Antipsychotic Agents: Synthesis and Structure—Activity Relationships"; J. Med. Chem., 1996, 39, pp. 3179–3187.

Gorgues, A. et al.: "Mono–hydrofluorination of Electrophilic Alkynes by the Liquid Biphasic $CsF–H_2O–DMF$ System (DMF = N,N–dimethylformamide)"; J. Chem. Soc. Chem. Commun., 1989, pp. 1493–1494.

Hauske, J.R. et al.: "Synthesis of 10,11–Anydroerythromycin"; J. Org. Chem. 1982, 47, pp. 1595–1596.

Kim, Dae–Kee et al.: "Synthesis and Anti–HIV–1 Activity of a Series of 1–Alkoxy–5–alkyl–6–(arylthio)uracils"; J. Med. Chem. 1997, 40, pp. 2363–2373.

Kim, M.S. et al.: "Photophysical Properties and Conformational Equilibrium of trans–6–Styrylquinoxaline"; Photochem. Photobiol., 1991, 54, pp. 7–15.

Kingsbury, W.P. et al.: "Synthesis of Structural Analogs of Leukotriene $B_4$ and Their Receptor Binding Activity"; J. Med. Chem. 1993, 36, pp. 3308–3320.

Kurabayashi, M. et al.: "The Reaction of 1,3,5–Triazine with Aromatic Nitrile Oxides. A New Synthesis of 3–Substituted 1,2,4–Oxadiazoles."; Bull. Chem. Soc. Jpn., 1978, 51, pp. 1484–1486.

Landquist, J.K. et al.: *"Quinoxaline N–Oxides Part IV.* Derivatives of Py–Hydroxyalkyl–,—Aminoalkyl–, and –Carboxy–quinoxalines."*; J. Chem. Soc., 1956, pp. 2052–2058.

Mukkala, Veli–Matti et al.: "New Heteroaromatic Complexing Agents and Luminescence of Their Europium(III) and Terbium(III) Chelates"; Helv. Chim. Acta, 1992, 75, pp. 1621–11632.

Muri, E.M.F. et al.: "Synthesis of New Benzylic Ethers of Oximes Derived From 1–Phenyl–Pyrazole Compounds"; Synth. Commun., 1998, 28, 1299–1321.

Nerenz, H. et al.: "Nonlinear optical chromophores with isoquinolines, thieno[2,3–c]–pyridines and 2–(2'–thienyl)pyridines as inherently polarized π–electron bridges"; J. Chem. Soc., Perkin Trans. 2, 1998, pp. 437–447.

Pontikis, R. et al.: "Synthesis and Anti–HIV Activity of Novel N–1 Side Chain–Modified Analogs of 1–[(2–Hydroxyethoxy)methyl]–6–(phenylthio)thymine (HEPT)"; J. Med. Chem. 1997, 40, pp. 1845–1854.

Sammelson, R.E. et al.: "Linear Tetraheterocycles Composed of Both Bidentate Diisoxazole and Bidentate Isoxazole—Furyl/Thienyl/Pyridyl Motifs[1]"; J. Org. Chem. 2000, 65, pp. 2225–2228.

Sano, S. et al.: "New Reaction Mode of the Horner–Wadsworth–Emmons Reaction for the Preparation of α–Fluoro–α,β–unsaturated Esters"; SYNLETT, 1998, pp. 777–779.

Sokolowski, A. et al.: "Phenoxyl Radical Complexes of Zinc(II)"; J. Am. Chem. Soc. 1997, 119, pp. 8889–8900.

Sutherland, J.D. et al.: "Studies on a Potentially Prebiotic Synthesis of RNA"; Tetrahedron, 1997, vol. 53, No. 34, pp. 11595–11626.

Tanaka, A. et al.: Inhibitors of Acyl–CoA:Cholesterol O–Acyltransferase. 2. Identification and Structure—Activity Relationships of a Novel Series of N–Alkyl–N–(heteroaryl–substituted benzyl)–N'–arylureas[1]; J. Med. Chem. 1998, 41, pp. 2390–2410.

Vacher, B. et al.: "Design and Snthesis of a Series of 6–Substituted–2–pyridinylmethylamine Derivatives as Novel, High–Affinity, Selective Agonists at $5–HT_{1A}$ Receptors"; J. Med. Chem. 1998, 41, pp. 5070–5083.

Wong, Ken–Tsung et al.: "Suzuki Coupling Approach for the Synthesis of Phenylene—Pyrimidine Alternating Oligomers for Blue Light–Emitting Material"; Org. Lett., 2202, 4, pp. 513–516.

* cited by examiner

6-O-ACYL KETOLIDE ANTIBACTERIALS

CROSS-REFERENCE TO RELATED APPLICATIONS

This application claims the benefit under 35 U.S.C. § 119(e) of provisional applications Ser. No. 60/392,513, filed Jun. 28, 2002, and No. 60/338,566, filed Dec. 5, 2001, both of which are incorporated herein by reference.

FIELD OF THE INVENTION

The present invention relates to the field of macrolide compounds having antibacterial activity, pharmaceutical compositions containing the compounds, and methods of treating bacterial infections with the compounds.

BACKGROUND OF THE INVENTION

Erythromycins are well-known antibacterial agents widely used to treat and prevent bacterial infection caused by Gram-positive and Gram-negative bacteria. However, due to their low stability in acidic environment, they often carry side effects such as poor and erratic oral absorption. As with other antibacterial agents, bacterial strains having resistance or insufficient susceptibility to erythromycin have developed over time and are identified in patients suffering from such ailments as community-acquired pneumonia, upper and lower respiratory tract infections, skin and soft tissue infections, meningitis, hospital-acquired lung infections, and bone and joint infections. Particularly problematic pathogens include methicillin-resistant *Staphylococcus aureus* (MRSA), vancomycin-resistant enterococci (VRE) and penicillin- and macrolide-resistant *Streptococcus pneumoniae*. Therefore, continuing efforts are called for to identify new erythromycin derivative compounds with improved antibacterial activity, and/or unanticipated selectivity against various target microorganisms, particularly erythromycin-resistant strains.

The following references relate to various erythromycin derivatives disclosed as having antibacterial activity:

EP 216,169 and U.S. Pat. No. 4,826,820 to Brain et al. disclose antibacterially active 6-carbamate erythromycin derivatives stated to "have antibacterial properties, in particular against Gram-positive bacteria but also against some Gram-negative bacteria."

U.S. Pat. Nos. 5,444,051, 5,561,118, and 5,770,579, all to Agouridas et al., disclose erythromycin compounds such as those of the formulae

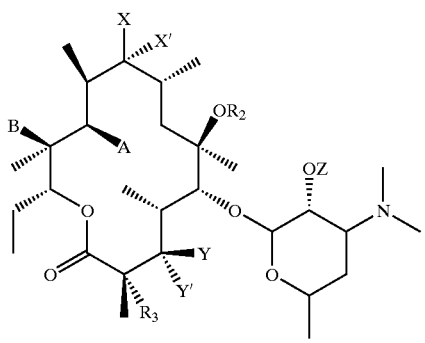

wherein substituents are as described in the respective references, which are all stated to be useful as antibiotics.

U.S. Pat. No. 5,866,549 to Or et al. and WO 98/09978 (Or et al.) disclose 6-O-substituted ketolides stated to have increased acid stability relative to erythromycin A and 6-O-methyl erythromycin A and enhanced activity toward gram negative bacteria and macrolide resistant gram positive bacteria.

WO 97/17356 (Or et al.) discloses tricyclic erythromycin derivatives stated to be useful in the treatment and prevention of bacterial infections.

WO 99/21871 (Phan et al.) discloses 2-halo-6-O-substituted ketolide derivatives of the formula

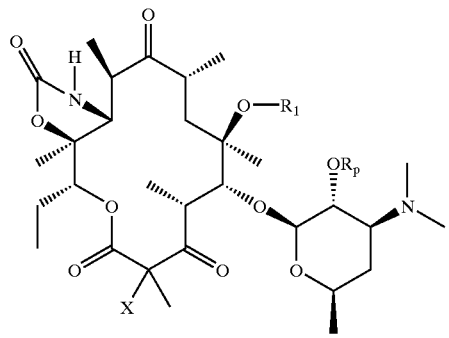

wherein substituents are as described in the respective reference, which are stated to possess antibacterial activity.

WO 99/21864 (Or et al.) discloses 6,11-bridged erythromycin derivatives having antibacterial activity.

WO 00/75156 (Phan et al.) discloses 6-O-carbamate ketolide derivatives that are useful as antibacterial agents for the treatment and prevention of infection in a mammal.

EP1146051 to Kaneko et al. discloses macrolide compounds of the following formula that are useful as antibacterial and antiprotozoal agents in mammals,

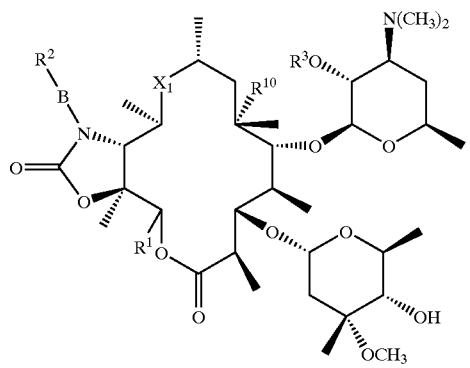

wherein substituents are as described in the reference.

EP1114826 to Kaneko and McMillen discloses novel erythromycin derivatives useful as antibacterial, antiprotozoal and/or prokinetic agents.

WO 00/71557 to Dirlam et al. discloses 13-methyl-erythromycin derivatives that are useful as antibacterial and antiprotozoal agents in mammals (including humans), fish and birds.

U.S. Pat. No. 6,355,620 to Ma et al. discloses C-2 modified erythromycin derivatives that are useful in treating bacterial infections.

WO 02/032918 to Hlasta et al. discloses a series of erythromycin ketolides that possess anti-infective activity and are useful for the treatment of bacterial and protozoal infections.

WO 00/062783 to Hlasta et al. discloses erythromycin analogs useful in the treatment of bacterial and protozoal infections and in the treatment of other conditions involving gastric motility.

U.S. Pat. No. 5,922,683 to Or et al. discloses multicyclic erythromycin compounds having antibacterial activity.

U.S. Pat. No. 6,034,069 to Or et al. discloses 3'-N-modified 6-O-substituted erythromycin ketolide compounds having antibacterial activity.

SUMMARY OF THE INVENTION

The invention provides compounds of Formula 1:

Formula 1

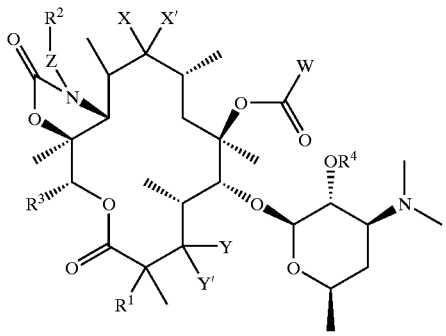

wherein $R^1$ is selected from the group consisting of hydrogen, halogen, and hydroxy;

Z is selected from the group consisting of —NH—$(CH_2)_n$—, —$(CH_2)_n$—, —O—$(CH_2)_n$—, —NH—$C_1$–$C_6$alkenyl-, —$C_1$–$C_6$alkenyl-, —O—$C_1$–$C_6$alkenyl-, NH$C_1$–$C_6$alkynyl-, —$C_1$–$C_6$alkynyl-, and —O—$C_1$–$C_6$alkynyl-, wherein n is an integer from 0 to 5;

$R^2$ is selected from the group consisting of hydrogen, aryl, and heteroaryl;

$R^3$ is selected from the group consisting of hydrogen, $C_1$–$C_{10}$alkyl, $C_2$–$C_{10}$-alkenyl, $C_2$–$C_{10}$-alkynyl, aryl, heteroaryl, heterocyclo, aryl($C_1$–$C_{10}$)alkyl, aryl($C_2$–$C_{10}$) alkenyl, aryl($C_2$–$C_{10}$)alkynyl, heterocyclo($C_1$–$C_{10}$)alkyl, heterocyclo($C_2$–$C_{10}$)alkenyl, and heterocyclo($C_2$–$C_{10}$) alkynyl, $C_3$–$C_6$-cycloalkyl, $C_5$–$C_8$-cycloalkenyl, alkoxyalkyl containing 1–6 carbon atoms in each alkyl or alkoxy group, and alkylthioalkyl containing 1–6 carbon atoms in each alkyl or thioalkyl group;

$R^4$ is hydrogen or a hydroxy protecting group;

W is selected from the group consisting of (1) a substituted pyrrole of the formula

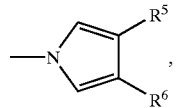

wherein $R^5$ and $R^6$ are independently selected from the group consisting of hydrogen, CN, —C(NH)CHR$^{10}$R$^{11}$, nitro, —C(O)R$^7$, —C(O)OR$^7$, —C(O)NR$^7$R$^8$, —SO$_2$R$^7$, $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, and heteroaryl, wherein $R^7$ and $R^8$ are independently selected from the group consisting of hydrogen, alkyl, alkenyl, alkynyl, cycloalkyl, aryl, heteroaryl, heterocyclo, aralkyl, heteroaralkyl, and heterocycloalkyl; and $R^{10}$ and $R^{11}$ are independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl, or $R^{10}$ and $R^{11}$, taken together with the atoms to which they are attached, form an optionally substituted 4–8 membered carbocyclic ring wherein the substituents are selected from the group consisting of $C_0$–$C_8$-alkyl, $C_2$–$C_8$-alkenyl, $C_2$–$C_8$-alkynyl, aryl, and heteroaryl;

(2) —OR$^9$, wherein $R^9$ is independently selected from the group consisting of $C_1$–$C_8$-alkyl, $C_3$–$C_8$-alkenyl, $C_3$–$C_8$-alkynyl, $C_3$–$C_8$-cycloalkyl, and $C_5$–$C_8$-cycloalkenyl;

(3) —NR$^{10}$OR$^{11}$, wherein $R^{10}$ and $R^{11}$ are independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl, or $R^{10}$ and $R^{11}$, taken together with the atoms to which they are attached, form an optionally substituted 5–8 membered heterocyclic ring wherein the substituents are selected from the group consisting of $C_1$–$C_8$-alkyl, $C_2$–$C_8$-alkenyl, $C_2$–$C_8$-alkynyl, aryl, and heteroaryl;

(4) —NR$^{12}$NR$^{13}$R$^{14}$, wherein $R^{12}$, $R^{13}$, and $R^{14}$ are independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl, or $R^{12}$ and $R^{13}$, taken together with the nitrogens to which they are attached, form an optionally substituted 5–8 membered heterocyclic ring, wherein the substituents are selected from the group consisting of $C_1$–$C_8$-alkyl, $C_2$–$C_8$-alkenyl, $C_2$–$C_8$-alkynyl, aryl, and heteroaryl;

or $R^{13}$ and $R^{14}$, taken together with the nitrogen to which they are attached, form an optionally substituted 3–8 membered heterocyclic ring or an optionally substituted 5–10 membered heteroaryl ring, wherein the substituents are selected from the group consisting of $C_1$–$C_8$-alkyl, $C_2$–$C_8$-alkenyl, $C_2$–$C_8$-alkynyl, aryl, and heteroaryl;

(5) —NR$^5$N=CHR$^{13a}$, wherein $R^{15}$ is independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl; and $R^{13a}$ is independently selected from the group consisting of $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, and heteroaryl;

(6) —NR$^{10}$NR$^{11}$C(O)R$^{16}$, wherein $R^{16}$ is independently selected from the group consisting of hydrogen, $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, and heteroaryl;

(7) —NR$^{10}$NR$^{11}$C(O)OR$^{17}$, wherein $R^{17}$ is independently selected from the group consisting of $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl;

(8) —NR$^{10}$NR$^{11}$C(O)NR$^{18}$R$^{19}$, wherein $R^{18}$ and $R^{19}$ are independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl, or $R^{18}$ and $R^{19}$, taken together with the nitrogen to which they are attached, form an optionally substituted 3–8 membered heterocyclic ring or an optionally substituted 5–10 membered heteroaryl ring, wherein the substituents are selected from the group consisting of $C_1$–$C_8$-alkyl, $C_2$–$C_8$-alkenyl, $C_2$–$C_8$-alkynyl, aryl, and heteroaryl;

(9) —$NR^{10}NR^{21}SO_2R^{20}$, wherein
   $R^{20}$ is independently selected from the group consisting of $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, and heteroaryl; and
   $R^{21}$ is independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, $C_2$–$C_6$ acyl, aryl, and heteroaryl;

(10) —$SR^9$, wherein
   $R^9$ is independently selected from the group consisting of $C_1$–$C_8$-alkyl, $C_3$–$C_8$-alkenyl, $C_3$–$C_8$-alkynyl, $C_3$–$C_8$-cycloalkyl, and $C_5$–$C_8$-cycloalkenyl;

(11) —$CHR^{10}R^{11}$, wherein
   $R^{10}$ and $R^{11}$ are independently selected from the group consisting of hydrogen, $C_1$–$C_8$-alkyl, $C_3$–$C_8$-alkenyl, $C_3$–$C_8$-alkynyl, $C_3$–$C_8$-cycloalkyl, $C_5$–$C_8$-cycloalkenyl, aryl, and heteroaryl, or $R^{10}$ and $R^{11}$, taken together with the atoms to which they are attached, form an optionally substituted 4–8 membered carbocyclic ring wherein the substituents are selected from the group consisting of $C_1$–$C_8$-alkyl, $C_2$–$C_8$-alkenyl, $C_2$–$C_8$-alkynyl, aryl, and heteroaryl; and

(12) a substituted pyrazole of the formula

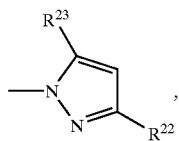

, wherein
   $R^{22}$ and $R^{23}$ are independently selected from the group consisting of hydrogen, —$C(O)OR^7$, —$C(O)NR^7R^8$, $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, and heteroaryl, wherein
      $R^7$ and $R^8$ are independently selected from the group consisting of hydrogen, alkyl, alkenyl, alkynyl, cycloalkyl, aryl, heteroaryl, heterocyclo, aralkyl, heteroaralkyl, and heterocycloalkyl;

X and X', together with the carbon atom to which they are attached, form C=O, C=$NR_c$, or C=$NOR_c$, wherein $R_c$ is independently selected from hydrogen, alkyl, alkenyl and alkynyl; and Y and Y', together with the carbon atom to which they are attached, form C=O, —CHOH, C=$NR_c$, or C=$NOR_c$, wherein $R_c$ is independently selected from hydrogen, alkyl, alkenyl and alkynyl;

or an optical isomer, enantiomer, diastereomer, racemate or racemic mixture thereof, or a pharmaceutically acceptable salt, esters or pro-drugs thereof.

Compounds of the above formula are useful as antibacterial agents for the treatment of bacterial infections in a subject such as human and animal.

The present invention is also directed to a method of treating a subject having a condition caused by or contributed to by bacterial infection, which comprises administering to said subject a therapeutically effective amount of the compound of Formula 1.

The present invention is further directed to a method of preventing a subject from suffering from a condition caused by or contributed to by bacterial infection, which comprises administering to the subject a prophylactically effective amount of the compound of Formula 1.

Other objects and advantages will become apparent to those skilled in the art from a review of the ensuing specification.

DETAILED DESCRIPTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon—carbon double bond. "Alkynyl" refers to a straight or branched chain hydrocarbon with at least one carbon—carbon triple bound. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. "Cycloalkenyl" groups contain 5 to 8 ring carbons and at least one carbon—carbon double bond. The alkyl, alkenyl, alkynyl, cycloalkyl, cycloalkenyl, and alkoxy group may be independently substituted with one or more members of the group including, but not limited to, halogen, alkyl, alkenyl, alkynyl, cycloalkyl, alkoxy, oxo, aryl, heteroaryl, heterocyclo, CN, nitro, —$OCOR_a$, —$OR_a$, —$SR_a$, —$SOR_a$, —$SO_2R_a$, —$COOR_a$, —$NR_aR_b$, —$CONR_aR_b$, —$OCONR_aR_b$, —$NHCOR_a$, —$NHCOOR_a$, and —$NHCONR_aR_b$, wherein $R_a$ and $R_b$ are independently selected from H, alkyl, alkenyl, alkynyl, cycloalkyl, aryl, heteroaryl, heterocyclo, aralkyl, heteroaralkyl, and heterocycloalkyl. "Aralkyl," "heteroaralkyl," and "heterocycloalkyl" are alkyl groups substituted with aryl, heteroaryl, and heterocyclo, respectively. "Arylalkenyl," "heteroarylalkenyl," and "heterocycloalkenyl" are alkenyl groups substituted with aryl, heteroaryl, and heterocyclo, respectively. "Arylalkynyl," "heteroarylalkynyl," and "heterocycloalkynyl" are alkynyl groups substituted with aryl, heteroaryl, and heterocyclo, respectively.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo and iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, $C_1$–$C_8$-alkyl, aryl, heteroaryl, heterocyclo, $C_1$–$C_8$-alkoxyl, $C_1$–$C_8$-alkylthio, $C_1$–$C_8$-alkyl-amino, di($C_1$–$C_8$-alkyl) amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0–3 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, indazolyl, indolizinyl, benzofuryl, cinnolinyl, quinoxalinyl, pyrrolopyridinyl, furopyridinyl (such as furo[2,3-c] pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with halogen, OH, CN, mercapto, nitro, amino, $C_1$–$C_8$-alkyl, aryl, heteroaryl, heterocyclo, $C_0$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully saturated, partially saturated, or non-aromatic cyclic group which is, for example, a 3- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzothiopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like. The heterocyclic group may be substituted by independent replacement of 1 to 3 of the hydrogen atoms thereon with OH, CN, mercapto, nitro, amino, $C_1$–$C_8$-alkyl, aryl, heteroaryl, heterocyclo, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl; acyl and aroyl such as acetyl, pivaloyl, benzoyl, 4-methoxybenzoyl, and 4-nitrobenzoyl; alkoxycarbonyl such as methoxycarbonyl, ethoxycarbonyl, and benzyloxycarbonyl.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Included within the scope of the invention are the hydrated forms of the compounds which contain various amounts of water, for instance, the hydrate, hemihydrate, and sesquihydrate forms. The present invention also includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" includes, without limitation, any animal or artificially modified animal. As a particular embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals.

Compounds of Formula 1 wherein R$^2$ is hydrogen and Z is —(CH$_2$)$_n$— wherein n is 0 are preferred embodiments of the present invention.

Compounds of Formula 1 wherein W is selected from groups (1), (2), (3), or (4) as described above are other preferred embodiments of the present invention.

Compounds of Formula 1 wherein R$^3$ is ethyl are still other preferred embodiments of the present invention.

Compounds of Formula 1 wherein R$^4$ is hydrogen are yet other embodiments of this invention. R$^4$ may also be selected from acyl and aroyl.

Compounds of Formula 1 wherein R is hydrogen and Z is —(CH$_2$)$_n$— wherein n is 0, W is selected from groups (1), (2), (3), or (4) as described above, R$^3$ is ethyl, and R$^4$ is hydrogen, are still other preferred embodiments of the present invention.

Especially preferred embodiments of compounds of Formula 1 are those compounds having Formula 1':

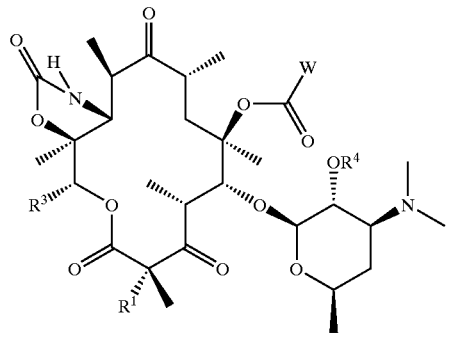

Formula 1' wherein, R$^1$, R$^3$, R$^4$ and W are as described above.

Compounds of Formula 1' whrerin R$^1$ is selected from the group consisting of H and F are preferred embodiments of the invention.

Compound of Formula 1' wherein R$^3$ is ethyl are also preferred embodiments of the invention.

Compound of Formula 1' wherein R$^4$ is selected from the group consisting of H and acyl are still other preferred embodiments of the invention.

Compounds of Formula 1' wherein W is selected from the group consisting of groups (1), (2), (3), (4), (10), (11) and (12) as defined above are also preferred embodiments of the invention.

Compounds of Formula 1' wherein R$^1$ is H and R$^3$ is ethyl are still other preferred embodiments of the invention.

Compounds of Formula 1' wherein R$^1$ is F and R$^3$ is ethyl are still other preferred embodiments of the invention.

Compounds of Formula 1' wherein R$^1$ is H, R$^3$ is ethyl and R$^4$ is H are also preferred embodiments of the invention.

Compounds of Formulal 1' wherein W is selected from group consisting of groups (1) and (2) as defined above are still other preferred embodiments of the invention.

This invention also provides processes for preparing the instant compounds.

The compounds of Formula 1 may be prepared from readily available starting materials such as erythromycin and erythromycin derivatives well known in the art. Outlined in Schemes 1 through 13 are representative procedures to prepare the compounds of the instant invention.

Scheme 1

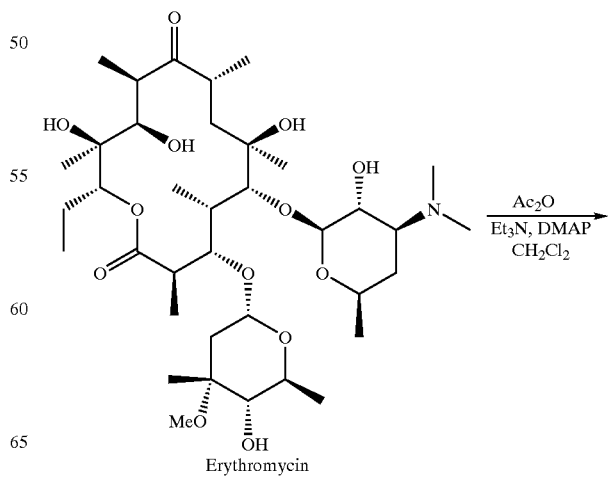

Erythromycin

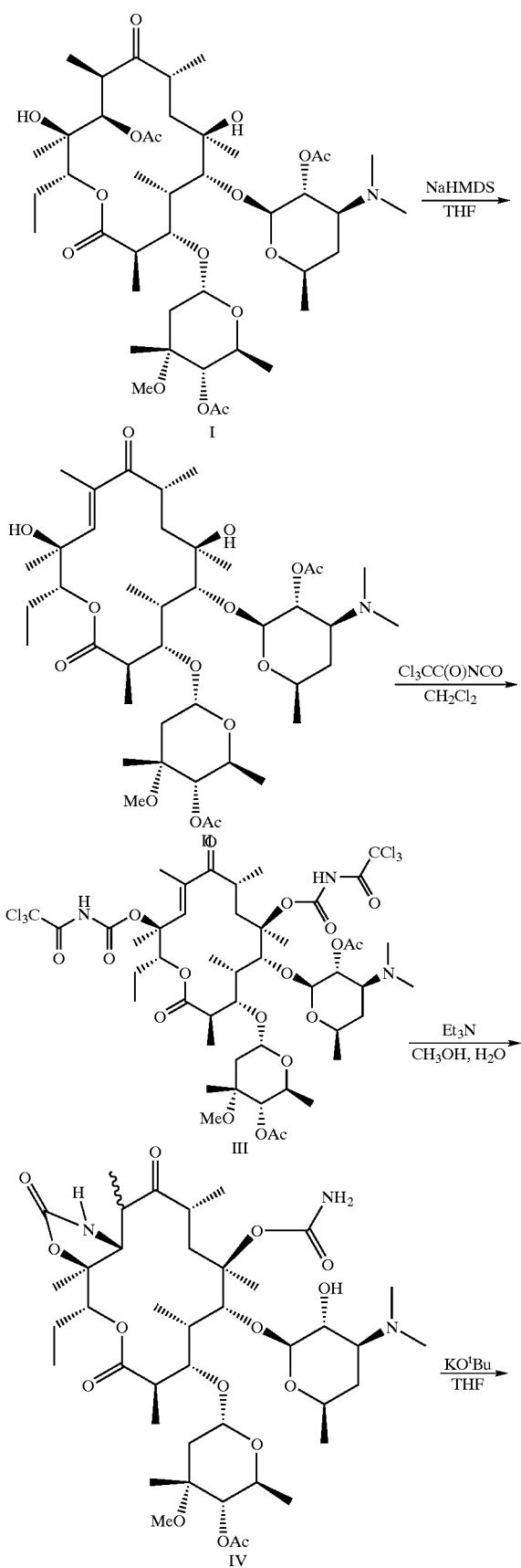
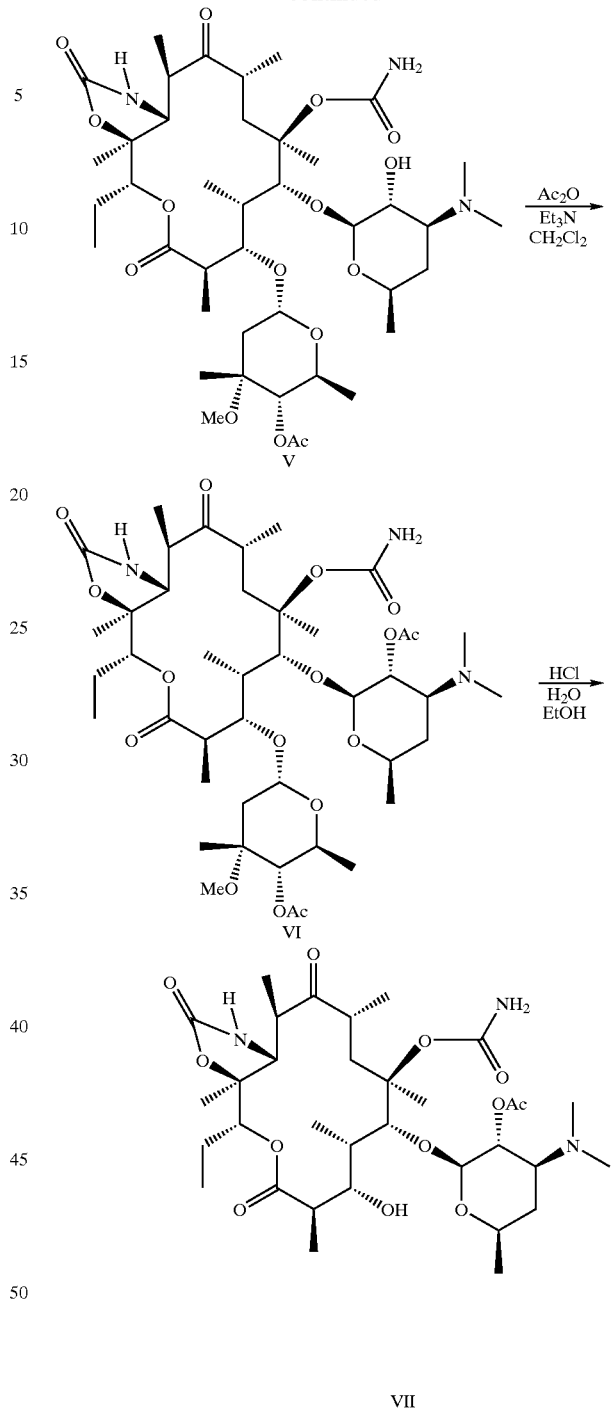

Scheme 1 illustrates the method of synthesis of the 2',4"-diacetyl-6-carbamyl-11,12-dideoxy-11,12-iminocarbonyloxyerythromycin A (VI) and the 2'-acetyl-6-carbamyl-11,12-dideoxy-3-O-descladinosyl-11,12-iminocarbonyloxyerythromycin A (VII) precursors to the compounds of the invention.

Erythromycin A is treated with acetic anhydride in the presence of a tertiary amine base, such as triethylamine, diisopropylethylamine, or pyridine, and an acylation catalyst, such as 4-(dimethylamino)pyridine (DMAP), in a suitable solvent such as methylene chloride, chloroform or tetrahydrofuran (THF) at a temperature ranging from −20°

C. to 37° C. for 2 to 48 hours to afford 2',4",11-triacetylerythromycin A (I). The 10,11-anhydro derivative (II) can be readily obtained by treatment of I with a base in an inert solvent such as THF, dioxane, 1,2-dimethoxyethane (DME), or dimethylformamide (DMF) at a temperature ranging from −78° C. to 80° C. for 1–24 hours. Suitable bases to effect the elimination reaction include, but are not limited to, sodium hexamethyldisilazide, potassium hexamethyldisilazide, lithium diisopropylamide (LDA), lithium tetramethylpiperidide, 1,8-diazabicyclo[5.4.0] undec-7-ene (DBU), and tetramethylguanidine. It will be apparent to one skilled in the art that alternative methods for synthesis of 2',4"-diacetyl-10,11-anhydroerythromycin A are available, including conversion of erythromycin A to the 11,12-cyclic carbonate derivative with ethylene carbonate, followed by elimination with tetramethylguanidine, as described in Hauske, J. R. and Kostek, G., *J. Org. Chem.* 1982, 47,1595. Selective protection of the 2' and 4"-hydroxyl groups can then be readily accomplished with acetic anhydride in the presence of a tertiary amine base. Likewise, alternative protecting group strategies may be employed. For example, erythromycin A may be treated with benzoic anhydride, propionic anhydride, or formic acetic anhydride under similar conditions as described above to obtain the 2',4",11-triacylated erythromycin A derivative followed by elimination to afford the corresponding 10,11-anhydro compound.

Once the suitably protected 10,11-anhydro derivative is obtained, derivatization of both tertiary hydroxyl groups can be carried out by treatment with trichloroacetylisocyanate in an inert solvent, such as methylene chloride, chloroform, or THF at a temperature ranging from −20° C. to 37° C. for 1–24 hours to yield the di-(N-trichloroacetyl)carbamate derivative (III). The N-trichloroacetylcarbamate functionalities can be hydrolyzed to the corresponding primary carbamates by treatment with a suitable base, such as triethylamine, in an aqueous solvent mixture, such as methanol/water for 1–24 hours at a temperature ranging from 20° C. to 80° C. Alternative bases may likewise be used to effect this conversion, such as sodium hydroxide, potassium hydroxide, sodium carbonate and potassium carbonate. Under the reaction conditions, the primary carbamate formed at the 12-position undergoes spontaneous Michael addition to the electrophilic 11-position of the α,β-unsaturated ketone and the 2'-acetoxy group is hydrolyzed to the corresponding hydroxyl to afford the cyclic carbamate derivative (IV). Compound IV is generally isolated as a mixture of methyl epimers at the C10-position, which can be readily converted to the desired C10-β-methyl epimer (V) by treatment with an equilibrating base, such as potassium t-butoxide, tetramethylguanidine, or DBU in a suitable solvent, such as THF, dioxane, DME, DMF or t-butanol at a temperature ranging from −78° C. to 80° C. for 1 to 24 hours. Reprotection of the 2'-hydroxyl group to give VI can be carried out by treatment with acetic anhydride in the presence of a tertiary amine base, such as triethylamine, diisopropylethylamine, or pyridine, and optionally an acylation catalyst, such as DMAP, in a suitable solvent such as methylene chloride, chloroform or THF at a temperature ranging from −20° C. to 37° C. for 2 to 48 hours. It is understood that an orthogonal protection strategy of the sugar hydroxyls may also be employed by treatment of V with alternate reagents such as benzoic anhydride, benzyl chloroformate, hexamethyldisilazane, or a trialkylsilyl chloride. Finally, selective removal of the cladinose sugar can be accomplished by reaction of VI with an acid, such as hydrochloric, sulfuric, chloroacetic, and trifluoroacetic, in the presence of alcohol and water to afford VII. Reaction time is typically 0.5–24 hours at a temperature ranging from −10° C. to 37° C.

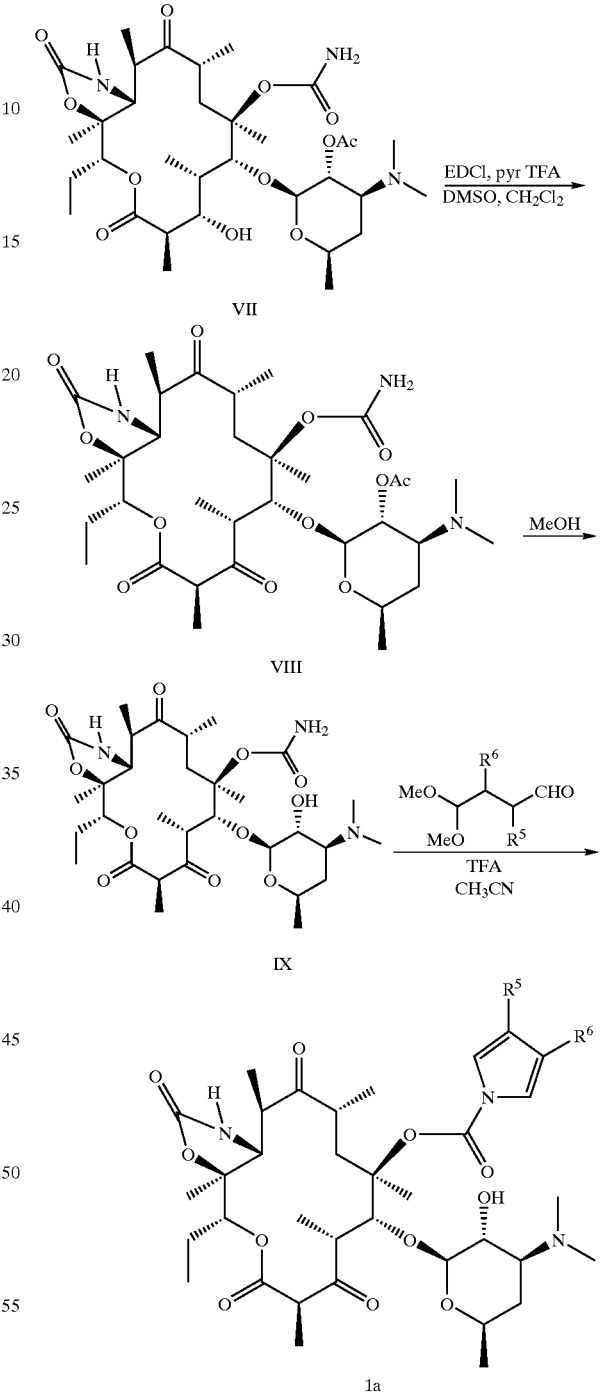

Scheme 2 depicts the synthesis of compounds of formulae VIII and IX and compounds of the instant invention of formula 1a. Oxidation of the 3-hydroxy group of VII to yield compound VIII can be effected with dimethylsulfoxide (DMSO) and a carbodiimide, such as 1-ethyl-3-(3-dimethylaminopropyl)carbodiimide (EDCI), in the presence of pyridinium trifluoroacetate in a suitable solvent, such as methylene chloride, for 1 to 24 hours at a temperature ranging from −20° C. to 37° C. Alternative methods of oxidation include N-chlorosuccinimide and dimethylsulfide complex followed by treatment with a tertiary amine base, Dess-Martin periodinane, or oxalyl chloride/DMSO followed by treatment with a tertiary amine base. Removal of the 2'-acetyl group of compound VIII is readily accomplished by transesterification with methanol for 2–48 hours at a temperature ranging from 15–20° C. to 60° C. to yield compound IX. Alternative methods for deprotection of the 2'-acetyl group include hydrolysis in the presence of an alkali metal hydroxide or alkali metal carbonate, such as sodium hydroxide or potassium carbonate, or ammonolysis with ammonia in methanol. Compounds of formula 1a can be obtained by reaction of IX with a suitably substituted 1,4-dialdehyde or its equivalent in the presence of an acid. Equivalents of 1,4-dialdehydes include 2,5-dialkoxytetrahydrofurans, 1,4-dialdehyde monoacetals, and 1,4-dialdehyde diacetals. A preferred acid for effecting this transformation is trifluoroacetic acid in a suitable solvent, like acetonitrile, methylene chloride, or toluene at −20° C. to 100° C. Typically, the reaction is conducted for from 2–96 hours. Preferred 1,4-dialdehydes or their equivalents include 2-formyl-4,4-dimethoxybutanenitrile, tetrahydro-2,5-dimethoxy-3-furancarboxaldehyde, tetrahydro-2,5-dimethoxy-3-furancarboxylic acid methyl ester, and tetrahydro-2,5-dimethoxy-3-furancarboxylic acid ethyl ester.

Compounds of formula 1a can be converted to other compounds of the instant invention by displacement of the pyrrole with hydrazines, hydroxylamines, and alcohols. Preferred substrates for this conversion are those in which the pyrrole is substituted with electron-withdrawing groups including, but not limited to, cyano, formyl, and alkoxycarbonyl. A particularly preferred substrate is compound 1a, where $R^5$=CN and $R^6$=H. Scheme 3 illustrates the conversion of compound 1a to compounds of formula 1b, 1c, and 1d, wherein $R^9$, $R^{10}$, $R^{11}$, $R^{12}$, $R^{13}$, and $R^{14}$ are as defined previously. Compounds of formula 1b can be prepared by reaction of 1a with hydrazine or a suitably substituted hydrazine in a suitable solvent, such as acetonitrile, dimethylformamide, dimethyl sulfoxide, or tetrahydrofuran, at a temperature ranging from −20° C. to 120° C. for 0.5 to 72 hours. Compounds of formula 1c can be prepared by reaction of 1a with hydroxylamine or a suitably substituted hydroxylamine in a suitable solvent, such as acetonitrile, dimethylformamide, dimethyl sulfoxide, or tetrahydrofuran, at a temperature ranging from −20° C. to 120° C. for 0.5 to 72 hours. The hydrazines and hydroxylamines used in the preparation of compounds of formulae 1b and 1c may be in the form of acid addition salts, in which case the reaction is preferably conducted in the presence of a base such as pyridine, triethylamine, or an alkali metal carbonate. Compounds of formula 1d can be prepared by reaction of 1a with a suitably substituted alcohol in the presence of a suitable Scheme 3

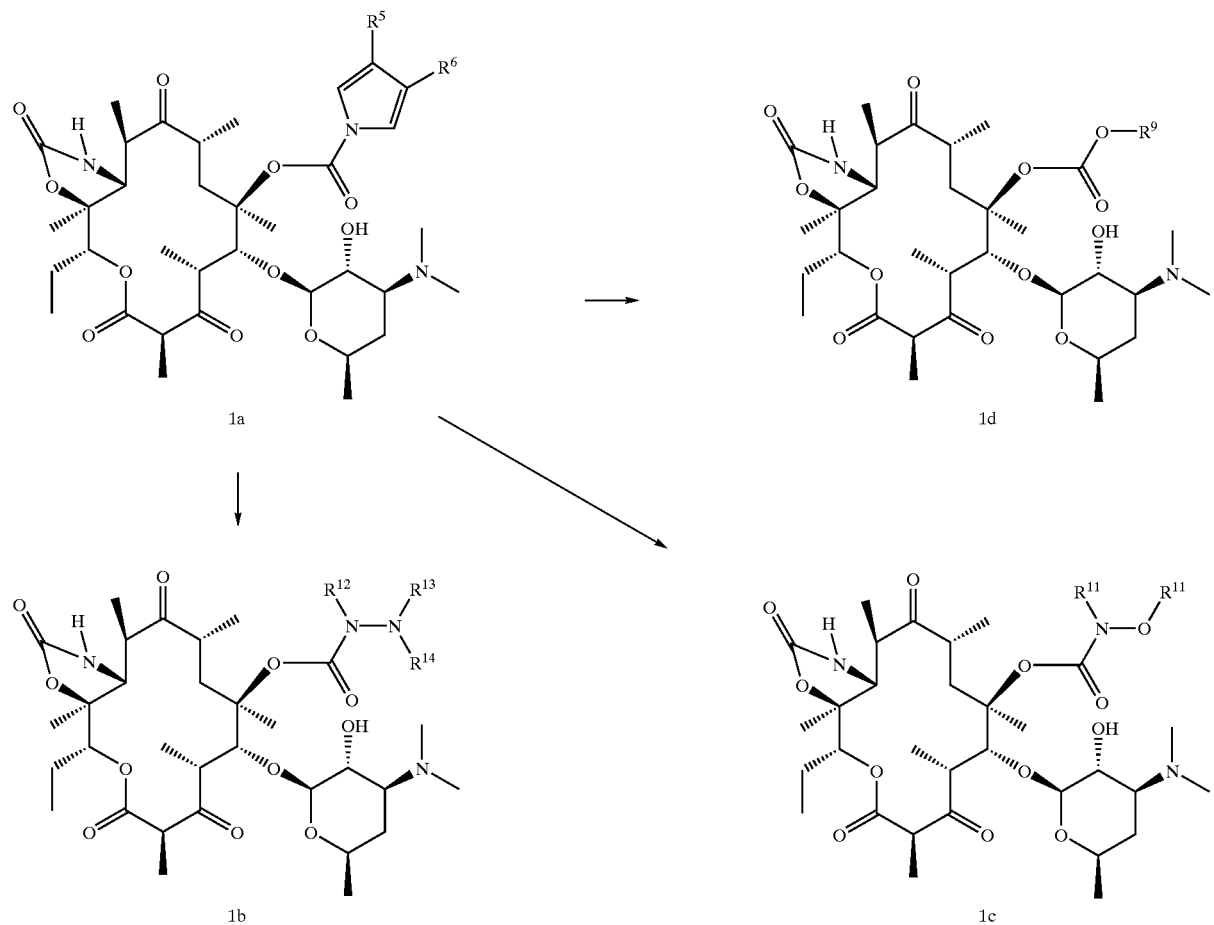

base such as DBU, DBN, tert-butyltetramethylguanidine, sodium hydride, potassium hydride, or an alkyllithium, in a suitable solvent, such as acetonitrile, dimethylformamide, dimethyl sulfoxide, or tetrahydrofuran, at a temperature ranging from −20° C. to 120° C. for 0.5 to 72 hours. Preformed alkali or alkaline earth metal alkoxides are also suitable reagents for the preparation of compounds of formula 1d.

compound 1e to compounds of formula 1g consists of treatment with a suitably substituted aldehyde in the, presence of acetic acid in methanol as solvent for 0.5 to 24 hours, and subsequently adding sodium cyanoborohydride and, if necessary, additional acetic acid to produce the compound of formula 1g after a period of from 0.5 to 72 hours. In the direct conversion of compound 1e to compounds of formula 1g, it is also possible to isolate compounds of formula 1h in Scheme 4

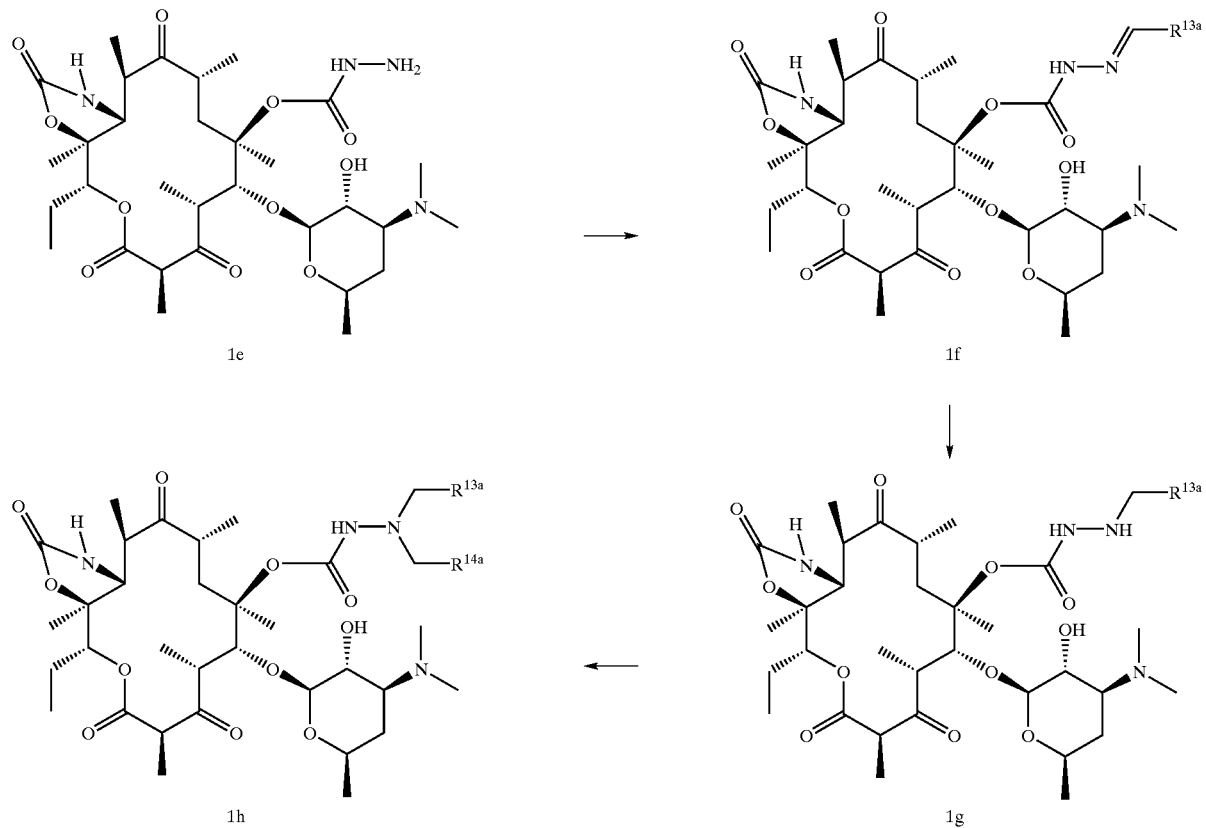

The compound of formula 1e, obtained by reaction of compound 1a with hydrazine as described in Scheme 3, can be further converted to other compounds of the instant invention as shown, for example, in Scheme 4. Compound 1e can be converted to compounds of formula 1f by reaction with a suitably substituted aldehyde, $R^{13a}$CHO, in a suitable solvent, including but not limited to methanol, ethanol, acetonitrile, THF, or dichloromethane, at a temperature ranging from −20° C. to 120° C. for 0.5 to 72 hours, and preferably in the presence of an acid catalyst, such as acetic acid, trifluoroacetic acid, or hydrochloric acid. Furthermore, reaction of 1e with a 1,3-dialdehyde or a 1,3-dialdehyde equivalent, such as a 2,5-dialkoxytetrahydrofuran, under similar conditions as above produces an optionally substituted pyrrole. Compound 1f can be converted to compounds of formula 1g by treatment with a variety of reducing agents including sodium cyanoborohydride in the presence of an acid catalyst such as acetic acid, triethylsilane in trifluoroacetic acid, and hydrogen in the presence of a noble metal catalyst such as palladium on carbon. The conversion of compound 1e to compounds of formula 1g can also be carried out without isolation of the intermediate compound of formula 1f. A preferred method for the conversion of which $R^{13a}$ and $R^{14a}$ are the same, which are also compounds of the instant invention, depending on the reactivity of the aldehyde and the number of equivalents of aldehyde employed. Additionally, compounds of formula 1h in which $R^{13a}$ and $R^{14a}$ are not necessarily the same may be prepared, for example, by reaction of compounds of formula 1g with an aldehyde, $R^{14a}$CHO, in the presence of acetic acid and sodium cyanoborohydride in methanol. The conversion of compound 1e to compounds of formula 1h can also be carried out without isolation of the intermediate compound of formula 1g. For example, compound 1e may be treated with a suitably substituted aldehyde, $R^{13a}$CHO, in the presence of acetic acid in methanol as solvent for from 0.5 to 24 hours, followed by addition of sodium cyanoborohydride and, if necessary, additional acetic acid. Following reaction for from 0.5 to 72 hours, a second suitably substituted aldehyde, $R^{14a}$CHO, is added, optionally in the presence of additional acetic acid and additional sodium cyanoborohydride, to produce the compound of formula 1h after a period of from 0.5 to 72 hours. Additionally, if a dialdehyde is used, compounds of formula 1h in which $R^{13a}$ and $R^{14a}$ are connected to form a ring may be prepared. For example, reaction of compound 1e with a 1,5-dialdehyde or a 1,5-dialdehyde equivalent such as a 3,4-dihydro-2-alkoxy-2H-pyran in the presence of triethylsilane and trifluoroacetic acid produces a compound of formula 1h in which $R^{13a}$ and $R^{14a}$ are connected to form a piperidine ring.

Scheme 5

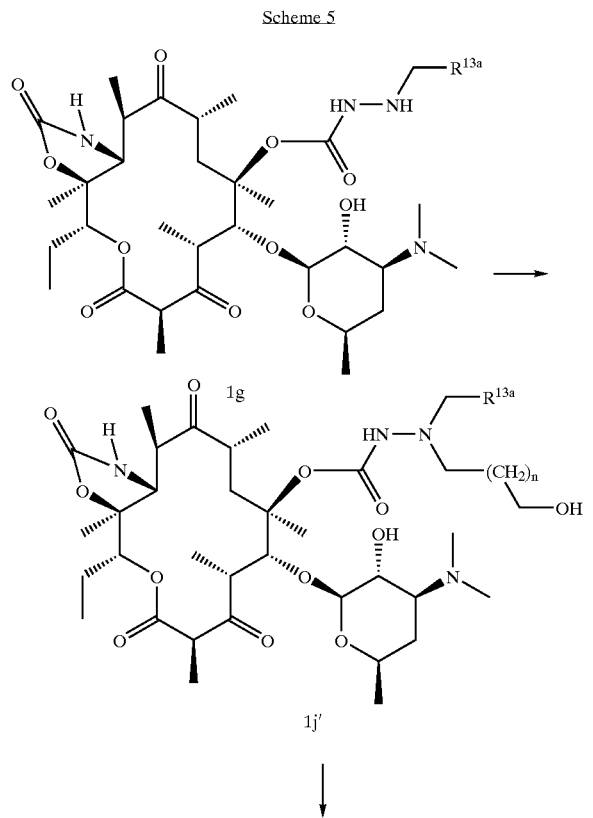

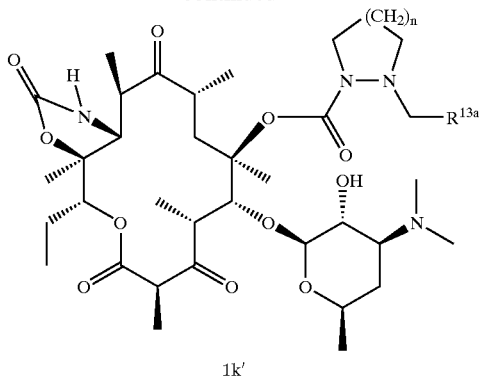

In the case where $R^{14a}$ contains a functionality that can be converted to a leaving group, intramolecular reaction with the alpha-nitrogen atom to form a heterocycle can occur under appropriate conditions. This is illustrated in Scheme 5. For example, the compound of formula 1j', in which n is an integer from 1–3, can be obtained by reaction of compound 1k' with a dialdehyde in the presence of a suitable reducing agent, such as sodium cyanoborohydride, and an acid catalyst, such as acetic acid at temperatures ranging from 0° C. to 60° C. for from 1 to 24 hours. Suitable dialdehydes to effect this conversion include, for example, glutaraldehyde, butanedial, and malondialdehyde. Alternatively, a suitable dialdehyde equivalent, such as 3,4-dihydro-2-methoxy-2H-pyran, 2,5-dimethoxytetrahydrofuran or 1,1,3,3-tetramethoxypropane may be employed. Conversion of compounds of formula 1j' to heterocycles of formula 1k' can be accomplished by reaction with a suitable sulfonyl chloride, such as p-toluenesulfonyl chloride or methanesulfonyl chloride, in an inert solvent in the presence of a base at temperatures ranging from –20° C. to 60° C. for from 1 to 120 hours. Suitable bases to effect this conversion include for example, triethylamine, diisopropylethylamine, or pyridine. Suitable solvents include, but are not limited to, methylene chloride, chloroform or tetrahydrofuran.

Scheme 6

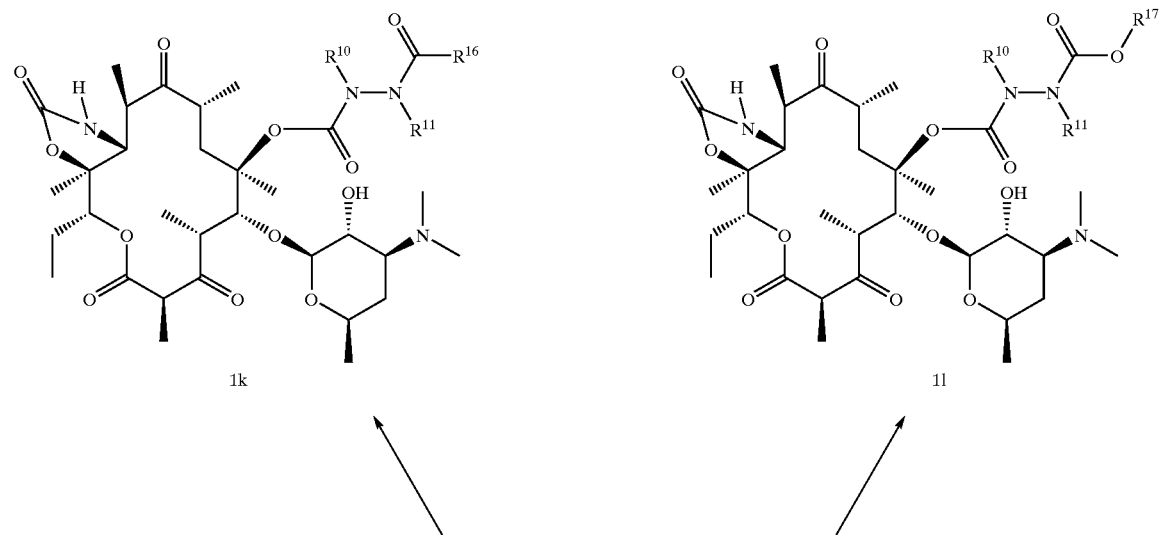

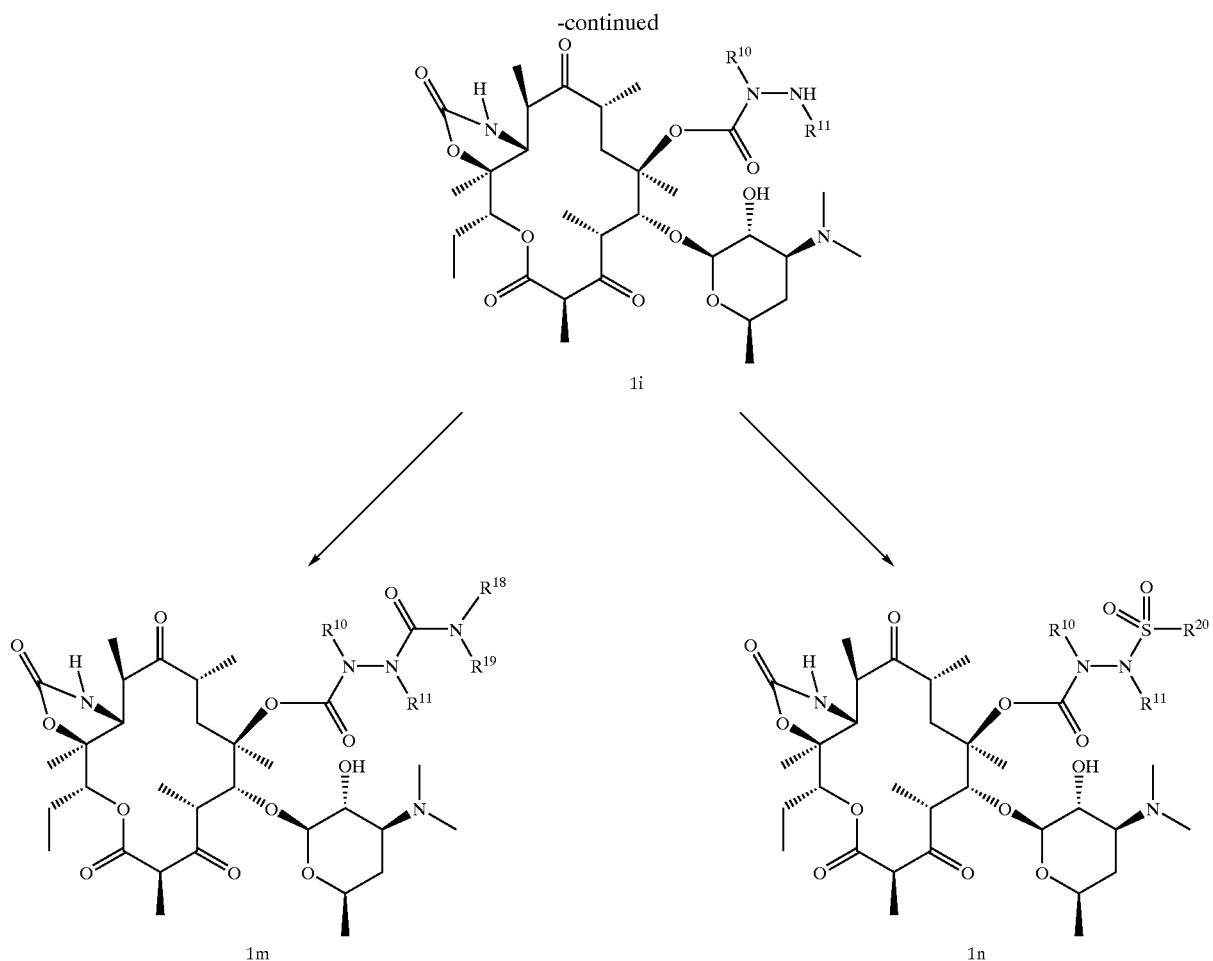

Scheme 6 shows methods for the conversion of compounds of formula 1i, prepared by the methods described above, into additional compounds of the invention of the formulae 1k, 1l, 1m, and 1n. For some of these conversions, derivatization of the 2'-hydroxyl may occur concurrently with the desired transformation. In suitable cases, as detailed below, the 2'-derivatized compound may be converted into the corresponding 2'-hydroxy compound.

Compounds of formula 1i may be converted into compounds of formula 1k by reaction with an excess of an acylating agent in the presence of a tertiary amine, followed by de-acylation of the 2'-hydroxyl by the methods described above, such as transesterification with methanol for 2–48 hours at a temperature ranging from –20° C. to 60° C. to yield compounds of formula 1k. Alternatively, compounds of formula 1k may be prepared directly from compounds of formula 1i by reaction with an acylating agent (1–4 equivalents, depending on the reactivity of the acylating agent), optionally in the presence of an amine base, such as pyridine, in an inert solvent such as dichloromethane, tetrahydrofuran or toluene at temperatures ranging from –20° C. to 60° C. for from 1–48 hours. Acylating agents include acid halides, acid anhydrides, and acids in the presence of an activating agent such as dicyclohexylcarbodiimide, EDCI, BOP-Cl, BOP, PyBOP, and the like. Compounds of formula 1i may be converted into compounds of formula 1l by reaction with an excess of a carbonylating agent in the presence of a tertiary amine, followed by de-acylation of the 2'-hydroxyl by the methods described above, such as transesterification with methanol for 2–48 hours at a temperature ranging from –20° C. to 60° C. to yield compounds of formula 1l. Alternatively, compounds of formula 1l may be prepared directly from compounds of formula 1i by reaction with a carbonylating agent (1–1.5 equivalents, depending on the reactivity of the carbonylating agent), optionally in the presence of an amine base, such as pyridine, in an inert solvent such as dichloromethane, tetrahydrofuran or toluene at temperatures ranging from –20° C. to 60° C. for from 1–48 hours. Carbonylating agents include chloroformates, fluoroformates, azidoformates, and pyrocarbonates. Compounds of formula 1i may be converted into compounds of formula 1m by reaction with a carbamoyl chloride in the presence of a tertiary amine or with an isocyanate (1–1.5 equivalents, depending on the reactivity of the carbamoyl chloride or isocyanate), optionally in the presence of an amine base, such as pyridine, in an inert solvent such as dichloromethane, tetrahydrofuran or toluene at temperatures ranging from –20° C. to 60° C. for from 1–120 hours. Compounds of formula 1i may be converted into compounds of formula 1n by reaction with a sulfonyl chloride or sulfonic anhydride (1–1.5 equivalents, depending on the reactivity of the sulfonyl chloride or sulfonic anhydride), optionally in the presence of an amine base, such as pyridine, in an inert solvent such as dichloromethane, tetrahydrofuran or toluene at temperatures ranging from –20° C. to 60° C. for from 1–48 hours.

Scheme 7

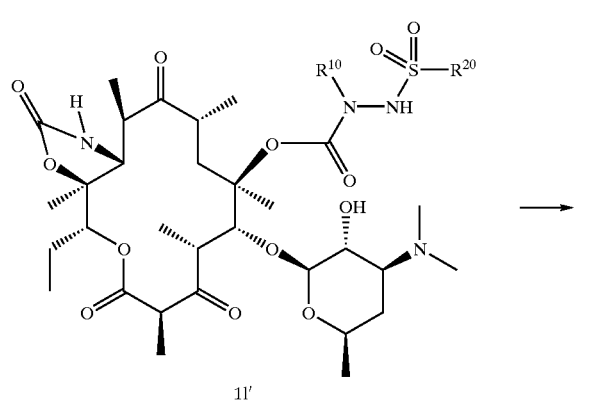

1l'

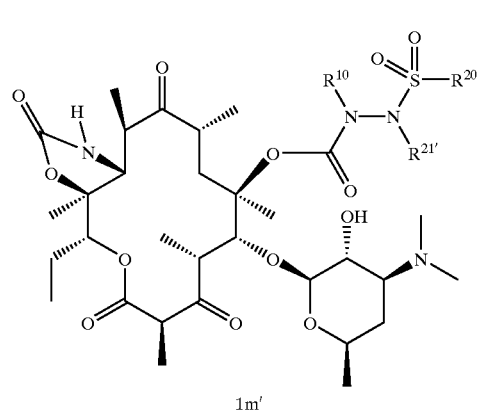

1m'

Compounds of formula 1m', in which $R^{21'}$ is $C_2$–$C_6$ acyl, may be prepared from compounds of formula 1l' in a two-step process involving reaction with an excess of an acylating agent in the presence of an amine base, such as pyridine, followed by de-acylation of the 2'-hydroxyl by the methods described above, such as transesterification with methanol for 2–48 hours at a temperature ranging from –20° C. to 60° C. (Scheme 7).

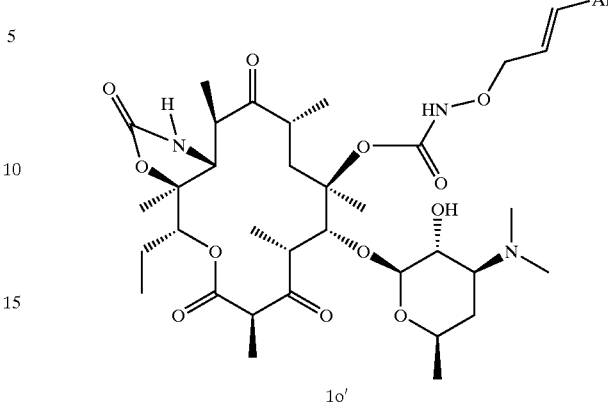

1o'

Scheme 8 illustrates an alternative method of synthesis of N-alkoxycarbamate compounds of formula 1o', wherein Ar is aryl or heteroaryl. The compound of formula 1n' (prepared as depicted in Scheme 3 by reaction of compounds of formula 1a with O-allylhydroxylamine) may be converted to compounds of formula 1o' under Heck reaction conditions, employing a aryl or heteroaryl halide or triflate (ArX) in the presence of a Pd(0) or Pd(II) catalyst, a phosphine ligand, and an amine or inorganic base, for from 2 to 72 hours at a temperature ranging from 20° C. to 120° C. Suitable palladium catalysts to effect this conversion include, for example, palladium(II)acetate, tetrakis(triphenylphosphine)palladium (0), and the like. Suitable phosphine ligands include, for example, triphenylphosphine, tri-o-tolylphosphine, and the like. Suitable bases include tertiary amines, such as triethylamine, sodium or potassium acetate, and sodium bicarbonate. Suitable solvents include, but are not limited to, N,N-dimethylformamide, acetonitrile and dimethylsulfoxide.

Scheme 8

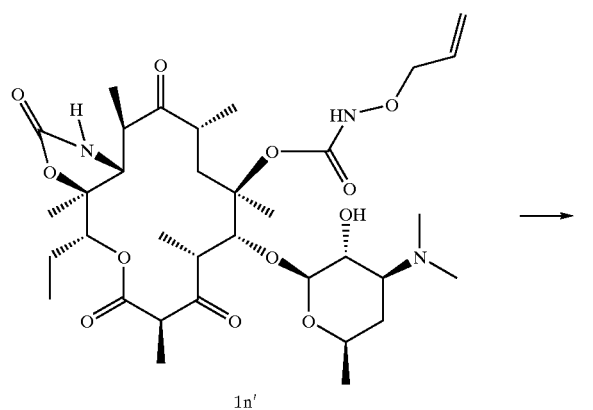

1n'

Scheme 9

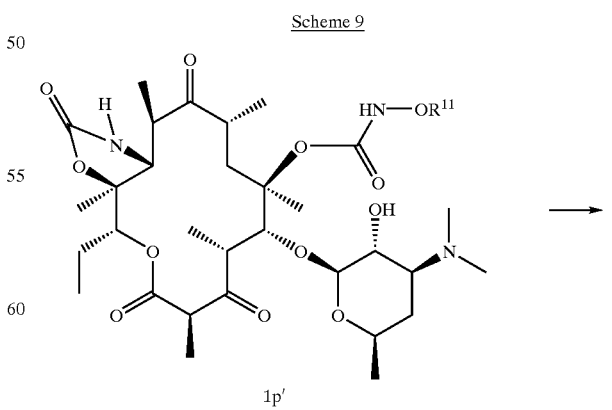

1p'

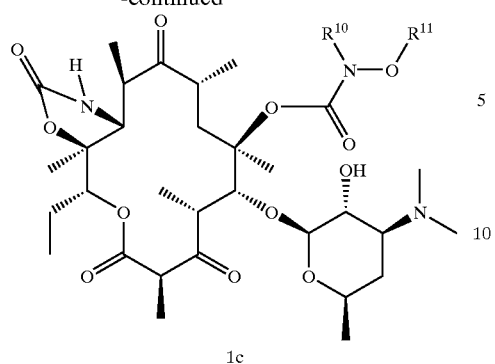

Scheme 9 illustrates a method for synthesis of N-alkoxycarbamate compounds of formula 1c, in which $R^{10}$ is $C_1$–$C_8$-alkyl, $C_3$–$C_8$-alkenyl and $C_3$–$C_8$-alkynyl and $R^{11}$ is as previously defined. The compound of formula 1p' (prepared by reaction of compounds of formula 1a with a suitably substituted hydroxylamine) may be converted to compounds of formula 1c by reaction with a suitably substituted aldehyde in the presence of a reducing agent and an acid catalyst, in a suitable solvent, such as acetonitrile, methylene chloride, or toluene, for from 2 to 72 hours at a temperature ranging from 0° C. to 100° C. A preferred reducing agent to effect this conversion is triethylsilane. A preferred acid catalyst is trifluoroacetic acid.

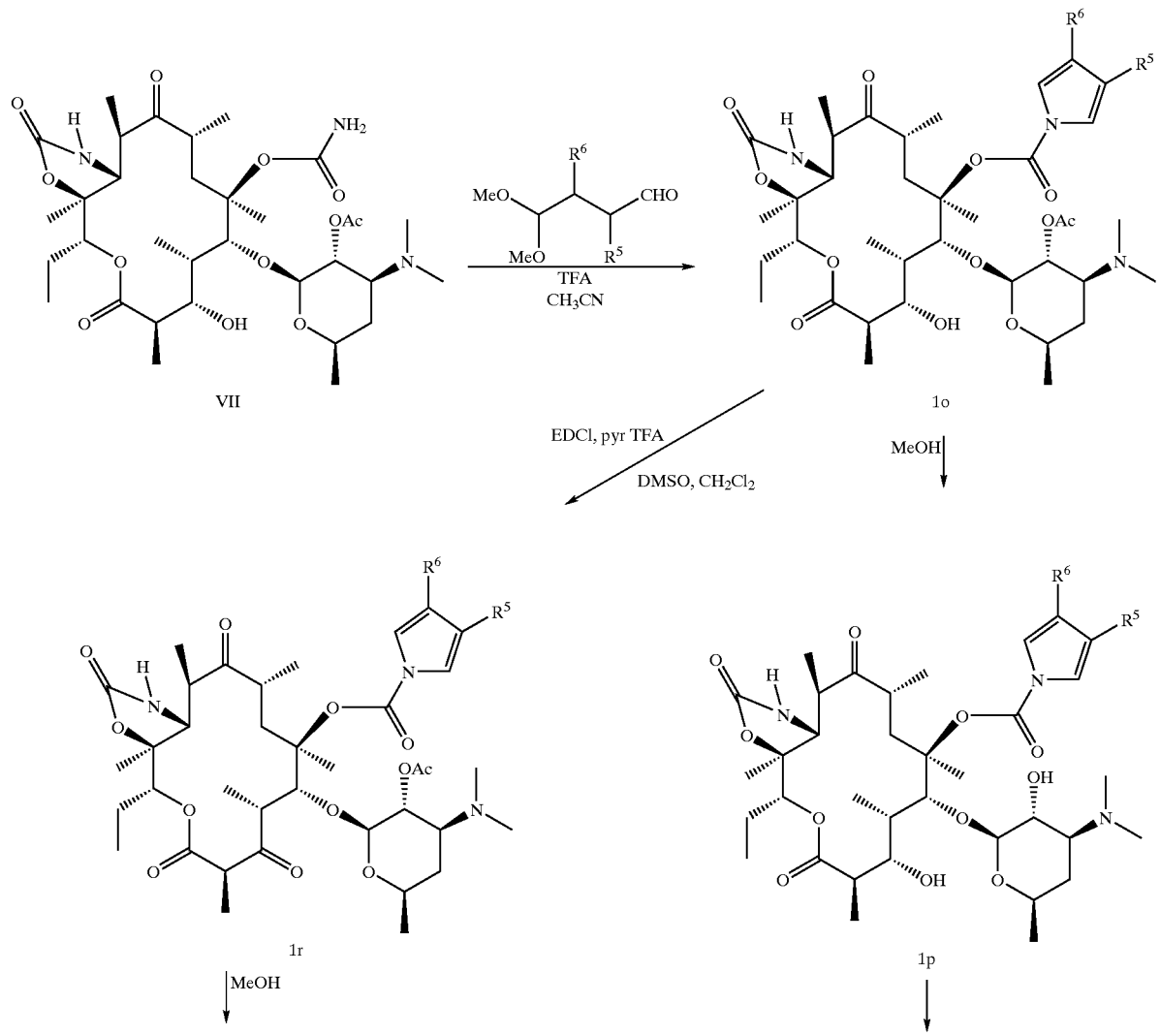

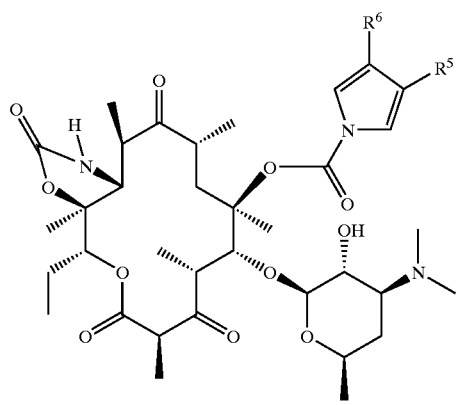

1a

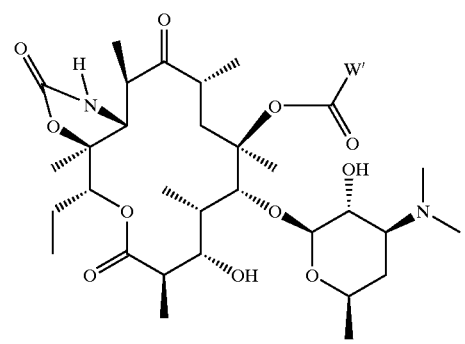

1q

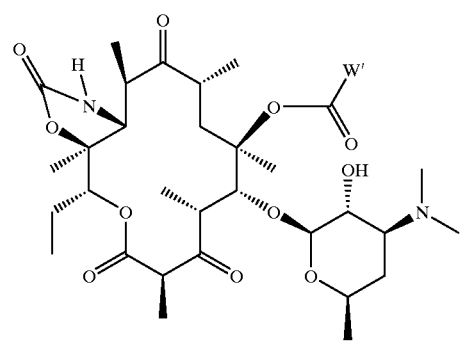

1s

It will be clear to one skilled in the art that the order of the steps in the synthetic sequence leading to compounds of the invention can be altered, provided that the functionality present in the molecule is compatible with the desired selective transformations. This is illustrated in Scheme 10 wherein W' is W other than

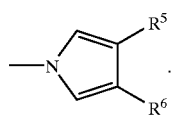

For example, compound VII can be converted to compound 1o under similar conditions as described above for the conversion of compound IX to compound 1a (Scheme 2). Removal of the 2'-acetyl group of compound 1o as described for the conversion of compound VIII to compound IX (Scheme 2) provides compound 1p. Compound 1p may then be converted to compounds of formula 1q by methods analogous to those described above in Schemes 3–9. Alternatively, oxidation of the 3-hydroxyl of compound 1o to the ketone of compound 1r can be conducted as described for the analogous transformation of VII to VIII in Scheme 2.

Deprotection of the 2'-acetyl group of 1r is readily effected as described for the conversion of compound VIII to compound IX (Scheme 2) to provide the compounds of formula 1a. Compound 1a may then be converted to compounds of formula 1s as described above in Schemes 3–9.

Scheme 11

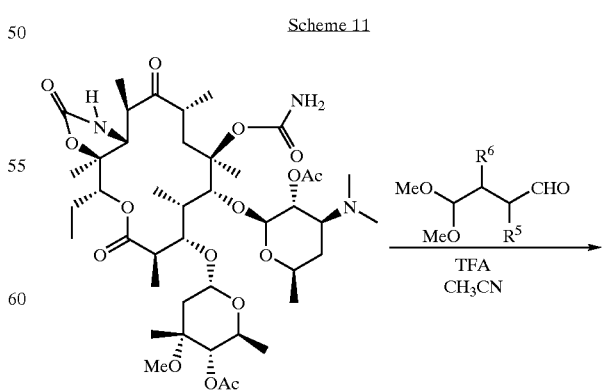

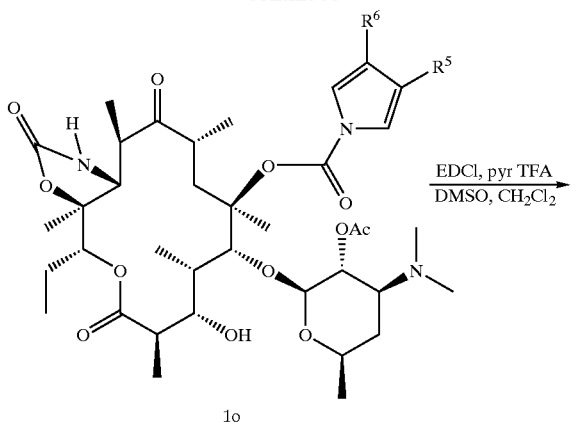

1o

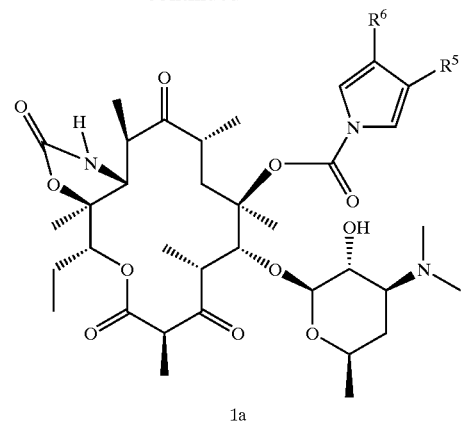

1a

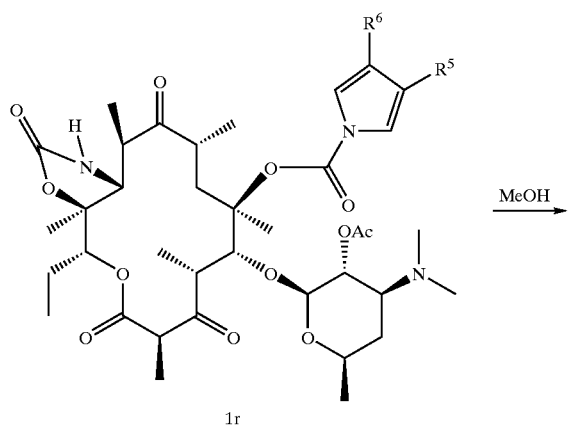

1r

Scheme 11 illustrates an alternate route for the preparation of the compounds of the invention (1a). Reaction of compound VI with a suitably substituted 1,4-dialdehyde or its equivalent in the presence of an acid, such as trifluoroacetic acid, in a suitable solvent, such as acetonitrile, methylene chloride, or toluene, at a temperature ranging from −20° C. to 100° C. for 2–96 hours leads to the simultaneous removal of the cladinose sugar and the formation of the pyrrole to afford compound 1o. Equivalents of 1,4-dialdehydes include 2,5-dialkoxytetrahydrofurans, 1,4-dialdehyde monoacetals, and 1,4-dialdehyde diacetals. Conversion of compound 1o to compound 1a then follows the procedure described above (Scheme 10).

Scheme 12

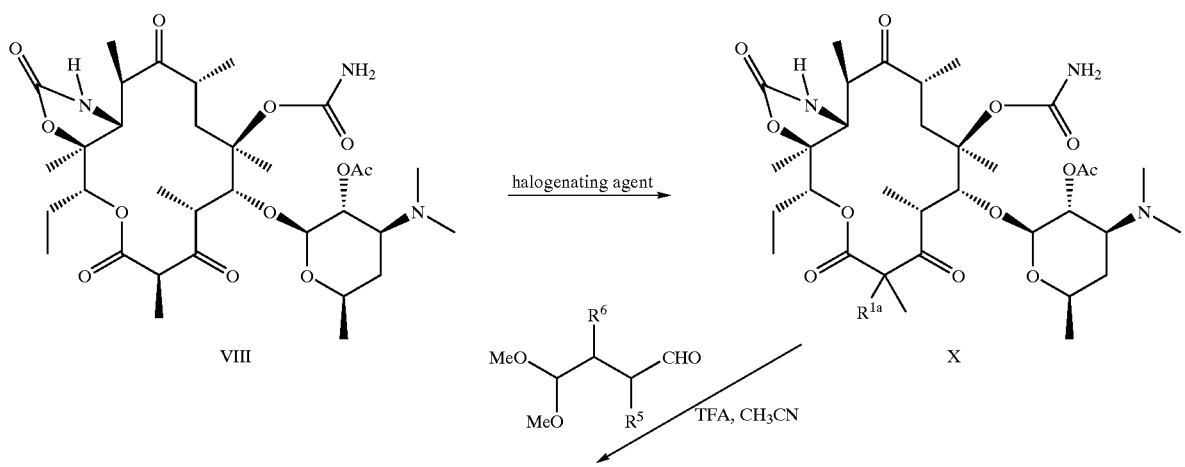

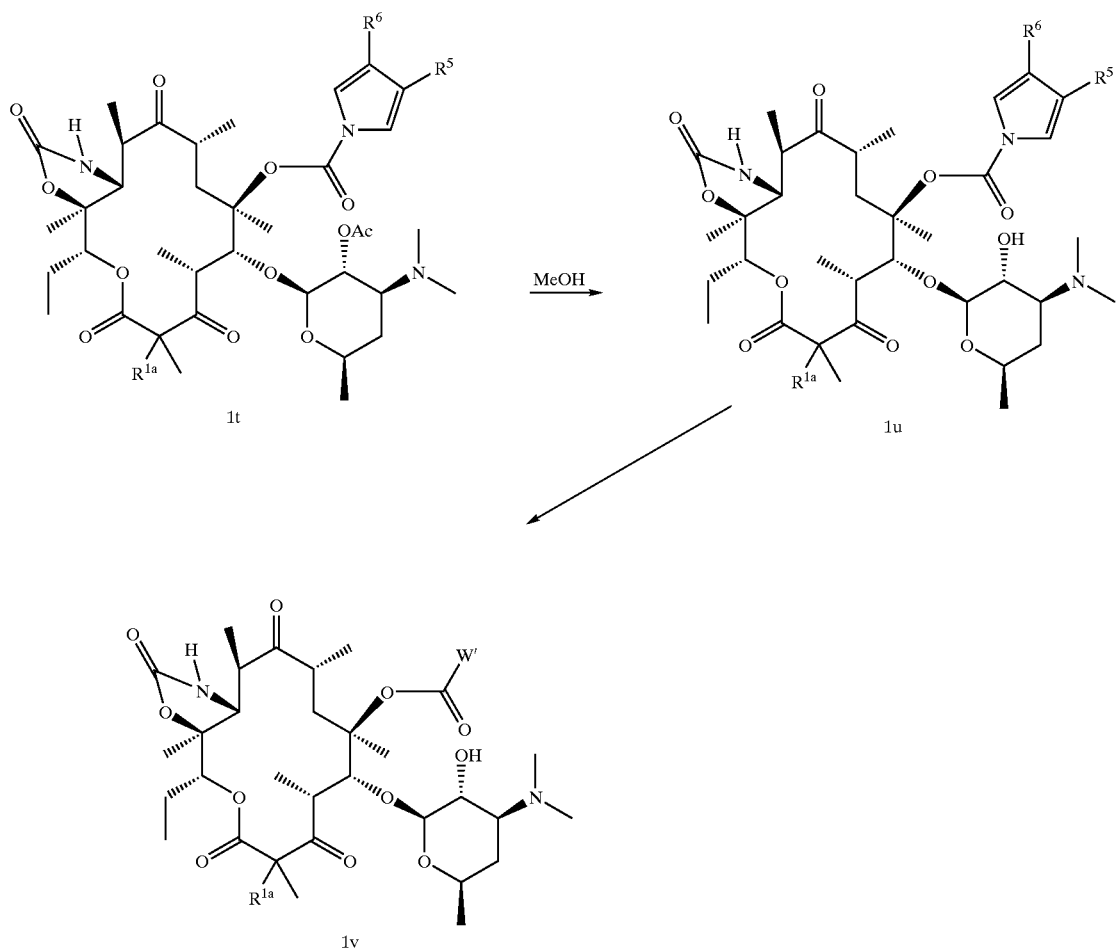

Scheme 12, wherein $R^{1a}$ is halogen, illustrates the procedures by which compounds of formula VIII can be converted to compounds of formula 1v.

Fluorination of compound VIII can be accomplished with any one of a number of fluorinating reagents, including N-fluorobenzenesulfonimide in the presence of base, 1-(chloromethyl)-4-fluoro-1,4-diazoniabicyclo[2.2.2]octane bis[tetrafluoroborate] (SELECTFLUOR™) in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, and N-fluoroperfluoropiperidine in the presence of base to give X wherein $R^{1a}$ is F. Chlorination of VIII can be effected with hexachloroethane in the presence of base, sulfuryl chloride, thionyl chloride, trifluoromethanesulfonyl chloride in the presence of base, chlorine, or sodium hypochlorite in the presence of acetic acid to give X wherein $R^{1a}$ is Cl. Suitable brominating agents would include pyridinium hydrobromide perbromide, bromine in acetic acid, N-bromosuccinimide in the presence of base, 1,2-dibromoethane in the presence of base, or carbon tetrabromide in the presence of base to give X wherein $R^{1a}$ is Br. Suitable iodinating agents include N-iodosuccinimide in the presence of base or iodine to give X wherein $R^{1a}$ is I.

Transformation of the halogenated derivatives X to the corresponding compounds of formula 1v can be accomplished through analogous synthetic routes as above for the non-halogenated compounds. For example, reaction of compounds of formula X with a suitably substituted 1,4-dialdehyde or its equivalent in the presence of an acid, such as trifluoroacetic acid, in a suitable solvent, such as acetonitrile, methylene chloride, or toluene, at a temperature ranging from −20° C. to 100° C. for 2–96 hours provides compounds of formula 1t. Equivalents of 1,4-dialdehydes include 2,5-dialkoxytetrahydrofurans, 1,4-dialdehyde monoacetals, and 1,4-dialdehyde diacetals. Deprotection of the 2'-acetyl group of compounds of formula 1t is readily effected as described for the conversion of compound VIII to compound IX (Scheme 2) to provide the compounds of formula 1u. Compounds of formula 1u may then be converted to compounds of formula 1v by procedures analogous to those described above in Schemes 3–9.

Scheme 13

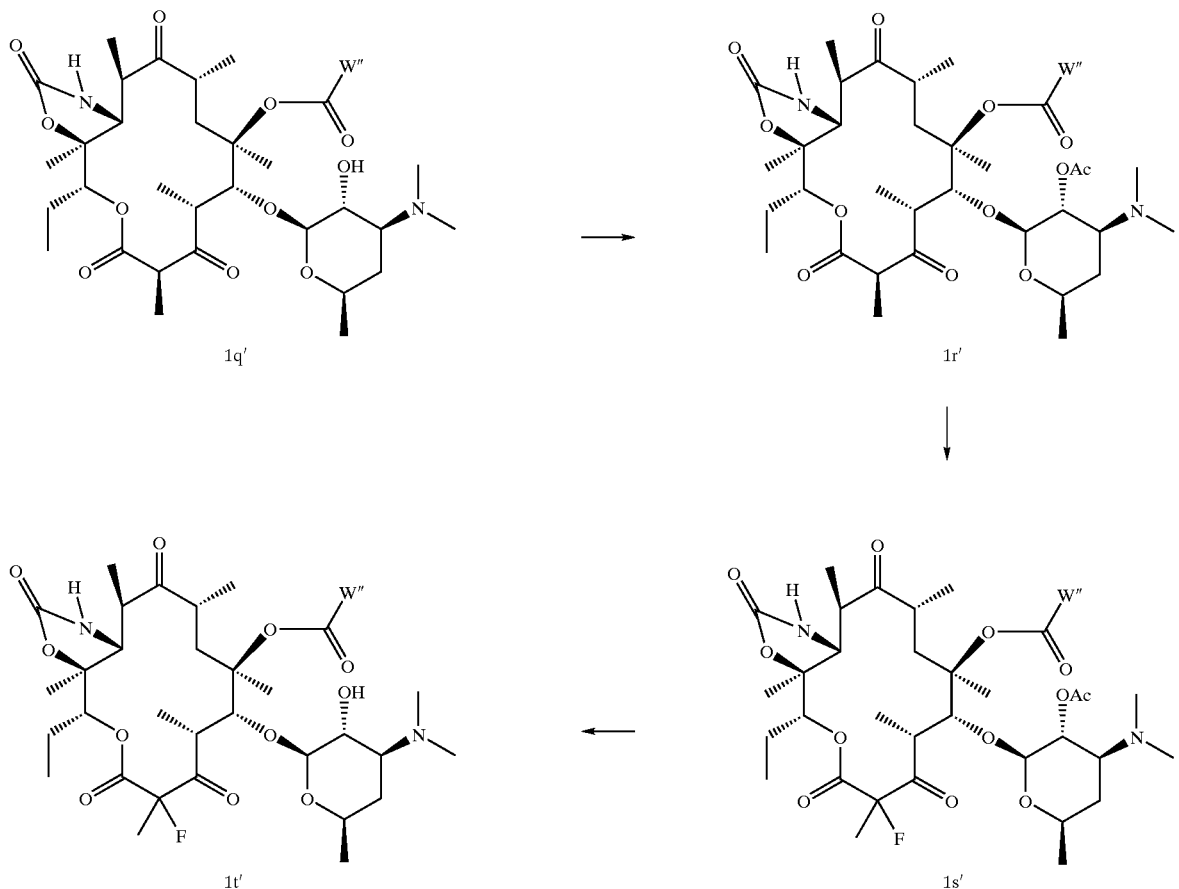

Once again, it will be apparent to one skilled in the art that by changing the order of steps compounds of formula 1t' may be obtained by reaction of suitably protected precursors with a suitable fluorinating agent, followed by deprotection. This is illustrated in Scheme 13 wherein W" is W other than

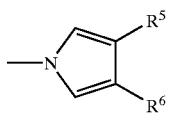

or —$NR^{12}NR^{13}R^{14}$, wherein $R^{13}$ or $R^{14}$ are hydrogen. For example, compounds of formula 1q' may be converted to compounds of formula 1r' by reaction with acetic anhydride in the presence of a tertiary amine base, such as triethylamine, diisopropylethylamine, or pyridine, and optionally an acylation catalyst, such as DMAP, in a suitable solvent such as methylene chloride, chloroform or THF at a temperature ranging from −20° C. to 37° C. for 2 to 48 hours. Fluorination of compounds of formula 1r', as described for the conversion of compounds of formula VIII to compounds of formula X, wherein $R^{1a}$ is fluoro (Scheme 12), provides compounds of formula 1s'. Finally, de-acylation of the 2'-hydroxyl by the methods described above, such as transesterification with methanol for 2–48 hours at a temperature ranging from −20° C. to 60° C., provides compounds of formula 1t'.

Scheme 14A

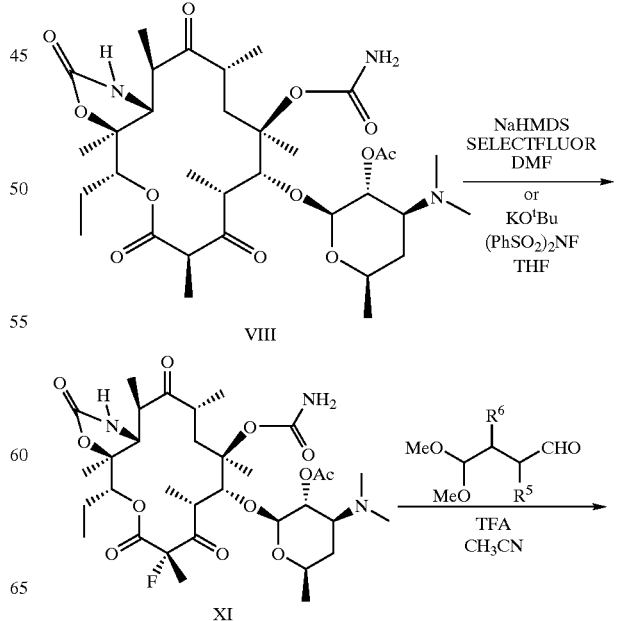

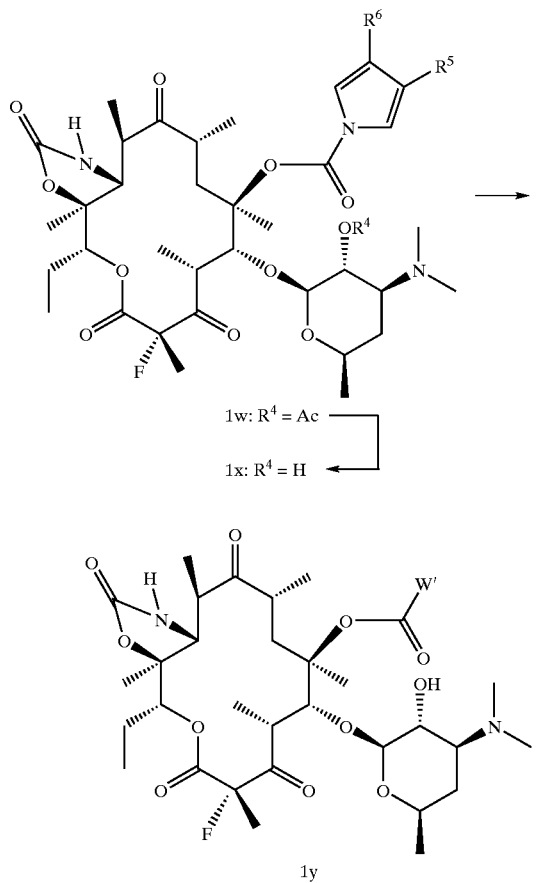

1w: R⁴ = Ac
1x: R⁴ = H

1y

Scheme 14B

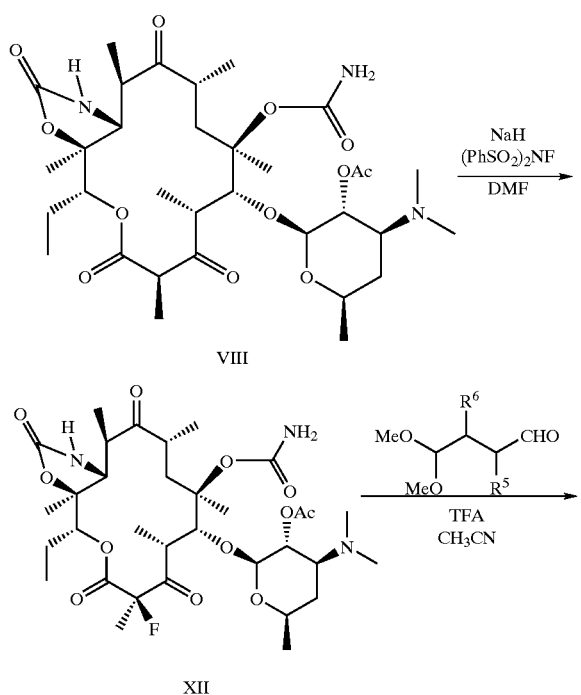

VIII

XII

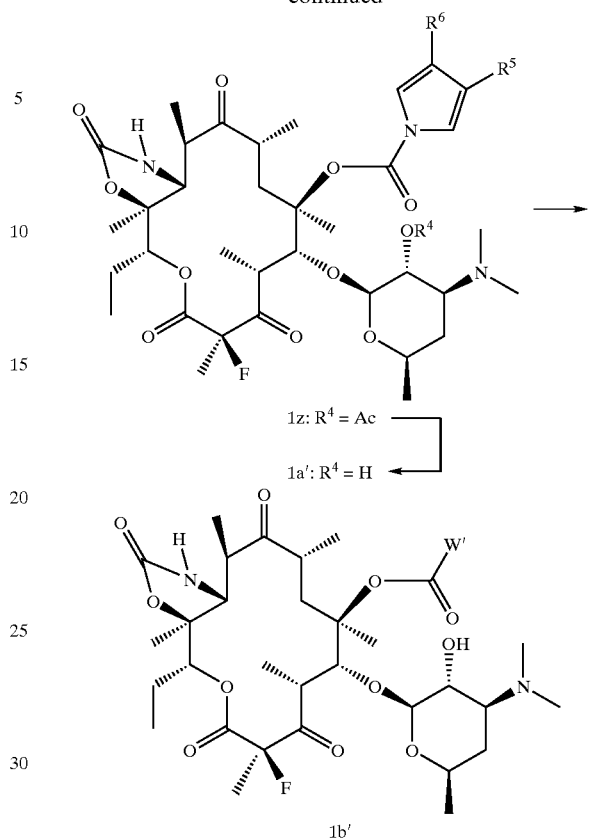

1z: R⁴ = Ac
1a': R⁴ = H

1b'

Schemes 14A and 14B illustrate the procedures by which compound VIII can be converted to 2α- and 2β-fluoro derivatives of formulae XI and XII. Fluorination of compound VIII can be accomplished as described herein above. Reagent combinations for the conversion of compound VIII to the 2α-fluoro derivative XI include SELECTFLUOR and sodium hexamethyldisilazide in DMF and N-fluorobenzenesulfonimide and potassium t-butoxide in THF. Typically, the reaction is conducted at −78° C. to −60° C. for 5 minutes to 24 hours. Reagent combinations for the conversion of compound VIII to the 2β-fluoro derivative XII include N-fluorobenzenesulfonimide and sodium hydride in DMF. Typically, this reaction is conducted at 0° C. to 20° C. for 1 to 24 hours.

Transformation of the fluorinated derivatives XI and XII to the corresponding compounds of the invention 1y and 1b', respectively, can be accomplished through analogous synthetic routes as above. For example, reaction of compounds of formula XI or XII with a suitably substituted 1,4-dialdehyde or its equivalent in the presence of an acid, such as trifluoroacetic acid, in a suitable solvent, such as acetonitrile, methylene chloride, or toluene, at a temperature ranging from −20° C. to 100° C. for 2–96 hours provides compounds of formula 1w or 1z, respectively. Equivalents of 1,4-dialdehydes include 2,5-dialkoxytetrahydrofurans, 1,4-dialdehyde monoacetals, and 1,4-dialdehyde diacetals. Deprotection of the 2'-acetyl group of compounds of formula 1w or 1z is readily effected as described for the conversion of compound VIII to compound IX (Scheme 2) to provide the compounds of formula 1x or 1a', respectively. Compounds of formula 1x or 1a' may then be converted to compounds of formula 1y or 1b', respectively, by procedures analogous to those described above in Schemes 3–9.

It will be understood by one skilled in the art of organic synthesis that the halogenation reaction can also be conducted at a later stage in the synthetic sequence. For example, halogenation of compound 1r (Scheme 10) affords the corresponding 2-halo derivative 1t, which likewise can be converted to compounds of the invention as shown in Scheme 12.

Scheme 15

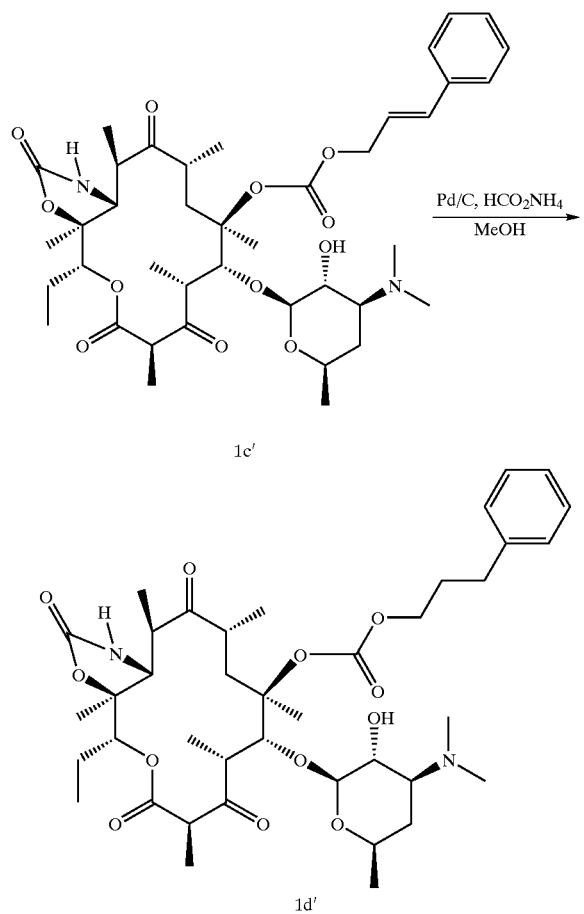

1c'

1d'

Compounds which contain an alkenyl or alkynyl function may be converted to the corresponding saturated compounds. For example, as illustrated in Scheme 15, a substituted O-propenylcarbonate derivative such as 1c' may be converted to the corresponding substituted O-propylcarbonate compound (1d'). Typically, this transformation is conducted via catalytic transfer hydrogenation, in which the olefin is reacted with ammonium formate in the presence of a suitable catalyst, such as palladium on carbon, in a suitable solvent, such as methanol or ethanol, at a temperature ranging from 20° C. to 60° C. for 15 minutes to 24 hours. Other methods for reduction of the double bond could also be applicable, for example treatment with hydrogen in the presence of a noble metal catalyst, such as palladium or platinum, or reaction with diimide. It will be obvious to one skilled in the art that the analogous O-propynylcarbonate may likewise be reduced to the corresponding O-propenylcarbonate or O-propylcarbonate under similar conditions.

Scheme 16

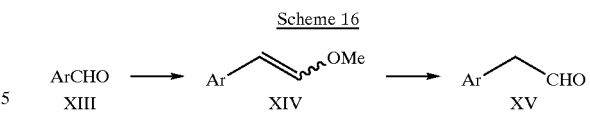

Scheme 16 illustrates a method for the preparation of certain arylacetaldehydes and heteroarylacetaldehydes (XV) used in the preparation of some of the compounds of the invention. In this method, an aryl or heteroaryl aldehyde XIII is allowed to react with (methoxymethylene) triphenylphosphorane in a suitable solvent to form the corresponding enol ether XIV. The (methoxymethylene) triphenylphosphorane reagent is generally generated in situ by reaction of the corresponding phosphonium salt with a strong base such as an alkyllithium, an alkali metal hydride, or an alkali metal amide. A preferred base for this transformation is sodium hexamethyldisilazide. The enol ether is then hydrolyzed to the desired aldehyde XV by treatment with aqueous acid. The hydrolysis step may be conducted on the isolated enol ether or, alternatively, the reaction solution containing the enol ether may be directly treated with aqueous acid to effect the hydrolysis.

Scheme 17

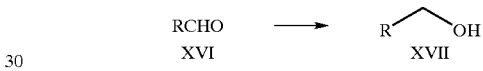

Scheme 17 illustrates a method for the preparation of certain alcohols (XVII) used in the preparation of some of the compounds of the invention. In this method, an aldehyde XVI is reduced to the alcohol XVII. A preferred reducing agent is sodium borohydride in an alcoholic solvent such as methanol or ethanol. Another preferred reducing agent is diisobutylaluminum hydride in an inert solvent such as dichloromethane, toluene, or tetrahydrofuran. It will be obvious to one skilled in the art that numerous methods for reducing an aldehyde to an alcohol are known, and any of these may be suitable provided that the method is compatible with other functional groups that may be present in the molecule.

Certain alcohols used in the preparation of compounds of the invention contain an alkene. Such alkenyl alcohols, including compounds in which the alkene is trisubstituted, may be made by methods known in the art. Methods are also known in the art for the preparation of alkenyl alcohols when one of the alkene substituents is a halogen and in particular when the alkene substituent is fluorine. Additionally, methods are known in the art for the preparation of trisubstituted, including fluorinated, alkenyl acids, esters, and aldehydes, such compounds being easily converted to the desired alcohols by reduction with typical hydride reducing agents such as sodium or lithium borohydride, lithium aluminum hydride, diisobutylaluminum hydride, and many others well known in the art. References which provide examples of the art known for the preparation of fluorinated alkenes relevant to the present invention include but are not limited to *Synleff* 1998, 777; *J. Chem. Soc. Chem. Comm.* 1989,1493; and *J. Chem. Soc. Chem. Comm.* 1985,961. In addition several examples of the preparation of alkenyl alcohols, including fluorinated alkenyl alcohols, are included as reference examples.

Scheme 18

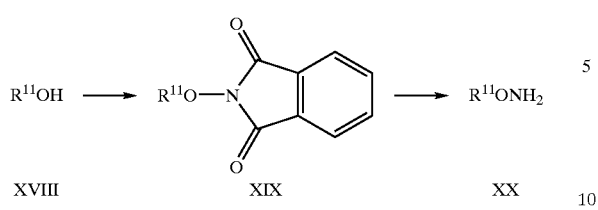

Scheme 18 illustrates a method for the preparation of certain hydroxylamines (XX) used in the preparation of some of the compounds of the invention. In this method, an alcohol XVIII is first converted to the phthalimide derivative XIX. A preferred method for this transformation involves treatment of the alcohol with N-hydroxyphthalimide in the presence of triphenylphosphine and diethyl azodicarboxylate. The phthalimide compound XIX is then converted to the hydroxylamine XX by reaction with hydrazine. The method is more fully described, for example, in *J. Med. Chem.* 1997, 40, 2363.

Scheme 19

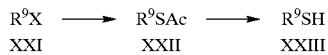

Scheme 19 illustrates a method for the preparation of certain thiols (XXIII) used in the preparation of some of the compounds in this invention. In this method, an alkyl halide XXI is first converted to the thiolacetate derivative XXII. A preferred method for this transformation involves reaction of the alkyl bromide with potassium thiolacetate in a suitable solvent, such as N,N-dimethyl acetamide (DMA), for from 1 to 24 hours at a temperature ranging from 0° C. to 100° C. The thiolacetate XXII is then converted to the corresponding thiol XXIII by treatment with aqueous base in a suitable solvent, such as methanol, for from 1 to 24 hours at a temperature ranging from 0° C. to 60° C. It will be obvious to one skilled in the art that numerous methods for reducing a thiolacetate to a thiol are known, and any of these may be suitable provided that the method is compatible with other functional groups that may be present in the molecule.

Scheme 20

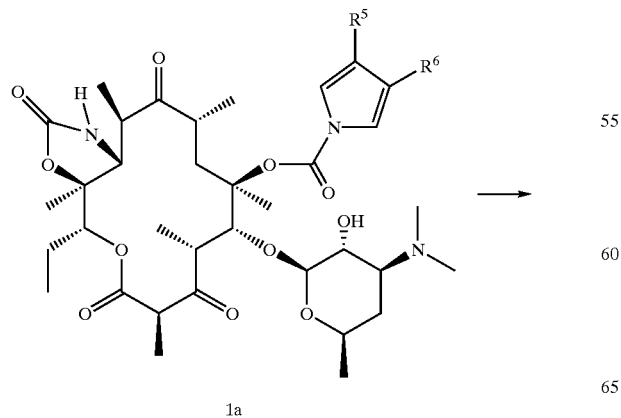

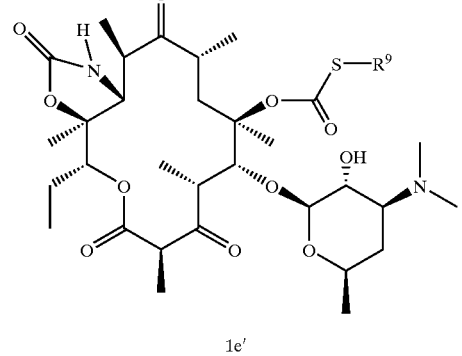

Scheme 20 illustrates the preparation of thiocarbonate compounds of formula 1e', wherein $R^9$ is as defined previously, by reaction of 1'a with a suitably substituted thiol in the presence of a suitable base such as DBU, DBN, tert-butyltetramethylguanidine, sodium hydride, potassium hydride, or an alkyllithium. This reaction is conducted in a suitable solvent, such as acetonitrile, dimethylformamide, or tetrahydrofuran at a temperature ranging from −20° C. to 120° C. for 0.5 to 72 hours. Preferred substrates for this conversion are those in which the pyrrole of 1a is substituted with electron-withdrawing groups including, but not limited to, cyano, formyl, and alkoxycarbonyl. A particularly preferred substrate is compound 1a, where $R^5$=CN and $R^6$=H. Preformed alkali or alkaline earth metal thiolates are also suitable reagents for the preparation of compounds of formula 1e'.

Scheme 21

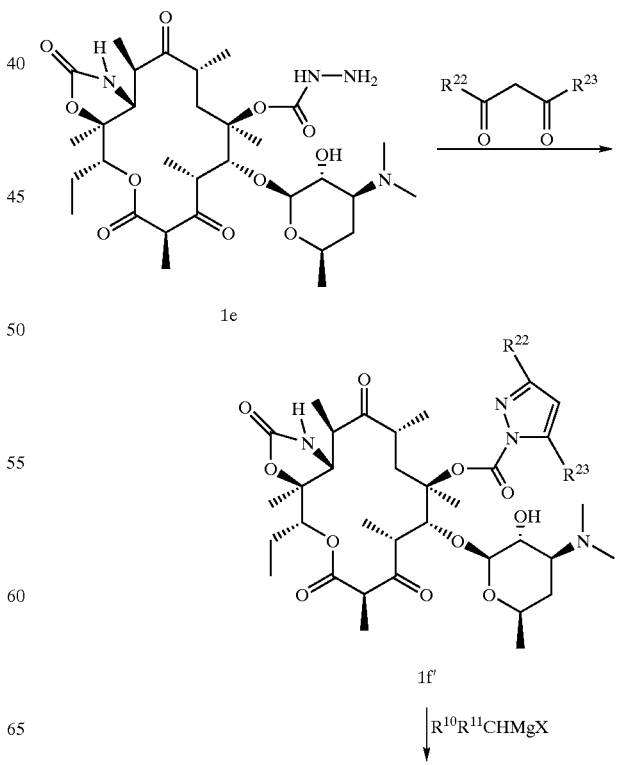

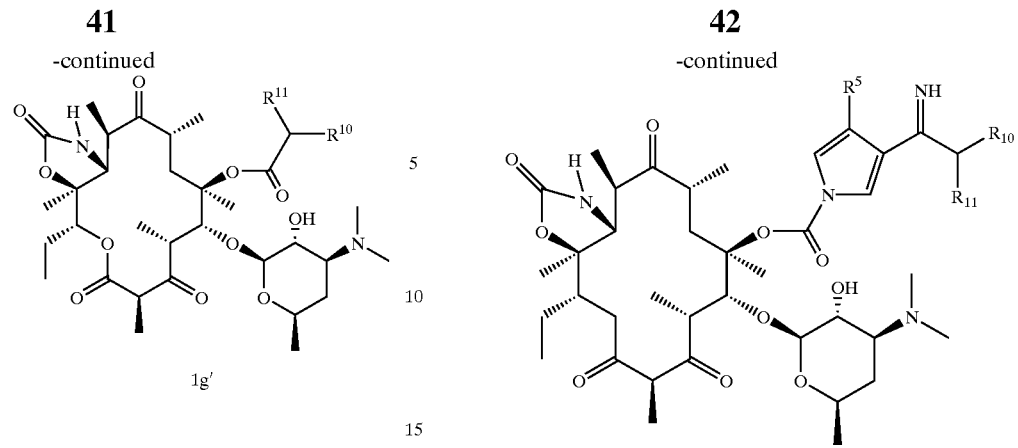

1g'

Scheme 21 depicts the synthesis of compounds of the instant invention of formulae 1f and 1g'. Compounds of formula 1f can be obtained by reaction of 1e with a suitably substituted β-dicarbonyl compound or its equivalent, optionally in the presence of an acid. Equivalents of β-dicarbonyl compounds include for example monoketals or monoacetals of a β-dicarbonyl compound, diketals or diacetals of a β-dicarbonyl compound, β-alkoxy or β-amino-α,β-unsaturated carbonyl compounds and α,β-acetylenic carbonyl compounds. A preferred acid for effecting this transformation is trifluoroacetic acid in a suitable solvent, like acetonitrile, methylene chloride, or toluene at −20° C. to 100° C. The reaction mixture may optionally contain an adsorbent such as molecular sieves to remove alcohol or water that may be generated during the reaction. Typically, the reaction is conducted for from 15 minutes to 24 hours. Preferred 1,3-dicarbonyl compounds or their equivalents include 1,3-malondialdehyde, 1,1,3,3-tetramethoxypropane and 3,3-dimethoxypropanal.

Compounds of formula 1f can be converted to esters of formula 1g' by displacement of the pyrazole with carbon nucleophiles, such as Grignard reagents, organolithium species, or organocuprates. A preferred class of carbon nucleophiles are the Grignard reagents. A preferred substrate for this conversion is the derivative of 1f in which the pyrazole ring is unsubstituted, that is where $R^{21}$ and $R^{22}$=H. Typically this reaction is conducted in an inert solvent such as THF, ether, dioxane or toluene at temperatures ranging from −78° C. to 65° C. for from 5 minutes to 24 hours.

Scheme 22

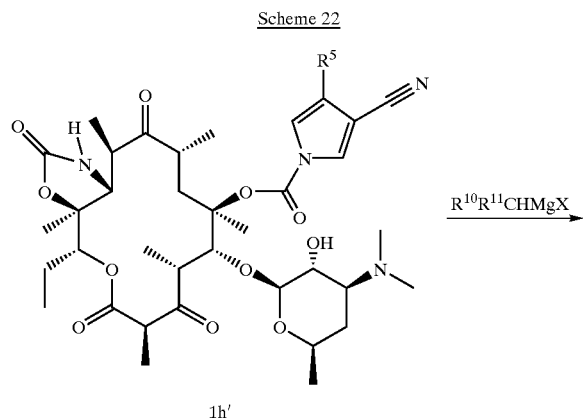

1h'

Scheme 22 illustrates the synthesis of compounds of the instant invention 1i', wherein $R^5$ is hydrogen, —C(O)NR$^7$R$^8$, —SO$_2$R$^7$, $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, or heteroaryl, by reaction of compounds of the instant invention 1h', wherein $R^5$ is hydrogen, —C(O)NR$^7$R$^8$, —SO$_2$R$^7$, $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, aryl, or heteroaryl, with a suitably substituted organometallic reagent, such as a Grignard reagent or an organolithium species. A preferred class of organometallic reagents for this conversion are the Grignard reagents. Typically, this transformation is conducted in an inert solvent, such as THF, ether, dioxane, or toluene at temperatures ranging from −78° C. to 25° C. for from 5 minutes to 24 hours.

Compounds of the invention wherein $R^4$ is a hydroxy protecting group other than acyl may be prepared by methods analogous to those shown in the above schemes with appropriate reagents that are either commercially available or may be made by known methods.

Compounds of the invention wherein $R^3$ is a group other than ethyl may be prepared beginning with modified erythromycin derivatives as starting materials as described in various publications including, but not limited to, WO99/35157, WO00/62783, WO00/63224, and WO00/63225, which are all incorporated by reference herein.

Compounds of the invention wherein $R^2$-Z is a group other than hydrogen may be prepared beginning with starting materials prepared as described in WO 00/75156 and EP1146051, which are both incorporated by reference herein.

These compounds have antimicrobial activity against susceptible and drug resistant Gram positive and Gram negative bacteria. In particular, they are useful as broad spectrum antibacterial agents for the treatment of bacterial infections in humans and animals. These compounds are particularly active against S. aureus, S. epidermidis, S. pneumoniae, S. pyogenes, Enterococci, Moraxella catarrhalis and H. influenzae. These compounds are particularly useful in the treatment of community-acquired pneumonia, upper and lower respiratory tract infections, skin and soft tissue infections, meningitis, hospital-acquired lung infections, and bone and joint infections.

Minimal inhibitory concentration (MIC) has been an indicator of in vitro antibacterial activity widely used in the art. The in vitro antimicrobial activity of the compounds was determined by the microdilution broth method following the test method from the National Committee for Clinical Laboratory Standards (NCCLS). This method is described in the NCCLS Document M7-A4, Vol.17, No.2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities depending on the organism tested.

Table 1 below sets forth the biological activity (MIC, µg/mL) of some compounds of the present invention.

TABLE 1

MIC Values (µg/mL) of Some Compounds of Formula I
(A: *E. coli* OC2605; B: *S. aureus* ATCC29213;
C: *E. faecalis* ATCC29212;
D: *S. pneumoniae* ATCC49619; E: *H. influenzae* ATCC49247)

| No. | A | B | C | D | E |
|---|---|---|---|---|---|
| 2 | >16 | >16 | 8 | 0.5 | >16 |
| 3 | >16 | >16 | 4 | 1 | >16 |
| 4 | >16 | >16 | 4 | 1 | >16 |
| 5 | >16 | 16 | 4 | 0.5 | 8 |
| 6 | 16 | 0.12 | 0.12 | 0.03 | 1 |
| 7 | 8 | 0.12 | 0.06 | 0.03 | 2 |
| 15 | ND[a] | 0.12 | 0.06 | 0.03 | 0.5 |
| 19 | ND[a] | 0.12 | 0.06 | ≦0.015 | ND[a] |
| 20 | 8 | 0.12 | 0.06 | 0.03 | 2 |
| 21 | ND[a] | 0.12 | 0.06 | ≦0.015 | ND[a] |
| 22 | ND[a] | 0.25 | 0.06 | ≦0.015 | 0.5 |
| 24 | ND[a] | 0.12 | 0.06 | ≦0.015 | 1 |
| 26 | ND[a] | 0.25 | 0.12 | 0.03 | 2 |
| 30 | ND[a] | 0.12 | 0.06 | ≦0.015 | 1 |
| 31 | ND[a] | 0.12 | 0.06 | 0.03 | 1 |
| 33 | ND[a] | 0.25 | 0.12 | 0.06 | 1 |
| 34 | ND[a] | 0.25 | 0.12 | 0.03 | 1 |
| 35 | ND[a] | 0.25 | 0.12 | 0.03 | 1 |
| 37 | ND[a] | 0.12 | 0.06 | ≦0.015 | 0.5 |
| 40 | ND[a] | 0.12 | 0.06 | 0.06 | ND[a] |
| 44 | ND[a] | 0.12 | 0.06 | ≦0.015 | ND[a] |
| 47 | ND[a] | 0.12 | 0.06 | ≦0.015 | 0.5 |
| 48 | ND[a] | 0.12 | 0.12 | 0.03 | 1 |
| 49 | ND[a] | 0.12 | 0.12 | 0.03 | 1 |
| 50 | ND[a] | 1 | 0.5 | 0.06 | 2 |
| 52 | ND[a] | 0.12 | 0.06 | ≦0.015 | 1 |
| 55 | ND[a] | 0.25 | 0.12 | 0.03 | 1 |
| 56 | ND[a] | 0.5 | 0.25 | 0.06 | 2 |
| 58 | ND[a] | 0.5 | 0.5 | 0.06 | 4 |
| 61 | ND[a] | 0.12 | 0.12 | 0.03 | 1 |
| 63 | ND[a] | 0.25 | 0.12 | 0.06 | 1 |
| 64 | ND[a] | 0.12 | 0.06 | 0.03 | 1 |
| 65 | ND[a] | 0.25 | 0.12 | 0.03 | 1 |
| 72 | ND[a] | 0.25 | 0.06 | 0.03 | 2 |
| 73 | ND[a] | 2 | 1 | 0.25 | 16 |
| 76 | ND[a] | 0.25 | 0.12 | 0.03 | 1 |
| 77 | 8 | 0.12 | 0.06 | 0.03 | 2 |
| 80 | 16 | 0.25 | 0.12 | 0.03 | 2 |
| 86 | 8 | 0.12 | 0.06 | 0.03 | 2 |
| 87 | 8 | 0.12 | 0.06 | 0.03 | 1 |
| 122 | ND[a] | 0.12 | 0.06 | ≦0.015 | 1 |
| 137 | ND[a] | 0.25 | 0.12 | 0.03 | 4 |
| 139 | ND[a] | 0.12 | 0.06 | 0.12 | ND |
| 159 | ND[a] | 0.25 | 0.12 | 0.03 | 1 |
| 160 | ND[a] | 0.12 | 0.06 | 0.03 | 1 |
| 168 | ND[a] | 0.12 | 0.06 | ≦0.015 | 0.5 |
| 224 | ND[a] | 0.12 | 0.06 | ≦0.015 | 2 |
| 286 | ND[a] | 0.25 | 0.25 | 0.06 | 4 |
| 288 | ND[a] | 0.25 | 0.12 | 0.06 | ND |
| 570 | >16 | 1 | 0.25 | 0.03 | 4 |
| 571 | >16 | 0.5 | 0.12 | 0.03 | 4 |
| 578 | ND[a] | 0.5 | 0.25 | 0.12 | ND[a] |
| 599 | 16 | 0.5 | 0.25 | 0.06 | 2 |
| 601 | ND[a] | 0.25 | 0.12 | 0.03 | 2 |
| 602 | ND[a] | 0.25 | 0.12 | 0.03 | ND[a] |
| 603 | ND[a] | 0.25 | 0.12 | 0.03 | 2 |
| 605 | 16 | 0.25 | 0.25 | 0.06 | 4 |
| 606 | ND[a] | 0.25 | 0.12 | 0.06 | ND[a] |
| 607 | ND[a] | 0.25 | 0.25 | 0.03 | ND[a] |
| 608 | >16 | 0.5 | 0.5 | 0.06 | 4 |
| 611 | >16 | 2 | 0.5 | 0.12 | 8 |
| 612 | >16 | 1 | 0.25 | 0.06 | 4 |
| 615 | ND[a] | 1 | 0.25 | 0.06 | ND[a] |
| 616 | ND[a] | 0.5 | 0.25 | 0.06 | ND[a] |
| 617 | ND[a] | 0.25 | 0.12 | 0.03 | ND[a] |
| 618 | ND[a] | 0.25 | 0.06 | 0.03 | 1 |
| 619 | ND[a] | 0.25 | 0.12 | 0.03 | ND[a] |
| 620 | ND[a] | 0.5 | 0.12 | 0.03 | ND[a] |
| 621 | ND[a] | 1 | 0.25 | 0.12 | ND[a] |
| 622 | ND[a] | 0.25 | 0.25 | 0.03 | 4 |
| 623 | ND[a] | 0.25 | 0.12 | 0.03 | 4 |
| 624 | >16 | 4 | 0.5 | 0.12 | 4 |
| 625 | >16 | 2 | 0.25 | 0.03 | 4 |
| 626 | >16 | 0.25 | 0.12 | 0.03 | 4 |
| 661 | >16 | 0.5 | 0.12 | 0.03 | 2 |
| 675 | 16 | 0.5 | 0.12 | 0.06 | 2 |
| 676 | 8 | 0.25 | 0.12 | 0.03 | 4 |
| 744 | >16 | 0.25 | 0.25 | 0.03 | 8 |
| 774 | >16 | 2 | 0.25 | 0.06 | 4 |
| 803 | >16 | 0.25 | 0.12 | 0.03 | 4 |
| 804 | >16 | 0.5 | 0.12 | 0.03 | 8 |
| 805 | 16 | 0.25 | 0.25 | 0.06 | 2 |
| 806 | >16 | 2 | 1 | 0.12 | 16 |
| 807 | >16 | 2 | 1 | 0.12 | 4 |
| 809 | ND[a] | 1 | 0.5 | 0.03 | 2 |
| 810 | ND[a] | 2 | 0.5 | 0.06 | 4 |
| 811 | ND[a] | 2 | 0.5 | 0.06 | 4 |
| 812 | ND[a] | >16 | 4 | 2 | >16 |
| 813 | ND[a] | 16 | 1 | 0.25 | 16 |
| 814 | ND[a] | 8 | 0.5 | 0.12 | 8 |
| 815 | ND[a] | 4 | 1 | 0.25 | 16 |
| 816 | ND[a] | 16 | 1 | 0.5 | 16 |
| 817 | ND[a] | 2 | 0.25 | 0.06 | 8 |
| 818 | ND[a] | 4 | 0.25 | 0.06 | 8 |
| 819 | ND[a] | 16 | 1 | 0.25 | >16 |
| 820 | ND[a] | 1 | 0.25 | 0.06 | 8 |
| 821 | ND[a] | 2 | 0.5 | 0.12 | 16 |
| 822 | ND[a] | 4 | 1 | 0.12 | 8 |
| 823 | ND[a] | 8 | 1 | 0.12 | >16 |
| 824 | ND[a] | 2 | 1 | 0.12 | 16 |
| 825 | ND[a] | 4 | 0.5 | 0.12 | 16 |
| 826 | ND[a] | 8 | 2 | 0.25 | 8 |
| 827 | ND[a] | 1 | 1 | 0.12 | 8 |
| 828 | ND[a] | 0.5 | 0.25 | 0.06 | 2 |
| 829 | ND[a] | 1 | 0.5 | 0.06 | 2 |
| 830 | ND[a] | 1 | 0.5 | 0.12 | 4 |
| 831 | ND[a] | 2 | 0.25 | 0.06 | 8 |
| 832 | ND[a] | 4 | 0.5 | 0.25 | 8 |
| 833 | ND[a] | 0.5 | 0.25 | 0.06 | 16 |
| 834 | ND[a] | 0.5 | 0.12 | <0.015 | 8 |
| 835 | ND[a] | 0.5 | 0.12 | 0.03 | 4 |

TABLE 1-continued

MIC Values (μg/mL) of Some Compounds of Formula I
(A: *E. coli* OC2605; B: *S. aureus* ATCC29213;
C: *E. faecalis* ATCC29212;
D: *S. pneumoniae* ATCC49619; E: *H. influenzae* ATCC49247)

| | MIC (μg/mL) | | | | |
|---|---|---|---|---|---|
| No. | A | B | C | D | E |
| 836 | ND[a] | 0.25 | 0.12 | 0.03 | 1 |
| 837 | ND[a] | 2 | 0.25 | 0.12 | 8 |
| 838 | ND[a] | 0.25 | 0.12 | 0.06 | 1 |
| 839 | ND[a] | 1 | 0.12 | 0.06 | 2 |
| 840 | ND[a] | 0.5 | 0.12 | 0.06 | 2 |
| 841 | ND[a] | 0.5 | 0.12 | 0.03 | 2 |
| 843 | ND[a] | 8 | 2 | 0.5 | 16 |
| 844 | ND[a] | 0.5 | 0.12 | 0.03 | 4 |
| 845 | ND[a] | >16 | >16 | 4 | >16 |
| 846 | ND[a] | 8 | 1 | 0.25 | 2 |

[a]Not determined

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, which may be given in divided doses two to four times a day, or in sustained release form. For most large mammals the total daily dosage is from about 0.07 g to 7.0 g, preferably from about 100 mg to 2000 mg. Dosage forms suitable for internal use comprise from about 100 mg to 1200 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Compound IX

Step A

Triethylamine (42.0 mL, 301 mmol), DMAP (0.6 g, 4.9 mmol), and acetic anhydride (28.5 mL, 302 mmol) were added to a 0° C. suspension of erythromycin (36.7 g, 50 mmol) in dichloromethane (250 mL). The mixture was allowed to warm to room temperature and stir for 18 h. Methanol (10 mL) was added and stirring was continued for 5 min. The mixture was diluted with ether (750 mL), washed with sat. aq. $NaHCO_3$, water, and brine (500 mL each), dried ($MgSO_4$), and concentrated to provide the title compound as a colorless foam. The material was used in the next step without further purification. MS 860 $(M+H)^+$.

Step B

Sodium hexamethyldisilazide (1.0M in THF, 60.0 mL, 60.00 mmol) was added over 25 min to a 0° C. solution of the compound from step A (50.0 mmol) in THF (500 mL). After 2 h at 0° C., the mixture was diluted with water (250 mL) and brine (250 mL) and extracted with ethyl acetate (3×250 mL). The combined organic layers were dried ($MgSO_4$) and concentrated. The material was used in the next step without further purification. If desired, pure material could be obtained by chromatography ($SiO_2$, 95:5:0.2 dichloromethane/methanol/conc. $NH_4OH$). MS 800 $(M+H)^+$.

Step C

Trichloroacetylisocyanate (18.0 mL, 151 mmol) was added over 20 min to a 0° C. solution of the compound from step B (50 mmol) in dichloromethane (350 mL). After 3 h at 0° C., the reaction was quenched by the addition of methanol (30 mL) and concentrated. The residue was dissolved in a mixture of methanol (450 mL), water (45 mL), and triethylamine (18 mL), heated to reflux for 2 h, and concentrated. The residue was dissolved in ethyl acetate (500 mL), washed with sat. aq. $NaHCO_3$ (250 mL) and brine (250 mL), dried ($MgSO_4$), and concentrated. The resulting mixture of C-10 epimers was dissolved in THF (500 mL) at 0° C. and potassium t-butoxide (1.0 M in THF, 60.0 mL, 60.0 mmol) was added over 15 min. The resulting mixture was stirred at 0° C. to 15° C. for 6 h. Sat. aq. $NaHCO_3$ (250 mL) was added, the bulk of the THF was removed in vacuo, and the resulting solution was extracted with ethyl acetate (3×250 mL). The combined organic extracts were washed with brine (250 mL), dried ($MgSO_4$), and concentrated. The material was used in the next step without further purification. If desired, pure material could be obtained by chromatography ($SiO_2$, 95:5:0.2 dichloromethane/methanol/conc. $NH_4OH$). MS 844 $(M+H)^+$.

Step D

A solution of the compound from step C (50 mmol), triethylamine (13.0 mL, 93.3 mmol), and acetic anhydride (8.8 mL, 93.3 mmol) in dichloromethane (250 mL) was stirred at room temperature for 20 h. The solution was washed with sat. aq. $NaHCO_3$ (2×250 mL) and brine (250 mL), dried ($MgSO_4$), and concentrated. The material was used in the next step without further purification. MS 886 $(M+H)^+$.

Step E

The compound from step D (50 mmol) was dissolved in 1.2 N HCl (400 mL) and ethanol (160 mL) and stirred at room temperature for 20 h. The mixture was cooled to 0° C., made basic with 10% NaOH, and extracted with ethyl acetate (3×300 mL). The combined organic layers were washed with water (300 mL) and brine (300 mL), dried ($MgSO_4$), and concentrated. Purification by chromatography ($SiO_2$, 94:6:0.5 dichloromethane/methanol/conc. $NH_4OH$) yields 10.4 g (30% based on erythromycin) of the title compound as a colorless solid. MS 686 $(M+H)^+$.

Step F

EDCI (3.92 g, 20.45 mmol) was added to a solution of the compound from step E (2.00 g, 2.92 mmol) and dimethyl sulfoxide (3.70 mL, 52.14 mmol) in dichloromethane (10 ml) at 0° C. A solution of pyridinium trifluoroacetate (3.94 g, 20.40 mmol) in dichloromethane (10 mL) was added over 10 min and the resulting solution was stirred at 0° C. for 2 h before being quenched with water (2 mL). After 5 min, the mixture was diluted with dichloromethane (50 mL), washed with water (50 mL) and brine (50 mL), dried ($MgSO_4$), and concentrated. The material was used in the next step without further purification. If desired, pure material could be obtained by chromatography ($SiO2$, 96:4:0.2 dichloromethane/methanol/conc. $NH_4OH$). MS 684 $(M+H)^+$.

Step G

The crude product from step F was allowed to stand in methanol (20 mL) for 24 h and then concentrated. Purification by chromatography ($SiO_2$, 94:6:0.2 dichloromethane/methanol/conc. $NH_4OH$) yields 1.39 g (74%) of the title compound as a colorless solid. MS 642 $(M+H)^+$.

EXAMPLE 2

Compound 2 (Formula 1a: $R^5$ is H, $R^6$ is H)

A solution Compound IX (1.00 g, 1.56 mmol), 2,5-dimethoxytetrahydrofuran (0.40 mL, 3.09 mmol), and trifluoroacetic acid (0.60 mL, 7.79 mmol) in $CH_3CN$ (10 mL) was stirred at room temperature for 24 h. Water (5 mL) was added and the solution was stirred for 20 h. The reaction mixture was diluted with ethyl acetate (75 mL), washed with sat. aq. $NaHCO_3$ (50 mL) and brine (50 mL), dried ($Na_2SO_4$), and concentrated. Purification by chromatography ($SiO_2$, 95:5:0.2 dichloromethane/methanol/conc. $NH_4OH$) yielded 550 mg (51%) of the title compound. MS 692 $(M+H)^+$.

EXAMPLE 3

Compound 3 (Formula 1a: $R^5$ is C(O)H, $R^6$ is H)

A solution of Compound IX (500 mg, 0.78 mmol), 2,5-dimethoxy-3-tetrahydrofurancarboxaldehyde (625 mg, 3.90 mmol), and trifluoroacetic acid (0.60 mL, 7.79 mmol) in $CH_3CN$ (5 mL) was stirred at room temperature for 18 h. The reaction mixture was diluted with ethyl acetate (50 mL), washed with sat. aq. $NaHCO_3$ (25 mL) and brine (25 mL), dried ($Na_2SO_4$), and concentrated. Purification by chromatography ($SiO_2$, 95:5:0.5 dichloromethane/methanol/conc. $NH_4OH$) yielded 255 mg (45%) of the title compound. MS 720 $(M+H)^+$.

EXAMPLE 4

Compound 4 (Formula 1a: $R^5$ is CN, $R^6$ is H)

A solution of Compound IX (5.00 g, 7.79 mmol), 2-formyl-4,4-dimethoxybutanenitrile, (5.40 g, 34.36 mmol, prepared as described in Reference Example 68), and trifluoroacetic acid (6.0 mL, 77.88 mmol) in $CH_3CN$ (40 mL) was heated to 60° C. for 24 h. The reaction mixture was diluted with ethyl acetate (250 mL), washed with sat. aq. $NaHCO_3$ (250 mL), water (250 mL), and brine (250 mL), dried ($Na_2SO_4$), and concentrated. Purification by chromatography ($SiO_2$, 95:5:0.5 dichloromethane/methanol/conc. $NH_4OH$) yielded 3.00 g (54%) of the title compound. MS 717 $(M+H)^+$.

EXAMPLE 5

Compound 5 (Formula 1b: $R^{12}$ is H, $R^{13}$ is H, $R^{14}$ is H)

Method A

Hydrazine (105 μL, 3.34 mmol) was added to a solution of Compound 4 (475 mg, 0.66 mmol) in $CH_3CN$ (5 mL) and the resulting solution was stirred for 30 min. Concentration and purification by chromatography ($SiO_2$, 94:6:0.2 dichloromethane/methanol/conc. $NH_4OH$) yielded 346 mg (80%) of the title compound. MS 657 $(M+H)^+$.

Method B

Hydrazine (110 μL, 3.50 mmol) was added to a solution of Compound 3 (500 mg, 0.69 mmol) in DMSO (2.5 mL) and the resulting solution was stirred at rt for 24 h. Additional hydrazine (110 μL, 3.50 mmol) was added and stirring at rt was continued for 4 h. The reaction mixture was diluted with water (20 mL) and extracted with ethyl acetate (3×20 mL). The combied organic layers were washed with water (2×30 mL) and brine (30 mL), dried (MgSO$_4$), and concentrated. Purification by chromatography (SiO$_2$, 94:6:0.5 dichloromethane/methanol/conc. NH$_4$OH) yielded 136 mg (30%) of the title compound. MS 657 (M+H)$^+$.

EXAMPLE 6

Compound 6 (Formula 1d: R$^9$ is (2E)-3-phenyl-2-propenyl)

Compound 4 (25 mg, 0.035 mmol) was added to a mixture of cinnamyl alcohol (26 mg, 0.19 mmol) and DBU (26 μL, 0.17 mmol) in CH$_3$CN (0.25 mL) and the resulting solution was stirred for 90 min at rt. The solution was diluted with ethyl acetate (10 mL), washed with 10% aq. NH$_4$Cl, sat. aq. NaHCO$_3$, and brine (10 ml each), dried (Na$_2$SO$_4$), and concentrated. Purification by chromatography (SiO$_2$, 96:4:0.2 dichloromethane/methanol/conc. NH$_4$OH) yielded 11 mg (42%) of the title compound. MS 759 (M+H)$^+$.

EXAMPLE 7

Compound 7 (Formula 1d: R$^9$ is (2E)-3-[4-(2-pyrimidinyl)phenyl]-2-propenyl)

DBU (420 μL, 2.81 mmol) was added to a solution of (2E)-3-[4-(2-pyrimidinyl)phenyl]-2-propen-1-ol (600 mg, 2.83 mmol, prepared as described in Reference Example 65) in THF (4.5 mL) and DMSO (0.5 mL), the mixture was stirred at rt for 5 min, and then cooled to 0° C. Compound 4 (500 mg, 0.70 mmol) was added and the resulting solution was stirred for 3 h at 0° C. The solution was diluted with ethyl acetate (50 mL), washed with 10% aq. NH$_4$Cl (50 mL—discarded), and extracted with 1.2 N HCl (3×10 mL). The combined acidic extracts were cooled to 0° C., made basic with 10% aq. NaOH, and extracted with ethyl acetate (3×25 mL). The combined organic layers were washed with brine (50 mL), dried (Na$_2$SO$_4$), and concentrated. Purification by chromatography (SiO$_2$, 96:4:0.2 dichloromethane/methanol/conc. NH$_4$OH) yielded 243 mg (42%) of the title compound. MS 837 (M+H)$^+$.

EXAMPLES 8–285

Compounds 8–285

Following the procedure of Example 7, except substituting the reagent of formula R$^9$OH for the (2E)-3-[4-(2-pyrimidinyl)phenyl]-2-propen-1-ol of Example 7, Compounds 8–48 shown in the table below of formula 1d, wherein R$^9$ is as described in the table, can be prepared.

| Compound No. | R$^9$ | MS [(M+H)$^+$] |
| --- | --- | --- |
| 8 | phenylmethyl | 733 |
| 9 | 2-phenylethyl | 747 |
| 10 | 3-phenyl-2-propynyl | 757 |
| 11 | 3-phenylpropyl | 761 |
| 12 | 4-phenylbutyl | 775 |
| 13 | (2E)-3-[4-(4-pyrimidinyl)phenyl]-2-propenyl | 837 |
| 14 | (2E)-3-[4-(5-pyrimidinyl)phenyl]-2-propenyl | 837 |
| 15 | (2E)-3-[3-(2-pyrimidinyl)phenyl]-2-propenyl | 837 |
| 16 | (2E)-3-[4-(2-pyridinyl)phenyl]-2-propenyl | 836 |
| 17 | (2E)-3-[4-(3-pyridinyl)phenyl]-2-propenyl | 836 |
| 18 | (2E)-3-[4-(4-pyridinyl)phenyl]-2-propenyl | 836 |
| 19 | (2E)-3-(4-pyrazinylphenyl)-2-propenyl | 837 |
| 20 | (2E)-3-[4-(3-pyridazinyl)phenyl]-2-propenyl | 837 |
| 21 | (2E)-3-[4-(1H-pyrazol-1-yl)phenyl]-2-propenyl | 825 |
| 22 | (2E)-3-[4-(1H-1,2,4-triazol-1-yl)phenyl]-2-propenyl | 826 |
| 23 | (2E)-3-[4-(4H-1,2,4-triazol-4-yl)phenyl]-2-propenyl | 826 |
| 24 | (2E)-3-[4-(1H-1,2,3-triazol-1-yl)phenyl]-2-propenyl | 826 |
| 25 | (2E)-3-[4-(1H-imidazol-1-yl)phenyl]-2-propenyl | 825 |
| 26 | (2E)-3-[4-(1-methyl-1H-pyrazol-3-yl)phenyl]-2-propenyl | 839 |
| 27 | (2E)-3-[4-(1-methyl-1H-pyrazol-5-yl)phenyl]-2-propenyl | 839 |
| 28 | (2E)-3-[3-methoxy-4-(1H-pyrazol-1-yl)phenyl]-2-propenyl | 855 |
| 29 | (2E)-3-[3-fluoro-4-(1H-pyrazol-1-yl)phenyl]-2-propenyl | 843 |
| 30 | (2E)-3-[2-fluoro-4-(1H-pyrazol-1-yl)phenyl]-2-propenyl | 843 |
| 31 | (2E)-3-[3-fluoro-4-(1H-1,2,4-triazol-1-yl)phenyl]-2-propenyl | 843 |
| 32 | (2E)-3-[6-(1H-pyrazol-1-yl)-3-pyridinyl]-2-propenyl | 826 |
| 33 | (2E)-3-(1-phenyl-1H-pyrazol-4-yl)-2-propenyl | 825 |
| 34 | (2E)-3-[1-(2-pyrimidinyl)-1H-imidazol-4-yl]-2-propenyl | 827 |
| 35 | (2E)-3-(1-pyrazinyl-1H-imidazol-4-yl)-2-propenyl | 827 |
| 36 | (2E)-3-(2-quinolinyl)-2-propenyl | 810 |
| 37 | (2E)-3-(3-quinolinyl)-2-propenyl | 810 |
| 38 | (2E)-3-(4-quinolinyl)-2-propenyl | 810 |
| 39 | (2E)-3-(5-quinolinyl)-2-propenyl | 810 |
| 40 | (2E)-3-(6-quinolinyl)-2-propenyl | 810 |
| 41 | (2E)-3-(7-quinolinyl)-2-propenyl | 810 |
| 42 | (2E)-3-(8-quinolinyl)-2-propenyl | 810 |
| 43 | (2E)-3-(2-quinoxalinyl)-2-propenyl | 811 |
| 44 | (2E)-3-(6-quinoxalinyl)-2-propenyl | 811 |

| Compound No. | R⁹ | MS [(M+H)⁺] |
|---|---|---|
| 45 | (2E)-3-(4-isoquinolinyl)-2-propenyl | 810 |
| 46 | (2E)-3-(6-bromo-3-pyridinyl)-2-propenyl | 838,840 |
| 47 | (2E)-3-[4-(2-oxazolyl)phenyl]-2-propenyl | 826 |
| 48 | (2E)-3-[4-(5-oxazolyl)phenyl]-2-propenyl | 826 |
| 49 | (2E)-3-[4-(2-thiazolyl)phenyl]-2-propenyl | 842 |
| 50 | (2E)-3-[4-(2-thienyl)phenyl]-2-propenyl | 841 |
| 51 | (2E)-3-[4-(3-isoxazolyl)phenyl]-2-propenyl | 826 |
| 52 | (2E)-3-[4-(1,3,4-oxadiazol-2-yl)phenyl]-2-propenyl | 827 |
| 53 | (2E)-3-[4-(1,2,4-oxadiazol-3-yl)phenyl]-2-propenyl | 827 |
| 54 | (2E)-3-[4-(1,2,4-oxadiazol-5-yl)phenyl]-2-propenyl | 827 |
| 55 | (2E)-3-(1-methyl-1H-benzimidazol-2-yl)-2-propenyl | 813 |
| 56 | (2E)-3-[4-(5-bromo-2-pyrimidinyl)phenyl]-2-propenyl | 915,917 |
| 57 | (2E)-3-[4-(5-fluoro-2-pyrimidinyl)phenyl]-2-propenyl | 855 |
| 58 | (2E)-3-[4-(5-ethyl-2-pyrimidinyl)phenyl]-2-propenyl | 865 |
| 59 | (2E)-3-[4-(4-methyl-2-pyrimidinyl)phenyl]-2-propenyl | 851 |
| 60 | (2E)-3-[4-(4-methoxy-2-pyrimidinyl)phenyl]-2-propenyl | 867 |
| 61 | (2E)-3-[4-(6-methyl-3-pyridazinyl)phenyl]-2-propenyl | 851 |
| 62 | (2E)-3-[4-(6-methoxy-3-pyridazinyl)phenyl]-2-propenyl | 867 |
| 63 | (2E)-3-[5-(2-pyridinyl)-2-thienyl]-2-propenyl | 842 |
| 64 | (2E)-3-[5-(2-pyrimidinyl)-2-thienyl]-2-propenyl | 843 |
| 65 | (2E)-3-(5-pyrazinyl-2-thienyl)-2-propenyl | 843 |
| 66 | (2E)-3-[4-(2-pyridinyl)-2-thienyl]-2-propenyl | 842 |
| 67 | (2E)-3-[4-(2-pyrimidinyl)-2-thienyl]-2-propenyl | 843 |
| 68 | (2E)-3-(4-pyrazinyl-2-thienyl)-2-propenyl | 843 |
| 69 | (2E)-3-[5-(2-pyridinyl)-3-thienyl]-2-propenyl | 842 |
| 70 | (2E)-3-[5-(2-pyrimidinyl)-3-thienyl]-2-propenyl | 843 |
| 71 | (2E)-3-(5-pyrazinyl-3-thienyl)-2-propenyl | 843 |
| 72 | (2E)-3-(2-phenyl-5-pyrimidinyl)-2-propenyl | 837 |
| 73 | (2E)-3-[2,2'-bithiophen]-5-yl-2-propenyl | 847 |
| 74 | (2E)-3-[4-(2-pyrimidinyloxy)phenyl]-2-propenyl | 853 |
| 75 | (2E)-3-[2-fluoro-4-(2-pyrimidinyl)phenyl]-2-propenyl | 855 |
| 76 | (2E)-3-[4-(2-pyrimidinyl)phenyl]-2-butenyl | 851 |
| 77 | [4-(2-pyrimidinyl)phenyl]methyl | 811 |
| 78 | [4-(3-pyridazinyl)phenyl]methyl | 811 |
| 79 | (4-pyrazinylphenyl)methyl | 811 |
| 80 | 3-[4-(2-pyrimidinyl)phenyl]-2-propynyl | 835 |
| 81 | 3-[4-(4-pyrimidinyl)phenyl]-2-propynyl | 835 |
| 82 | 3-[4-(5-pyrimidinyl)phenyl]-2-propynyl | 835 |
| 83 | 3-[4-(2-pyridinyl)phenyl]-2-propynyl | 834 |
| 84 | 3-[4-(3-pyridinyl)phenyl]-2-propynyl | 834 |
| 85 | 3-[4-(4-pyridinyl)phenyl]-2-propynyl | 834 |
| 86 | 3-(4-pyrazinylphenyl)-2-propynyl | 835 |
| 87 | 3-[4-(3-pyridazinyl)phenyl]-2-propynyl | 835 |
| 88 | 3-[4-(1H-pyrazol-1-yl)phenyl]-2-propynyl | 823 |
| 89 | 3-[4-(1H-1,2,4-triazol-1-yl)phenyl]-2-propynyl | 824 |
| 90 | 3-[4-(4H-1,2,4-triazol-4-yl)phenyl]-2-propynyl | 824 |
| 91 | 3-[4-(1H-1,2,3-triazol-1-yl)phenyl]-2-propynyl | 824 |
| 92 | 3-[4-(1H-imidazol-1-yl)phenyl]-2-propynyl | 823 |
| 93 | 3-[4-(1-methyl-1H-pyrazol-3-yl)phenyl]-2-propynyl | 837 |
| 94 | 3-[4-(1-methyl-1H-pyrazol-5-yl)phenyl]-2-propynyl | 837 |
| 95 | 3-(1-phenyl-1H-pyrazol-4-yl)-2-propynyl | 823 |
| 96 | 3-(2-quinolinyl)-2-propynyl | 808 |
| 97 | 3-(3-quinolinyl)-2-propynyl | 808 |
| 98 | 3-(4-quinolinyl)-2-propynyl | 808 |
| 99 | 3-(5-quinolinyl)-2-propynyl | 808 |
| 100 | 3-(6-quinolinyl)-2-propynyl | 808 |
| 101 | 3-(7-quinolinyl)-2-propynyl | 808 |
| 102 | 3-(8-quinolinyl)-2-propynyl | 808 |
| 103 | 3-(2-quinoxalinyl)-2-propynyl | 809 |
| 104 | 3-(6-quinoxalinyl)-2-propynyl | 809 |
| 105 | 3-(4-isoquinolinyl)-2-propynyl | 808 |
| 106 | 3-[4-(2-oxazolyl)phenyl]-2-propynyl | 824 |
| 107 | 3-[4-(5-oxazolyl)phenyl]-2-propynyl | 824 |
| 108 | 3-[4-(2-thiazolyl)phenyl]-2-propynyl | 840 |
| 109 | 3-[4-(2-thienyl)phenyl]-2-propynyl | 839 |
| 110 | 3-[4-(3-isoxazolyl)phenyl]-2-propynyl | 824 |
| 111 | 3-[4-(1,3,4-oxadiazol-2-yl)phenyl]-2-propynyl | 825 |
| 112 | 3-[4-(1,2,4-oxadiazol-3-yl)phenyl]-2-propynyl | 825 |
| 113 | 3-[4-(1,2,4-oxadiazol-5-yl)phenyl]-2-propynyl | 825 |
| 114 | 3-(1-methyl-1H-benzimidazol-2-yl)-2-propynyl | 811 |
| 115 | 3-[4-(5-bromo-2-pyrimidinyl)phenyl]-2-propynyl | 913,915 |
| 116 | 3-[4-(5-fluoro-2-pyrimidinyl)phenyl]-2-propynyl | 853 |
| 117 | 3-[4-(5-ethyl-2-pyrimidinyl)phenyl]-2-propynyl | 863 |
| 118 | 3-[4-(4-methyl-2-pyrimidinyl)phenyl]-2-propynyl | 849 |
| 119 | 3-[4-(4-methoxy-2-pyrimidinyl)phenyl]-2-propynyl | 865 |
| 120 | 3-[4-(6-methyl-3-pyridazinyl)phenyl]-2-propynyl | 849 |

-continued

| Compound No. | R⁹ | MS [(M+H)⁺] |
|---|---|---|
| 121 | 3-[4-(6-methoxy-3-pyridazinyl)phenyl]-2-propynyl | 865 |
| 122 | 3-[3-(2-pyridinyl)-5-isoxazolyl]-2-propynyl | 825 |
| 123 | 3-[5-(2-pyridinyl)-2-thienyl]-2-propynyl | 840 |
| 124 | 3-[5-(3-pyridinyl)-2-thienyl]-2-propynyl | 840 |
| 125 | 3-[5-(4-pyridinyl)-2-thienyl]-2-propynyl | 840 |
| 126 | 3-[5-(2-pyrimidinyl)-2-thienyl]-2-propynyl | 841 |
| 127 | 3-(5-pyrazinyl-2-thienyl)-2-propynyl | 841 |
| 128 | 3-[4-(2-pyridinyl)-2-thienyl]-2-propynyl | 840 |
| 129 | 3-[4-(3-pyridinyl)-2-thienyl]-2-propynyl | 840 |
| 130 | 3-[4-(4-pyridinyl)-2-thienyl]-2-propynyl | 840 |
| 131 | 3-[4-(2-pyrimidinyl)-2-thienyl]-2-propynyl | 841 |
| 132 | 3-[5-(2-pyridinyl)-3-thienyl]-2-propynyl | 840 |
| 133 | 3-[5-(3-pyridinyl)-3-thienyl]-2-propynyl | 840 |
| 134 | 3-(2-phenyl-5-pyrimidinyl)-2-propynyl | 835 |
| 135 | 3-[2,2'-bithiophen]-5-yl-2-propynyl | 845 |
| 136 | 3-[4-(2-pyrimidinyloxy)phenyl]-2-propynyl | 851 |
| 137 | 4-[4-(2-pyrimidinyl)phenyl]-3-butynyl | 849 |
| 138 | 5-[4-(2-pyrimidinyl)phenyl]-4-pentynyl | 863 |
| 139 | 3-[4-(2-pyrimidinyl)phenyl]propyl | 839 |
| 140 | 3-(4-pyrazinylphenyl)propyl | 839 |
| 141 | 3-[4-(3-pyridazinyl)phenyl]propyl | 839 |
| 142 | 3-[4-(2-pyridinyl)phenyl]propyl | 838 |
| 143 | 3-[4-(1H-pyrazol-1-yl)phenyl]propyl | 827 |
| 144 | 3-[4-(1H-1,2,4-triazol-1-yl)phenyl]propyl | 828 |
| 145 | 3-[4-(1H-1,2,3-triazol-1-yl)phenyl]propyl | 828 |
| 146 | 3-[4-(1-methyl-1H-pyrazol-3-yl)phenyl]propyl | 841 |
| 147 | 3-(2-quinolinyl)propyl | 812 |
| 148 | 3-(3-quinolinyl)propyl | 812 |
| 149 | 3-(4-quinolinyl)propyl | 812 |
| 150 | 3-(5-quinolinyl)propyl | 812 |
| 151 | 3-(6-quinolinyl)propyl | 812 |
| 152 | 3-(7-quinolinyl)propyl | 812 |
| 153 | 3-(8-quinolinyl)propyl | 812 |
| 154 | 3-(2-quinoxalinyl)propyl | 813 |
| 155 | 3-(6-quinoxalinyl)propyl | 813 |
| 156 | 3-[4-(2-oxazolyl)phenyl]propyl | 828 |
| 157 | 3-[5-(2-pyridinyl)-2-thienyl]propyl | 844 |
| 158 | 3-[5-(2-pyrimidinyl)-2-thienyl]propyl | 845 |
| 159 | 3-(1H-benzimidazol-1-yl)propyl | 801 |
| 160 | (2Z)-2-fluoro-3-[4-(2-pyrimidinyl)phenyl]-2-propenyl | 855 |
| 161 | (2Z)-2-fluoro-3-[4-(4-pyrimidinyl)phenyl]-2-propenyl | 855 |
| 162 | (2Z)-2-fluoro-3-[4-(5-pyrimidinyl)phenyl]-2-propenyl | 855 |
| 163 | (2Z)-2-fluoro-3-[3-(2-pyrimidinyl)phenyl]-2-propenyl | 855 |
| 164 | (2Z)-2-fluoro-3-[4-(2-pyridinyl)phenyl]-2-propenyl | 854 |
| 165 | (2Z)-2-fluoro-3-[4-(3-pyridinyl)phenyl]-2-propenyl | 854 |
| 166 | (2Z)-2-fluoro-3-[4-(4-pyridinyl)phenyl]-2-propenyl | 854 |
| 167 | (2Z)-2-fluoro-3-(4-pyrazinylphenyl)-2-propenyl | 855 |
| 168 | (2Z)-2-fluoro-3-[4-(3-pyridazinyl)phenyl]-2-propenyl | 855 |
| 169 | (2Z)-2-fluoro-3-[4-(1H-pyrazol-1-yl)phenyl]-2-propenyl | 843 |
| 170 | (2Z)-2-fluoro-3-[4-(1H-1,2,4-triazol-1-yl)phenyl]-2-propenyl | 844 |
| 171 | (2Z)-2-fluoro-3-[4-(4H-1,2,4-triazol-4-yl)phenyl]-2-propenyl | 844 |
| 172 | (2Z)-2-fluoro-3-[4-(1H-1,2,3-triazol-1-yl)phenyl]-2-propenyl | 844 |
| 173 | (2Z)-2-fluoro-3-[4-(1H-imidazol-1-yl)phenyl]-2-propenyl | 843 |
| 174 | (2Z)-2-fluoro-3-[4-(1-methyl-1H-pyrazol-3-yl)phenyl]-2-propenyl | 857 |
| 175 | (2Z)-2-fluoro-3-[4-(1-methyl-1H-pyrazol-5-yl)phenyl]-2-propenyl | 857 |
| 176 | (2Z)-2-fluoro-3-[3-methoxy-4-(1H-pyrazol-1-yl)phenyl]-2-propenyl | 873 |
| 177 | (2Z)-2-fluoro-3-[3-fluoro-4-(1H-pyrazol-1-yl)phenyl]-2-propenyl | 861 |
| 178 | (2Z)-2-fluoro-3-[2-fluoro-4-(1H-pyrazol-1-yl)phenyl]-2-propenyl | 861 |
| 179 | (2Z)-2-fluoro-3-[3-fluoro-4-(1H-1,2,4-triazol-1-yl)phenyl]-2-propenyl | 862 |
| 180 | (2Z)-2-fluoro-3-(1-phenyl-1H-pyrazol-4-yl)-2-propenyl | 843 |
| 181 | (2Z)-2-fluoro-3-[1-(2-pyrimidinyl)-1H-imidazol-4-yl]-2-propenyl | 845 |
| 182 | (2Z)-2-fluoro-3-(1-pyrazinyl-1H-imidazol-4-yl)-2-propenyl | 845 |
| 183 | (2Z)-2-fluoro-3-(2-quinolinyl)-2-propenyl | 828 |
| 184 | (2Z)-2-fluoro-3-(3-quinolinyl)-2-propenyl | 828 |
| 185 | (2Z)-2-fluoro-3-(4-quinolinyl)-2-propenyl | 828 |
| 186 | (2Z)-2-fluoro-3-(5-quinolinyl)-2-propenyl | 828 |

-continued

| Compound No. | R⁹ | MS [(M+H)⁺] |
|---|---|---|
| 187 | (2Z)-2-fluoro-3-(6-quinolinyl)-2-propenyl | 828 |
| 188 | (2Z)-2-fluoro-3-(7-quinolinyl)-2-propenyl | 828 |
| 189 | (2Z)-2-fluoro-3-(8-quinolinyl)-2-propenyl | 828 |
| 190 | (2Z)-2-fluoro-3-(2-quinoxalinyl)-2-propenyl | 829 |
| 191 | (2Z)-2-fluoro-3-(6-quinoxalinyl)-2-propenyl | 829 |
| 192 | (2Z)-2-fluoro-3-(4-isoquinolinyl)-2-propenyl | 828 |
| 193 | (2Z)-2-fluoro-3-(6-bromo-3-pyridinyl)-2-propenyl | 856,858 |
| 194 | (2Z)-2-fluoro-3-[4-(2-oxazolyl)phenyl]-2-propenyl | 844 |
| 195 | (2Z)-2-fluoro-3-[4-(5-oxazolyl)phenyl]-2-propenyl | 844 |
| 196 | (2Z)-2-fluoro-3-[4-(2-thiazolyl)phenyl]-2-propenyl | 860 |
| 197 | (2Z)-2-fluoro-3-[4-(2-thienyl)phenyl]-2-propenyl | 859 |
| 198 | (2Z)-2-fluoro-3-[4-(3-isoxazolyl)phenyl]-2-propenyl | 844 |
| 199 | (2Z)-2-fluoro-3-[4-(1,3,4-oxadiazol-2-yl)phenyl]-2-propenyl | 845 |
| 200 | (2Z)-2-fluoro-3-[4-(1,2,4-oxadiazol-3-yl)phenyl]-2-propenyl | 845 |
| 201 | (2Z)-2-fluoro-3-[4-(1,2,4-oxadiazol-5-yl)phenyl]-2-propenyl | 845 |
| 202 | (2Z)-2-fluoro-3-(1-methyl-1H-benzimidazol-2-yl)-2-propenyl | 831 |
| 203 | (2Z)-2-fluoro-3-[4-(5-fluoro-2-pyrimidinyl)phenyl]-2-propenyl | 873 |
| 204 | (2Z)-2-fluoro-3-[4-(4-methyl-2-pyrimidinyl)phenyl]-2-propenyl | 869 |
| 205 | (2Z)-2-fluoro-3-[4-(4-methoxy-2-pyrimidinyl)phenyl]-2-propenyl | 885 |
| 206 | (2Z)-2-fluoro-3-[4-(6-methoxy-3-pyridazinyl)phenyl]-2-propenyl | 869 |
| 207 | (2Z)-2-fluoro-3-[5-(2-pyridinyl)-2-thienyl]-2-propenyl | 860 |
| 208 | (2Z)-2-fluoro-3-[5-(3-pyridinyl)-2-thienyl]-2-propenyl | 860 |
| 209 | (2Z)-2-fluoro-3-[5-(4-pyridinyl)-2-thienyl]-2-propenyl | 860 |
| 210 | (2Z)-2-fluoro-3-[5-(2-pyrimidinyl)-2-thienyl]-2-propenyl | 861 |
| 211 | (2Z)-2-fluoro-3-(5-pyrazinyl-2-thienyl)-2-propenyl | 861 |
| 212 | (2Z)-2-fluoro-3-[4-(2-pyridinyl)-2-thienyl]-2-propenyl | 860 |
| 213 | (2Z)-2-fluoro-3-[4-(3-pyridinyl)-2-thienyl]-2-propenyl | 860 |
| 214 | (2Z)-2-fluoro-3-[4-(4-pyridinyl)-2-thienyl]-2-propenyl | 860 |
| 215 | (2Z)-2-fluoro-3-[4-(2-pyrimidinyl)-2-thienyl]-2-propenyl | 861 |
| 216 | (2Z)-2-fluoro-3-(4-pyrazinyl-2-thienyl)-2-propenyl | 861 |
| 217 | (2Z)-2-fluoro-3-[5-(2-pyridinyl)-3-thienyl]-2-propenyl | 860 |
| 218 | (2Z)-2-fluoro-3-[5-(2-pyrimidinyl)-3-thienyl]-2-propenyl | 861 |
| 219 | (2Z)-2-fluoro-3-(5-pyrazinyl-3-thienyl)-2-propenyl | 861 |
| 220 | (2Z)-2-fluoro-3-(2-phenyl-5-pyrimidinyl)-2-propenyl | 855 |
| 221 | (2Z)-2-fluoro-3-[2,2'-bithiophen]-5-yl-2-propenyl | 865 |
| 222 | (2Z)-2-fluoro-3-[4-(2-pyrimidinyloxy)phenyl]-2-propenyl | 871 |
| 223 | (2Z)-2-fluoro-3-[2-fluoro-4-(2-pyrimidinyl)phenyl]-2-propenyl | 873 |
| 224 | (2Z)-3-fluoro-3-[4-(2-pyrimidinyl)phenyl]-2-propenyl | 855 |
| 225 | (2Z)-3-fluoro-3-[4-(4-pyrimidinyl)phenyl]-2-propenyl | 855 |
| 226 | (2Z)-3-fluoro-3-[4-(5-pyrimidinyl)phenyl]-2-propenyl | 855 |
| 227 | (2Z)-3-fluoro-3-[4-(2-pyridinyl)phenyl]-2-propenyl | 854 |
| 228 | (2Z)-3-fluoro-3-[4-(3-pyridinyl)phenyl]-2-propenyl | 854 |
| 229 | (2Z)-3-fluoro-3-[4-(4-pyridinyl)phenyl]-2-propenyl | 854 |
| 230 | (2Z)-3-fluoro-3-(4-pyrazinylphenyl)-2-propenyl | 855 |
| 231 | (2Z)-3-fluoro-3-[4-(3-pyridazinyl)phenyl]-2-propenyl | 855 |
| 232 | (2Z)-3-fluoro-3-[4-(1H-pyrazol-1-yl)phenyl]-2-propenyl | 843 |
| 233 | (2Z)-3-fluoro-3-[4-(1H-1,2,4-triazol-1-yl)phenyl]-2-propenyl | 844 |
| 234 | (2Z)-3-fluoro-3-[4-(4H-1,2,4-triazol-4-yl)phenyl]-2-propenyl | 844 |
| 235 | (2Z)-3-fluoro-3-[4-(1H-1,2,3-triazol-1-yl)phenyl]-2-propenyl | 844 |
| 236 | (2Z)-3-fluoro-3-[4-(1H-imidazol-1-yl)phenyl]-2-propenyl | 843 |
| 237 | (2Z)-3-fluoro-3-[4-(1-methyl-1H-pyrazol-3-yl)phenyl]-2-propenyl | 857 |
| 238 | (2Z)-3-fluoro-3-[4-(1-methyl-1H-pyrazol-5-yl)phenyl]-2-propenyl | 857 |
| 239 | (2Z)-3-fluoro-3-(1-phenyl-1H-pyrazol-4-yl)-2-propenyl | 843 |
| 240 | (2Z)-3-fluoro-3-(2-quinolinyl)-2-propenyl | 828 |
| 241 | (2Z)-3-fluoro-3-(3-quinolinyl)-2-propenyl | 828 |
| 242 | (2Z)-3-fluoro-3-(4-quinolinyl)-2-propenyl | 828 |
| 243 | (2Z)-3-fluoro-3-(5-quinolinyl)-2-propenyl | 828 |
| 244 | (2Z)-3-fluoro-3-(6-quinolinyl)-2-propenyl | 828 |
| 245 | (2Z)-3-fluoro-3-(7-quinolinyl)-2-propenyl | 828 |
| 246 | (2Z)-3-fluoro-3-(8-quinolinyl)-2-propenyl | 828 |
| 247 | (2Z)-3-fluoro-3-(2-quinoxalinyl)-2-propenyl | 829 |
| 248 | (2Z)-3-fluoro-3-(6-quinoxalinyl)-2-propenyl | 829 |

-continued

| Compound No. | R$^9$ | MS [(M+H)$^+$] |
|---|---|---|
| 249 | (2Z)-3-fluoro-3-(4-isoquinolinyl)-2-propenyl | 828 |
| 250 | (2Z)-3-fluoro-3-[4-(2-oxazolyl)phenyl]-2-propenyl | 844 |
| 251 | (2Z)-3-fluoro-3-[4-(5-oxazolyl)phenyl]-2-propenyl | 844 |
| 252 | (2Z)-3-fluoro-3-[4-(2-thiazolyl)phenyl]-2-propenyl | 860 |
| 253 | (2Z)-3-fluoro-3-[4-(2-thienyl)phenyl]-2-propenyl | 859 |
| 254 | (2Z)-3-fluoro-3-[4-(3-isoxazolyl)phenyl]-2-propenyl | 844 |
| 255 | (2Z)-3-fluoro-3-[4-(1,3,4-oxadiazol-2-yl)phenyl]-2-propenyl | 845 |
| 256 | (2Z)-3-fluoro-3-[4-(1,2,4-oxadiazol-3-yl)phenyl]-2-propenyl | 845 |
| 257 | (2Z)-3-fluoro-3-[4-(1,2,4-oxadiazol-5-yl)phenyl]-2-propenyl | 845 |
| 258 | (2Z)-3-fluoro-3-(1-methyl-1H-benzimidazol-2-yl)-2-propenyl | 831 |
| 259 | (2Z)-3-fluoro-3-[4-(5-bromo-2-pyrimidinyl)phenyl]-2-propenyl | 933,935 |
| 260 | (2Z)-3-fluoro-3-[4-(5-fluoro-2-pyrimidinyl)phenyl]-2-propenyl | 873 |
| 261 | (2Z)-3-fluoro-3-[4-(5-ethyl-2-pyrimidinyl)phenyl]-2-propenyl | 883 |
| 262 | (2Z)-3-fluoro-3-[4-(4-methyl-2-pyrimidinyl)phenyl]-2-propenyl | 869 |
| 263 | (2Z)-3-fluoro-3-[4-(4-methoxy-2-pyrimidinyl)phenyl]-2-propenyl | 885 |
| 264 | (2Z)-3-fluoro-3-[4-(6-methyl-3-pyridazinyl)phenyl]-2-propenyl | 869 |
| 265 | (2Z)-3-fluoro-3-[4-(6-methoxy-3-pyridazinyl)phenyl]-2-propenyl | 885 |
| 266 | (2Z)-3-fluoro-3-[5-(2-pyridinyl)-2-thienyl]-2-propenyl | 860 |
| 267 | (2Z)-3-fluoro-3-[5-(3-pyridinyl)-2-thienyl]-2-propenyl | 860 |
| 268 | (2Z)-3-fluoro-3-[5-(4-pyridinyl)-2-thienyl]-2-propenyl | 860 |
| 269 | (2Z)-3-fluoro-3-[5-(2-pyrimidinyl)-2-thienyl]-2-propenyl | 861 |
| 270 | (2Z)-3-fluoro-3-[5-(4-pyrimidinyl)-2-thienyl]-2-propenyl | 861 |
| 271 | (2Z)-3-fluoro-3-[5-(5-pyrimidinyl)-2-thienyl]-2-propenyl | 861 |
| 272 | (2Z)-3-fluoro-3-(5-pyrazinyl-2-thienyl)-2-propenyl | 861 |
| 273 | (2Z)-3-fluoro-3-[4-(2-pyridinyl)-2-thienyl]-2-propenyl | 860 |
| 274 | (2Z)-3-fluoro-3-[4-(3-pyridinyl)-2-thienyl]-2-propenyl | 860 |
| 275 | (2Z)-3-fluoro-3-[4-(4-pyridinyl)-2-thienyl]-2-propenyl | 860 |
| 276 | (2Z)-3-fluoro-3-[4-(2-pyrimidinyl)-2-thienyl]-2-propenyl | 861 |
| 277 | (2Z)-3-fluoro-3-[4-(4-pyrimidinyl)-2-thienyl]-2-propenyl | 861 |
| 278 | (2Z)-3-fluoro-3-[4-(5-pyrimidinyl)-2-thienyl]-2-propenyl | 861 |
| 279 | (2Z)-2-fluoro-3-[5-(2-pyridinyl)-3-thienyl]-2-propenyl | 860 |
| 280 | (2Z)-2-fluoro-3-[5-(3-pyridinyl)-3-thienyl]-2-propenyl | 860 |
| 281 | (2Z)-3-fluoro-3-(2-phenyl-5-pyrimidinyl)-2-propenyl | 855 |
| 282 | (2Z)-3-fluoro-3-[2,2'-bithiophen]-5-yl-2-propenyl | 865 |
| 283 | (2Z)-3-fluoro-3-[4-(2-pyrimidinyloxy)phenyl]-2-propenyl | 871 |
| 284 | (2Z)-2-fluoro-3-[3-(2-pyridinyl)-5-isoxazolyl]-2-propenyl | 845 |
| 285 | (2Z)-3-fluoro-3-[3-(2-pyridinyl)-5-isoxazolyl]-2-propenyl | 845 |

EXAMPLE 286

Compound 286 (Formula 1d: R$^9$ is 4-[4-(2-pyrimidinyl)phenyl]butyl)

A mixture of Compound 137 (63 mg, 0.074 mmol), 10% Pd/C (30 mg), and ammonium formate (47 mg, 0.074 mmol) in methanol (1 mL) was stirred for 20 min at room temperature. Solids were removed by filtration through Celite, the filter pad was rinsed with additional methanol, and the filtrate was concentrated. Purification by chromatography (SiO$_2$, 96:4:0.2 dichloromethane/methanol/conc. NH$_4$OH) yielded 43 mg (68%) of the title compound. MS 853 (M+H)$^+$.

EXAMPLE 287

Compound 287 (Formula 1d: R$^9$ is 5-[4-(2-pyrimidinyl)phenyl]pentyl)

The title compound is prepared by a procedure analogous to Example 286 by substituting Compound 138 for the Compound 137 of Example 286. MS 867 (M+H)$^+$.

EXAMPLE 288

Compound 288 (Formula 1y: W' is OR$^9$, and R$^9$ is (2E)-3-[4-(2-Pyrimidinyl)phenyl]-2-propenyl)

Step A:

A mixture of the Compound 7 (100 mg, 0.12 mmol), triethylamine (35 μL, 0.25 mmol), and acetic anhydride (23 μL, 0.24 mmol) in dichloromethane (1 mL) was stirred for 18 h at room temperature. The reaction mixture was diluted with dichloromethane (15 mL) washed with sat. aq. NaHCO$_3$ (10 mL), dried (Na$_2$SO$_4$), and concentrated. MS 879 (M+H)$^+$.

Step B:

Sodium hexamethyldisilazide (1.0M in THF, 180 μL, 0.18 mmol) was added dropwise to a solution of the product from step A (0.12 mmol) in DMF (1.5 mL) at −60° C. The mixture was stirred for 30 min at −60° C. and then SELECT-FLUOR™ (51 mg, 0.14 mmol) was added. The resulting mixture was stirred for 10 min at −60° C. and then diluted with ethyl acetate (15 mL) and 10% aq. NH$_4$Cl (10 mL). The organic layer was washed with sat. aq. NaHCO$_3$ (10 mL) and brine (10 mL), dried (Na$_2$SO$_4$), and concentrated. MS 897 (M+H)$^+$.

Step C:

The material from Step B was allowed to stand in methanol for 18 h and then concentrated. Purification by chromatography (SiO$_2$, 96:4:0.2 dichloromethane/methanol/conc. NH$_4$OH) yielded 66 mg (65%) of the title compound. MS 855(M+H)$^+$.

EXAMPLES 289–569

Compounds 289–569

By a procedure analogous to that of Example 288, Compounds 289–569 shown in the table below of formula 1y, wherein W' is OR$^9$, and R$^9$ is as described in the table, can be prepared.

| Compound No. | R$^9$ | MS [(M+H)$^+$] |
|---|---|---|
| 289 | phenylmethyl | 751 |
| 290 | 2-phenylethyl | 765 |
| 291 | 3-phenyl-2-propynyl | 775 |
| 292 | 3-phenylpropyl | 779 |
| 293 | 4-phenylbutyl | 793 |
| 294 | (2E)-3-phenyl-2-propenyl | 777 |
| 295 | (2E)-3-[4-(4-pyrimidinyl)phenyl]-2-propenyl | 855 |
| 296 | (2E)-3-[4-(5-pyrimidinyl)phenyl]-2-propenyl | 855 |
| 297 | (2E)-3-[3-(2-pyrimidinyl)phenyl]-2-propenyl | 855 |
| 298 | (2E)-3-[4-(2-pyridinyl)phenyl]-2-propenyl | 854 |
| 299 | (2E)-3-[4-(3-pyridinyl)phenyl]-2-propenyl | 854 |
| 300 | (2E)-3-[4-(4-pyridinyl)phenyl]-2-propenyl | 854 |
| 301 | (2E)-3-(4-pyrazinylphenyl)-2-propenyl | 855 |
| 302 | (2E)-3-[4-(3-pyridazinyl)phenyl]-2-propenyl | 855 |
| 303 | (2E)-3-[4-(1H-pyrazol-1-yl)phenyl]-2-propenyl | 843 |
| 304 | (2E)-3-[4-(1H-1,2,4-triazol-1-yl)phenyl]-2-propenyl | 844 |
| 305 | (2E)-3-[4-(4H-1,2,4-triazol-4-yl)phenyl]-2-propenyl | 844 |
| 306 | (2E)-3-[4-(1H-1,2,3-triazol-1-yl)phenyl]-2-propenyl | 844 |
| 307 | (2E)-3-[4-(1H-imidazol-1-yl)phenyl]-2-propenyl | 843 |
| 308 | (2E)-3-[4-(1-methyl-1H-pyrazol-3-yl)phenyl]-2-propenyl | 857 |
| 309 | (2E)-3-[4-(1-methyl-1H-pyrazol-5-yl)phenyl]-2-propenyl | 857 |
| 310 | (2E)-3-[3-methoxy-4-(1H-pyrazol-1-yl)phenyl]-2-propenyl | 873 |
| 311 | (2E)-3-[3-fluoro-4-(1H-pyrazol-1-yl)phenyl]-2-propenyl | 861 |
| 312 | (2E)-3-[2-fluoro-4-(1H-pyrazol-1-yl)phenyl]-2-propenyl | 861 |
| 313 | (2E)-3-[3-fluoro-4-(1H-1,2,4-triazol-1-yl)phenyl]-2-propenyl | 861 |
| 314 | (2E)-3-[6-(1H-pyrazol-1-yl)-3-pyridinyl]-2-propenyl | 844 |
| 315 | (2E)-3-(1-phenyl-1H-pyrazol-4-yl)-2-propenyl | 843 |
| 316 | (2E)-3-[1-(2-pyrimidinyl)-1H-imidazol-4-yl]-2-propenyl | 845 |
| 317 | (2E)-3-(1-pyrazinyl-1H-imidazol-4-yl)-2-propenyl | 845 |
| 318 | (2E)-3-(2-quinolinyl)-2-propenyl | 828 |
| 319 | (2E)-3-(3-quinolinyl)-2-propenyl | 828 |
| 320 | (2E)-3-(4-quinolinyl)-2-propenyl | 828 |
| 321 | (2E)-3-(5-quinolinyl)-2-propenyl | 828 |
| 322 | (2E)-3-(6-quinolinyl)-2-propenyl | 828 |
| 323 | (2E)-3-(7-quinolinyl)-2-propenyl | 828 |
| 324 | (2E)-3-(8-quinolinyl)-2-propenyl | 828 |
| 325 | (2E)-3-(2-quinoxalinyl)-2-propenyl | 829 |
| 326 | (2E)-3-(6-quinoxalinyl)-2-propenyl | 829 |
| 327 | (2E)-3-(4-isoquinolinyl)-2-propenyl | 828 |
| 328 | (2E)-3-(6-bromo-3-pyridinyl)-2-propenyl | 856,858 |
| 329 | (2E)-3-[4-(2-oxazolyl)phenyl]-2-propenyl | 844 |
| 330 | (2E)-3-[4-(5-oxazolyl)phenyl]-2-propenyl | 844 |
| 331 | (2E)-3-[4-(2-thiazolyl)phenyl]-2-propenyl | 860 |
| 332 | (2E)-3-[4-(2-thienyl)phenyl]-2-propenyl | 859 |
| 333 | (2E)-3-[4-(3-isoxazolyl)phenyl]-2-propenyl | 844 |
| 334 | (2E)-3-[4-(1,3,4-oxadiazol-2-yl)phenyl]-2-propenyl | 845 |
| 335 | (2E)-3-[4-(1,2,4-oxadiazol-3-yl)phenyl]-2-propenyl | 845 |
| 336 | (2E)-3-[4-(1,2,4-oxadiazol-5-yl)phenyl]-2-propenyl | 845 |
| 337 | (2E)-3-(1-methyl-1H-benzimidazol-2-yl)-2-propenyl | 831 |
| 338 | (2E)-3-[4-(5-bromo-2-pyrimidinyl)phenyl]-2-propenyl | 933,835 |
| 339 | (2E)-3-[4-(5-fluoro-2-pyrimidinyl)phenyl]-2-propenyl | 873 |
| 340 | (2E)-3-[4-(5-ethyl-2-pyrimidinyl)phenyl]-2-propenyl | 883 |
| 341 | (2E)-3-[4-(4-methyl-2-pyrimidinyl)phenyl]-2-propenyl | 869 |
| 342 | (2E)-3-[4-(4-methoxy-2-pyrimidinyl)phenyl]-2-propenyl | 885 |
| 343 | (2E)-3-[4-(6-methyl-3-pyridazinyl)phenyl]-2-propenyl | 869 |
| 344 | (2E)-3-[4-(6-methoxy-3-pyridazinyl)phenyl]-2-propenyl | 885 |
| 345 | (2E)-3-[5-(2-pyridinyl)-2-thienyl]-2-propenyl | 860 |
| 346 | (2E)-3-[5-(2-pyrimidinyl)-2-thienyl]-2-propenyl | 861 |
| 347 | (2E)-3-(5-pyrazinyl-2-thienyl)-2-propenyl | 861 |
| 348 | (2E)-3-[4-(2-pyridinyl)-2-thienyl]-2-propenyl | 860 |
| 349 | (2E)-3-[4-(2-pyrimidinyl)-2-thienyl]-2-propenyl | 861 |
| 350 | (2E)-3-(4-pyrazinyl-2-thienyl)-2-propenyl | 861 |
| 351 | (2E)-3-[5-(2-pyridinyl)-3-thienyl]-2-propenyl | 860 |
| 352 | (2E)-3-[5-(2-pyrimidinyl)-3-thienyl]-2-propenyl | 861 |
| 353 | (2E)-3-(5-pyrazinyl-3-thienyl)-2-propenyl | 861 |

-continued

| Compound No. | R⁹ | MS [(M+H)⁺] |
|---|---|---|
| 354 | (2E)-3-(2-phenyl-5-pyrimidinyl)-2-propenyl | 855 |
| 355 | (2E)-3-[2,2'-bithiophen]-5-yl-2-propenyl | 865 |
| 356 | (2E)-3-[4-(2-pyrimidinyloxy)phenyl]-2-propenyl | 871 |
| 357 | (2E)-3-[2-fluoro-4-(2-pyrimidinyl)phenyl]-2-propenyl | 873 |
| 358 | (2E)-3-[4-(2-pyrimidinyl)phenyl]-2-butenyl | 869 |
| 359 | [4-(2-pyrimidinyl)phenyl]methyl | 829 |
| 360 | [4-(3-pyridazinyl)phenyl]methyl | 829 |
| 361 | (4-pyrazinylphenyl)methyl | 829 |
| 362 | 3-[4-(2-pyrimidinyl)phenyl]-2-propynyl | 853 |
| 363 | 3-[4-(4-pyrimidinyl)phenyl]-2-propynyl | 853 |
| 364 | 3-[4-(5-pyrimidinyl)phenyl]-2-propynyl | 853 |
| 365 | 3-[4-(2-pyridinyl)phenyl]-2-propynyl | 852 |
| 366 | 3-[4-(3-pyridinyl)phenyl]-2-propynyl | 852 |
| 367 | 3-[4-(4-pyridinyl)phenyl]-2-propynyl | 852 |
| 368 | 3-(4-pyrazinylphenyl)-2-propynyl | 853 |
| 369 | 3-[4-(3-pyridazinyl)phenyl]-2-propynyl | 853 |
| 370 | 3-[4-(1H-pyrazol-1-yl)phenyl]-2-propynyl | 841 |
| 371 | 3-[4-(1H-1,2,4-triazol-1-yl)phenyl]-2-propynyl | 842 |
| 372 | 3-[4-(4H-1,2,4-triazol-4-yl)phenyl]-2-propynyl | 842 |
| 373 | 3-[4-(1H-1,2,3-triazol-1-yl)phenyl]-2-propynyl | 842 |
| 374 | 3-[4-(1H-imidazol-1-yl)phenyl]-2-propynyl | 841 |
| 375 | 3-[4-(1-methyl-1H-pyrazol-3-yl)phenyl]-2-propynyl | 855 |
| 376 | 3-[4-(1-methyl-1H-pyrazol-5-yl)phenyl]-2-propynyl | 855 |
| 377 | 3-(1-phenyl-1H-pyrazol-4-yl)-2-propynyl | 841 |
| 378 | 3-(2-quinolinyl)-2-propynyl | 826 |
| 379 | 3-(3-quinolinyl)-2-propynyl | 826 |
| 380 | 3-(4-quinolinyl)-2-propynyl | 826 |
| 381 | 3-(5-quinolinyl)-2-propynyl | 826 |
| 382 | 3-(6-quinolinyl)-2-propynyl | 826 |
| 383 | 3-(7-quinolinyl)-2-propynyl | 826 |
| 384 | 3-(8-quinolinyl)-2-propynyl | 826 |
| 385 | 3-(2-quinoxalinyl)-2-propynyl | 827 |
| 386 | 3-(6-quinoxalinyl)-2-propynyl | 827 |
| 387 | 3-(4-isoquinolinyl)-2-propynyl | 826 |
| 388 | 3-[4-(2-oxazolyl)phenyl]-2-propynyl | 842 |
| 389 | 3-[4-(5-oxazolyl)phenyl]-2-propynyl | 842 |
| 390 | 3-[4-(2-thiazolyl)phenyl]-2-propynyl | 858 |
| 391 | 3-[4-(2-thienyl)phenyl]-2-propynyl | 857 |
| 392 | 3-[4-(3-isoxazolyl)phenyl]-2-propynyl | 842 |
| 393 | 3-[4-(1,3,4-oxadiazol-2-yl)phenyl]-2-propynyl | 843 |
| 394 | 3-[4-(1,2,4-oxadiazol-3-yl)phenyl]-2-propynyl | 843 |
| 395 | 3-[4-(1,2,4-oxadiazol-5-yl)phenyl]-2-propynyl | 843 |
| 396 | 3-(1-methyl-1H-benzimidazol-2-yl)-2-propynyl | 829 |
| 397 | 3-[4-(5-bromo-2-pyrimidinyl)phenyl]-2-propynyl | 931,933 |
| 398 | 3-[4-(5-fluoro-2-pyrimidinyl)phenyl]-2-propynyl | 871 |
| 399 | 3-[4-(5-ethyl-2-pyrimidinyl)phenyl]-2-propynyl | 881 |
| 400 | 3-[4-(4-methyl-2-pyrimidinyl)phenyl]-2-propynyl | 867 |
| 401 | 3-[4-(4-methoxy-2-pyrimidinyl)phenyl]-2-propynyl | 883 |
| 402 | 3-[4-(6-methyl-3-pyridazinyl)phenyl]-2-propynyl | 867 |
| 403 | 3-[4-(6-methoxy-3-pyridazinyl)phenyl]-2-propynyl | 883 |
| 404 | 3-[3-(2-pyridinyl)-5-isoxazolyl]-2-propynyl | 843 |
| 405 | 3-[5-(2-pyridinyl)-2-thienyl]-2-propynyl | 858 |
| 406 | 3-[5-(3-pyridinyl)-2-thienyl]-2-propynyl | 858 |
| 407 | 3-[5-(4-pyridinyl)-2-thienyl]-2-propynyl | 858 |
| 408 | 3-[5-(2-pyrimidinyl)-2-thienyl]-2-propynyl | 859 |
| 409 | 3-(5-pyrazinyl-2-thienyl)-2-propynyl | 859 |
| 410 | 3-[4-(2-pyridinyl)-2-thienyl]-2-propynyl | 858 |
| 411 | 3-[4-(3-pyridinyl)-2-thienyl]-2-propynyl | 858 |
| 412 | 3-[4-(4-pyridinyl)-2-thienyl]-2-propynyl | 858 |
| 413 | 3-[4-(2-pyrimidinyl)-2-thienyl]-2-propynyl | 859 |
| 414 | 3-[5-(2-pyridinyl)-3-thienyl]-2-propynyl | 858 |
| 415 | 3-[5-(3-pyridinyl)-3-thienyl]-2-propynyl | 858 |
| 416 | 3-(2-phenyl-5-pyrimidinyl)-2-propynyl | 853 |
| 417 | 3-[2,2'-bithiophen]-5-yl-2-propynyl | 863 |
| 418 | 3-[4-(2-pyrimidinyloxy)phenyl]-2-propynyl | 869 |
| 419 | 4-[4-(2-pyrimidinyl)phenyl]-3-butynyl | 867 |
| 420 | 5-[4-(2-pyrimidinyl)phenyl]-4-pentynyl | 881 |
| 421 | 3-[4-(2-pyrimidinyl)phenyl]propyl | 857 |
| 422 | 3-(4-pyrazinylphenyl)propyl | 857 |
| 423 | 3-[4-(3-pyridazinyl)phenyl]propyl | 857 |
| 424 | 3-[4-(2-pyridinyl)phenyl]propyl | 856 |
| 425 | 3-[4-(1H-pyrazol-1-yl)phenyl]propyl | 845 |
| 426 | 3-[4-(1H-1,2,4-triazol-1-yl)phenyl]propyl | 846 |
| 427 | 3-[4-(1H-1,2,3-triazol-1-yl)phenyl]propyl | 846 |
| 428 | 3-[4-(1-methyl-1H-pyrazol-3-yl)phenyl]propyl | 859 |
| 429 | 3-(2-quinolinyl)propyl | 830 |

-continued

| Compound No. | R⁹ | MS [(M+H)⁺] |
|---|---|---|
| 430 | 3-(3-quinolinyl)propyl | 830 |
| 431 | 3-(4-quinolinyl)propyl | 830 |
| 432 | 3-(5-quinolinyl)propyl | 830 |
| 433 | 3-(6-quinolinyl)propyl | 830 |
| 434 | 3-(7-quinolinyl)propyl | 830 |
| 435 | 3-(8-quinolinyl)propyl | 830 |
| 436 | 3-(2-quinoxalinyl)propyl | 831 |
| 437 | 3-(6-quinoxalinyl)propyl | 831 |
| 438 | 3-[4-(2-oxazolyl)phenyl]propyl | 846 |
| 439 | 3-[5-(2-pyridinyl)-2-thienyl]propyl | 862 |
| 440 | 3-[5-(2-pyrimidinyl)-2-thienyl]propyl | 863 |
| 441 | 3-(1H-benzimidazol-1-yl)propyl | 819 |
| 442 | (2Z)-2-fluoro-3-[4-(2-pyrimidinyl)phenyl]-2-propenyl | 873 |
| 443 | (2Z)-2-fluoro-3-[4-(4-pyrimidinyl)phenyl]-2-propenyl | 873 |
| 444 | (2Z)-2-fluoro-3-[4-(5-pyrimidinyl)phenyl]-2-propenyl | 873 |
| 445 | (2Z)-2-fluoro-3-[3-(2-pyrimidinyl)phenyl]-2-propenyl | 873 |
| 446 | (2Z)-2-fluoro-3-[4-(2-pyridinyl)phenyl]-2-propenyl | 872 |
| 447 | (2Z)-2-fluoro-3-[4-(3-pyridinyl)phenyl]-2-propenyl | 872 |
| 448 | (2Z)-2-fluoro-3-[4-(4-pyridinyl)phenyl]-2-propenyl | 872 |
| 449 | (2Z)-2-fluoro-3-(4-pyrazinylphenyl)-2-propenyl | 873 |
| 450 | (2Z)-2-fluoro-3-[4-(3-pyridazinyl)phenyl]-2-propenyl | 873 |
| 451 | (2Z)-2-fluoro-3-[4-(1H-pyrazol-1-yl)phenyl]-2-propenyl | 861 |
| 452 | (2Z)-2-fluoro-3-[4-(1H-1,2,4-triazol-1-yl)phenyl]-2-propenyl | 862 |
| 453 | (2Z)-2-fluoro-3-[4-(4H-1,2,4-triazol-4-yl)phenyl]-2-propenyl | 862 |
| 454 | (2Z)-2-fluoro-3-[4-(1H-1,2,3-triazol-1-yl)phenyl]-2-propenyl | 862 |
| 455 | (2Z)-2-fluoro-3-[4-(1H-imidazol-1-yl)phenyl]-2-propenyl | 861 |
| 456 | (2Z)-2-fluoro-3-[4-(1-methyl-1H-pyrazol-3-yl)phenyl]-2-propenyl | 875 |
| 457 | (2Z)-2-fluoro-3-[4-(1-methyl-1H-pyrazol-5-yl)phenyl]-2-propenyl | 875 |
| 458 | (2Z)-2-fluoro-3-[3-methoxy-4-(1H-pyrazol-1-yl)phenyl]-2-propenyl | 891 |
| 459 | (2Z)-2-fluoro-3-[3-fluoro-4-(1H-pyrazol-1-yl)phenyl]-2-propenyl | 879 |
| 460 | (2Z)-2-fluoro-3-[2-fluoro-4-(1H-pyrazol-1-yl)phenyl]-2-propenyl | 879 |
| 461 | (2Z)-2-fluoro-3-[3-fluoro-4-(1H-1,2,4-triazol-1-yl)phenyl]-2-propenyl | 880 |
| 462 | (2Z)-2-fluoro-3-(1-phenyl-1H-pyrazol-4-yl)-2-propenyl | 861 |
| 463 | (2Z)-2-fluoro-3-[1-(2-pyrimidinyl)-1H-imidazol-4-yl]-2-propenyl | 863 |
| 464 | (2Z)-2-fluoro-3-(1-pyrazinyl-1H-imidazol-4-yl)-2-propenyl | 863 |
| 465 | (2Z)-2-fluoro-3-(2-quinolinyl)-2-propenyl | 846 |
| 466 | (2Z)-2-fluoro-3-(3-quinolinyl)-2-propenyl | 846 |
| 467 | (2Z)-2-fluoro-3-(4-quinolinyl)-2-propenyl | 846 |
| 468 | (2Z)-2-fluoro-3-(5-quinolinyl)-2-propenyl | 846 |
| 469 | (2Z)-2-fluoro-3-(6-quinolinyl)-2-propenyl | 846 |
| 470 | (2Z)-2-fluoro-3-(7-quinolinyl)-2-propenyl | 846 |
| 471 | (2Z)-2-fluoro-3-(8-quinolinyl)-2-propenyl | 846 |
| 472 | (2Z)-2-fluoro-3-(2-quinoxalinyl)-2-propenyl | 847 |
| 473 | (2Z)-2-fluoro-3-(6-quinoxalinyl)-2-propenyl | 847 |
| 474 | (2Z)-2-fluoro-3-(4-isoquinolinyl)-2-propenyl | 846 |
| 475 | (2Z)-2-fluoro-3-(6-bromo-3-pyridinyl)-2-propenyl | 874,876 |
| 476 | (2Z)-2-fluoro-3-[4-(2-oxazolyl)phenyl]-2-propenyl | 862 |
| 477 | (2Z)-2-fluoro-3-[4-(5-oxazolyl)phenyl]-2-propenyl | 862 |
| 478 | (2Z)-2-fluoro-3-[4-(2-thiazolyl)phenyl]-2-propenyl | 878 |
| 479 | (2Z)-2-fluoro-3-[4-(2-thienyl)phenyl]-2-propenyl | 877 |
| 480 | (2Z)-2-fluoro-3-[4-(3-isoxazolyl)phenyl]-2-propenyl | 862 |
| 481 | (2Z)-2-fluoro-3-[4-(1,3,4-oxadiazol-2-yl)phenyl]-2-propenyl | 863 |
| 482 | (2Z)-2-fluoro-3-[4-(1,2,4-oxadiazol-3-yl)phenyl]-2-propenyl | 863 |
| 483 | (2Z)-2-fluoro-3-[4-(1,2,4-oxadiazol-5-yl)phenyl]-2-propenyl | 863 |
| 484 | (2Z)-2-fluoro-3-(1-methyl-1H-benzimidazol-2-yl)-2-propenyl | 849 |
| 485 | (2Z)-2-fluoro-3-[4-(5-fluoro-2-pyrimidinyl)phenyl]-2-propenyl | 891 |
| 486 | (2Z)-2-fluoro-3-[4-(4-methyl-2-pyrimidinyl)phenyl]-2-propenyl | 887 |
| 487 | (2Z)-2-fluoro-3-[4-(4-methoxy-2-pyrimidinyl)phenyl]-2-propenyl | 903 |

-continued

| Compound No. | R⁹ | MS [(M+H)⁺] |
|---|---|---|
| 488 | (2Z)-2-fluoro-3-[4-(6-methoxy-3-pyridazinyl)phenyl]-2-propenyl | 887 |
| 489 | (2Z)-2-fluoro-3-[5-(2-pyridinyl)-2-thienyl]-2-propenyl | 878 |
| 490 | (2Z)-2-fluoro-3-[5-(3-pyridinyl)-2-thienyl]-2-propenyl | 878 |
| 491 | (2Z)-2-fluoro-3-[5-(4-pyridinyl)-2-thienyl]-2-propenyl | 878 |
| 492 | (2Z)-2-fluoro-3-[5-(2-pyrimidinyl)-2-thienyl]-2-propenyl | 879 |
| 493 | (2Z)-2-fluoro-3-(5-pyrazinyl-2-thienyl)-2-propenyl | 879 |
| 494 | (2Z)-2-fluoro-3-[4-(2-pyridinyl)-2-thienyl]-2-propenyl | 878 |
| 495 | (2Z)-2-fluoro-3-[4-(3-pyridinyl)-2-thienyl]-2-propenyl | 878 |
| 496 | (2Z)-2-fluoro-3-[4-(4-pyridinyl)-2-thienyl]-2-propenyl | 878 |
| 497 | (2Z)-2-fluoro-3-[4-(2-pyrimidinyl)-2-thienyl]-2-propenyl | 879 |
| 498 | (2Z)-2-fluoro-3-(4-pyrazinyl-2-thienyl)-2-propenyl | 879 |
| 499 | (2Z)-2-fluoro-3-[5-(2-pyridinyl)-3-thienyl]-2-propenyl | 878 |
| 500 | (2Z)-2-fluoro-3-[5-(2-pyrimidinyl)-3-thienyl]-2-propenyl | 879 |
| 501 | (2Z)-2-fluoro-3-(5-pyrazinyl-3-thienyl)-2-propenyl | 879 |
| 502 | (2Z)-2-fluoro-3-(2-phenyl-5-pyrimidinyl)-2-propenyl | 873 |
| 503 | (2Z)-2-fluoro-3-[2,2'-bithiophen]-5-yl-2-propenyl | 883 |
| 504 | (2Z)-2-fluoro-3-[4-(2-pyrimidinyloxy)phenyl]-2-propenyl | 889 |
| 505 | (2Z)-2-fluoro-3-[2-fluoro-4-(2-pyrimidinyl)phenyl]-2-propenyl | 891 |
| 506 | (2Z)-3-fluoro-3-[4-(2-pyrimidinyl)phenyl]-2-propenyl | 873 |
| 507 | (2Z)-3-fluoro-3-[4-(4-pyrimidinyl)phenyl]-2-propenyl | 873 |
| 508 | (2Z)-3-fluoro-3-[4-(5-pyrimidinyl)phenyl]-2-propenyl | 873 |
| 509 | (2Z)-3-fluoro-3-[4-(2-pyridinyl)phenyl]-2-propenyl | 872 |
| 510 | (2Z)-3-fluoro-3-[4-(3-pyridinyl)phenyl]-2-propenyl | 872 |
| 511 | (2Z)-3-fluoro-3-[4-(4-pyridinyl)phenyl]-2-propenyl | 872 |
| 512 | (2Z)-3-fluoro-3-(4-pyrazinylphenyl)-2-propenyl | 873 |
| 513 | (2Z)-3-fluoro-3-[4-(3-pyridazinyl)phenyl]-2-propenyl | 873 |
| 514 | (2Z)-3-fluoro-3-[4-(1H-pyrazol-1-yl)phenyl]-2-propenyl | 861 |
| 515 | (2Z)-3-fluoro-3-[4-(1H-1,2,4-triazol-1-yl)phenyl]-2-propenyl | 862 |
| 516 | (2Z)-3-fluoro-3-[4-(4H-1,2,4-triazol-4-yl)phenyl]-2-propenyl | 862 |
| 517 | (2Z)-3-fluoro-3-[4-(1H-1,2,3-triazol-1-yl)phenyl]-2-propenyl | 862 |
| 518 | (2Z)-3-fluoro-3-[4-(1H-imidazol-1-yl)phenyl]-2-propenyl | 861 |
| 519 | (2Z)-3-fluoro-3-[4-(1-methyl-1H-pyrazol-3-yl)phenyl]-2-propenyl | 875 |
| 520 | (2Z)-3-fluoro-3-[4-(1-methyl-1H-pyrazol-5-yl)phenyl]-2-propenyl | 875 |
| 521 | (2Z)-3-fluoro-3-(1-phenyl-1H-pyrazol-4-yl)-2-propenyl | 861 |
| 522 | (2Z)-3-fluoro-3-(2-quinolinyl)-2-propenyl | 846 |
| 523 | (2Z)-3-fluoro-3-(3-quinolinyl)-2-propenyl | 846 |
| 524 | (2Z)-3-fluoro-3-(4-quinolinyl)-2-propenyl | 846 |
| 525 | (2Z)-3-fluoro-3-(5-quinolinyl)-2-propenyl | 846 |
| 526 | (2Z)-3-fluoro-3-(6-quinolinyl)-2-propenyl | 846 |
| 527 | (2Z)-3-fluoro-3-(7-quinolinyl)-2-propenyl | 846 |
| 528 | (2Z)-3-fluoro-3-(8-quinolinyl)-2-propenyl | 846 |
| 529 | (2Z)-3-fluoro-3-(2-quinoxalinyl)-2-propenyl | 847 |
| 530 | (2Z)-3-fluoro-3-(6-quinoxalinyl)-2-propenyl | 847 |
| 531 | (2Z)-3-fluoro-3-(4-isoquinolinyl)-2-propenyl | 846 |
| 532 | (2Z)-3-fluoro-3-[4-(2-oxazolyl)phenyl]-2-propenyl | 862 |
| 533 | (2Z)-3-fluoro-3-[4-(5-oxazolyl)phenyl]-2-propenyl | 862 |
| 534 | (2Z)-3-fluoro-3-[4-(2-thiazolyl)phenyl]-2-propenyl | 878 |
| 535 | (2Z)-3-fluoro-3-[4-(2-thienyl)phenyl]-2-propenyl | 877 |
| 536 | (2Z)-3-fluoro-3-[4-(3-isoxazolyl)phenyl]-2-propenyl | 862 |
| 537 | (2Z)-3-fluoro-3-[4-(1,3,4-oxadiazol-2-yl)phenyl]-2-propenyl | 863 |
| 538 | (2Z)-3-fluoro-3-[4-(1,2,4-oxadiazol-3-yl)phenyl]-2-propenyl | 863 |
| 539 | (2Z)-3-fluoro-3-[4-(1,2,4-oxadiazol-5-yl)phenyl]-2-propenyl | 863 |
| 540 | (2Z)-3-fluoro-3-(1-methyl-1H-benzimidazol-2-yl)-2-propenyl | 849 |
| 541 | (2Z)-3-fluoro-3-[4-(5-bromo-2-pyrimidinyl)phenyl]-2-propenyl | 951,953 |
| 542 | (2Z)-3-fluoro-3-[4-(5-fluoro-2-pyrimidinyl)phenyl]-2-propenyl | 891 |
| 543 | (2Z)-3-fluoro-3-[4-(5-ethyl-2-pyrimidinyl)phenyl]-2-propenyl | 901 |
| 544 | (2Z)-3-fluoro-3-[4-(4-methyl-2-pyrimidinyl)phenyl]-2-propenyl | 887 |
| 545 | (2Z)-3-fluoro-3-[4-(4-methoxy-2-pyrimidinyl)phenyl]-2-propenyl | 903 |
| 546 | (2Z)-3-fluoro-3-[4-(6-methyl-3-pyridazinyl)phenyl]-2-propenyl | 887 |

-continued

| Compound No. | R⁹ | MS [(M+H)⁺] |
|---|---|---|
| 547 | (2Z)-3-fluoro-3-[4-(6-methoxy-3-pyridazinyl)phenyl]-2-propenyl | 903 |
| 548 | (2Z)-3-fluoro-3-[5-(2-pyridinyl)-2-thienyl]-2-propenyl | 878 |
| 549 | (2Z)-3-fluoro-3-[5-(3-pyridinyl)-2-thienyl]-2-propenyl | 878 |
| 550 | (2Z)-3-fluoro-3-[5-(4-pyridinyl)-2-thienyl]-2-propenyl | 878 |
| 551 | (2Z)-3-fluoro-3-[5-(2-pyrimidinyl)-2-thienyl]-2-propenyl | 879 |
| 552 | (2Z)-3-fluoro-3-[5-(4-pyrimidinyl)-2-thienyl]-2-propenyl | 879 |
| 553 | (2Z)-3-fluoro-3-[5-(5-pyrimidinyl)-2-thienyl]-2-propenyl | 879 |
| 554 | (2Z)-3-fluoro-3-(5-pyrazinyl-2-thienyl)-2-propenyl | 879 |
| 555 | (2Z)-3-fluoro-3-[4-(2-pyridinyl)-2-thienyl]-2-propenyl | 878 |
| 556 | (2Z)-3-fluoro-3-[4-(3-pyridinyl)-2-thienyl]-2-propenyl | 878 |
| 557 | (2Z)-3-fluoro-3-[4-(4-pyridinyl)-2-thienyl]-2-propenyl | 878 |
| 558 | (2Z)-3-fluoro-3-[4-(2-pyrimidinyl)-2-thienyl]-2-propenyl | 879 |
| 559 | (2Z)-3-fluoro-3-[4-(4-pyrimidinyl)-2-thienyl]-2-propenyl | 879 |
| 560 | (2Z)-3-fluoro-3-[4-(5-pyrimidinyl)-2-thienyl]-2-propenyl | 879 |
| 561 | (2Z)-2-fluoro-3-[5-(2-pyridinyl)-3-thienyl]-2-propenyl | 878 |
| 562 | (2Z)-2-fluoro-3-[5-(3-pyridinyl)-3-thienyl]-2-propenyl | 878 |
| 563 | (2Z)-3-fluoro-3-(2-phenyl-5-pyrimidinyl)-2-propenyl | 873 |
| 564 | (2Z)-3-fluoro-3-[2,2'-bithiophen]-5-yl-2-propenyl | 883 |
| 565 | (2Z)-3-fluoro-3-[4-(2-pyrimidinyloxy)phenyl]-2-propenyl | 889 |
| 566 | 4-[4-(2-pyrimidinyl)phenyl]butyl | 871 |
| 567 | 5-[4-(2-pyrimidinyl)phenyl]pentyl | 885 |
| 568 | (2Z)-2-fluoro-3-[3-(2-pyridinyl)-5-isoxazolyl]-2-propenyl | 863 |
| 569 | (2Z)-3-fluoro-3-[3-(2-pyridinyl)-5-isoxazolyl]-2-propenyl | 863 |

EXAMPLE 570

Compound 570 (Formula 1c: $R^{10}$ is H, $R^{11}$ is phenylmethyl)

A mixture of O-benzylhydroxylamine (22 mg, 0.18 mmol) and Compound 4 (25 mg, 0.070 mmol) in DMSO (0.25 mL) was heated to 60° C. for 18 h. The solution was diluted with ethyl acetate (15 mL), washed with water (2×10 mL) and brine (10 ml), dried ($Na_2SO_4$), and concentrated. Purification by chromatography ($SiO_2$, 95:5:0.2 dichloromethane/methanol/conc. $NH_4OH$) yielded 8.3 mg (32%) of the title compound. MS 748 (M+H)⁺.

EXAMPLES 571–619

Compounds 571–619

Following the procedure of Example 570, except substituting the reagent of formula $R^{11}ONH_2$ for the O-benzylhydroxylamine of Example 570, the compounds 571–619 shown in the table below of formula 1c wherein $R^{10}$ is H and $R^{11}$ is as described in the table, can be prepared.

| Compound No. | R¹¹ | MS [(M+H)⁺] |
|---|---|---|
| 571 | 2-[4-(2-pyrimidinyl)phenyl]ethyl | 840 |
| 572 | 2-[4-(4-pyrimidinyl)phenyl]ethyl | 840 |
| 573 | 2-[4-(5-pyrimidinyl)phenyl]ethyl | 840 |
| 574 | 2-[3-(2-pyrimidinyl)phenyl]ethyl | 840 |
| 575 | 2-[4-(2-pyridinyl)phenyl]ethyl | 839 |
| 576 | 2-[4-(3-pyridinyl)phenyl]ethyl | 839 |
| 577 | 2-[4-(4-pyridinyl)phenyl]ethyl | 839 |
| 578 | 2-(4-pyrazinylphenyl)ethyl | 840 |
| 579 | 2-[4-(3-pyridazinyl)phenyl]ethyl | 840 |
| 580 | 2-[4-(1H-pyrazol-1-yl)phenyl]ethyl | 828 |
| 581 | 2-[4-(1H-1,2,4-triazol-1-yl)phenyl]ethyl | 829 |
| 582 | 2-[4-(1H-1,2,3-triazol-1-yl)phenyl]ethyl | 829 |
| 583 | 2-[4-(1H-imidazol-1-yl)phenyl]ethyl | 828 |
| 584 | 2-[4-(1-methyl-1H-pyrazol-3-yl)phenyl]ethyl | 842 |
| 585 | 2-[4-(1-methyl-1H-pyrazol-5-yl)phenyl]ethyl | 842 |
| 586 | 2-[3-fluoro-4-(1H-pyrazol-1-yl)phenyl]ethyl | 846 |
| 587 | 2-[2-fluoro-4-(1H-pyrazol-1-yl)phenyl]ethyl | 846 |
| 588 | 2-(1-phenyl-1H-pyrazol-4-yl)ethyl | 828 |
| 589 | 2-[1-(2-pyrimidinyl)-1H-imidazol-4-yl]ethyl | 830 |
| 590 | 2-(2-quinolinyl)ethyl | 813 |
| 591 | 2-(3-quinolinyl)ethyl | 813 |
| 592 | 2-(4-quinolinyl)ethyl | 813 |
| 593 | 2-(5-quinolinyl)ethyl | 813 |
| 594 | 2-(6-quinolinyl)ethyl | 813 |
| 595 | 2-(7-quinolinyl)ethyl | 813 |
| 596 | 2-(8-quinolinyl)ethyl | 813 |
| 597 | 2-(2-quinoxalinyl)ethyl | 814 |
| 598 | 2-(6-quinoxalinyl)ethyl | 814 |
| 599 | [4-(2-pyrimidinyl)phenyl]methyl | 826 |
| 600 | [4-(3-pyridazinyl)phenyl]methyl | 826 |
| 601 | (4-pyrazinylphenyl)methyl | 826 |
| 602 | 3-[4-(2-pyrimidinyl)phenyl]-2-propynyl | 850 |
| 603 | 3-(4-pyrazinylphenyl)-2-propynyl | 850 |
| 604 | 3-[4-(3-pyridazinyl)phenyl]-2-propynyl | 850 |
| 605 | (2E)-3-[4-(2-pyrimidinyl)phenyl]-2-propenyl | 852 |
| 606 | (2E)-3-(4-pyrazinylphenyl)-2-propenyl | 852 |
| 607 | (2E)-3-[4-(3-pyridazinyl)phenyl]-2-propenyl | 852 |
| 608 | 3-[4-(2-pyrimidinyl)phenyl]propyl | 854 |
| 609 | 3-(4-pyrazinylphenyl)propyl | 854 |
| 610 | 3-[4-(3-pyridazinyl)phenyl]propyl | 854 |
| 611 | 2-phenylethyl | 762 |
| 612 | 3-phenylpropyl | 776 |
| 613 | (2E)-3-phenyl-2-propenyl | 774 |
| 614 | 3-phenyl-2-propynyl | 772 |
| 615 | (2E)-3-(3-pyridinyl)-2-propenyl | 775 |
| 616 | (2E)-3-[3-(2-pyrimidinyl)phenyl]-2-propenyl | 852 |
| 617 | (2E)-3-[4-(2-pyridinyl)phenyl]-2-propenyl | 851 |
| 618 | 3-(3-quinolinyl)-2-propynyl | 823 |
| 619 | (2E)-3-[4-(1H-pyrazol-1-yl)phenyl]-2-propenyl | 840 |

EXAMPLE 620

Compound 620 (Formula 1o': Ar is 3-quinolinyl

Step A

Following the procedure of Example 570, except substituting the reagent of O-allylhydroxylamine hydrochloride for the O-benzylhydroxylamine of Example 570, the compound of formula 1c wherein $R^{10}$ is H and $R^{11}$ is 2-propenyl can be prepared.

Step B

The compound from step A (90 mg, 0.13 mmol), tri-o-tolylphosphine (4 mg, 0.013 mmol) and triethylamine (53 mg, 0.52 mmol) in 3 mL DMF was degassed with nitrogen for 5 minutes. Palladium acetate (2 mg, 0.0065 mmol) and 3-bromoquinoline (81 mg, 0.39 mmol) were added. The reaction mixture was heated at 100° C. for 24 hrs. Water (10 mL) was added and the mixture was extracted with ethyl acetate (3×15 mL). The organic layer was collected, dried and concentrated. Purification by chromatography ($SiO_2$, 95:5:0.2 dichloromethane/methanol/conc. $NH_4OH$) yielded 18 mg (17%) of the title compound. MS 825 (M+H)$^+$.

EXAMPLE 621

Compound 621 (Formula 1c: $R^{10}$ is $CH_3$, $R^{11}$ is 2-[4-(2-pyrimidinyl)phenyl]ethyl)

Compound 571 (100 mg, 0.12 mmol) and parafomaldehyde (36 mg, 1.2 mmol) were dissolved in 1 mL acetonitrile. To this reaction mixture was added TFA (120 μL, 1.2 mmol) followed by triethylsilane (240 μL, 1.2 mmol). The reaction mixture was heated at 60° C. for 24 h. Saturated $NaHCO_3$ was added and the mixture was extracted with ethyl acetate. The organic layer was dried and concentrated. Purification by chromatography ($SiO_2$, 95:5:0.2 dichloromethane/methanol/conc. $NH_4OH$) followed by HPLC separation yielded 6 mg (6%) of the title compound. MS 855 (M+H)$^+$.

EXAMPLE 622

Compound 622 (Formula 1y: W' is $NR^{10}OR^{11}$, $R^{10}$ is H, and $R^{11}$ is (2E)-3-[(4-(2-pyrimidinyl)phenyl)]-2-propenyl Step A Compound 605 (30 mg, 0.034 mmol) was converted to its 2'-acetate derivative by a procedure analogous to Example 1, step D.

Step B

Sodium hexamethyldisilazide (1.0 M in THF, 51 μL, 0.051 mmol) was added dropwise to a solution of the product from Step A (0.034 mmol) in DMF (1 mL) at −60° C. The mixture was stirred for 20 min at this temperature and then SELECTFLUOR™ (15 mg, 0.041 mmol) was added. The resulting mixture was stirred for one hour at −60° C., diluted with ethyl acetate, washed with water and brine, dried and concentrated. This material was allowed to stand in methanol for 24 h and then concentrated. Purification by chromatography ($SiO_2$, 95:5:0.2 dichloromethane/methanol/conc. $NH_4OH$) yielded 18 mg (62%) of the title compound. MS 870 (M+H)$^+$.

EXAMPLE 623

Compound 623 (Formula 1y: W' is $NR^{10}OR^{11}$, $R^{10}$ is H, and $R^{11}$ is 3-(3-quinolinyl)-2-propynyl The title compound was prepared by procedures analogous to Example 622 by substituting the compound of Example 618 for the compound of Example 605. MS 841 (M+H)$^+$.

EXAMPLE 624

Compound 624 (Formula 1b: $R^{12}$ is H, $R^{13}$ is phenyl, $R^{14}$ is H)

Phenylhydrazine (70 μL, 0.71 mmol) was added to a solution of Compound 4 (50 mg, 0.070 mmol) in DMSO (0.5 mL) and the resulting solution was stirred for 5 days. The solution was diluted with ethyl acetate (10 mL), washed with water and brine (5 mL each), dried ($Na2SO_4$), and concentrated. Purification by chromatography ($SiO_2$, 96:4:0.2 dichloromethane/methanol/conc. $NH_4OH$) yielded 15 mg (29%) of the title compound. MS 733 (M+H)$^+$.

EXAMPLE 625

Compound 625 (Formula 1b: $R^{12}$ is H, $R^{13}$ is phenylmethyl, $R^{14}$ is H)

A mixture of Compound 5 (50 mg, 0.076 mmol), benzaldehyde (9 μL, 0.089 mmol), and acetic acid (18 μL, 0.31 mmol) in methanol (0.5 mL) was stirred at rt for 1 h. Sodium cyanoborohydride (19 mg, 0.30 mmol) was added, followed by a small amount of bromocresol green, and then acetic acid dropwise until the color of the solution remained yellow. After 18 h at rt, the solution was diluted with ethyl acetate (15 mL), washed with 1 N NaOH, water, and brine (10 mL each), dried ($Na_2SO_4$), and concentrated. Purification by chromatography ($SiO_2$, 95:5:0.2 dichloromethane/methanol/conc. $NH_4OH$) yielded 40 mg (70%) of the title compound. MS 747 (M+H)$^+$.

EXAMPLE 626

Compound 626 (Formula 1b: $R^{12}$ is H, $R^{13}$ is 2-[4-(2-pyrimidinyl)phenyl]ethyl, $R^{14}$ is H)

A mixture of Compound 5 (200 mg, 0.30 mmol), 4-(2-pyrimidinyl)benzeneacetaldehyde (72 mg, 0.36 mmol, prepared as described in Reference Example 64), and acetic acid (75 μL, 1.31 mmol) in methanol (2 mL) was stirred at rt for 1 h. Sodium cyanoborohydride (80 mg, 1.27 mmol) was added, followed by a small amount of bromocresol green, and then acetic acid dropwise until the color of the solution remained yellow. After 18 h at rt, the solution was diluted with ethyl acetate (30 mL), washed with 1 N NaOH and brine (15 mL each), dried ($Na_2SO_4$), and concentrated. Purification by chromatography ($SiO_2$, 95:5:0.2 dichloromethane/methanol/conc. $NH_4OH$) yielded 186 mg (72%) of the title compound. MS 839 (M+H)$^+$.

EXAMPLES 627–743

Compounds 627–743

Following the procedure of Example 625, except substituting the reagent below for the benzaldehyde of Example 625, the compounds 627-743 shown in the table below of formula 1b wherein $R^{12}$ is H, $R^{14}$ is H, and $R^{13}$ is as described in the table, can be prepared.

| Compound No. | Reagent | R¹³ | MS [(M+H)⁺] |
|---|---|---|---|
| 627 | 4-(4-pyrimidinyl)benzeneacetaldehyde | 2-[4-(4-pyrimidinyl)phenyl]ethyl | 839 |
| 628 | 4-(5-pyrimidinyl)benzeneacetaldehyde | 2-[4-(5-pyrimidinyl)phenyl]ethyl | 839 |
| 629 | 3-(2-pyrimidinyl)benzeneacetaldehyde | 2-[3-(2-pyrimidinyl)phenyl]ethyl | 839 |
| 630 | 4-(2-pyridinyl)benzeneacetaldehyde | 2-[4-(2-pyridinyl)phenyl]ethyl | 838 |
| 631 | 4-(3-pyridinyl)benzeneacetaldehyde | 2-[4-(3-pyridinyl)phenyl]ethyl | 838 |
| 632 | 4-(4-pyridinyl)benzeneacetaldehyde | 2-[4-(4-pyridinyl)phenyl]ethyl | 838 |
| 633 | 4-pyrazinylbenzeneacetaldehyde | 2-(4-pyrazinylphenyl)ethyl | 839 |
| 634 | 4-(3-pyridazinyl)benzeneacetaldehyde | 2-[4-(3-pyridazinyl)phenyl]ethyl | 839 |
| 635 | 4-(1H-pyrazol-1-yl)benzeneacetaldehyde | 2-[4-(1H-pyrazol-1-yl)phenyl]ethyl | 827 |
| 636 | 4-(1H-1,2,4-triazol-1-yl)benzeneacetaldehyde | 2-[4-(1H-1,2,4-triazol-1-yl)phenyl]ethyl | 828 |
| 637 | 4-(1H-1,2,3-triazol-1-yl)benzeneacetaldehyde | 2-[4-(1H-1,2,3-triazol-1-yl)phenyl]ethyl | 828 |
| 638 | 4-(1H-imidazol-1-yl)benzeneacetaldehyde | 2-[4-(1H-imidazol-1-yl)phenyl]ethyl | 827 |
| 639 | 4-(1-methyl-1H-pyrazol-3-yl)benzeneacetaldehyde | 2-[4-(1-methyl-1H-pyrazol-3-yl)phenyl]ethyl | 841 |
| 640 | 4-(1-methyl-1H-pyrazol-5-yl)benzeneacetaldehyde | 2-[4-(1-methyl-1H-pyrazol-5-yl)phenyl]ethyl | 841 |
| 641 | 3-fluoro-4-(1H-pyrazol-1-yl)benzeneacetaldehyde | 2-[3-fluoro-4-(1H-pyrazol-1-yl)phenyl]ethyl | 845 |
| 642 | 2-fluoro-4-(1H-pyrazol-1-yl)benzeneacetaldehyde | 2-[2-fluoro-4-(1H-pyrazol-1-yl)phenyl]ethyl | 845 |
| 643 | 2-(1-phenyl-1H-pyrazol-4-yl)acetaldehyde | 2-(1-phenyl-1H-pyrazol-4-yl)ethyl | 827 |
| 644 | 2-[1-(2-pyrimidinyl)-1H-imidazol-4-yl]acetaldehyde | 2-[1-(2-pyrimidinyl)-1H-imidazol-4-yl]ethyl | 829 |
| 645 | 2-(2-quinolinyl)acetaldehyde | 2-(2-quinolinyl)ethyl | 812 |
| 646 | 2-(3-quinolinyl)acetaldehyde | 2-(3-quinolinyl)ethyl | 812 |
| 647 | 2-(4-quinolinyl)acetaldehyde | 2-(4-quinolinyl)ethyl | 812 |
| 648 | 2-(5-quinolinyl)acetaldehyde | 2-(5-quinolinyl)ethyl | 812 |
| 649 | 2-(6-quinolinyl)acetaldehyde | 2-(6-quinolinyl)ethyl | 812 |
| 650 | 2-(7-quinolinyl)acetaldehyde | 2-(7-quinolinyl)ethyl | 812 |
| 651 | 2-(8-quinolinyl)acetaldehyde | 2-(8-quinolinyl)ethyl | 812 |
| 652 | 2-(2-quinoxalinyl)acetaldehyde | 2-(2-quinoxalinyl)ethyl | 813 |
| 653 | 2-(6-quinoxalinyl)acetaldehyde | 2-(6-quinoxalinyl)ethyl | 813 |
| 654 | 3-[4-(2-pyrimidinyl)phenyl]-2-propynal | 3-[4-(2-pyrimidinyl)phenyl]-2-propynyl | 849 |
| 655 | 3-[4-(3-pyridazinyl)phenyl]-2-propynal | 3-[4-(3-pyridazinyl)phenyl]-2-propynyl | 849 |
| 656 | 3-(4-pyrazinylphenyl)-2-propynal | 3-(4-pyrazinylphenyl)-2-propynyl | 849 |
| 657 | 4-(2-pyrimidinyl)benzenepropanal | 3-[4-(2-pyrimidinyl)phenyl]propyl | 853 |
| 658 | 4-(3-pyridazinyl)benzenepropanal | 3-[4-(3-pyridazinyl)phenyl]propyl | 853 |
| 659 | 4-pyrazinylbenzenepropanal | 3-(4-pyrazinylphenyl)propyl | 853 |
| 660 | 4-phenylbutanal | 4-phenylbutyl | 789 |
| 661 | 6-quinolinecarboxaldehyde | 6-quinolinylmethyl | 798 |
| 662 | 3-(1H-pyrazol-1-yl)benzaldehyde | [3-(1H-pyrazol-1-yl)phenyl]methyl | 813 |
| 663 | 4-(4-methyl-1H-pyrazol-1-yl)benzaldehyde | [4-(4-methyl-1H-pyrazol-1-yl)phenyl]methyl | 827 |
| 664 | 3-methoxy-4-(1H-pyrazol-1-yl)benzaldehyde | [3-methoxy-4-(1H-pyrazol-1-yl)phenyl]methyl | 843 |
| 665 | 3-fluoro-4-(1H-pyrazol-1-yl)benzaldehyde | [3-fluoro-4-(1H-pyrazol-1-yl)phenyl]methyl | 831 |
| 666 | 3-fluoro-4-(1H-1,2,4-triazol-1-yl)benzaldehyde | [3-fluoro-4-(1H-1,2,4-triazol-1-yl)phenyl]methyl | 832 |
| 667 | 2-fluoro-4-(1H-pyrazol-1-yl)benzaldehyde | [2-fluoro-4-(1H-pyrazol-1-yl)phenyl]methyl | 831 |
| 668 | 4-(2-pyrimidinyloxy)benzaldehyde | [4-(2-pyrimidinyloxy)phenyl]methyl | 841 |
| 669 | 1-(2-pyrimidinyl)-1H-imidazole-4-carboxaldehyde | [1-(2-pyrimidinyl)-1H-imidazol-4-yl]methyl | 815 |
| 670 | 3-(2-pyridinyl)benzaldehyde | [3-(2-pyridinyl)phenyl]methyl | 824 |
| 671 | 3-(2-pyrimidinyl)benzaldehyde | [3-(2-pyrimidinyl)phenyl]methyl | 825 |
| 672 | 4-(4-methoxy-2-pyrimidinyl)benzaldehyde | [4-(4-methoxy-2-pyrimidinyl)phenyl]methyl | 855 |
| 673 | 4-(4-methyl-2-pyrimidinyl)benzaldehyde | [4-(4-methyl-2-pyrimidinyl)phenyl]methyl | 839 |
| 674 | 2-fluoro-4-(2-pyrimidinyl)benzaldehyde | [2-fluoro-4-(2-pyrimidinyl)phenyl]methyl | 843 |
| 675 | 4-(3-pyridazinyl)benzaldehyde | [4-(3-pyridazinyl)phenyl]methyl | 825 |
| 676 | 4-(2-pyrimidinyl)benzaldehyde | [4-(2-pyrimidinyl)phenyl]methyl | 825 |
| 677 | 4-pyrazinylbenzaldehyde | [4-pyrazinylphenyl]methyl | 825 |

-continued

| Compound No. | Reagent | R¹³ | MS [(M+H)⁺] |
|---|---|---|---|
| 678 | 4-(4-pyrimidinyl)benzaldehyde | [4-(4-pyrimidinyl)phenyl]methyl | 825 |
| 679 | 4-(5-nitro-2-pyridinyl)benzaldehyde | [4-(5-nitro-2-pyridinyl)phenyl]methyl | 869 |
| 680 | 3-[4-(1H-pyrazol-1-yl)phenyl]-2-propynal | 3-[4-(1H-pyrazol-1-yl)phenyl]-2-propynyl | 837 |
| 681 | 3-(3-quinolinyl)-2-propynal | 3-(3-quinolinyl)-2-propynyl | 847 |
| 682 | (2E)-3-[6-(1H-pyrazol-1-yl)-3-pyridinyl]-2-propenal | (2E)-3-[6-(1H-pyrazol-1-yl)-3-pyridinyl]-2-propenyl | 840 |
| 683 | (2E)-3-(6-bromo-3-pyridinyl)-2-propenal | (2E)-3-(6-bromo-3-pyridinyl)-2-propenyl | 852,854 |
| 684 | (2E)-3-[4-(3-pyridinyl)phenyl]-2-propenal | (2E)-3-[4-(3-pyridinyl)phenyl]-2-propenyl | 850 |
| 685 | (2E)-3-[2-fluoro-4-(1H-pyrazol-1-yl)phenyl]-2-propenal | (2E)-3-[2-fluoro-4-(1H-pyrazol-1-yl)phenyl]-2-propenyl | 857 |
| 686 | (2E)-3-[3-methoxy-4-(1H-pyrazol-1-yl)phenyl]-2-propenal | (2E)-3-[3-methoxy-4-(1H-pyrazol-1-yl)phenyl]-2-propenyl | 869 |
| 687 | (2E)-3-(6-quinoxalinyl)-2-propenal | (2E)-3-(6-quinoxalinyl)-2-propenyl | 825 |
| 688 | (2E)-3-(6-quinolinyl)-2-propenal | (2E)-3-(6-quinolinyl)-2-propenyl | 824 |
| 689 | (2E)-3-[4-(1H-pyrazol-1-yl)phenyl]-2-propenal | (2E)-3-[4-(1H-pyrazol-1-yl)phenyl]-2-propenyl | 839 |
| 690 | (2E)-3-[6-(1H-1,2,4-triazol-1-yl)-2-pyridinyl]-2-propenal | (2E)-3-[6-(1H-1,2,4-triazol-1-yl)-2-pyridinyl]-2-propenyl | 841 |
| 691 | (2E,4E)-5-[6-(1H-1,2,4-triazol-1-yl)-2-pyridinyl]-2,4-pentadienal | (2E,4E)-5-[6-(1H-1,2,4-triazol-1-yl)-2-pyridinyl]-2,4-pentadienyl | 867 |
| 692 | (2E)-3-[4-(2-pyridinyl)phenyl]-2-propenal | (2E)-3-[4-(2-pyridinyl)phenyl]-2-propenyl | 850 |
| 693 | (2E)-3-[4-(4-pyridinyl)phenyl]-2-propenal | (2E)-3-[4-(4-pyridinyl)phenyl]-2-propenyl | 850 |
| 694 | (2E)-3-[4-(5-pyrimidinyl)phenyl]-2-propenal | (2E)-3-[4-(5-pyrimidinyl)phenyl]-2-propenyl | 851 |
| 695 | (2E)-3-[4-(1H-1,2,4-triazol-1-yl)phenyl]-2-propenal | (2E)-3-[4-(1H-1,2,4-triazol-1-yl)phenyl]-2-propenyl | 840 |
| 696 | (2E)-3-[4-(1H-1,2,3-triazol-1-yl)phenyl]-2-propenal | (2E)-3-[4-(1H-1,2,3-triazol-1-yl)phenyl]-2-propenyl | 840 |
| 697 | (2E)-3-[4-(1H-imidazol-1-yl)phenyl]-2-propenal | (2E)-3-[4-(1H-imidazol-1-yl)phenyl]-2-propenyl | 839 |
| 698 | (2E)-3-(4-quinolinyl)-2-propenal | (2E)-3-(4-quinolinyl)-2-propenyl | 824 |
| 699 | (2E)-3-[3-(2-pyridinyl)phenyl]-2-propenal | (2E)-3-[3-(2-pyridinyl)phenyl]-2-propenyl | 850 |
| 700 | (2E)-3-[3-(2-pyrimidinyl)phenyl]-2-propenal | (2E)-3-[3-(2-pyrimidinyl)phenyl]-2-propenyl | 851 |
| 701 | (2E)-3-[4-(4-methyl-2-pyrimidinyl)phenyl]-2-propenal | (2E)-3-[4-(4-methyl-2-pyrimidinyl)phenyl]-2-propenyl | 865 |
| 702 | (2E)-3-[3-(1H-pyrazol-1-yl)phenyl]-2-propenal | (2E)-3-[3-(1H-pyrazol-1-yl)phenyl]-2-propenyl | 839 |
| 703 | (2E)-3-[4-(1-methyl-1H-pyrazol-3-yl)phenyl]-2-propenal | (2E)-3-[4-(1-methyl-1H-pyrazol-3-yl)phenyl]-2-propenyl | 853 |
| 704 | (2E)-3-[4-(1-methyl-1H-pyrazol-5-yl)phenyl]-2-propenal | (2E)-3-[4-(1-methyl-1H-pyrazol-5-yl)phenyl]-2-propenyl | 853 |
| 705 | (2E)-3-[4-(5-nitro-2-pyridinyl)phenyl]-2-propenal | (2E)-3-[4-(5-nitro-2-pyridinyl)phenyl]-2-propenyl | 895 |
| 706 | (2E)-3-(8-quinolinyl)-2-propenal | (2E)-3-(8-quinolinyl)-2-propenyl | 824 |
| 707 | (2E)-3-(7-quinolinyl)-2-propenal | (2E)-3-(7-quinolinyl)-2-propenyl | 824 |
| 708 | (2E)-3-[6-(1H-pyrazol-1-yl)-2-pyridinyl]-2-propenal | (2E)-3-[6-(1H-pyrazol-1-yl)-2-pyridinyl]-2-propenyl | 840 |
| 709 | (2E)-3-(4-isoquinolinyl)-2-propenal | (2E)-3-(4-isoquinolinyl)-2-propenyl | 824 |
| 710 | (2E)-3-[3-fluoro-4-(1H-pyrazol-1-yl)phenyl]-2-propenal | (2E)-3-[3-fluoro-4-(1H-pyrazol-1-yl)phenyl]-2-propenyl | 857 |
| 711 | (2E)-3-[3-fluoro-4-(1H-1,2,4-triazol-1-yl)phenyl]-2-propenal | (2E)-3-[3-fluoro-4-(1H-1,2,4-triazol-1-yl)phenyl]-2-propenyl | 858 |
| 712 | (2E)-3-[5-(2-pyridinyl)-2-thienyl]-2-propenal | (2E)-3-[5-(2-pyridinyl)-2-thienyl]-2-propenyl | 856 |
| 713 | (2E,4E)-5-[4-(1H-pyrazol-1-yl)phenyl]-2,4-pentadienal | (2E,4E)-5-[4-(1H-pyrazol-1-yl)phenyl]-2,4-pentadienyl | 865 |
| 714 | (2E)-3-(1-phenyl-1H-pyrazol-4-yl)-2-propenal | (2E)-3-(1-phenyl-1H-pyrazol-4-yl)-2-propenyl | 839 |
| 715 | (2E)-3-[4-(4-methyl-1H-pyrazol-1-yl)phenyl]-2-propenal | (2E)-3-[4-(4-methyl-1H-pyrazol-1-yl)phenyl]-2-propenyl | 853 |
| 716 | (2E)-3-[4-(4-methoxy-2-pyrimidinyl)phenyl]-2-propenal | (2E)-3-[4-(4-methoxy-2-pyrimidinyl)phenyl]-2-propenyl | 881 |
| 717 | (2E)-3-(4-pyrazinylphenyl)-2-propenal | (2E)-3-(4-pyrazinylphenyl)-2-propenyl | 851 |
| 718 | (2E)-3-[4-(4-pyrimidinyl)phenyl]-2-propenal | (2E)-3-[4-(4-pyrimidinyl)phenyl]-2-propenyl | 851 |

-continued

| Compound No. | Reagent | R[13] | MS [(M+H)+] |
|---|---|---|---|
| 719 | (2E)-3-[4-(2-pyrimidinyloxy)phenyl]-2-propenal | (2E)-3-[4-(2-pyrimidinyloxy)phenyl]-2-propenyl | 865 |
| 720 | (2E)-3-[2-fluoro-4-(2-pyrimidinyl)phenyl]-2-propenal | (2E)-3-[2-fluoro-4-(2-pyrimidinyl)phenyl]-2-propenyl | 869 |
| 721 | (2E)-3-[4-(3-pyridazinyl)phenyl]-2-propenal | (2E)-3-[4-(3-pyridazinyl)phenyl]-2-propenyl | 851 |
| 722 | (2E)-3-[1-(2-pyrimidinyl)-1H-imidazol-4-yl]-2-propenal | (2E)-3-[1-(2-pyrimidinyl)-1H-imidazol-4-yl]-2-propenyl | 841 |
| 723 | [[4-(2-pyrimidinyl)phenyl]methoxy]acetaldehyde | [[4-(2-pyrimidinyl)phenyl]methoxy]ethyl | 869 |
| 724 | (2E)-3-[4-(2-pyrimidinyl)phenyl]-2-propenal | (2E)-3-[4-(2-pyrimidinyl)phenyl]-2-propenyl | 851 |
| 725 | 4-(1H-pyrazol-1-yl)benzaldehyde | [4-(1H-pyrazol-1-yl)phenyl]methyl | 813 |
| 726 | 4-(2-pyridinyl)benzaldehyde | [4-(2-pyridinyl)phenyl]methyl | 824 |
| 727 | 4-(1H-1,2,4-triazol-1-yl)benzaldehyde | [4-(1H-1,2,4-triazol-1-yl)phenyl]methyl | 814 |
| 728 | 3-[4-(2-pyridinyl)phenyl]-2-propynal | 3-[4-(2-pyridinyl)phenyl]-2-propynyl | 848 |
| 729 | 2-fluoro-4-(2-pyrimidinyl)benzeneacetaldehyde | 2-[2-fluoro-4-(2-pyrimidinyl)phenyl]ethyl | 857 |
| 730 | 4-(2-thiazolyl)benzeneacetaldehyde | 2-[4-(2-thiazolyl)phenyl]ethyl | 844 |
| 731 | 4-(2-oxazolyl)benzeneacetaldehyde | 2-[4-(2-oxazolyl)phenyl]ethyl | 828 |
| 732 | 4-(4-morpholinyl)benzeneacetaldehyde | 2-[4-(4-morpholinyl)phenyl]ethyl | 846 |
| 733 | 2-Phenyl-5-pyrimidineacetaldehyde | 2-(2-phenyl-5-pyrimidinyl)ethyl | 839 |
| 734 | 4-methyl-2-phenyl-5-pyrimidineacetaldehyde | 2-(4-methyl-2-phenyl-5-pyrimidinyl)ethyl- | 853 |
| 735 | 4-(5-ethyl-2-pyrimidinyl)-benzeneacetaldehyde | 2-[4-(5-ethyl-2-pyrimidinyl)phenyl]ethyl | 867 |
| 736 | 5-methyl-3-phenyl-4-isoxazoleacetaldehyde | 2-(5-methyl-3-phenyl-4-isoxazolyl)ethyl | 842 |
| 737 | 4-(5-fluoro-2-pyrimidinyl)-benzeneacetaldehyde | 2-[4-(5-fluoro-2-pyrimidinyl)phenyl]ethyl | 857 |
| 738 | 5-(2-pyrimidinyl)-2-thiophenecarboxaldehyde | [5-(2-pyrimidinyl)-2-thienyl]methyl | 831 |
| 739 | 5-(2-pyrimidinyl)-2-thiopheneacetaldehyde | [5-(2-pyrimidinyl)-2-thienyl]ethyl | 845 |
| 740 | 5-(2-pyrimidinyl)-2-furancarboxaldehyde | [5-(2-pyrimidinyl)-2-furanyl]methyl | 815 |
| 741 | 5-(2-pyrimidinyl)-2-furanacetaldehyde | [5-(2-pyrimidinyl)-2-furanyl]ethyl | 829 |
| 742 | 1-(2-pyrimidinyl)-1H-imidazole-4-carboxaldehyde | 2-[1-(2-pyrimidinyl)-1H-imidazol-4-yl]methyl | 815 |
| 743 | 1-(2-pyrimidinyl)-1H-imidazole-4-acetaldehyde | 2-[1-(2-pyrimidinyl)-1H-imidazol-4-yl]ethyl | 829 |

EXAMPLE 744

Compound 744 (Formula 1b: $R^{12}$ is H, $R^{13}$ is (2E)-3-[4-(2-pyrimidinyl)phenyl]-2-propenyl, $R^{14}$ is $CH_3$)

A mixture of Compound 5 (50 mg, 0.076 mmol), (2E)-3-[4-(2-pyrimidinyl)phenyl)phenyl]-2-propenal (17 mg, 0.081 mmol, prepared as described in Reference Example 29), and acetic acid (18 μL, 0.31 mmol) in methanol (0.5 mL) was stirred at rt for 1 h. Sodium cyanoborohydride (20 mg, 0.32 mmol) was added, followed by a small amount of bromocresol green, and then acetic acid dropwise until the color of the solution remained yellow. After 18 h at rt, formaldehyde (37 wt. % solution, 12 μL, 0.16 mmol) and sodium cyanoborohydride (10 mg, 0.16 mmol) were added, followed by a small amount of bromocresol green, and then acetic acid dropwise until the color of the solution remained yellow. After 2 h, the solution was diluted with ethyl acetate (15 mL), washed with 1N NaOH, water, and brine (10 mL each), dried ($Na_2SO_4$), and concentrated. Purification by chromatography ($SiO_2$, 95:5:0.2 dichloromethane/methanol/conc. $NH_4OH$) yielded 25 mg of material that was further purified by HPLC (C18 column, 10–90% $CH_3CN/H_2O$+ 0.1% TFA). The lyophilized fractions were taken up in dichloromethane, washed with sat. aq. $NaHCO_3$, dried ($Na_2SO_4$), and concentrated to provide 8.3 mg (13%) of the title compound. MS 865 (M+H)+.

EXAMPLES 745–802

Compounds 745–802

Following the procedure of Example 744, except substituting the reagent below for the (2E)-3-[4-(2-pyrimidinyl)phenyl]-2-propenal of Example 744, the compounds 745–802 shown in the table below of formula 1b wherein $R^{12}$, is H, $R^{14}$ is $CH_3$, and $R^{13}$ is as described in the table, can be prepared.

| Compound No. | Reagent | R$^{13}$ | MS [(M + H)$^+$] |
|---|---|---|---|
| 745 | 4-(4-pyrimidinyl)benzeneacetaldehyde | 2-[4-(4-pyrimidinyl)phenyl]ethyl | 853 |
| 746 | 4-(5-pyrimidinyl)benzeneacetaldehyde | 2-[4-(5-pyrimidinyl)phenyl]ethyl | 853 |
| 747 | 3-(2-pyrimidinyl)benzeneacetaldehyde | 2-[3-(2-pyrimidinyl)phenyl]ethyl | 853 |
| 748 | 4-(2-pyridinyl)benzeneacetaldehyde | 2-[4-(2-pyridinyl)phenyl]ethyl | 852 |
| 749 | 4-(3-pyridinyl)benzeneacetaldehyde | 2-[4-(3-pyridinyl)phenyl]ethyl | 852 |
| 750 | 4-(4-pyridinyl)benzeneacetaldehyde | 2-[4-(4-pyridinyl)phenyl]ethyl | 852 |
| 751 | 4-pyrazinylbenzeneacetaldehyde | 2-(4-pyrazinylphenyl)ethyl | 853 |
| 752 | 4-(3-pyridazinyl)benzeneacetaldehyde | 2-[4-(3-pyridazinyl)phenyl]ethyl | 853 |
| 753 | 4-(1H-pyrazol-1-yl)benzeneacetaldehyde | 2-[4-(1H-pyrazol-1-yl)phenyl]ethyl | 841 |
| 754 | 4-(1H-1,2,4-triazol-1-yl)benzeneacetaldehyde | 2-[4-(1H-1,2,4-triazol-1-,yl)phenyl]ethyl | 842 |
| 755 | 4-(1H-1,2,3-triazol-1-yl)benzeneacetaldehyde | 2-[4-(1H-1,2,3-triazol-1-yl)phenyl]ethyl | 842 |
| 756 | 4-(1H-imidazol-1-yl)benzeneacetaldehyde | 2-[4-(1H-imidazol-1-yl)phenyl]ethyl | 841 |
| 757 | 4-(1-methyl-1H-pyrazol-3-yl)benzeneacetaldehyde | 2-[4-(1-methyl-1H-pyrazol-3-yl)phenyl]ethyl | 855 |
| 758 | 4-(1-methyl-1H-pyrazol-5-yl)benzeneacetaldehyde | 2-[4-(1-methyl-1H-pyrazol-5-yl)phenyl]ethyl | 855 |
| 759 | 3-fluoro-4-(1H-pyrazol-1-yl)benzeneacetaldehyde | 2-[3-fluoro-4-(1H-pyrazol-1-yl)phenyl]ethyl | 859 |
| 760 | 2-fluoro-4-(1H-pyrazol-1-yl)benzeneacetaldehyde | 2-[2-fluoro-4-(1H-pyrazol-1-yl)phenyl]ethyl | 859 |
| 761 | 2-(1-phenyl-1H-pyrazol-4-yl)acetaldehyde | 2-(1-phenyl-1H-pyrazol-4-yl)ethyl | 841 |
| 762 | 2-[1-(2-pyrimidinyl)-1H-imidazol-4-yl]acetaldehyde | 2-[1-(2-pyrimidinyl)-1H-imidazol-4-yl]ethyl | 843 |
| 763 | 2-(2-quinolinyl)acetaldehyde | 2-(2-quinolinyl)ethyl | 826 |
| 764 | 2-(3-quinolinyl)acetaldehyde | 2-(3-quinolinyl)ethyl | 826 |
| 765 | 2-(4-quinolinyl)acetaldehyde | 2-(4-quinolinyl)ethyl | 826 |
| 766 | 2-(5-quinolinyl)acetaldehyde | 2-(5-quinolinyl)ethyl | 826 |
| 767 | 2-(6-quinolinyl)acetaldehyde | 2-(6-quinolinyl)ethyl | 826 |
| 768 | 2-(7-quinolinyl)acetaldehyde | 2-(7-quinolinyl)ethyl | 826 |
| 769 | 2-(8-quinolinyl)acetaldehyde | 2-(8-quinolinyl)ethyl | 826 |
| 770 | 2-(2-quinoxalinyl)acetaldehyde | 2-(2-quinoxalinyl)ethyl | 827 |
| 771 | 2-(6-quinoxalinyl)acetaldehyde | 2-(6-quinoxalinyl)ethyl | 827 |
| 772 | (2E)-3-(4-pyrazinylphenyl)-2-propenal | (2E)-3-(4-pyrazinylphenyl)-2-propenyl | 865 |
| 773 | (2E)-3-[4-(3-pyridazinyl)phenyl]-2-propenal | (2E)-3-[4-(3-pyridazinyl)phenyl]-2-propenyl | 865 |
| 774 | 4-(2-pyrimidinyl)benzaldehyde | [4-(2-pyrimidinyl)phenyl]methyl | 839 |
| 775 | 4-(3-pyridazinyl)benzaldehyde | [4-(3-pyridazinyl)phenyl]methyl | 839 |
| 776 | 4-pyrazinylbenzaldehyde | (4-pyrazinylphenyl)methyl | 839 |
| 777 | 3-[4-(2-pyrimidinyl)phenyl]-2-propynal | 3-[4-(2-pyrimidinyl)phenyl]-2-propynyl | 863 |
| 778 | 3-[4-(3-pyridazinyl)phenyl]-2-propynal | 3-[4-(3-pyridazinyl)phenyl]-2-propynyl | 863 |
| 779 | 3-(4-pyrazinylphenyl)-2-propynal | 3-(4-pyrazinylphenyl)-2-propynyl | 863 |
| 780 | 4-(2-pyrimidinyl)benzenepropanal• | 3-[4-(2-pyrimidinyl)phenyl]propyl | 867 |
| 781 | 4-(3-pyridazinyl)benzenepropanal | 3-[4-(3-pyridazinyl)phenyl]propyl | 867 |
| 782 | 4-pyrazinylbenzenepropanal | 3-(4-pyrazinylphenyl)propyl | 867 |
| 783 | 4-(1H-1,2,4-triazol-1-yl)benzaldehyde | [4-(1H-1,2,4-triazol-1-yl)phenyl]methyl | 828 |
| 784 | 4-(1-methyl-1H-pyrazol-3-yl)benzaldehyde | [4-(1-methyl-1H-pyrazol-3-yl)phenyl]methyl | 827 |
| 785 | 4-(1H-pyrazol-1-yl)benzaldehyde | [4-(1H-pyrazol-1-yl)phenyl]methyl | 827 |
| 786 | 4-(2-pyridinyl)benzaldehyde | [4-(2-pyridinyl)phenyl]methyl | 838 |
| 787 | 3-[4-(2-pyridinyl)phenyl]-2-propynal | 3-[4-(2-pyridinyl)phenyl]-2-propynyl | 862 |
| 788 | 2-fluoro-4-(2-pyrimidinyl)benzeneacetaldehyde | 2-[2-fluoro-4-(2-pyrimidinyl)phenyl]ethyl | 871 |
| 789 | 4-(2-thiazolyl)benzeneacetaldehyde | 2-[4-(2-thiazolyl)phenyl]ethyl | 858 |
| 790 | 4-(2-oxazolyl)benzeneacetaldehyde | 2-[4-(2-oxazolyl)phenyl]ethyl | 842 |
| 791 | 4-(4-morpholinyl)benzeneacetaldehyde | 2-[4-(4-morpholinyl)phenyl]ethyl | 860 |
| 792 | 2-Phenyl-5-pyrimidineacetaldehyde | 2-(2-phenyl-5-pyrimidinyl)ethyl | 853 |

| Compound No. | Reagent | R13 | MS [(M + H)+] |
|---|---|---|---|
| 793 | 4-methyl-2-phenyl-5-pyrimidineacetaldehyde | 2-(4-methyl-2-phenyl-5-pyrimidinyl)ethyl | 867 |
| 794 | 4-(5-ethyl-2-pyrimidinyl)-benzeneacetaldehyde | 2-[4-(5-ethyl-2-pyrimidinyl)phenyl]ethyl | 881 |
| 795 | 5-methyl-3-phenyl-4-isoxazoleacetaldehyde | 2-(5-methyl-3-phenyl-4-isoxazolyl)ethyl | 856 |
| 796 | 4-(5-fluoro-2-pyrimidinyl)-benzeneacetaldehyde | 2-[4-(5-fluoro-2-pyrimidinyl)phenyl]ethyl | 871 |
| 797 | 5-(2-pyrimidinyl)-2-thiophenecarboxaldehyde | [5-(2-pyrmidinyl)-2-thienyl]methyl | 845 |
| 798 | 5-(2-pyrimidinyl)-2-thiopheneacetaldehyde | [5-(2-pyrimidinyl)-2-thienyl]ethyl | 859 |
| 799 | 5-(2-pyrimidinyl)-2-furancarboxaldehyde | [5-(2-pyrimidinyl)-2-furanyl]methyl | 829 |
| 800 | 5-(2-pyrimidinyl)-2-furanacetaldehyde | [5-(2-pyrimidinyl)-2-furanyl]ethyl | 843 |
| 801 | 1-(2-pyrimidinyl)-1H-imidazole-4-carboxaldehyde | 2-[1-(2-pyrimidinyl)-1H-imidazol-4-yl]methyl | 829 |
| 802 | 1-(2-pyrimidinyl)-1H-imidazole-4-acetaldehyde | 2-[1-(2-pyrimidinyl)-1H-imidazol-4-yl]ethyl | 843 |

EXAMPLE 803

Compound 803 (Formula 1b: $R^{12}$ is H, $R^{13}$ is 2-[4-(2-pyrimidinyl)phenyl]ethyl, $R^{14}$ is $CH_3$)

Sodium cyanoborohydride (19 mg, 0.30 mmol) was added to a mixture of Compound 626 (50 mg, 0.060 mmol), formaldehyde (37 wt. % solution, 12 µL, 0.16 mmol), and acetic acid (15 µL, 0.26 mmol) in methanol (0.5 mL) and the resulting solution was stirred at rt for 3 h. The solution was diluted with ethyl acetate (15 mL), washed with 1 N NaOH, water, and brine (10 mL each), dried ($Na_2SO_4$), and concentrated. Purification by chromatography ($SiO_2$, 95:5:0.2 dichloromethane/methanol/conc. $NH_4OH$) yielded 38 mg (75%) of the title compound. MS 853 (M+H)+.

EXAMPLE 804

Compound 804 (Formula 1b: $R^{12}$ is H, $R^{13}$ is 2-[4-(2-pyrimidinyl)phenyl]ethyl, $R^{14}$ is $CH_2CH_3$)

Sodium cyanoborohydride (19 mg, 0.30 mmol) was added to a mixture of Compound 626 (50 mg, 0.060 mmol), acetaldehyde (10 µL, 0.18 mmol), and acetic acid (15 µL, 0.26 mmol) in methanol (0.5 mL) and the resulting solution was stirred at rt for 3 h. The solution was diluted with ethyl acetate (15 mL), washed with 1 N NaOH, water, and brine (10 mL each), dried ($Na_2SO_4$), and concentrated. Purification by chromatography ($SiO_2$, 95:5:0.2 dichloromethane/methanol/conc. $NH_4OH$) yielded 41 mg (79%) of the title compound. MS 867 (M+H)+.

EXAMPLE 805

Compound 805 (Formula 1b: $R^{12}$ is H, $R^{13}$ is (2E)-3-[4-(2-pyrimidinyl)phenyl]-2-propenyl, $R^{14}$ is H) and Compound 806 (Formula 1b: $R^{12}$ is H, $R^{13}$ is (2E)-3-[4-(2-pyrimidinyl)phenyl]-2-propenyl, $R^{14}$ is (2E)-3-[4-(2-pyrimidinyl)phenyl]-2-propenyl)

A mixture of Compound 5 (100 mg, 0.15 mmol), (2E)-3-[4-(2-pyrimidinyl)phenyl]-2-propenal (37 mg, 0.18 mmol, prepared as described in Reference Example 29), and acetic acid (35 µL, 0.61 mmol) in methanol (1 mL) was stirred at rt for 1 h. Sodium cyanoborohydride (1.0 M in THF, 0.61 mL, 0.61 mmol) was added followed by a small amount of bromocresol green, and then acetic acid dropwise until the color of the solution remained yellow. After 18 h, solid sodium cyanoborohydride (20 mg, 0.32 mmol) was added and the mixture was stirred for 96 h. The solution was diluted with ethyl acetate (15 mL), washed with 1N NaOH, water, and brine (10 ml each), dried ($Na_2SO_4$), and concentrated. Purification by chromatography ($SiO_2$, 95:5:0.2 dichloromethane/methanol/conc. $NH_4OH$) yielded 47 mg (70%) of a mixture of compounds. This mixture was further purified by HPLC (C18 column, 10–90% $CH_3CN/H_2O$+ 0.1% TFA). The lyophilized fractions were taken up in dichloromethane, washed with sat. aq. $NaHCO_3$, dried ($Na_2SO_4$), and concentrated to provide Compound 235 (14 mg, MS 851 (M+H)+) and Compound 236 (10 mg, MS 1045 (M+H)+).

EXAMPLE 806

Compounds 807 and 808

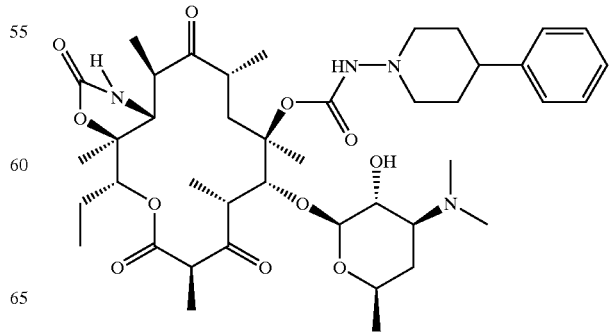

Compound 807

-continued

Compound 808

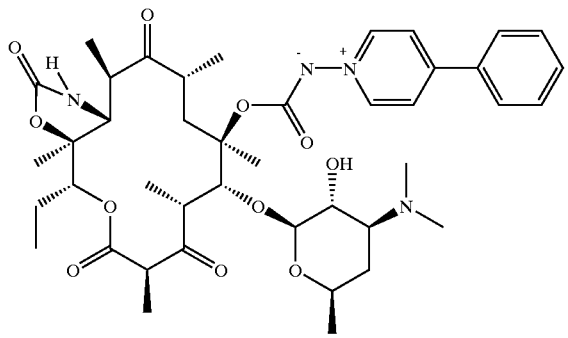

A mixture of Compound 5 (50 mg, 0.076 mmol), 2-butoxy-3,4-dihydro-4-phenyl-2H-pyran (90 mg, 0.39 mmol, prepared as described in Reference Example 67), triethylsilane (125 µL, 0.78 mmol), and trifluoroacetic acid (60 µL, 0.78 mmol) in acetonitrile (0.5 mL) was stirred at rt for 1 h. The reaction mixture was diluted with ethyl acetate (15 mL), washed with sat. aq. NaHCO$_3$ (10 mL) and brine (10 mL), dried (Na$_2$SO$_4$), and concentrated. Purification by chromatography (SiO$_2$, 95:5:0.5 dichloromethane/methanol/conc. NH$_4$OH) yielded 15 mg (25%) of compound 807 (MS 801 (M+H)$^+$) and 15 mg (25%) of compound 808 (MS 796 (M+H)$^+$). Compound 807 was further purified by chromatography (SiO$_2$, 98.5:1.5 acetonitrile/conc. NH$_4$OH) to yield 8 mg (13%).

EXAMPLE 807

Compound 809 [Formula 1n: R$^{11}$ is H, R$^{20}$ is 4-methylphenyl]

To a solution of Compound 5 (150 mg, 0.23 mmol) in dichloromethane (2 mL) at room temperature was added p-toluenesulfonyl chloride (48 mg, 0.25 mmol). The reaction mixture was stirred overnight, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 123 mg (66%) of the title compound. MS 811 (M+H)$^+$.

EXAMPLE 808

Compound 810 [Formula 1m': R$^{10}$ is H, R$^{20}$ is 4-methylphenyl, R$^{21'}$ is acetyl]

Step A:
Acetic anhydride (0.1 mL) was added to a solution of compound 809 (54 mg, 0.07 mmol) in pyridine (0.3 mL), and the reaction mixture was stirred at room temperature for 1 h. Excess pyridine and acetic anhydride were removed in vacuo, the residue dissolved in dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 50 mg (83%) of product. MS 895 (M+H)$^+$.

Step B:
The product from step A (20 mg, 0.02 mmol) was stirred in MeOH (1 mL) at rt for 18 h. Solvent was evaporated in vacuo, and the crude product was purified by medium pressure liquid chromatography (SiO$_2$, 95:5:0.2 dichloromethane/methanol/conc. NH$_4$OH) to give 15 mg (79%) of the title compound. MS 853 (M+H)$^+$.

EXAMPLE 809

Compound 811

[Formula 1n: R$^{13}$ is H, R$^{20}$ is 4-(1H-pyrazol-1-yl)-phenyl]

To a solution of Compound 5 (100 mg, 0.15 mmol) in dichloromethane (1.2 mL) at room temperature was added 4-(1H-pyrazol-1-yl)-benzenesulfonyl chloride (51 mg, 0.21 mmol). The reaction mixture was stirred overnight, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 45 mg (35%) of the title compound. MS 863 (M+H)$^+$.

EXAMPLE 810

Compound 812 (Formula 1k: R$^{13}$ is H, R$^{16}$ is methyl)

Method A:
Acetic anhydride (32 µL, 0.33 mmol) was added dropwise to a solution of Compound 5 (200 mg, 0.30 mmol) in dichloromethane (3 mL) at 0° C. The reaction mixture was stirred at 0° C. for 1 h, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 186 mg (88%) of the title compound. MS 699 (M+H)$^+$.

Method B:
Acetyl chloride (3 µL, 45 µmol) was added dropwise to a solution of Compound 5 (25 mg, 38 µmol) in dichloromethane (0.3 mL) at rt. The reaction mixture was stirred at rt for 1 h, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 17 mg (63%) of the title compound. MS 699 (M+H)$^+$.

Method C:
Acetic anhydride (0.1 mL, 1.06 mmol) was added to a solution of Compound 5 (50 mg, 0.08 mmol) in pyridine (0.3 mL) at rt. The reaction mixture was stirred at rt for 4 h, diluted with dichloromethane, washed with sat. aq. NaHCO$_3$, dried with Na$_2$SO$_4$, and concentrated in vacuo. The resulting product was stirred in methanol (1 mL) overnight, and concentrated in vacuo. Purification by medium pressure liquid chromatography (SiO$_2$, 95:5:0.2 dichloromethane/methanol/conc. NH$_4$OH) gave 23 mg (66%) of the title compound. MS 699 (M+H)$^+$.

EXAMPLE 811

Compound 813 (Formula 1k: R$^{13}$ is H, R$^{16}$ is Phenyl)

Benzoic anhydride (135 mg, 0.60 mmol) was added to a solution of Compound 5 (100 mg, 0.15 mmol) in dichloromethane (0.8 mL) and pyridine (0.8 mL) at rt. The reaction mixture was stirred at rt for 18 h, diluted with dichloromethane, washed with sat. aq. NaHCO$_3$, dried with Na$_2$SO$_4$, and concentrated in vacuo. The resulting product was refluxed in methanol (3 mL) for 7 h, and concentrated in vacuo. Purification by medium pressure liquid chromatography (SiO$_2$, 95:5:0.2 dichloromethane/methanol/conc. NH$_4$OH) gave 52 mg (45%) of the title compound. MS 761 (M+H)$^+$.

EXAMPLE 812

Compound 814 (Formula 1l: R$^{13}$ is H, R$^{17}$ is benzyl)

Benzyl chloroformate (16 µL, 114 µmol) was added to a solution of Compound 5 (50 mg, 76 µmol) in dichloromethane (0.7 mL) at rt. The reaction mixture was stirred overnight, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 31 mg (52%) of the title compound. MS 791 (M+H)$^+$.

EXAMPLE 813

Compound 815 (Formula 1m: R$^{13}$ is H, R$^{18}$ is Me, R$^{19}$ is Phenyl)

N-Methyl-N-phenyl carbamoyl chloride (34 mg, 0.19 mmol) was added to a solution of Compound 5 (100 mg, 0.15 mmol) in dichloromethane (2 mL) at room temperature. The reaction mixture was stirred at room temperature for 4 days, diluted with dichloromethane, washed with sat. aq. NaHCO$_3$, dried with Na$_2$SO$_4$, and concentrated in vacuo. Purification by medium pressure liquid chromatography (SiO$_2$, 95:5:0.2 dichloromethane/methanol/conc. NH$_4$OH) gave 56 mg (47%) of the title compound. MS 790 (M+H)$^+$.

EXAMPLE 814

Compound 816 (Formula 1h: R$^{13a}$,R$^{14a}$ is —(CH$_2$)$_3$—)

To a solution of Compound 5 (100 mg, 0.15 mmol) in methanol (1 mL) at room temperature was added glutaraldehyde (50 wt % in water, 84 mg), and acetic acid (0.1 mL). The reaction mixture was stirred at room temperature for 1 h, sodium cyanoborohydride (100 mg, 1.61 mmol) was added followed by a small amount of bromocresol green, and then acetic acid was added dropwise until the color of the solution remained yellow. The reaction mixture was stirred at room temperature for 1 h, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 55 mg (50%) of the title compound. MS 725 (M+H)$^+$.

EXAMPLE 815

Compound 817 [Formula 1b: R$^{12}$ is Me, R$^{13}$ is (4-pyrazinylphenyl)methyl, R$^{14}$ is H] and Compound 776 [Formula 1b: R$^{12}$ is H, R$^{13}$ is (4-pyrazinylphenyl)methyl, R$^{14}$ is Me]

Step A: Compound of formula 1b, wherein R$^{12}$ is H, R$^{13}$ is H, R$^{14}$ is Me and compound of formula 1b, wherein R$^{12}$ is Me, R$^{13}$ is H, R$^{14}$ is H)

To a solution of Compound 4 (800 mg, 1.11 mmol) in dichloromethane at 0° C. was added dropwise a solution of methylhydrazine (0.30 mL, 5.55 mmol). The reaction mixture was stirred at 0° C. for an additional 15 min, at room temperature for 1 h, and concentrated in vacuo. Purification by medium pressure liquid chromatography (SiO$_2$, 95:5:0.2 dichloromethane/methanol/conc. NH$_4$OH) gave 550 mg (67%) of a 1:1 mixture of the title compounds. MS 671 (M+H)$^+$.

Step B: Compound 817 and Compound 776

To a solution of a 1:1 mixture of compounds from step A (100 mg, 0.15 mmol) in methanol (1 mL) at room temperature was added 4-pyrazinylbenzaldehyde (27 mg, 0.15 mmol, prepared as described in Reference Example 17) and acetic acid (0.1 mL). The reaction mixture was stirred at room temperature for 30 min, sodium cyanoborohydride (50 mg, 0.80 mmol) was added followed by a small amount of bromocresol green, and then acetic acid was added dropwise until the color of the solution remained yellow. The reaction mixture was stirred at room temperature for 1 h, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 46 mg (44%) of a 1:1 mixture of the title compounds [MS 839 (M+H)$^+$]. This mixture was separated by reverse phase HPLC (C18 column, 30–70% CH$_3$CN/H$_2$O+0.1% TFA). The lyophilized fractions were taken up in dichloromethane, washed with sat. aq. NaHCO$_3$, dried with Na$_2$SO$_4$, and concentrated in vacuo to provide 10 mg of Compound 817 and 10 mg of Compound 776.

EXAMPLE 816

Compound 818 {Formula 1b: R$^{12}$ is Me, R$^{13}$ is [4-(2-pyridinyl)phenyl]methyl, R$^{14}$ is H} and Compound 786 {Formula 1b: R$^{12}$ is H, R$^{13}$ is [4-(2-pyridinyl)phenyl]methyl, R$^{14}$ is Me}

The title compounds were prepared by a procedure analogous to Example 815, by substituting 4-(2-pyridinyl) benzaldehyde for 4-pyrazinylbenzaldehyde. MS 838 (M+H)$^+$.

EXAMPLE 817

Compound 819 [Formula 1b: R$^{12}$ is Me, R$^{13}$ is (4-pyrazinylphenyl)methyl, R$^{14}$ is Me] and Compound 776 [Formula 1b: R$^{12}$ is H, R$^{13}$ is (4-pyrazinylphenyl)methyl, R$^{14}$ is Me]

To a solution of a 1:1 mixture of compounds from step A of Example 815 (100 mg, 0.15 mmol) in methanol (1 mL) at room temperature was added 4-pyrazinylbenzaldehyde (50 mg, 0.30 mmol, prepared as described in Reference Example 17)) and acetic acid (0.1 mL). The reaction mixture was stirred at room temperature for 30 min, sodium cyanoborohydride (50 mg, 0.80 mmol) was added followed by a small amount of bromocresol green, and then acetic acid was added dropwise until the color of the solution remained yellow. The reaction mixture was stirred at room temperature for 1 h, carefully quenched with sat. aq. NaHCO$_3$, extracted with dichloromethane, dried with Na$_2$SO$_4$, and concentrated in vacuo. To a solution of this crude reaction mixture in methanol (1 mL) was added formaldehyde (37 wt % in H$_2$O, 0.1 mL) and acetic acid (0.1 mL). The reaction mixture was stirred at room temperarture for 15 min, sodium cyanoborohydride (50 mg, 0.80 mmol) was added followed by a small amount of bromocresol green, and then acetic acid was added dropwise until the color of the solution remained yellow. The reaction mixture was stirred at room temperature for 30 min, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 76 mg of a 1:1 mixture of the title compounds. This mixture was separated by reverse phase HPLC (C18 column, 30–70% CH$_3$CN/H$_2$O+0.1% TFA). The lyophilized fractions were taken up in dichloromethane, washed with sat. aq. NaHCO$_3$, dried with Na$_2$SO$_4$, concentrated in vacuo to provide 15 mg of compound 776 [(M+H)+839] and 15 mg of compound 819 [(M+H)$^+$853].

EXAMPLE 818

Compound 820 [Formula 1b: R$^{12}$ is Me, R$^{13}$ is 2-(4-pyrazinylphenyl)ethyl, R$^{14}$ is H] and Compound 751 [Formula 1b: R$^{12}$ is H, R$^{13}$ is 2-(4-pyrazinylphenyl)ethyl, R$^{14}$ is Me]

The title compounds were prepared by a procedure analogous to Example 815 by substituting 4-pyrazinylbenzeneacetaldehyde (prepared as described in Reference Example 420) for 4-pyrazinylbenzaldehyde. MS 853 (M+H)$^+$.

EXAMPLE 819

Compound 821 [Formula 1b: $R^{12}$ is Me, $R^{13}$ is 2-(4-pyrazinylphenyl)ethyl, $R^{14}$ is Me] and
Compound 751 [Formula 1b: $R^{12}$ is H, $R^{13}$ is 2-(4-pyrazinylphenyl)ethyl, $R^{14}$ is Me]

The title compounds were prepared by a procedure analogous to Example 817 by substituting 4-pyrazinylbenzeneacetaldehyde (prepared as described in Reference Example 420) for 4-pyrazinylbenzaldehyde. Compound 821, MS 867 (M+H)$^+$; and Compound 751, MS 853 (M+H)$^+$.

EXAMPLE 820

Compound 822 [Formula 1j': $R^{13a}$ is 2-(4-pyrazinylphenyl)methyl, n is 3]

To compound 751 (120 mg, 0.14 mmol) in methanol (1 mL) at room temperature was added glutaraldehyde (50 wt % in water, 50 µL) and acetic acid (0.1 mL). The reaction mixture was stirred at room temperature for 1 h, sodium cyanoborohydride (50 mg, 0.81 mmol) was added followed by a small amount of bromocresol green, and then acetic acid was added dropwise until the color of the solution remained yellow. The reaction mixture was stirred at room temperature for 1 h, carefully quenched with sat. aq. NaHCO$_3$, extracted with dichloromethane, the organic layer dried with Na$_2$SO$_4$, and concentrated in vacuo to give 120 mg (91%) of the title compound. MS 925 (M+H)$^+$.

EXAMPLE 821

Compound 823 [Formula 1k': $R^{13a}$ is 2-(4-pyrazinylphenyl)methyl, n is 3]

To Compound 822 (100 mg, 0.11 mmol) in dichloromethane (1.4 mL) at room temperature was added p-toluenesulfonyl chloride (27 mg, 0.14 mmol) and triethylamine (39 µL, 0.28 mmol). The reaction mixture was stirred at room temperature for four days, quenched with sat. aq. NaHCO$_3$, extracted with dichloromethane, dried with Na$_2$SO$_4$ and concentrated in vacuo. Purification by medium pressure liquid chromatography (SiO$_2$, 95:5:0.2 dichloromethane/methanol/conc. NH$_4$OH) gave 60 mg (61%) of the title compound. MS 907 (M+H)$^+$.

EXAMPLE 822

Compound 824 {Formula 1b: $R^{12}$ is H, and $R^{13}$, $R^{14}$ together with the nitrogen to which they are attached is 3-[4-(2-pyrimidinyl)phenyl]pyrrole}

Trifluoroacetic acid (61 µL, 0.80 mmol) was added to a solution of Compound 5 (39 mg, 0.06 mmol) and 2-[4-(tetrahydro-2,5-dimethoxy-3-furanyl)phenyl]pyrimidine (24 mg, 0.08 mmol, prepared as described in Reference Example 441) in acetonitrile (1 mL) at room temperature. The reaction mixture was stirred at 55° C. for 3 h, cooled to room temperature, quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 22 mg (70%) of the title compound. MS 861 (M+H)$^+$.

EXAMPLE 823

Compound 825 [Formula 1f: $R^{13a}$ is 4-(2-pyrimidinyl)phenyl]

To a solution of Compound 5 (100 mg, 0.15 mmol) in methanol (1 mL) at room temperature was added 4-(2-pyrimidinyl)benzaldehyde (34 mg, 0.18 mmol, prepared as described in WO 9828264), and acetic acid (50 µL). The reaction mixture was stirred at room temperature for 1 h, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 43 mg (34%) of the title compound. MS 823 (M+H)$^+$.

EXAMPLE 824

Compound 826 {Formula 1f: $R^{13a}$ is [4-(2-pyrimidinyl)phenyl]methyl}

To a solution of Compound 5 (100 mg, 0.15 mmol) in methanol (1 mL) at room temperature was added 4-(2-pyrimidinyl)benzeneacetaldehyde (40 mg, 0.20 mmol, prepared as described in Example 64), and acetic acid (50 µL). The reaction mixture was stirred at room temperature for 1 h, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 48 mg (38%) of the title compound. MS 837 (M+H)$^+$.

EXAMPLE 825

Compound 827 {Formula 1f: $R^{13a}$ is 2-[4-(2-pyrimidinyl)phenyl]ethenyl}

To a solution of Compound 5 (100 mg, 0.15 mmol) in methanol (1 mL) at room temperature was added (2E)-3-[4-(2-pyrimidinyl)phenyl]-2-propenal (32 mg, 0.15 mmol, prepared as described in Reference Example 29), and acetic acid (50 µL). The reaction mixture was stirred at room temperature for 1 h, carefully quenched with sat. aq. NaHCO$_3$, extracted with dichloromethane, dried with Na$_2$SO$_4$, and concentrated in vacuo. Purification by medium pressure liquid chromatography (SiO$_2$, 95:5:0.2 dichloromethane/methanol/conc. NH$_4$OH) gave 41 mg (32%) of the title compound. MS 849 (M+H)$^+$.

EXAMPLE 826

Compound 828 {Formula 1t': W' is 1-methyl-1-[2-(4-pyrazinylphenyl)ethyl]hydrazinyl}

Step A:
To Compound 751 (106 mg, 0.12 mmol) in dichloromethane (1 mL) at room temperature was added acetic anhydride (113 µL, 1.20 mmol) and triethylamine (333 µL, 2.40 mmol). The reaction was stirred at room temperature for 1 h, diluted with dichloromethane, washed with sat. aq. NH$_4$Cl, dried with Na$_2$SO$_4$, and concentrated in vacuo. Purification by medium pressure liquid chromatography (SiO$_2$, 95:5:0.2 dichloromethane/methanol/conc. NH$_4$OH) gave 82 mg (74%) of product. MS 895 (M+H)$^+$.
Step B:
Product from step A (82 mg, 0.09 mmol) in DMF (1 mL) under nitrogen was cooled to −60° C. and NaHMDS (420 µL, 0.42 mmol, 1M solution in THF) was added dropwise.

EXAMPLE 827

Compound 829 {Formula 1t': W' is 1-methyl-1-[2-(4-pyridazinylphenyl)ethyl]hydrazinyl}

The title compound was prepared by following the procedure used for Example 826, except substituting Compound 752 for Compound 751. MS 871 (M+H)$^+$.

EXAMPLE 828

Compound 830 (Formula 1e': R$^9$ is (2E)-3-phenyl-2-propenyl)

DBU (64 mg, 0.42 mmol) was added to a solution of (2E)-3-phenyl-2-propene-1-thiol (63 mg, 0.42 mmol, prepared as described in Reference Example 473) in THF (1 mL), the mixture was stirred at room temperature for 5 min, and then cooled to 0° C. Compound 4 (100 mg, 0.14 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) yielded 13 mg (12%) of the title compound. MS 775 (M+H)$^+$.

EXAMPLE 829

Compound 831 (Formula 1e': R$^9$ is phenylmethyl)

DBU (78 mg, 0.51 mmol) was added to a solution of benzyl mercaptan (63 mg, 0.51 mmol) in THF (2 mL), the mixture was stirred at room temperature for 5 min, and then cooled to 0° C. Compound 4 (120 mg, 0.17 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) yielded 26 mg (20%) of the title compound. MS 749 (M+H)$^+$.

EXAMPLE 830

Compound 832 (Formula 1e': R$^9$ is 2-propenyl)

DBU (320 mg, 2.1 mmol) was added to a solution of allyl mercaptan (156 mg, 2.1 mmol) in THF (2.5 mL), the mixture was stirred at room temperature for 5 min, and then cooled to 0° C. Compound 4 (500 mg, 0.7 mmol) was added and the resulting solution was stirred for 3 h at 0° C. The solution was diluted with ethyl acetate (60 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) yielded 133 mg (27%) of the title compound. MS 699 (M+H)$^+$.

EXAMPLE 831

Compound 833 (Formula 1e': R$^9$ is (2E)-3-[(4-(2-pyrimidinyl)phenyl)]-2-propenyl)

DBU (110 µL, 0.75 mmol) was added to a solution of (2E)-3-[(4-(2-pyrimidinyl)phenyl)]-2-propene-1-thiol (170 mg, 0.75 mmol, prepared as described in Reference Example 472) in THF (2 mL), the mixture was stirred at room temperature for 5 min, and then cooled to 0° C. Compound 4 (180 mg, 0.25 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 96:4:0.2 dichloromethane/methanol/conc. NH$_4$OH) yielded 96 mg (45%) of the title compound. MS 854 (M+H)$^+$.

EXAMPLE 832

Compound 834 (Formula 1e': R$^9$ is [4-(2-pyrimidinyl)phenyl]methyl)

DBU (75 µL, 0.5 mmol) was added to a solution of 4-(2-pyrimidinyl)benzenemethanethiol (100 mg, 0.5 mmol, prepared as described in Reference Example 464) in THF (2 mL), the mixture was stirred at room temperature for 5 min, and then cooled to 0° C. Compound 4 (180 mg, 0.25 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) followed by HPLC separation yielded 26 mg (13%) of the title compound. MS 828 (M+H)$^+$.

EXAMPLE 833

Compound 835 (Formula 1e': R$^9$ is 2-[4-(2-pyrimidinyl)phenyl]ethyl)

DBU (55 µL, 0.37 mmol) was added to a solution of 4-(2-pyrimidinyl)benzenemethanethiol (80 mg, 0.37 mmol, prepared as described in Reference Example 465) in THF (2 mL), the mixture was stirred at room temperature for 5 min, and then cooled to 0° C. Compound 4 (132 mg, 0.18 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) followed by HPLC separation yielded 10 mg (7%) of the title compound. MS 842 (M+H)$^+$.

EXAMPLE 834

Compound 836 (Formula 1e': R$^9$ is [4-(1H-1,2,4-triazol-1-yl)phenyl]ethyl)

DBU (40 µL, 0.27 mmol) was added to a solution of 4-(1H-1,2,4-triazol-1-yl)benzenemethanethiol (55 mg, 0.27 mmol, prepared as described in Reference Example 466) in THF (1 mL), the mixture was stirred at room temperature for 5 min, and then cooled to 0° C. Compound 4(100 mg, 0.14 mmol) was added and the resulting solution was stirred for 3 h at 0° C. The solution was diluted with ethyl acetate (20 mL), washed with 10% aq. NH$_4$Cl, sat. NaHCO$_3$ and brine. The organic layer was dried (Na$_2$SO$_4$), and concentrated. Purification by chromatography (SiO$_2$, 95:5:0.2 dichloromethane/methanol/conc. NH$_4$OH) followed by HPLC separation yielded 7 mg (6%) of the title compound. MS 831 (M+H)$^+$.

EXAMPLE 835

Compound 837 (Formula 1e': R$^9$ is (2E)-3-(3-quinolinyl)-2-propenyl)

DBU (40 µL, 0.27 mmol) was added to a solution of (2E)-3-(3-quinolinyl)-2-propene-1-thiol (54 mg, 0.27 mmol, prepared as described in Reference Example 467) in THF (1 mL), the mixture was stirred at room temperature for 5 min, and then cooled to 0° C. Compound 4 (100 mg, 0.14 mmol) was added and the resulting solution was stirred for 3 h at 0° C. The solution was diluted with ethyl acetate (20 mL), washed with 10% aq. $NH_4Cl$, sat. $NaHCO_3$ and brine. The organic layer was dried ($Na_2SO_4$), and concentrated. Purification by chromatography ($SiO_2$, 95:5:0.2 dichloromethane/methanol/conc. $NH_4OH$) yielded 6 mg (6%) of the title compound. MS 827 $(M+H)^+$.

EXAMPLE 836

Compound 838 (Formula 1e': $R^9$ is 3-quinolinylmethyl)

DBU (94 µL, 0.63 mmol) was added to a solution of 3-quinolinemethanethiol (110 mg, 0.63 mmol, prepared as described in Reference Example 468) in THF (2 mL), the mixture was stirred at room temperature for 5 min, and then cooled to 0° C. Compound 4 (225 mg, 0.32 mmol) was added and the resulting solution was stirred for 3 h at 0° C. The solution was diluted with ethyl acetate (20 mL), washed with 10% aq. $NH_4Cl$, sat. $NaHCO_3$ and brine. The organic layer was dried ($Na_2SO_4$), and concentrated. Purification by chromatography ($SiO_2$, 95:5:0.2 dichloromethane/methanol/conc. $NH_4OH$) followed by HPLC separation yielded 27 mg (11%) of the title compound. MS 800 $(M+H)^+$.

EXAMPLE 837

Compound 839 (Formula 1e': $R^9$ is [5-(2-pyridinyl)-2-thienyl]methyl)

DBU (140 µL, 0.92 mmol) was added to a solution of 5-(2-pyridinyl)-2-thiophenemethanethiol (190 mg, 0.92 mmol, prepared as described in Reference Example 469) in THF (2 mL), the mixture was stirred at rt for 5 min, and then cooled to 0° C. The compound from Example 4 (220 mg, 0.31 mmol) was added and the resulting solution was stirred for 3 h at 0° C. The solution was diluted with ethyl acetate (20 mL), washed with 10% aq. $NH_4Cl$, sat. $NaHCO_3$ and brine. The organic layer was dried ($Na_2SO_4$), and concentrated. Purification by chromatography ($SiO_2$, 95:5:0.2 dichloromethane/methanol/conc. $NH_4OH$) followed by HPLC separation yielded 23 mg (9%) of the title compound. MS 833 $(M+H)^+$.

EXAMPLE 838

Compound 840 (Formula 1e': $R^9$ is [4-(1H-1,2,4-triazol-1-yl)phenyl]methyl)

DBU (120 µL, 0.84 mmol) was added to a solution of 4-(1H-1,2,4-triazol-1-yl)benzenemethanethiol (160 mg, 0.84 mmol, prepared as described in Reference Example 470) in THF (2 mL), the mixture was stirred at room temperature for 5 min, and then cooled to 0° C. Compound 4 (200 mg, 0.28 mmol) was added and the resulting solution was stirred for 3 h at 0° C. The solution was diluted with ethyl acetate (20 mL), washed with 10% aq. $NH_4Cl$, sat. $NaHCO_3$ and brine. The organic layer was dried ($Na_2SO_4$), and concentrated. Purification by chromatography ($SiO_2$, 95:5:0.2 dichloromethane/methanol/conc. $NH_4OH$) followed by HPLC separation yielded 20 mg (9%) of the title compound. MS 816 $(M+H)^+$.

EXAMPLE 839

Compound 841 (Formula 1e': $R^9$ is [1-(2-pyrimidinyl)-1H-imidazol-4-yl]methyl)

DBU (120 µL, 0.84 mmol) was added to a solution of 1-(2-pyrimidinyl)-1H-imidazole-4-methanethiol (160 mg, 0.84 mmol, prepared as described in Reference Example 471) in THF (2 mL), the mixture was stirred at room temperature for 5 min, and then cooled to 0° C. Compound 4 (200 mg, 0.28 mmol) was added and the resulting solution was stirred for 3 h at 0° C. The solution was diluted with ethyl acetate (20 mL), washed with 10% aq. $NH_4Cl$, sat. $NaHCO_3$ and brine. The organic layer was dried ($Na_2SO_4$), and concentrated. Purification by chromatography ($SiO_2$, 95:5:0.2 dichloromethane/methanol/conc. $NH_4OH$) followed by HPLC separation yielded 32 mg (14%) of the title compound. MS 817 $(M+H)^+$.

EXAMPLE 840

Compound 842 (Formula 1f': $R^{22}$ and $R^{23}$ are H)

1,1,3,3-Tetramethoxypropane (0.49 mL, 2.94 mmol), trifluoroacetic acid (0.45 mL, 6.1 mmol), and 4 Å molecular sieves (2.0 g) were added to a solution of Compound 5 (1.280 g, 1.96 mmol) in dichloromethane (8 mL). This mixture was heated at 60° C. in a sealed culture tube for 30 min. The reaction mixture was cooled to room temperature, diluted with dichloromethane, and the molecular sieves removed by filtration. The filtrate was washed with sat. aq. $NaHCO_3$, dried with $Na_2SO_4$, and concentrated in vacuo. Purification by medium pressure liquid chromatography ($SiO_2$, 95:5:0.5 dichloromethane/methanol/conc. $NH_4OH$) gave 854 mg (63%) of the title compound. MS 693 $(M+H)^+$.

EXAMPLE 841

Compound 843 (Formula 1g': $R^{10}$ is phenyl, $R^{11}$ is H)

To a solution of Compound 842 (100 mg, 0.15 mmol) in THF (0.5 mL) under nitrogen at room temperature was added dropwise a solution of benzylmagnesium chloride (2.0 M in THF, 0.22 mL, 0.45 mmol). The reaction mixture was stirred at rt for 5 min and carefully quenched with sat. aq. $NH_4Cl$, extracted three times with dichloromethane, dried with $Na_2SO_4$, and concentrated in vacuo. Purification by medium pressure liquid chromatography ($SiO_2$, 95:5:0.5 dichloromethane/methanol/conc. $NH_4OH$) gave 46 mg (45%) of the title compound. MS 717 $(M+H)^+$.

EXAMPLE 842

Compound 844 (Formula 1g': $R^{10}$ is 3-phenylethyl, $R^{11}$ is H)

To a suspension of magnesium powder (240 mg, 10 mmol) in THF (5 mL) was added 1-bromo-3-phenylpropane (1.68 mL, 11 mmol) dropwise. One drop of dibromoethane was added and the reaction mixture stirred at rt until all the magnesium powder dissolved (30 min). In a separate flask, to a solution of Compound 842 (80 mg, 0.12 mmol) in THF (1 mL) at room temperature was added the above prepared Grignard solution (1 mL, 2 mmol) dropwise. This mixture was stirred at room temperature for 15 min, carefully quenched with sat. aq. $NH_4Cl$, extracted three times with dichloromethane, dried with $Na_2SO_4$, and concentrated in vacuo. Purification by medium pressure liquid chromatography ($SiO_2$, 95:5:0.5 dichloromethane/methanol/conc. $NH_4OH$) gave 20 mg (23%) of the title compound. MS 745 $(M+H)^+$.

EXAMPLE 843

Compound 845 (Formula 1i': $R^5$ is H, $R^{10}$ is phenyl, $R^{11}$ is H)

To a solution of Compound 4 (195 mg, 0.27 mmol) in THF (2.0 mL) under nitrogen at room temperature was added dropwise a solution of benzylmagnesium chloride (2.0 M in THF, 0.54 mL, 1.08 mmol). The reaction mixture was stirred at room temperature for 5 min and carefully quenched with sat. aq. NH$_4$Cl, extracted three times with dichloromethane, dried with Na$_2$SO$_4$, and concentrated in vacuo. Purification by medium pressure liquid chromatography (SiO$_2$, 95:5:0.5 dichloromethane/methanol/conc. NH$_4$OH) gave 46 mg (33% based on recovered starting material) of the title compound. MS 809 (M+H)$^+$.

EXAMPLE 844

Compound 846 (Formula 1i': R$^5$ is H, R$^{10}$ is 2-phenylethyl, R$^{11}$ is H)

To a suspension of magnesium powder (240 mg, 10 mmol) in THF (5 mL) was added 1-bromo-3-phenylpropane (1.68 mL, 11 mmol) dropwise. One drop of dibromoethane was added and the reaction mixture stirred at room temperature until all the magnesium powder dissolved (30 min). In a separate flask, to a solution of Compound 4 (165 mg, 0.23 mmol) in THF (1 mL) at room temperature was added the above prepared Grignard solution (2 mL, 4 mmol) dropwise. This mixture was stirred at room temperature for 4 h, carefully quenched with sat. aq. NH$_4$Cl, extracted three times with dichloromethane, dried with Na$_2$SO$_4$, and concentrated in vacuo. Purification by medium pressure liquid chromatography (SiO$_2$, 95:5:0.5 dichloromethane/methanol/conc. NH$_4$OH) gave 51 mg (43% based on recovered starting material) of the title compound. MS 837 (M+H)$^+$.

REFERENCE EXAMPLE 1

4-Phenylbutanal

4-Phenylbutanol (700 mg, 4.66 mmol) was added to a solution of the Dess-Martin reagent (2.40 g, 5.66 mol) in dichloromethane (35 mL). After 30 min at RT, the solution was quenched with 10% aq. Na$_2$S$_2$O$_3$, washed with sat. aq. NaHCO$_3$ and brine, dried (Na$_2$SO$_4$), and concentrated. Purification by chromatography (SiO$_2$, 9:1 hexane/ethyl acetate) yielded the title compound. MS 149 (M+H)$^+$.

REFERENCE EXAMPLE 2

4-Pyridinepropanal

4-Pyridinepropanol (0.60 mL, 4.65 mmol) was added to a solution of the Dess-Martin reagent (2.37 g, 5.58 mol) in dichloromethane (30 mL). After 60 min at RT, the solution was quenched with 10% aq. Na$_2$S$_2$O$_3$, washed with sat. aq. NaHCO$_3$ and brine, dried (Na$_2$SO$_4$), and concentrated. Purification by chromatography (SiO$_2$, 4:1 hexane/ethyl acetate) yielded the title compound. MS 136 (M+H)$^+$.

REFERENCE EXAMPLE 3

3-(1H-Pyrazol-1-yl)benzaldehyde

A mixture of 3-formylphenylboronic acid (2.00 g, 13.34 mmol), pyrazole (0.46 g, 6.67 mmol), copper(II) acetate (1.82 g, 10.01 mmol), pyridine (1.10 mL, 13.34 mmol), and powdered 4A molecular sieves (2.5 g) in dichloromethane (20 mL) was stirred under an air atmosphere for 24 h. The mixture was then filtered through Celite, the filtered solids were washed with methanol, and the combined filtrate was concentrated. Purification by chromatography (SiO$_2$, 3:1 hexane/ethyl acetate) yielded the title compound. MS 173 (M+H)$^+$.

REFERENCE EXAMPLE 4

4-(4-Methyl-1H-pyrazol-1-yl)benzaldehyde

A solution of 4-methylpyrazole (1.98 g, 24.11 mmol) in DMF (8 mL) was added to sodium hydride (60% in oil, 0.97 g, 24.25 mmol) in DMF (6 mL) and the resulting mixture was stirred 2 h at RT. 4-Fluorobenzaldehyde (1.26 g, 7.45 mmol) was added dropwise and the resulting mixture heated to 80° C. for 3 h. The reaction mixture was poured into ice-water and extracted with ethyl acetate. The combined organic layers were washed with water and brine, dried (MgSO$_4$), and concentrated. Purification by chromatography (SiO$_2$, 4:1 hexane/ethyl acetate) followed by recrystallization from hexane yielded the title compound. MS 187 (M+H)$^+$.

REFERENCE EXAMPLE 5

3-Methoxy-4-(1H-pyrazol-1-yl)benzaldehyde

A mixture of 4-fluoro-3-methoxybenzaldehyde (2.00 g, 12.98 mmol), pyrazole (1.32 g, 19.39 mmol), and powdered K$_2$CO$_3$ (2.68 g, 19.39 mmol) in DMF (20 mL) was heated to 120° C. for 20 h. The cooled reaction mixture was diluted with ethyl acetate (200 mL), washed with water (3×200 mL), dried (Na$_2$SO$_4$), and concentrated. Purification by chromatography (SiO$_2$, 4:1 hexane/ethyl acetate) yielded 1.52 g (58%) of the title compound as a yellow oil. MS 203 (M+H)$^+$.

REFERENCE EXAMPLE 6

3-Fluoro-4-(1H-pyrazol-1-yl)benzaldehyde

The title compound was prepared by a procedure analogous to Reference Example 5 by substituting 3,4-difluorobenzaldehyde for the 4-fluoro-3-methoxybenzaldehyde of Reference Example 5. MS 191 (M+H)$^+$.

REFERENCE EXAMPLE 7

3-Fluoro-4-(1H-1,2,4-triazol-1-yl)benzaldehyde

The title compound was prepared by a procedure analogous to Reference Example 5 by substituting 3,4-difluorobenzaldehyde and 1,2,4-triazole, respectively, for the 4-fluoro-3-methoxybenzaldehyde and pyrazole of Reference Example 5. MS 192 (M+H)$^+$.

REFERENCE EXAMPLE 8

2-Fluoro-4-(1H-pyrazol-1-yl)benzaldehyde
Step A: 2-Fluoro-4-(1H-pyrazol-1-yl)benzonitrile A mixture of 2-fluoro-4-hydrazinobenzonitrile (3.03 g, 20.05 mmol, prepared as described in U.S. Pat. No. 5,006,148), malonaldehyde bis(diethyl)acetal (4.80 mL, 20.02 mmol), and conc. HCl (1 mL) in ethanol (20 mL) was heated to reflux for 1 h. Upon cooling to RT, the reaction mixture solidified. Water (40 mL) was added and the mixture was cooled to 0° C. and made basic with 10% NaOH. The solids were removed by filtration, washed with water, and dried in vacuo to yield 3.59 g (96%) of the title compound as a light brown solid.
Step B: 2-Fluoro-4-(1H-pyrazol-1-yl)benzaldehyde Diisobutylaluminum hydride (1.0 M in toluene, 11.00 mL, 11.00 mol) was added dropwise over 10 min to a vigorously stirred suspension of the compound from step A (1.88 g, 10.04 mmol) in toluene (100 mL) at −78° C. After 1 h at −78° C., methanol (1 mL) was added, the mixture was stirred for 5 min, and then poured into a stirred, cold (0° C.) mixture of 1.2 N HCl (100 mL) and ethyl acetate (100 mL). After stirring for 30 min at RT, the layers were separated and the aqueous layer was extracted with additional ethyl acetate (100 mL). The combined organic layers were washed with sat. aq. NaHCO$_3$ (100 mL) and brine (100 mL), dried (MgSO$_4$), and concentrated. Recrystallization from IPA followed by chromatography (SiO$_2$, dichloromethane) provided 1.25 g (65%) of the title compound as a colorless solid. MS 191 (M+H)$^+$.

REFERENCE EXAMPLE 9

4-(2-Pyrimidinyloxy)benzaldehyde

Sodium hydride (60% in oil, 1.44 g, 36.00 mmol) was added to a 0° C. solution of 4-hydroxybenzaldehyde (4.40 g, 36.03 mmol) in DMF (16 mL). After stirring for 20 min at 0° C., the mixture was allowed to warm to RT and a solution of 2-chloropyrimidine (4.12 g, 35.97 mmol) in DMF (8 mL) was added. The resulting mixture was heated to 100° C. for 18 h. The solvent was evaporated, the residue was dissolved in ethyl acetate, washed with water and brine, dried (MgSO$_4$), and concentrated to provide 6.20 g (86%) of the title compound. MS 201 (M+H)$^+$.

REFERENCE EXAMPLE 10

1-(2-Pyrimidinyl)-1H-imidazole-4-carboxaldehyde

The title compound was prepared by a procedure analogous to Reference Example 9 by substituting 1H-imidazole-4-carboxaldehyde for the 4-hydroxybenzaldehyde of Reference Example 9. MS 175 (M+H)$^+$.

REFERENCE EXAMPLE 11

3-(2-pyridinyl)benzaldehyde 2M aq. Na$_2$CO$_3$ (5 mL) and a solution of 3-formylphenylboronic acid (1.14 g, 7.60 mmol) in methanol (5 mL) were added to a solution of 2-bromopyridine (1.00 g, 6.33 mmol) and tetrakis(triphenylphosphine)palladium(0) (0.22 g, 0.19 mmol) in toluene (10 mL) and the mixture was heated to reflux for 18 h. The cooled reaction mixture was diluted with dichloromethane, washed with sat. aq. NaHCO$_3$ and brine, dried (MgSO$_4$), and concentrated. Purification by chromatography (SiO$_2$, 4:1 hexane/ethyl acetate) yielded 1.03 g (89%) of the title compound. MS 184 (M+H)$^+$.

REFERENCE EXAMPLE 12

3-(2-Pyrimidinyl)benzaldehyde

A mixture of Na$_2$CO$_3$ (4.74 g, 44.72 mmol) and 3-formylphenylboronic acid (3.40 g, 22.67 mmol) in water (15 mL) were added to a solution of 2-bromopyrimidine (3.00 g, 18.87 mmol) and tetrakis(triphenylphosphine)palladium(0) (0.72 g, 0.62 mmol) in DME (30 mL) and the mixture was heated to reflux for 24 h. The cooled reaction mixture was diluted with dichloromethane, washed with sat. aq. NaHCO$_3$ and brine, dried (MgSO$_4$), and concentrated. Purification by chromatography (SiO$_2$, 1:1 hexane/ethyl acetate) yielded 2.20 g (63%) of the title compound. MS 185 (M+H)$^+$.

REFERENCE EXAMPLE 13

4-(4-Methoxy-2-pyrimidinyl)benzaldehyde 1M aq. Na$_2$CO$_3$ (20 mL) and ethanol (10 mL) were added to a solution of 2-chloro-4-methoxypyrimidine (2.90 g, 20.06 mmol, prepared as described in *Tetrahedron* 1997, 53, 11595), 4-formylphenylboronic acid (3.90 g, 26.01 mmol) and [1,4-bis(diphenylphosphino)butane]palladium(II) dichloride (0.60 g, 0.99 mmol) in toluene (40 mL) and the mixture was heated to reflux for 18 h. The cooled reaction mixture was diluted with ethyl acetate, washed with sat. aq. NaHCO$_3$ and brine, dried (MgSO$_4$), and concentrated. Purification by chromatography (SiO$_2$, 4:1 hexane/ethyl acetate) yielded 1.80 g (42%) of the title compound. MS 215 (M+H)$^+$.

REFERENCE EXAMPLE 14

4-(4-Methyl-2-pyrimidinyl)benzaldehyde

The title compound was prepared by a procedure analogous to Reference Example 12 by substituting 4-formylphenylboronic acid and 2-bromo-4-methylpyrimidine (prepared as described in *Helv. Chim. Acta* 1992, 75, 1621) for the 3-formylphenylboronic acid and 2-bromopyridine, respectively, of Reference Example 12. MS 199 (M+H)$^+$.

REFERENCE EXAMPLE 15

2-Fluoro-4-(2-pyrimidinyl)benzaldehyde

Step A:
Dimethyl sulfoxide (70 mL) and 4-bromo-2-fluorobenzaldehyde (2.44 g, 12.02 mmol) were added to a mixture of potassium acetate (3.54 g, 36.07 mmol), bis(pinacolato)diboron (3.36 g, 13.23 mmol), and [1,1'-bis(diphenylphosphino)ferrocene]dichloropalladium(II) (294 mg, 0.36 mmol). The mixture was heated to 80° C. for 18 h. The cooled reaction mixture was diluted with benzene, washed with water, dried (MgSO$_4$), and concentrated. The material was used in the next step without further purification.

Step B:
The title compound was prepared by a procedure analogous to Reference Example 12 by substituting the product of step A for the 3-formylphenylboronic acid of Reference Example 12. MS 203 (M+H)$^+$.

REFERENCE EXAMPLE 16

4-(3-Pyridazinyl)benzaldehyde

The title compound was prepared by a procedure analogous to Reference Example 13 by substituting 3-chloropyridazine (prepared as described in WO 9724124) for the 2-chloro-4-methoxypyrimidine of Reference Example 13. MS 185 (M+H)$^+$.

REFERENCE EXAMPLE 17

4-Pyrazinylbenzaldehyde

The title compound was prepared by a procedure analogous to Reference Example 13 by substituting chloropyrazine for the 2-chloro-4-methoxypyrimidine of Reference Example 13. MS 185 (M+H)$^+$.

REFERENCE EXAMPLE 18

4-(4-Pyrimidinyl)benzaldehyde

The title compound was prepared by a procedure analogous to Reference Example 13 by substituting 4-chloropyrimidine hydrochloride (prepared as described in WO 9821188) for the 2-chloro-4-methoxypyrimidine of Reference Example 13. MS 185 (M+H)$^+$.

REFERENCE EXAMPLE 19

4-(5-Nitro-2-pyridinyl)benzaldehyde

The title compound was prepared by a procedure analogous to Reference Example 11 by substituting 4-formylphenylboronic acid and 2-bromo-5-nitropyridine for the 3-formylphenylboronic acid and 2-bromopyridine, respectively, of Reference Example 11. MS 229 (M+H)$^+$.

REFERENCE EXAMPLE 20

3-[4-(1H-Pyrazol-1-yl)phenyl]-2-propynal

Step A: 3-[4-(1H-pyrazol-1-yl)phenyl]-2-propyn-1-ol

A mixture of 1-(4-bromophenyl)-1H-pyrazole (prepared as described in *Bull. Soc. Chim. Fr.* 1966, 2832) (2.24 g, 10.04 mmol), Pd(Ph$_3$P)$_2$Cl$_2$ (180 mg, 0.26 mmol), and copper(I) iodide (95 mg, 0.50 mmol) in TEA (20 mL) was stirred for 5 min, propargyl alcohol (0.70 mL, 12.02 mmol) was added, and the mixture was heated to 80° C. for 48 h. The volatiles were evaporated, ethyl acetate (50 mL) and water (50 mL) were added to the residue, and the mixture was filtered through a pad of Celite. The organic layer from the filtrate was washed with brine (50 mL), dried (Na$_2$SO$_4$), and concentrated. Purification by chromatography (SiO$_2$, 3:2 hexane/ethyl acetate) yielded 0.73 g (37%) of the title compound as a brown solid. MS 199 (M+H)$^+$.

Step B: 3-[4-(1H-pyrazol-1-yl)phenyl]-2-propynal

A mixture of the compound from step A (0.71 g, 3.58 mmol) and MnO$_2$ (3.10 g, 35.66 mmol) in acetone (40 mL) was heated to reflux for 3 h. The cooled reaction mixture was filtered through Celite and the filtrate was concentrated. Purification by chromatography (SiO$_2$, 6:1 hexane/ethyl acetate) yielded 0.19 g (27%) of the title compound as an off-white solid. MS 197 (M+H)$^+$.

REFERENCE EXAMPLE 21

3-(3-Quinolinyl)-2-propynal

A mixture of 3-(3-quinolinyl)-2-propyn-1-ol (prepared as described in *J. Med Chem.* 1996, 39, 3179) (360 mg, 1.96 mmol) and the Dess-Martin reagent (1.00 g, 2.36 mmol) in dichloromethane (10 mL) was stirred at RT for 1.5 h. The solution was washed with sat. aq. NaHCO$_3$ and brine, dried (MgSO$_4$), and concentrated. Purification by chromatography (SiO$_2$, 1:4 hexane/ethyl acetate) yielded 258 mg (72%) of the title compound. MS 182 (M+H)$^+$.

REFERENCE EXAMPLE 22

(2E)-3-[6-(1H-Pyrazol-1-yl)-3-pyridinyl]-2-propenal

Step A: 5-Bromo-2-(1H-pyrazol-1-yl)pyridine

Pyrazole (2.05 g, 30.11 mol) was added in portions to sodium hydride (60% in oil, 1.20 g, 30.00 mmol) in DMF (40 mL) and the resulting mixture was stirred for 1 h at RT. 2,5-Dibromopyridine (4.75 g, 20.05 mmol) was added and the mixture was heated to 100° C. for 2 h. Ice-water (100 mL) was added to the cooled reaction mixture and the precipitated solids were removed by filtration and allowed to air-dry. Recrystallization from hexane provided 3.31 g (74%) of the title compound as a tan solid. MS 224 (M+H)$^+$.

Step B: Methyl (2E)-3-([6-(1H-pyrazol-1-yl)pyridin-3-yl]-2-propenoate

A solution of the compound from step A (450 mg, 2.01 mmol) and tri(o-tolyl)phosphine (123 mg, 0.40 mmol) in DMF (8 mL) was cooled to 0° C. and purged with nitrogen for 15 min. TEA (0.56 mL, 4.02 mmol) and methyl acrylate (0.36 mL, 4.00 mmol) were added and purging was continued for 5 min. Palladium acetate (45 mg, 0.20 mmol) was added and the flask was stoppered and heated to 120° C. for 24 h. The cooled reaction mixture was diluted with ether (50 mL) and washed with water (2×25 mL) and brine (25 mL), dried (MgSO$_4$), and concentrated. Purification by chromatography (SiO$_2$, 4:1 hexane/ethyl acetate) yielded 356 mg (77%) of the title compound. MS 230 (M+H)$^+$.

Step C: (2E)-3-[6-(1H-pyrazol-1-yl)-3-pyridinyl]-2-propen-1-ol

DIBAL (1.0 M solution in toluene, 3.10 mL, 3.10 mmol) was added dropwise to a suspension of the compound from step B (350 mg, 1.53 mmol) in toluene (10 mL) and dichloromethane (4 mL) at −78° C. and the mixture was stirred for 2 h at that temperature. Methanol (1 mL) was added and the mixture was poured into a stirring mixture of ethyl acetate (20 mL) and 10% aq. potassium sodium tartrate (20 mL) and stirred for 1 h at RT. The organic layer was washed with brine (20 mL), dried (Na$_2$SO$_4$), and concentrated. Purification by chromatography (SiO$_2$, 1:1 hexane/ethyl acetate) yielded 185 mg (59%) of the title compound. MS 202 (M+H)$^+$.

Step D: (2E)-3-[6-(1H-pyrazol-1-yl)-3-pyridinyl]-2-propenal

A mixture of the compound from step C (185 mg, 0.92 mmol) and MnO$_2$ (1.60 g, 18.40 mmol) in acetone (15 mL) was heated to reflux for 1 h. The cooled reaction mixture was filtered through Celite and the filtrate was concentrated. Purification by chromatography (SiO$_2$, 2:1 hexane/ethyl acetate) yielded 78 mg (43%) of the title compound. MS 200 (M+H)$^+$.

REFERENCE EXAMPLE 23

(2E)-3-(6-Bromo-3-pyridinyl)-2-propenal

2-Propylmagnesium chloride (2.0 M in THF, 5.00 mL 10.00 mmol) was added to a solution of 2,5-dibromopyridine (2.37 g, 10.00 mmol) in THF (5.0 mL) at RT. The resulting brown suspension was stirred for 1 h and then cooled to 0° C. 3-Dimethylaminoacrolein (95%, 1.30 mL, 12.36 mmol) was added and the mixture was warmed to RT and stirred for 2 h. 2 N HCl was added and after 5 min the mixture was cooled to 0° C. The precipitated solids were removed by filtration and partitioned between ethyl acetate (75 mL) and 10% NaOH (25 mL). The ethyl acetate layer was washed with brine (25 mL), dried (MgSO$_4$), and concentrated. Recrystallization from ethyl acetate provided 550 mg (26%) of the title compound as shiny brown flakes. MS 211 (M+H)$^+$.

REFERENCE EXAMPLE 24

(2E)-3-[4-(3-Pyridinyl)phenyl]-2-propenal 2M aq. Na$_2$CO$_3$ (1 mL) and a solution of 3-pyridinylboronic acid (148 mg, 1.20 mmol) in methanol (1 mL) were added to a solution of 4-bromocinnamaldehyde (211 mg, 1.00 mmol, prepared as described in *Tetrahedron* 1998, 54, 10761) and tetrakis(triphenylphosphine)palladium (0) (35 mg, 0.030 mmol) in toluene (2 mL) and the mixture was heated to reflux for 36 h. The cooled reaction mixture was diluted with dichloromethane, washed with sat. aq. NaHCO$_3$ and brine, dried (MgSO$_4$), and concentrated. Purification by chromatography (SiO$_2$, 1:1 hexane/ethyl acetate) yielded the title compound. MS 210 (M+H)$^+$.

REFERENCE EXAMPLE 25

(2E)-3-[2-Fluoro-4-(1H-pyrazol-1-yl)phenyl]-2-propenal

A mixture of 2-fluoro-4-(1H-pyrazol-1-yl)benzaldehyde (1.06 g, 5.57 mmol, prepared as described in Reference Example 8), (1,3-dioxolan-2-ylmethyl) triphenylphosphonium bromide (3.60 g, 8.39 mmol), and TDA-1 (1.80 mL, 5.63 mmol) in dichloromethane (30 mL) and sat. aq. $K_2CO_3$ (30 mL) was heated to reflux for 20 h. The layers were separated and the aqueous layer was extracted with dichloromethane (2×15 mL). The combined organic layers were washed with water (30 mL) and brine (30 mL), dried ($Na_2SO_4$), and concentrated. THF (15 mL) and 10% HCl (15 mL) were added and the mixture was stirred for 1 h at rt. The mixture was cooled to 0° C., the precipitated solids were removed by filtration, washed with water and dried in vacuo. Recrystallization from IPA provided 0.84 g (70%) of the title compound as tan needles. MS 217 $(M+H)^+$.

REFERENCE EXAMPLE 26

(2E)-3-[3-Methoxy-4-(1H-pyrazol-1-yl)phenyl]-2-propenal

A mixture of 3-methoxy-4-(1H-pyrazol-1-yl) benzaldehyde (1.52 g, 7.52 mmol, prepared as described in Reference Example 5), (1,3-dioxolan-2-ylmethyl) triphenylphosphonium bromide (4.85 g, 11.30 mmol), and TDA-1 (2.40 mL, 7.50 mmol) in dichloromethane (35 mL) and sat. aq. $K_2CO_3$ (35 mL) was heated to reflux for 18 h. The layers were separated and the aqueous layer was extracted with dichloromethane (2×20 mL). The combined organic layers were washed with water (50 mL) and brine (50 mL), dried ($MgSO_4$), and concentrated. THF (20 mL) and 10% HCl (20 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried ($MgSO_4$), and concentrated. Purification by chromatography ($SiO_2$, 2:1 hexane/ethyl acetate) provided 1.47 g (86%) of the title compound as a yellow solid. MS 229 $(M+H)^+$.

REFERENCE EXAMPLE 27

(2E)-3-(6-Quinoxalinyl)-2-propenal

A mixture of 6-quinoxalinecarboxaldehyde (0.62 g, 3.92 mmol, prepared as described in *Photochem. Photobiol.* 1991, 54, 7), (1,3-dioxolan-2-ylmethyl) triphenylphosphonium bromide (2.50 g, 5.82 mmol), and TDA-1 (1.20 mL, 3.75 mmol) in dichloromethane (20 mL) and sat. aq. $K_2CO_3$ (20 mL) was heated to reflux for 4 h. The layers were separated and the aqueous layer was extracted with dichloromethane (2×20 mL). The combined organic layers were washed with water (50 mL) and brine (50 mL), dried ($Na_2SO_4$), and concentrated. THF (10 mL) and 10% HCl (10 mL) were added and the mixture was stirred for 1 h at rt. The mixture was cooled to 0° C., the precipitated solids were removed by filtration, washed with water and dried in vacuo to give 0.47 g (65%) of the title compound as a tan solid. MS 185 $(M+H)^+$.

REFERENCE EXAMPLE 28

(2E)-3-(6-Quinolinyl)-2-propenal

A mixture of 6-quinolinecarboxaldehyde (1.58 g, 10.05 mmol, prepared as described in U.S. Pat. No. 5,559,256), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. $K_2CO_3$ (50 mL) was heated to reflux for 5 h. The layers were separated and the aqueous layer was extracted with dichloromethane (2×25 mL). The combined organic layers were washed with water (50 mL) and brine (50 mL), dried ($MgSO_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried ($MgSO_4$), and concentrated. Chromatography ($SiO_2$, 1:1 hexane/ethyl acetate+0.2% triethylamine) provided a yellow solid that was partioned between ethyl acetate (20 mL) and 10% HCl (15 mL). The aqueous layer was washed with ethyl acetate (2×20 mL) and then made basic with 10% NaOH. The precipitated solids were collected by filtration, washed with water, and dried in vacuo to give 1.20 g (65%) of the title compound as a light yellow solid. MS 184 $(M+H)^+$.

REFERENCE EXAMPLE 29

(2E)-3-[4-(2-Pyrimidinyl)phenyl]-2-propenal

A mixture of 4-(2-pyrimidinyl)-benzaldehyde (1.83 g, 9.94 mmol, prepared as described in WO 9828264), (1,3-dioxolan-2-ylmethyl)triphenylphosphonium bromide (6.45 g, 15.02 mmol), and TDA-1 (3.20 mL, 10.00 mmol) in dichloromethane (50 mL) and sat. aq. $K_2CO_3$ (50 mL) was heated to reflux for 20 h. The layers were separated and the aqueous layer was extracted with dichloromethane (2×25 mL). The combined organic layers were washed with water (50 mL) and brine (50 mL), dried ($MgSO_4$), and concentrated. THF (25 mL) and 10% HCl (25 mL) were added and the mixture was stirred for 1 h at rt. The mixture was cooled to 0° C., the precipitated solids were removed by filtration, washed with water and air-dried. Recrystallization from 2-propanol provided 1.20 g (57%) of the title compound as a light yellow solid. MS 211 $(M+H)^+$.

REFERENCE EXAMPLE 30

(2E)-3-[4-(1H-Pyrazol-1-yl)phenyl]-2-propenal

A mixture of 4-(1H-pyrazol-1-yl)-benzaldehyde (prepared as described in *J. Med Chem.* 1998, 41, 2390) (1.65 g, 9.58 mmol), (1,3-dioxolan-2-ylmethyl) triphenylphosphonium bromide (6.45 g, 15.02 mmol), and TDA-1 (3.20 mL, 10.00 mmol) in dichloromethane (50 mL) and sat. aq. $K_2CO_3$ (50 mL) was heated to reflux for 20 h. The layers were separated and the aqueous layer was extracted with dichloromethane (2×25 mL). The combined organic layers were washed with water (50 mL) and brine (50 mL), dried ($MgSO_4$), and concentrated. THF (25 mL) and 10% HCl (25 mL) were added and the mixture was stirred for 1 h at rt. The reaction mixture was cooled to 0° C., made basic with 10% NaOH, and extracted with ethyl acetate (3×25 mL). The combined organic layers were washed with water (50 mL) and brine (50 mL), dried ($MgSO_4$), and concentrated. Purification by chromatography ($SiO_2$, 3:1 hexane/ethyl acetate) provided 1.69 g (89%) of the title compound as a yellow solid. MS 199 $(M+H)^+$.

REFERENCE EXAMPLE 31

(2E)-3-[6-(1H-1,2,4-Triazol-1-yl)-2-pyridinyl]-2-propenal and (2E,4E)-5-[6-(1H-1,2,4-triazol-1-yl)-2-pyridinyl]-2,4-pentadienal Step A:
A solution of 1,2,4-triazole (1.55 g, 22.35 mmol) in DMF (7 mL) was added to sodium hydride (60% in oil, 0.90 g, 22.50 mmol) in DMF (7 mL) and the resulting mixture was stirred 2 h at RT. 2-(1,3-Dioxolan-2-yl)-6-fluoropyridine (1.26 g, 7.45 mmol, prepared as described in *J. Med. Chem.* 1998, 41, 5070) was added dropwise and the resulting mixture heated to 80° C. for 3 h. The reaction mixture was poured into ice-water and extracted with ethyl acetate. The combined organic layers were washed with water and brine, dried (MgSO$_4$), and concentrated. The residue obtained was dissolved in a mixture of formic acid (12 mL) and water (3 mL), CuSO$_4$5H$_2$O (0.19 g, 0.76 mmol) was added, and the mixture was heated to 65° C. for 5 h. The reaction mixture was concentrated, diluted with 10% aq. NaOH to pH>10, and extracted with ethyl acetate. The combined organic extracts were washed with dilute aq. ammonium hydroxide and brine, dried (MgSO$_4$), and concentrated. The material was used in the next step without further purification.

Step B:

A mixture of the product from step A (0.80 g, 4.59 mmol), (1,3-dioxolan-2-ylmethyl)triphenylphosphonium bromide (3.00 g, 6.99 mmol), and TDA-1 (2.00 mL, 6.25 mmol) in dichloromethane (20 mL) and sat. aq. K$_2$CO$_3$ (20 mL) was heated to reflux for 20 h. The layers were separated and the aqueous layer was extracted with dichloromethane (2×20 mL). The combined organic layers were washed with water (50 mL) and brine (50 mL), dried (Na$_2$SO$_4$), and concentrated. THF (10 mL) and 10% HCl (10 mL) were added and the mixture was stirred for 1 h at rt. The reaction mixture was cooled to 0° C., made basic with 10% NaOH, and extracted with ethyl acetate (3×15 mL). The combined organic layers were washed with water (20 mL) and brine (20 mL), dried (MgSO$_4$), and concentrated. Purification by chromatography (SiO$_2$, 2:1 hexane/ethyl acetate) provided 0.40 g (43%) of an inseparable mixture of 3-[6-(1H-1,2,4-triazol-1-yl)-2-pyridinyl]-2-propenal [MS 201 (M+H)$^+$] and 5-[6-(1H-1,2,4-triazol-1-yl)-2-pyridinyl]-2,4-pentadienal [MS 227 (M+H)$^+$].

REFERENCE EXAMPLE 32

(2E)-3-[4-(2-Pyridinyl)phenyl]-2-propenal

The title compound was prepared by a procedure analogous to Reference Example 30 by substituting 4-(2-pyridinyl)-benzaldehyde for the 4-(1H-pyrazol-1-yl)-benzaldehyde of Reference Example 30. MS 210 (M+H)$^+$.

REFERENCE EXAMPLE 33

(2E)-3-[4-(4-Pyridinyl)phenyl]-2-propenal

The title compound was prepared by a procedure analogous to Reference Example 30 by substituting 4-(4-pyridinyl)-benzaldehyde (prepared as described in WO 9828264) for the 4-(1H-pyrazol-1-yl)-benzaldehyde of Reference Example 30. MS 210 (M+H)$^+$.

REFERENCE EXAMPLE 34

(2E)-3-[4-(5-Pyrimidinyl)phenyl]-2-propenal

The title compound was prepared by a procedure analogous to Reference Example 30 by substituting 4-(5-pyrimidinyl)-benzaldehyde (prepared as described in WO 9828264) for the 4-(1H-pyrazol-1-yl)-benzaldehyde of Reference Example 30. MS 211 (M+H)$^+$.

REFERENCE EXAMPLE 35

(2E)-3-[4-(1H-1,2,4-Triazol-1-yl)phenyl]-2-propenal

The title compound was prepared by a procedure analogous to Reference Example 30 by substituting 4-(1H-1,2,4-triazol-1-yl)-benzaldehyde (prepared as described in *J. Med Chem.* 1998, 41, 2390) for the 4-(1H-pyrazol-1-yl)-benzaldehyde of Reference Example 30. MS 200 (M+H)$^+$.

REFERENCE EXAMPLE 36

(2E)-3-[4-(1H-1,2,3-Triazol-1-yl)phenyl]-2-propenal

The title compound was prepared by a procedure analogous to Reference Example 30 by substituting 4-(1H-1,2,3-triazol-1-yl)-benzaldehyde (prepared as described in *J. Med Chem.* 1998, 41, 2390) for the 4-(1H-pyrazol-1-yl)-benzaldehyde of Reference Example 30. MS 200 (M+H)$^+$.

REFERENCE EXAMPLE 37

(2E)-3-[4-(1H-Imidazol-1-yl)phenyl]-2-propenal

The title compound was prepared by a procedure analogous to Reference Example 30 by substituting 4-(1H-imidazol-1-yl)-benzaldehyde (prepared as described in *J. Med Chem.* 1998, 41, 2390) for the 4-(1H-pyrazol-1-yl)-benzaldehyde of Reference Example 30. MS 199 (M+H)$^+$.

REFERENCE EXAMPLE 38

(2E)-3-(4-Quinolinyl)-2-propenal

The title compound was prepared by a procedure analogous to Reference Example 30 by substituting 4-quinolinecarboxaldehyde for the 4-(1H-pyrazol-1-yl)-benzaldehyde of Reference Example 30. MS 184 (M+H)$^+$.

REFERENCE EXAMPLE 39

(2E)-3-[3-(2-Pyridinyl)phenyl]-2-propenal

The title compound was prepared by a procedure analogous to Reference Example 30 by substituting 3-(2-pyridinyl)benzaldehyde (prepared as described in Reference Example 11) for the 4-(1H-pyrazol-1-yl)-benzaldehyde of Reference Example 30. MS 210 (M+H)$^+$.

REFERENCE EXAMPLE 40

(2E)-3-[3-(2-Pyrimidinyl)phenyl]-2-propenal

The title compound was prepared by a procedure analogous to Reference Example 30 by substituting 3-(2-pyrimidinyl)benzaldehyde (prepared as described in Reference Example 12) for the 4-(1H-pyrazol-1-yl)-benzaldehyde of Reference Example 30. MS 211 (M+H)$^+$.

REFERENCE EXAMPLE 41

(2E)-3-[4-(4-Methyl-2-pyrimidinyl)phenyl]-2-propenal

The title compound was prepared by a procedure analogous to Reference Example 30 by substituting 4-(4-methyl-2-pyrimidinyl)benzaldehyde (prepared as described in Reference Example 14) for the 4-(1H-pyrazol-1-yl)-benzaldehyde of Reference Example 30. MS 225 (M+H)$^+$.

REFERENCE EXAMPLE 42

(2E)-3-[3-(1H-Pyrazol-1-yl)phenyl]-2-propenal

The title compound was prepared by a procedure analogous to Reference Example 30 by substituting 3-(1H-pyrazol-1-yl)-benzaldehyde (prepared as described in Reference Example 3) for the 4-(1H-pyrazol-1-yl)-benzaldehyde of Reference Example 30. MS 199 (M+H)$^+$.

REFERENCE EXAMPLE 43

(2E)-3-[4-(1-Methyl-1H-pyrazol-3-yl)phenyl]-2-propenal

The title compound was prepared by a procedure analogous to Reference Example 30 by substituting 4-(1-methyl-1H-pyrazol-3-yl)benzaldehyde (prepared as described in *J. Med. Chem.* 1998, 41, 2390) for the 4-(1H-pyrazol-1-yl)-benzaldehyde of Reference Example 30. MS 213 (M+H)$^+$.

REFERENCE EXAMPLE 44

(2E)-3-[4-(1-Methyl-1H-pyrazol-5-yl)phenyl]-2-propenal

The title compound was prepared by a procedure analogous to Reference Example 30 by substituting 4-(1-methyl-1H-pyrazol-5-yl)benzaldehyde (prepared as described in *J. Med. Chem.* 1998, 41, 2390) for the 4-(1H-pyrazol-1-yl)-benzaldehyde of Reference Example 30. MS 213 (M+H)$^+$.

REFERENCE EXAMPLE 45

(2E)-3-[4-(5-Nitro-2-pyridinyl)phenyl]-2-propenal

The title compound was prepared by a procedure analogous to Reference Example 30 by substituting 4-(5-nitro-2-pyridinyl)benzaldehyde (prepared as described in Reference Example 19) for the 4-(1H-pyrazol-1-yl)-benzaldehyde of Reference Example 30. MS 255 (M+H)$^+$.

REFERENCE EXAMPLE 46

(2E)-3-(8-Quinolinyl)-2-propenal

The title compound was prepared by a procedure analogous to Reference Example 30 by substituting 8-quinolinecarboxaldehyde (prepared as described in *J. Am. Chem. Soc.* 1997, 119, 8891) for the 4-(1H-pyrazol-1-yl)-benzaldehyde of Reference Example 30. MS 184 (M+H)$^+$.

REFERENCE EXAMPLE 47

(2E)-3-(7-Quinolinyl)-2-propenal

The title compound was prepared by a procedure analogous to Reference Example 30 by substituting 7-quinolinecarboxaldehyde (prepared as described in *J. Med. Chem.* 1993, 36, 3308) for the 4-(1H-pyrazol-1-yl)-benzaldehyde of Reference Example 30. MS 184 (M+H)$^+$.

REFERENCE EXAMPLE 48

(2E)-3-[6-(1H-Pyrazol-1-yl)-2-pyridinyl]-2-propenal

The title compound was prepared by a procedure analogous to Reference Example 30 by substituting 6-(1H-pyrazol-1-yl)-2-pyridinecarboxaldehyde (prepared as described in *J. Med. Chem.* 1998, 41, 5070) for the 4-(1H-pyrazol-1-yl)-benzaldehyde of Reference Example 30. MS 200 (M+H)$^+$.

REFERENCE EXAMPLE 49

(2E)-3-(4-Isoquinolinyl)-2-propenal

The title compound was prepared by a procedure analogous to Reference Example 30 by substituting 4-isoquinolinecarboxaldehyde for the 4-(1H-pyrazol-1-yl)-benzaldehyde of Reference Example 30. MS 184 (M+H)$^+$.

REFERENCE EXAMPLE 50

(2E)-3-[3-Fluoro-4-(1H-pyrazol-1-yl)phenyl]-2-propenal

The title compound was prepared by a procedure analogous to Reference Example 30 by substituting 3-fluoro-4-(1H-pyrazol-1-yl)benzaldehyde (prepared as described in Reference Example 6) for the 4-(1H-pyrazol-1-yl)-benzaldehyde of Reference Example 30. MS 217 (M+H)$^+$.

REFERENCE EXAMPLE 51

(2E)-3-[3-Fluoro-4-(1H-1,2,4-triazol-1-yl)phenyl]-2-propenal

The title compound was prepared by a procedure analogous to Reference Example 30 by substituting 3-fluoro-4-(1H-1,2,4-triazol-1-yl)benzaldehyde (prepared as described in Reference Example 7) for the 4-(1H-pyrazol-1-yl)-benzaldehyde of Reference Example 30. MS 218 (M+H)$^+$.

REFERENCE EXAMPLE 52

(2E)-3-[5-(2-Pyridinyl)-2-thienyl]-2-propenal

The title compound was prepared by a procedure analogous to Reference Example 30 by substituting 5-(2-pyridinyl)-2-thiophenecarboxaldehyde (prepared as described in *J. Chem Soc., Perkin Trans.* 2 1998, 437) for the 4-(1H-pyrazol-1-yl)-benzaldehyde of Reference Example 30. MS 216 (M+H)$^+$.

REFERENCE EXAMPLE 53

(2E,4E)-5-[4-(1H-Pyrazol-1-yl)phenyl]-2,4-pentadienal

The title compound was prepared by a procedure analogous to Reference Example 30 by substituting 3-[4-(1H-pyrazol-1-yl)phenyl]-2-propenal (prepared as described in Reference Example 30) for the 4-(1H-pyrazol-1-yl)-benzaldehyde of Reference Example 30. MS 225 (M+H)$^+$.

REFERENCE EXAMPLE 54

(2E)-3-(1-Phenyl-1H-pyrazol-4-yl)-2-propenal

The title compound was prepared by a procedure analogous to Reference Example 30 by substituting 1-phenyl-1H-pyrazol-4-ylcarboxaldehyde (prepared as described in *Synth. Commun.* 1998, 28, 1299) for the 4-(1H-pyrazol-1-yl)-benzaldehyde of Reference Example 30. MS 199 (M+H)$^+$.

REFERENCE EXAMPLE 55

(2E)-3-[4-(4-Methyl-1H-pyrazol-1-yl)phenyl]-2-propenal

The title compound was prepared by a procedure analogous to Reference Example 30 by substituting 4-(4-methyl-1H-pyrazol-1-yl)-benzaldehyde (prepared as described in Reference Example 4) for the 4-(1H-pyrazol-1-yl)-benzaldehyde of Reference Example 30. MS 213 (M+H)$^+$.

REFERENCE EXAMPLE 56

(2E)-3-[4-(4-Methoxy-2-pyrimidinyl)phenyl]-2-propenal

The title compound was prepared by a procedure analogous to Reference Example 30 by substituting 4-(4-methoxy-2-pyrimidinyl)benzaldehyde (prepared as described in Reference Example 13) for the 4-(1H-pyrazol-1-yl)-benzaldehyde of Reference Example 30. MS 241 (M+H)$^+$.

REFERENCE EXAMPLE 57

(2E)-3-(4-Pyrazinylphenyl)-2-propenal

The title compound was prepared by a procedure analogous to Reference Example 30 by substituting 4-pyrazinylbenzaldehyde (prepared as described in Reference Example 17) for the 4-(1H-pyrazol-1-yl)-benzaldehyde of Reference Example 30. MS 211 (M+H)$^+$.

REFERENCE EXAMPLE 58

(2E)-3-[4-(4-Pyrimidinyl)phenyl]-2-propenal

The title compound was prepared by a procedure analogous to Reference Example 30 by substituting 4-(4-pyrimidinyl)benzaldehyde (prepared as described in Reference Example 18) for the 4-(1H-pyrazol-1-yl)-benzaldehyde of Reference Example 30. MS 211 (M+H)$^+$.

REFERENCE EXAMPLE 59

(2E)-3-[4-(2-Pyrimidinyloxy)phenyl]-2-propenal

The title compound was prepared by a procedure analogous to Reference Example 30 by substituting 4-(2-pyrimidinyloxy)benzaldehyde (prepared as described in Reference Example 9) for the 4-(1H-pyrazol-1-yl)-benzaldehyde of Reference Example 30. MS 227 (M+H)$^+$.

REFERENCE EXAMPLE 60

(2E)-3-[2-Fluoro-4-(2-pyrimidinyl)phenyl]-2-propenal

The title compound was prepared by a procedure analogous to Reference Example 30 by substituting 2-fluoro-4-(2-pyrimidinyl)benzaldehyde (prepared as described in Reference Example 15) for the 4-(1H-pyrazol-1-yl)-benzaldehyde of Reference Example 30. MS 229 (M+H)$^+$.

REFERENCE EXAMPLE 61

(2E)-3-[4-(3-Pyridazinyl)phenyl]-2-propenal

The title compound was prepared by a procedure analogous to Reference Example 30 by substituting 4-(3-pyridazinyl)benzaldehyde (prepared as described in Reference Example 16) for the 4-(1H-pyrazol-1-yl)-benzaldehyde of Reference Example 30. MS 211 (M+H)$^+$.

REFERENCE EXAMPLE 62

(2E)-3-[1-(2-Pyrimidinyl)-1H-imidazol-4-yl]-2-propenal

The title compound was prepared by a procedure analogous to Reference Example 30 by substituting 1-(2-pyrimidinyl)-1H-imidazole-4-carboxaldehyde (prepared as described in Reference Example 10) for the 4-(1H-pyrazol-1-yl)-benzaldehyde of Reference Example 30. MS 201 (M+H)$^+$.

REFERENCE EXAMPLE 63

[[4-(2-Pyrimidinyl)phenyl]methoxy]acetaldehyde
Step A: 4-(2-pyrimidinyl)benzenemethanol The title compound was prepared by a procedure analogous to Reference Example 12 by substituting 4-(hydroxymethyl)phenylboronic acid for the 3-formylphenylboronic acid of Reference Example 12. MS 187 (M+H)$^+$.

Step B: [[4-(2-Pyrimidinyl)phenyl]methoxy]acetaldehyde

A solution of the product from step A (559 mg, 3.00 mmol) in DMF (4 mL) was added dropwise to a suspension of sodium hydride (60% in mineral oil, 144 mg, 3.60 mmol) at 0° C. The solution was stirred for 30 min at 0° C., bromoacetaldehyde diethyl acetal (0.55 mL, 3.66 mmol) and tetrabutylammonium iodide (111 mg, 0.30 mmol) were added, and the resulting mixture was stirred at 70° C. for 12 h. Additional sodium hydride (60% in mineral oil, 70 mg, 1.75 mmol) and bromoacetaldehyde diethyl acetal (0.55 mL, 3.66 mmol) were added and heating at 70° C. was continued for 12 h. The reaction mixture was concentrated, the residue was diluted with water and extracted with ethyl acetate, the combined organic layers were dried (MgSO$_4$), and concentrated. Purification by chromatography (SiO$_2$, 1:1 hexane/ethyl acetate) gave material which was taken up in ethanol (2 mL) and 10% aq. HCl (10 mL) and stirred for 12 h. The reaction mixture was made basic with aq. NaOH, extracted with ethyl acetate, dried (MgSO$_4$), and concentrated. Purification by chromatography (SiO$_2$, 1:1 hexane/ethyl acetate) provided 80 mg (12%) of the title compound. MS 229 (M+H)$^+$.

REFERENCE EXAMPLE 64

4-(2-Pyrimidinyl)benzeneacetaldehyde

Sodium hexamethyldisilazide (1.0M in THF, 2.65 mL, 2.65 mmol) was added to a suspension of methoxymethyltriphenylphosphonium chloride (0.93 g, 2.71 mmol) in THF (13 mL) at 0° C., and the red-orange mixture was stirred for 15 min at 0° C. A solution of 4-(2-pyrimidinyl)benzaldehyde (250 mg, 1.36 mmol, prepared as described in WO 9828264) in THF (5 mL) was added, and stirring was continued at 0° C. for 1 h. 10% aq. HCl (13 mL) was added and the mixture was heated to 50° C. for 1 h. The reaction mixture was then cooled to 0° C. and solid Na$_2$CO$_3$ was added cautiously until the solution was basic. The mixture was extracted with ethyl acetate (2×25 mL) and the combined organic extracts were washed with brine (2×25 mL), dried (MgSO$_4$), and concentrated. Purification by chromatography (SiO$_2$, 2:1 hexane/ethyl acetate) yielded 141 mg (52%) of the title compound. MS 199 (M+H)$^+$.

REFERENCE EXAMPLE 65

(2E)-3-[4-(2-Pyrimidinyl)phenyl]-2-propen-1-ol

DIBAL (1.0 M in THF, 18.0 mL) was added over 10 min to a −78° C. suspension of (2E)-3-[4-(2-pyrimidinyl)phenyl]-2-propenal (2.50 g, 11.89 mmol, prepared as described in Reference Example 29) in dichloromethane (100 mL). The resulting suspension was stirred for 30 min at −78° C., methanol (2 mL) was added cautiously, and stirring was continued for 5 min at −78° C. The mixture was poured into a mixture of 10% aq. citric acid (300 mL) and dichloromethane (200 mL) and allowed to stir for 1 h. The organic layer was separated, washed with sat. aq. NaHCO$_3$ (200 mL) and brine (200 mL), dried (MgSO$_4$), filtered through Celite, and concentrated. The resulting material was triturated with ether and dried in vacuo to provide 2.08 g (82%) of the title compound. MS 213 (M+H)$^+$.

REFERENCE EXAMPLE 66

(2E)-3-[4-(3-Pyridazinyl)phenyl]-2-propen-1-ol

Sodium borohydride (90 mg, 2.38 mmol) was added to a suspension of (2E)-3-[4-(3-pyridazinyl)phenyl]-2-propenal (400 mg, 1.90 mmol, prepared as described in Reference Example 61) in ethanol (5 mL) maintained in a room temperature water bath. After 20 min, the reaction was quenched with water (10 mL), allowed to stir for 10 min, and then concentrated to remove the ethanol. The solids were removed by filtration, washed with water, and dried in vacuo to provide 360 mg (89%) of the title compound. MS 213 (M+H)$^+$.

REFERENCE EXAMPLE 67

2-Butoxy-3,4-dihydro-4-phenyl-2H-pyran

A neat mixture of cinnamaldehyde (0.66 g, 4.99 mmol), butyl vinyl ether (1.30 mL, 10.05 mmol), and Yb(fod)$_3$ (265 mg, 0.25 mmol) was stirred at rt for 72 h and then heated to 50° C. for 18 h. Purification by chromatography (SiO$_2$, 95:5 hexane/ethyl acetate) yielded 0.89 g (77%) of the title compound. MS 233 (M+H)$^+$.

REFERENCE EXAMPLE 68

2-Formyl-4,4-dimethoxybutanenitrile

Lithium diisopropylamide mono(tetrahydrofuran) (1.5 M in cyclohexane, 22.0 mL, 33.00 mmol) was added to THF (100 mL) at −30° C. and the resulting solution was stirred for 10 min before 3-cyanopropionaldehyde dimethyl acetal (3.90 mL, 29.90 mmol) was added dropwise over 5 min. After 15 min, methyl formate (2.80 mmol, 45.42 mmol) was added and the resulting solution was stirred at −20° C. to −15° C. for 2 h. The reaction mixture was quenched with water (100 mL) and washed with ether (2×50 mL, discarded). The aqueous layer was acidified with 10% HCl and extracted with ether (3×50 mL). The combined ether extracts were washed with brine (3×50 mL), dried (MgSO$_4$), and concentrated. The residue was dissolved in dichloromethane and concentrated to remove traces of THF and provide 2.28 g (49%) of the title compound as a pale yellow oil.

REFERENCE EXAMPLE 69

4-(5-Fluoro-2-pyrimidinyl)benzaldehyde

A suspension of 2M aq. Na$_2$CO$_3$ (7 mL) and 4-formylphenylboronic acid (1.35 g, 9.0 mmol) in ethanol (4 mL) was added to a solution of 2-chloro-5-fluoropyrimidine (922 mg, 7.0 mmol, prepared as described in *Org. Prep. Proc. Int.* 1995, 27, 600), and [1,4-bis(diphenylphosphino) butane]palladium(II) dichloride (0.209 g, 0.35 mmol) in toluene (15 mL). The reaction mixture was heated to reflux for 6 h, cooled to room temperature, diluted with ethyl acetate, washed with sat. aq. NaHCO$_3$ and brine, dried with Na$_2$SO$_4$, and concentrated in vacuo. Purification by medium pressure liquid chromatography (SiO$_2$, 20:1 hexanes/ethyl acetate) gave 732 mg (52%) of the title compound. MS 203 (M+H)$^+$.

REFERENCE EXAMPLE 70

4-(5-Ethyl-2-pyrimidinyl)benzaldehyde

A suspension of saturated aq. Na$_2$CO$_3$ (10 mL) and 4-formylphenylboronic acid (1.80 g, 12.0 mmol) in ethanol (5 mL) was added to a solution of 2-chloro-5-ethylpyrimidine (1.20 mL, 10.0 mmol) and [1,4-bis(diphenylphosphino)butane]palladium(II) dichloride (0.300 g, 0.5 mmol) in toluene (20 mL). The reaction mixture was heated to reflux for 5 h, cooled to room temperature, diluted with ethyl acetate, washed with sat. aq. NaHCO$_3$ and brine, dried with Na$_2$SO$_4$, and concentrated in vacuo. Purification by medium pressure liquid chromatography (SiO$_2$, 3:1 hexanes/ethyl acetate) gave 1.62 g (76%) of the title compound. MS 213 (M+H)$^+$.

REFERENCE EXAMPLE 71

2-Phenyl-5-pyrimidinecarboxyaldehyde

To a solution of 5-bromo-2-phenylpyrimidine (850 mg, 3.65 mmol, prepared as described in *Org. Lett.* 2002, 4, 513) in THF (15 mL) at −100° C. was added dropwise n-BuLi (1.60 mL, 4.00 mmol, 2.5 M solution in hexanes). The reaction mixture was stirred at −100° C. for 15 min, and methyl formate (0.26 mL, 4.20 mmol) was added dropwise. The reaction mixture was stirred for an additional 15 min at −100° C., carefully quenched with a 1M HCl solution in diethyl ether (4.50 mL, 4.50 mmol), warmed to room temperature, and concentrated in vacuo. The crude reaction mixture was partitioned between dichloromethane and sat. aq. NaHCO$_3$, the organic layer dried with Na$_2$SO$_4$, and concentrated in vacuo. Purification by medium pressure liquid chromatography (SiO$_2$, 4:1 hexanes/ethyl acetate) gave 226 mg (34%) of the title compound. MS 185 (M+H)$^+$.

REFERENCE EXAMPLE 72

4-(2-Thiazolyl)benzaldehyde

A mixture of NaHCO$_3$ (3.83 g, 45.6 mmol) and 4-formylphenylboronic acid (2.69 g, 18.0 mmol) in water (60 mL) was added to a solution of 2-bromothiazole (2.50 g, 15.2 mmol) and tetrakis(triphenylphosphine)palladium(0) (500 mg, 0.43 mmol) in DME (60 mL). The reaction mixture was heated to reflux for 18 h, cooled to room temperature, diluted with ethyl acetate, washed with sat. aq. NaHCO$_3$ and brine, dried with Na$_2$SO$_4$, and concentrated in vacuo. Two consecutive recrystallizations from hexanes/ethyl acetate yielded 998 mg (35%) of the title compound. MS 190 (M+H)$^+$.

REFERENCE EXAMPLE 73

4-(2-Oxazolyl)benzaldehyde

Step A: 2-(4-Methylphenyl)oxazole

Polyphosphoric acid (20 g), vinylene carbonate (5.73 mL, 90.0 mmol) and p-toluamide (12.2 g, 90.0 mmol) were combined and heated at 170° C. for 2 h. The reaction mixture was allowed to cool to ~80° C., water (~100 mL) was carefully added, and stirred for ~10 min. This mixture was extracted three times with ethyl acetate, combined organic extracts were dried with Na$_2$SO$_4$, and concentrated in vacuo. Purification by medium pressure liquid chromatography (SiO$_2$, 97:3 hexanes/acetone) gave 6.41 g (45%) of the title compound. MS 160 (M+H)$^+$.

Step B: 4-(2-Oxazolyl)benzaldehyde

To 2-(4-methylphenyl)oxazole (6.41 g, 40.3 mmol) and N-bromosuccinimide (14.7 g, 82.6 mmol) in carbon tetrachloride (300 mL) was added 2,2'-azobisisobutyronitrile (500 mg, 3.1 mmol) and the reaction mixture was heated at 100° C. for 12 h. The reaction mixture was cooled to 0° C., filtered through a fritted funnel, and concentrated in vacuo. To this crude reaction mixture was added 95% ethanol (300 mL) and silver nitrate (15.1 g, 88.8 mmol), and the reaction mixture was refluxed for 4 h, cooled to room temperature, filtered through a fritted funnel, and concentrated in vacuo. Purification by medium pressure liquid chromatography (SiO$_2$, 10:1 hexanes/ethyl acetate) gave 880 mg (13%, 2 steps) of the title compound. MS 174 (M+H)$^+$.

REFERENCE EXAMPLE 74

4-(3-isoxazolyl)benzaldehyde

The title compound is prepared by a procedure analogous to Step B of Reference Example 73 by substituting 3-(4- methylphenyl)isoxazole (prepared as described in *J. Organomet. Chem.* 1966, 6, 598) for the 2-(4-methylphenyl)oxazole of Step B of Reference Example 73. MS 174 (M+H)+.

REFERENCE EXAMPLE 75

4-(1,2,4-Oxadiazol-3-yl)benzaldehyde

The title compound is prepared by a procedure analogous to Step B of Reference Example 73 by substituting 3-(4-methylphenyl)-1,2,4-oxadiazole (prepared as described in *Bull. Chem. Soc. Jpn.* 1978, 51,1484) for the 2-(4-methylphenyl)oxazole of Step B of Reference Example 73. MS 175 (M+H)+.

REFERENCE EXAMPLE 76

4-(1,2,4-Oxadiazol-5-yl)benzaldehyde
Step A: 5-(4-methylphenyl)-1,2,4-oxadiazole To a solution of 3.54 g (0.0510 mol) of hydroxylamine hydrochloride in a mixture of 10.2 mL (0.0510 mol) of 5 N NaOH, dioxane (50 mL), and 70% aq. acetic acid (100 mL), is added 6.79 g (0.0424) of N-[(dimethylamino)methylene]-4-methylbenzamide (prepared as described in *J. Chem. Soc. Perkin. Trans.* 1 1989, 589). The mixture is stirred at 90° C. for 1.5 h and the product is isolated from the cooled reaction mixture. MS 161 (M+H)+.
Step B: 4-(1,2,4-Oxadiazol-5-yl)benzaldehyde The title compound is prepared by a procedure analogous to Step B of Reference Example 73 by substituting the 5-(4-methylphenyl)-1,2,4-oxadiazole from Step A above for the 2-(4-methylphenyl)oxazole of Step B of Reference Example 73. MS 175 (M+H)+.

REFERENCE EXAMPLE 77

4-(1,3,4-Oxadiazol-2-yl)benzaldehyde
Step A: Dimethoxymethyl Benzoic Acid Hydrazide Triethylamine (11.8 mL, 84.6 mmol) was added to a solution of 4-(dimethoxymethyl)benzoic acid (11.0 g, 56.4 mmol, prepared as described in *Tetrahedron* 1998, 54,15679–15690) in dichloromethane (120 mL) at room temperature. The reaction mixture was cooled to −40° C., ethyl chloroformate (6.7 mL, 70.0 mmol) was added dropwise, and stirring continued at −40° C. for 30 min. Hydrazine (8.85 mL, 282 mmol) was added and the reaction mixture was warmed to room temperature and stirred for an additional 1 h. The reaction mixture was diluted with dichloromethane, washed with water, dried with $Na_2SO_4$, and concentrated in vacuo to give 9.06 g (77%) of the title compound, which was used in the next step without further purification. MS 211 (M+H)+.
Step B: 2-[4-(Dimethoxymethyl)phenyl]-1,3,4-oxadiazole Methyl orthoformate (20 mL) was added to the product from step A (9.06 g, 43.1 mmol), and this mixture was heated under Dean-stark conditions for 48 h. Excess methyl orthoformate was removed in vacuo, and the residue purified by medium pressure liquid chromatography ($SiO_2$, 3:1 hexanes/ethyl acetate) to give 5.26 g (56%) of the title compound. MS 221 (M+H)+.
Step C: 4-(1,3,4-Oxadiazol-2-yl)benzaldehyde To the product from step B (175 mg, 0.80 mmol) in a 1:1 mixture of tetrahydrofuran/water (2 mL) at room temperature was added p-toluenesulfonic acid (50 mg, 0.3 mmol). The reaction mixture was stirred at room temperature for 1 h, and partitioned between dichloromethane and sat. aq. $NaHCO_3$. The organic layer was dried with $Na_2SO_4$, and concentrated in vacuo to give 100 mg (72%) of the title product, which was used without further purification. MS 175 (M+H)+.

REFERENCE EXAMPLE 78

(2E)-3-[4-(1,3,4-Oxadiazol-2-yl)phenyl]-2-propenal

The title compound was prepared by a procedure analogous to Reference Example 30 by substituting 4-(1,3,4-oxadiazol-2-yl)benzaldehyde (prepared as described in Reference Example 77) for the 4-(1H-pyrazol-1-yl)-benzaldehyde of Reference Example 30. MS 201 (M+H)+.

REFERENCE EXAMPLE 79

(2E)-3-[4-(5-oxazolyl)phenyl]-2-propenal

The title compound was prepared by a procedure analogous to Reference Example 30 by substituting 4-(5-oxazolyl)benzaldehyde (prepared as described in *J. Med. Chem.* 1998, 41, 2390) for the 4-(11H-pyrazol-1-yl)-benzaldehyde of Reference Example 30. MS 200 (M+H)+.

REFERENCE EXAMPLE 80

(2E)-3-[4-(3-isoxazolyl)phenyl]-2-propenal

The title compound is prepared by a procedure analogous to Reference Example 30 by substituting 4-(3-isoxazolyl)benzaldehyde (prepared as described in Reference Example 74) for the 4-(1H-pyrazol-1-yl)-benzaldehyde of Reference Example 30. MS 200 (M+H)+.

REFERENCE EXAMPLE 81

(2E)-3-[4-(1,2,4-Oxadiazol-3-yl)phenyl]-2-propenal

The title compound is prepared by a procedure analogous to Reference Example 30 by substituting 4-(1,2,4-oxadiazol-3-yl)benzaldehyde (prepared as described in Reference Example 75) for the 4-(1H-pyrazol-1-yl)-benzaldehyde of Reference Example 30. MS 201 (M+H)+.

REFERENCE EXAMPLE 82

(2E)-3-[4-(1,2,4-Oxadiazol-5-yl)phenyl]-2-propenal

The title compound is prepared by a procedure analogous to Reference Example 30 by substituting 4-(1,2,4-oxadiazol-5-yl)benzaldehyde (prepared as described in Reference Example 76) for the 4-(1H-pyrazol-1-yl)-benzaldehyde of Reference Example 30. MS 201 (M+H)+.

REFERENCE EXAMPLE 83

(2E)-3-[4-(2-thienyl)phenyl]-2-propenal

The title compound was prepared by a procedure analogous to Reference Example 30 by substituting 4-(2-thienyl)benzaldehyde (prepared as described in *J. Med. Chem.* 1998, 41, 2390) for the 4-(1H-pyrazol-1-yl)-benzaldehyde of Reference Example 30. MS 215 (M+H)+.

REFERENCE EXAMPLE 84

(2E)-3-(1-methyl-1H-benzimidazol-2-yl)-2-propenal

The title compound was prepared by a procedure analogous to Reference Example 30 by substituting 1-methyl-1H-benzimidazole-2-carboxaldehyde for the 4-(1H-pyrazol-1-yl)-benzaldehyde of Reference Example 30. MS 187 (M+H)+.

REFERENCE EXAMPLE 85

(2E)-3-[2,2'-bithiophen]-5-yl-2-propenal

The title compound was prepared by a procedure analogous to Reference Example 30 by substituting [2,2'-bithiophene]-5-carboxaldehyde for the 4-(1H-pyrazol-1-yl)-benzaldehyde of Reference Example 30. MS 221 (M+H)$^+$.

REFERENCE EXAMPLE 86

5-(2-pyrimidinyl)-2-thiophenecarboxaldehyde

A mixture of Na$_2$CO$_3$ (3.16 g) and 5-formyl-2-thiopheneboronic acid (2.4 g, 15.1 mmol) in water (15 mL) were added to a solution of 2-bromopyrimidine (2 g, 12.58 mmol) and tetrakis(triphenylphosphine)palladium(0) (480 mg, 0.46 mmol) in DME (30 mL) and the mixture was heated to reflux for 24 hr. The cooled reaction mixture was diluted with dichloromethane, washed with sat. aq. NaHCO$_3$ and brine, dried (MgSO$_4$), and concentrated. Purification by chromatography (SiO$_2$, 1:1 hexane/ethyl acetate) yielded 620 mg (26%) of the title compound. MS 191 (M+H)$^+$.

REFERENCE EXAMPLE 87

5-pyrazinyl-2-thiophenecarboxaldehyde

The title compound was prepared by a procedure analogous to Reference Example 86 by substituting 2-chloropyrazine for the 2-bromopyrimidine of Reference Example 86. MS 191 (M+H)$^+$.

REFERENCE EXAMPLE 88

(2E)-3-[5-(2-pyrimidinyl)-2-thienyl]-2-propenal

The title compound was prepared by a procedure analogous to Reference Example 30 by substituting 5-(2-pyrimidinyl)-2-thiophenecarboxaldehyde (prepared as described in Reference Example 86) for the 4-(1H-pyrazol-1-yl)-benzaldehyde of Reference Example 30. MS 217 (M+H)$^+$.

REFERENCE EXAMPLE 89

(2E)-3-(5-pyrazinyl-2-thienyl)-2-propenal

The title compound was prepared by a procedure analogous to Reference Example 30 by substituting 5-pyrazinyl-2-thiophenecarboxaldehyde (prepared as described in Reference Example 87) for the 4-(1H-pyrazol-1-yl)-benzaldehyde of Reference Example 30. MS 217 (M+H)$^+$.

REFERENCE EXAMPLE 90

4-(2-pyrimidinyl)-2-thiophenecarboxaldehyde

A mixture of Na$_2$CO$_3$ (3.16 g) and 5-formyl-3-thiopheneboronic acid (2.4 g, 15.1 mmol) in water (15 mL) are added to a solution of 2-bromopyrimidine (2 g, 12.58 mmol) and tetrakis(triphenylphosphine)palladium(0) (480 mg, 0.46 mmol) in DME (30 mL) and the mixture is heated to reflux for 24 hr. The cooled reaction mixture is diluted with dichloromethane, washed with sat. aq. NaHCO$_3$ and brine, dried (MgSO$_4$), and concentrated. Purification by chromatography yields the title compound. MS 191 (M+H)$^+$.

REFERENCE EXAMPLE 91

4-(2-pyridinyl)-2-thiophenecarboxaldehyde

The title compound is prepared by a procedure analogous to Reference Example 90 by substituting 2-bromopyridine for the 2-bromopyrimidine of Reference Example 90. MS 190 (M+H)$^+$.

REFERENCE EXAMPLE 92

4-pyrazinyl-2-thiophenecarboxaldehyde

The title compound is prepared by a procedure analogous to Reference Example 90 by substituting chloropyrazine for the 2-bromopyrimidine of Reference Example 90. MS 191 (M+H)$^+$.

REFERENCE EXAMPLE 93

5-(2-pyrimidinyl)-3-thiophenecarboxaldehyde

The title compound is prepared by a procedure analogous to Reference Example 15 by substituting 5-bromo-3-thiophenecarboxaldehyde (prepared as described in Chem. Pharm. Bull. 1999, 47,1393) for the 4-bromo-2-fluorobenzaldehyde of Reference Example 15. MS 191 (M+H)$^+$.

REFERENCE EXAMPLE 94

5-(2-pyridinyl)-3-thiophenecarboxaldehyde

The title compound is prepared by a procedure analogous to Reference Example 15 by substituting 5-bromo-3-thiophenecarboxaldehyde (prepared as described in Chem. Pharm. Bull. 1999, 47,1393) and 2-bromopyridine, respectively, for the 4-bromo-2-fluorobenzaldehyde and 2-bromopyrimidine of Reference Example 15. MS 190 (M+H)$^+$.

REFERENCE EXAMPLE 95

5-pyrazinyl-3-thiophenecarboxaldehyde

The title compound is prepared by a procedure analogous to Reference Example 15 by substituting 5-bromo-3-thiophenecarboxaldehyde (prepared as described in Chem. Pharm. Bull. 1999, 47,1393) and chloropyrazine, respectively, for the 4-bromo-2-fluorobenzaldehyde and 2-bromopyrimidine of Reference Example 15. MS 191 (M+H)$^+$.

REFERENCE EXAMPLE 96

(2E)-3-[4-(2-pyrimidinyl)-2-thienyl]-2-propenal

The title compound is prepared by a procedure analogous to Reference Example 30 by substituting 4-(2-pyrimidinyl)-2-thiophenecarboxaldehyde (prepared as described in Reference Example 90) for the 4-(1H-pyrazol-1-yl)-benzaldehyde of Reference Example 30. MS 217 (M+H)$^+$.

REFERENCE EXAMPLE 97

(2E)-3-[4-(2-pyridinyl)-2-thienyl]-2-propenal

The title compound is prepared by a procedure analogous to Reference Example 30 by substituting 4-(2-pyridinyl)-2-thiophenecarboxaldehyde (prepared as described in Reference Example 91) for the 4-(1H-pyrazol-1-yl)-benzaldehyde of Reference Example 30. MS 216 (M+H)$^+$.

REFERENCE EXAMPLE 98

(2E)-3-(4-pyrazinyl-2-thienyl)-2-propenal

The title compound is prepared by a procedure analogous to Reference Example 30 by substituting 4-pyrazinyl-2-thiophenecarboxaldehyde (prepared as described in Reference Example 92) for the 4-(1H-pyrazol-1-yl)-benzaldehyde of Reference Example 30. MS 217 (M+H)$^+$.

REFERENCE EXAMPLE 99

(2E)-3-[5-(2-pyrimidinyl)-3-thienyl]-2-propenal

The title compound is prepared by a procedure analogous to Reference Example 30 by substituting 5-(2-pyrimidinyl)-3-thiophenecarboxaldehyde (prepared as described in Reference Example 93) for the 4-(1H-pyrazol-1-yl)-benzaldehyde of Reference Example 30. MS 217 (M+H)$^+$.

REFERENCE EXAMPLE 100

(2E)-3-[5-(2-pyridinyl)-3-thienyl]-2-propenal

The title compound is prepared by a procedure analogous to Reference Example 30 by substituting 5-(2-pyridinyl)-3-thiophenecarboxaldehyde (prepared as described in Reference Example 94) or the 4-(1H-pyrazol-1-yl)-benzaldehyde of Reference Example 30. MS 216 (M+H)$^+$.

REFERENCE EXAMPLE 101

(2E)-3-(5-pyrazinyl-3-thienyl)-2-propenal

The title compound is prepared by a procedure analogous to Reference Example 30 by substituting 5-pyrazinyl-3-thiophenecarboxaldehyde (prepared as described in Reference Example 95) for the 4-(1H-pyrazol-1-yl)-benzaldehyde of Reference Example 30. MS 217 (M+H)$^+$.

REFERENCE EXAMPLE 102

(2E)-3-(2-quinoxalinyl)-2-propenal

The title compound is prepared by a procedure analogous to Reference Example 30 by substituting 2-quinoxalinecarboxaldehyde (prepared as described in *J. Chem. Soc.* 1956, 2052) for the 4-(1H-pyrazol-1-yl)-benzaldehyde of Reference Example 30. MS 185 (M+H)$^+$.

REFERENCE EXAMPLE 103

(2E)-3-[4-(4H-1,2,4-Triazol-4-yl)phenyl]-2-propenal

The title compound was prepared by a procedure analogous to Reference Example 30 by substituting 4-(4H-1,2,4-triazol-4-yl)-benzaldehyde (prepared as described in WO 98/03476) for the 4-(1H-pyrazol-1-yl)-benzaldehyde of Reference Example 30. MS 200 (M+H)$^+$.

REFERENCE EXAMPLE 104

(2E)-3-[4-(2-pyridinyl)phenyl]-2-propen-1-ol (2E)-3-[4-(2-pyridinyl)phenyl]-2-propenal (500 mg, 2.4 mmol, prepared as described in Reference Example 32) was dissolved in THF (10 mL) and methanol (10 mL) at 0° C. Sodium borohydride (109 mg, 2.9 mmol) was added and the mixture was stirred at 0° C. for 30 min. The reaction mixture was concentrated. Water (10 mL) was added and the mixture was extracted with ethyl acetate (3×15 mL). The organic layer was collected, dried and concentrated. MS 212 (M+H)$^+$.

REFERENCE EXAMPLES 105–126

The compounds of Reference Examples 105–126, listed in the table below, are prepared by the method of Reference Example 104 by substituting the appropriate aldehyde for the (2E)-3-[4-(2-pyridinyl)phenyl]-2-propenal of Reference Example 104.

| Ref. Ex. | Compound | MS [(M + H)$^+$] |
| --- | --- | --- |
| 105 | (2E)-3-[4-(5-oxazolyl)phenyl]-2-propen-1-ol | 202 |
| 106 | (2E)-3-[4-(2-thienyl)phenyl]-2-propen-1-ol | 217 |
| 107 | (2E)-3-(1-methyl-1H-benzimidazol-2-yl)-2-propen-1-ol | 189 |
| 108 | (2E)-3-[2,2'-bithiophen]-5-yl-2-propen-1-ol | 223 |
| 109 | (2E)-3-[5-(2-pyrimidinyl)-2-thienyl]-2-propen-1-ol | 219 |
| 110 | (2E)-3-(5-pyrazinyl-2-thienyl)-2-propen-1-ol | 219 |
| 111 | (2E)-3-[5-(2-pyridinyl)-2-thienyl]-2-propen-1-ol | 218 |
| 112 | (2E)-3-[4-(2-thiazolyl)phenyl]-2-propen-1-ol | 218 |
| 113 | (2E)-3-(1-phenyl-1H-pyrazol-4-yl)-2-propen-1-ol | 201 |
| 114 | (2E)-3-[1-(2-pyrimidinyl)-1H-imidazol-4-yl]-2-propen-1-ol | 203 |
| 115 | (2E)-3-(1-pyrazinyl-1H-imidazol-4-yl)-2-propen-1-ol | 203 |
| 116 | (2E)-3-[4-(1-methyl-1H-pyrazol-3-yl)phenyl]-2-propen-1-ol | 215 |
| 117 | (2E)-3-[4-(1-methyl-1H-pyrazol-5-yl)phenyl]-2-propen-1-ol | 215 |
| 118 | (2E)-3-[3-fluoro-4-(1H-1,2,4-triazol-1-yl)phenyl]-2-propen-1-ol | 220 |
| 119 | (2E)-3-[4-(1H-1,2,4-triazol-1-yl)phenyl]-2-propen-1-ol | 202 |
| 120 | (2E)-3-[4-(4H-1,2,4-triazol-4-yl)phenyl]-2-propen-1-ol | 202 |
| 121 | (2E)-3-[4-(1H-1,2,3-triazol-1-yl)phenyl]-2-propen-1-ol | 202 |
| 122 | (2E)-3-[4-(1,3,4-oxadiazol-2-yl)phenyl]-2-propen-1-ol | 203 |
| 123 | (2E)-3-[4-(1,2,4-oxadiazol-3-yl)phenyl]-2-propen-1-ol | 203 |
| 124 | (2E)-3-[4-(1,2,4-oxadiazol-5-yl)phenyl]-2-propen-1-ol | 203 |
| 125 | (2E)-3-[4-(3-isoxazolyl)phenyl]-2-propen-1-ol | 202 |
| 126 | 4-pyrazinylbenzenemethanol | 187 |

REFERENCE EXAMPLES 127–154

The compounds of Reference Examples 127–154, listed in the table below, are prepared by the method of Reference Example 65 by substituting the appropriate aldehyde for the (2E)-3-[4-(2-pyrimidinyl)phenyl]-2-propenal of Reference Example 65.

| Ref. Ex. | Compound | MS [(M + H)$^+$] |
| --- | --- | --- |
| 127 | (2E)-3-[4-(4-pyrimidinyl)phenyl]-2-propen-1-ol | 213 |
| 128 | (2E)-3-[4-(5-pyrimidinyl)phenyl]-2-propen-1-ol | 213 |
| 129 | (2E)-3-[3-(2-pyrimidinyl)phenyl]-2-propen-1-ol | 213 |
| 130 | (2E)-3-[4-(3-pyridinyl)phenyl]-2-propen-1-ol | 212 |
| 131 | (2E)-3-[4-(4-pyridinyl)phenyl]-2-propen-1-ol | 212 |
| 132 | (2E)-3-(4-pyrazinylphenyl)-2-propen-1-ol | 213 |
| 133 | (2E)-3-[4-(1H-pyrazol-1-yl)phenyl]-2-propen-1-ol | 201 |
| 134 | (2E)-3-[4-(1H-imidazol-1-yl)phenyl]-2-propen-1-ol | 201 |
| 135 | (2E)-3-[3-methoxy-4-(1H-pyrazol-1-yl)phenyl]-2-propen-1-ol | 231 |
| 136 | (2E)-3-[3-fluoro-4-(1H-pyrazol-1-yl)phenyl]-2-propen-1-ol | 219 |
| 137 | (2E)-3-[2-fluoro-4-(1H-pyrazol-1-yl)phenyl]-2-propen-1-ol | 219 |
| 138 | (2E)-3-(3-quinolinyl)-2-propen-1-ol | 186 |
| 139 | (2E)-3-(4-quinolinyl)-2-propen-1-ol | 186 |
| 140 | (2E)-3-(5-quinolinyl)-2-propen-1-ol | 186 |
| 141 | (2E)-3-(6-quinolinyl)-2-propen-1-ol | 186 |
| 142 | (2E)-3-(7-quinolinyl)-2-propen-1-ol | 186 |
| 143 | (2E)-3-(2-quinoxalinyl)-2-propen-1-ol | 187 |
| 144 | (2E)-3-(6-quinoxalinyl)-2-propen-1-ol | 187 |
| 145 | (2E)-3-(4-isoquinolinyl)-2-propen-1-ol | 186 |
| 146 | (2E)-3-[4-(2-oxazolyl)phenyl]-2-propen-1-ol | 202 |
| 147 | (2E)-3-[4-(2-pyridinyl)-2-thienyl]-2-propen-1-ol | 218 |
| 148 | (2E)-3-[4-(2-pyrimidinyl)-2-thienyl]-2-propen-1-ol | 219 |
| 149 | (2E)-3-(4-pyrazinyl-2-thienyl)-2-propen-1-ol | 219 |
| 150 | (2E)-3-[5-(2-pyridinyl)-3-thienyl]-2-propen-1-ol | 218 |
| 151 | (2E)-3-[5-(2-pyrimidinyl)-3-thienyl]-2-propen-1-ol | 219 |
| 152 | (2E)-3-(5-pyrazinyl-3-thienyl)-2-propen-1-ol | 219 |
| 153 | (2E)-3-[4-(2-pyrimidinyloxy)phenyl]-2-propen-1-ol | 229 |
| 154 | (2E)-3-[2-fluoro-4-(2-pyrimidinyl)phenyl]-2-propen-1-ol | 231 |

REFERENCE EXAMPLE 155

4-(2-pyrimidinyl)benzenepropanol

A mixture of (2E)-3-[4-(2-pyrimidinyl)phenyl]-2-propen-1-ol (300 mg, 1.41 mmol, prepared as described in Reference Example 65), ammonium formate (445 mg, 7.06 mmol), and 10% Pd/C (100 mg) in methanol (5 mL) was stirred for 1 h at room temperature. Solids were removed by filtration through Celite and washed with additional methanol (20 mL). The filtrate was concentrated and the residue was taken up in ethyl acetate (30 mL), washed with water (20 mL), dried (MgSO$_4$) and concentrated. Purification by chromatography (SiO$_2$, 1:1 dichloromethane/ethyl acetate) provided 240 mg (79%) of the title compound as a colorless oil. MS 215 (M+H)$^+$.

REFERENCE EXAMPLES 156–170

The compounds of Reference Examples 156–170, listed in the table below, are prepared by the method of Reference Example 155 by substituting the appropriate alkene for the (2E)-3-[4-(2-pyrimidinyl)phenyl]-2-propen-1-ol of Reference Example 155.

| Ref. Ex. | Compound | MS [(M + H)$^+$] |
|---|---|---|
| 156 | 4-pyrazinylbenzenepropanol | 215 |
| 157 | 4-(3-pyridazinyl)benzenepropanol | 215 |
| 158 | 4-(2-pyridinyl)benzenepropanol | 214 |
| 159 | 4-(1H-pyrazol-1-yl)benzenepropanol | 203 |
| 160 | 4-(1H-1,2,4-triazol-1-yl)benzenepropanol | 204 |
| 161 | 4-(1H-1,2,3-triazol-1-yl)benzenepropanol | 204 |
| 162 | 4-(1-methyl-1H-pyrazol-3-yl)benzenepropanol | 217 |
| 163 | 3-(2-quinolinyl)propanol | 188 |
| 164 | 3-(5-quinolinyl)propanol | 188 |
| 165 | 3-(6-quinolinyl)propanol | 188 |
| 166 | 3-(7-quinolinyl)propanol | 188 |
| 167 | 3-(6-quinoxalinyl)propanol | 189 |
| 168 | 4-(2-oxazolyl)benzenepropanol | 204 |
| 169 | 5-(2-pyridinyl)-2-thiophenepropanol | 220 |
| 170 | 5-(2-pyrimidinyl)-2-thiophenepropanol | 221 |

REFERENCE EXAMPLE 171

(2Z)-2-Fluoro-3-[4-(2-pyrimidinyl)phenyl]-2-propen-1-ol

Step A: (2Z)-2-Fluoro-3-[4-(2-pyrimidinyl)phenyl]-2-propenoic Acid Ethyl Ester

Triethyl 2-fluoro-2-phosphonoacetate (1.55 mL, 7.64 mmol) was added to a suspension of MgBr$_2$ (1.68 g, 9.12 mmol) in THF (20 mL). The resulting mixture was cooled to 0° C., triethylamine (1.20 mL, 8.61 mmol) was added, and stirring was continued for 1 h at 0° C. A solution of 4-(2-pyrimidinyl)-benzaldehyde (1.00 g, 5.43 mmol, prepared as described in WO 9828264) in THF (10 mL) was aded via cannula and an additional amount of THF (5 mL) was used to rinse the transfer flask and cannula. The resulting mixture was stirred for 3 h at 0° C., quenched with 10% aq. ammonium chloride (5 mL), and concentrated to a small volume. The concentrate was diluted with ethyl acetate (50 mL), washed with 10% aq. ammonium chloride, sat. aq. NaHCO$_3$, and brine (50 mL each), dried (MgSO$_4$), and concentrated. Purification by chromatography (SiO$_2$, 3:1 hexane/ethyl acetate) provided 1.27 g of the title compound as a 3:1 mixture with its E isomer. Recrystallization from 2-propanol provided 0.76 g (51%) of the title compound containing ca. 1% of the E isomer. MS 273 (M+H)$^+$.

Step B: (2Z)-2-Fluoro-3-[4-(2-pyrimidinyl)phenyl]-2-propen-1-ol

Diisobutylaluminum hydride (1.0 M solution in THF, 5.5 mL, 5.50 mmol) was added dropwise to a 0° C. solution of the product from step A (500 mg, 1.84 mmol) in methylene chloride (15 mL). The resulting solution was stirred for 10 min at 0° C., quenched with methanol (0.25 mL) followed by 15% aq. Rochelle salt (20 mL), and allowed to stir at room temperature for 4 h. The layers were separated and the aqueous layer was extracted with methylene chloride (20 mL). The combined organic layers were dried (MgSO$_4$) and concentrated to provide 415 mg (98%) of the title compound as a colorless solid. MS 231 (M+H)$^+$.

REFERENCE EXAMPLES 172–234

The compounds of Reference Examples 172–234, listed in the table below, are prepared by the method of Reference Example 171 by substituting the appropriate aldehyde for the 4-(2-pyrimidinyl)benzaldehyde of Reference Example 171.

| Ref. Ex. | Compound | [(M + H)$^+$] |
|---|---|---|
| 172 | (2Z)-2-fluoro-3-[4-(4-pyrimidinyl)phenyl]-2-propen-1-ol | 231 |
| 173 | (2Z)-2-fluoro-3-[4-(5-pyrimidinyl)phenyl]-2-propen-1-ol | 231 |
| 174 | (2Z)-2-fluoro-3-[3-(2-pyrimidinyl)phenyl]-2-propen-1-ol | 231 |
| 175 | (2Z)-2-fluoro-3-[4-(2-pyridinyl)phenyl]-2-propen-1-ol | 230 |
| 176 | (2Z)-2-fluoro-3-[4-(3-pyridinyl)phenyl]-2-propen-1-ol | 230 |
| 177 | (2Z)-2-fluoro-3-[4-(4-pyridinyl)phenyl]-2-propen-1-ol | 230 |
| 178 | (2Z)-2-fluoro-3-(4-pyrazinylphenyl)-2-propen-1-ol | 231 |
| 179 | (2Z)-2-fluoro-3-[4-(3-pyridazinyl)phenyl]-2-propen-1-ol | 231 |
| 180 | (2Z)-2-fluoro-3-[4-(1H-pyrazol-1-yl)phenyl]-2-propen-1-ol | 219 |
| 181 | (2Z)-2-fluoro-3-[4-(1H-1,2,4-triazol-1-yl)phenyl]-2-propen-1-ol | 220 |
| 182 | (2Z)-2-fluoro-3-[4-(4H-1,2,4-triazol-4-yl)phenyl]-2-propen-1-ol | 220 |
| 183 | (2Z)-2-fluoro-3-[4-(1H-1,2,3-triazol-1-yl)phenyl]-2-propen-1-ol | 220 |
| 184 | (2Z)-2-fluoro-3-[4-(1H-imidazol-1-yl)phenyl]-2-propen-1-ol | 219 |
| 185 | (2Z)-2-fluoro-3-[4-(1-methyl-1H-pyrazol-3-yl)phenyl]-2-propen-1-ol | 233 |
| 186 | (2Z)-2-fluoro-3-[4-(1-methyl-1H-pyrazol-5-yl)phenyl]-2-propen-1-ol | 233 |
| 187 | (2Z)-2-fluoro-3-[3-methoxy-4-(1H-pyrazol-1-yl)phenyl]-2-propen-1-ol | 249 |
| 188 | (2Z)-2-fluoro-3-[3-fluoro-4-(1H-pyrazol-1-yl)phenyl]-2-propen-1-ol | 237 |
| 189 | (2Z)-2-fluoro-3-[2-fluoro-4-(1H-pyrazol-1-yl)phenyl]-2-propen-1-ol | 237 |
| 190 | (2Z)-2-fluoro-3-[3-fluoro-4-(1H-1,2,4-triazol-1-yl)phenyl]-2-propen-1-ol | 237 |
| 191 | (2Z)-2-fluoro-3-(1-phenyl-1H-pyrazol-4-yl)-2-propen-1-ol | 219 |
| 192 | (2Z)-2-fluoro-3-[1-(2-pyrimidinyl)-1H-imidazol-4-yl]-2-propen-1-ol | 221 |
| 193 | (2Z)-2-fluoro-3-(1-pyrazinyl-1H-imidazol-4-yl)-2-propen-1-ol | 221 |

-continued

| Ref. Ex. | Compound | [(M + H)+] |
|---|---|---|
| 194 | (2Z)-2-fluoro-3-(2-quinolinyl)-2-propen-1-ol | 204 |
| 195 | (2Z)-2-fluoro-3-(3-quinolinyl)-2-propen-1-ol | 204 |
| 196 | (2Z)-2-fluoro-3-(4-quinolinyl)-2-propen-1-ol | 204 |
| 197 | (2Z)-2-fluoro-3-(5-quinolinyl)-2-propen-1-ol | 204 |
| 198 | (2Z)-2-fluoro-3-(6-quinolinyl)-2-propen-1-ol | 204 |
| 199 | (2Z)-2-fluoro-3-(7-quinolinyl)-2-propen-1-ol | 204 |
| 200 | (2Z)-2-fluoro-3-(8-quinolinyl)-2-propen-1-ol | 204 |
| 201 | (2Z)-2-fluoro-3-(2-quinoxalinyl)-2-propen-1-ol | 205 |
| 202 | (2Z)-2-fluoro-3-(6-quinoxalinyl)-2-propen-1-ol | 205 |
| 203 | (2Z)-2-fluoro-3-(4-isoquinolinyl)-2-propen-1-ol | 204 |
| 204 | (2Z)-2-fluoro-3-(6-bromo-3-pyridinyl)-2-propen-1-ol | 232,234 |
| 205 | (2Z)-2-fluoro-3-[4-(2-oxazolyl)phenyl]-2-propen-1-ol | 220 |
| 206 | (2Z)-2-fluoro-3-[4-(5-oxazolyl)phenyl]-2-propen-1-ol | 220 |
| 207 | (2Z)-2-fluoro-3-[4-(2-thiazolyl)phenyl]-2-propen-1-ol | 236 |
| 208 | (2Z)-2-fluoro-3-[4-(2-thienyl)phenyl]-2-propen-1-ol | 235 |
| 209 | (2Z)-2-fluoro-3-[4-(3-isoxazolyl)phenyl]-2-propen-1-ol | 220 |
| 210 | (2Z)-2-fluoro-3-[4-(1,3,4-oxadiazol-2-yl)phenyl]-2-propen-1-ol | 221 |
| 211 | (2Z)-2-fluoro-3-[4-(1,2,4-oxadiazol-3-yl)phenyl]-2-propen-1-ol | 221 |
| 212 | (2Z)-2-fluoro-3-[4-(1,2,4-oxadiazol-5-yl)phenyl]-2-propen-1-ol | 221 |
| 213 | (2Z)-2-fluoro-3-(1-methyl-1H-benzimidazol-2-yl)-2-propen-1-ol | 207 |
| 214 | (2Z)-2-fluoro-3-[4-(5-fluoro-2-pyrimidinyl)phenyl]-2-propen-1-ol | 249 |
| 215 | (2Z)-2-fluoro-3-[4-(4-methyl-2-pyrimidinyl)phenyl]-2-propen-1-ol | 245 |
| 216 | (2Z)-2-fluoro-3-[4-(4-methoxy-2-pyrimidinyl)phenyl]-2-propen-1-ol | 261 |
| 217 | (2Z)-2-fluoro-3-[4-(6-methoxy-3-pyridazinyl)phenyl]-2-propen-1-ol | 261 |
| 218 | (2Z)-2-fluoro-3-[5-(2-pyridinyl)-2-thienyl]-2-propen-1-ol | 236 |
| 219 | (2Z)-2-fluoro-3-[5-(3-pyridinyl)-2-thienyl]-2-propen-1-ol | 236 |
| 220 | (2Z)-2-fluoro-3-[5-(4-pyridinyl)-2-thienyl]-2-propen-1-ol | 236 |
| 221 | (2Z)-2-fluoro-3-[5-(2-pyrimidinyl)-2-thienyl]-2-propen-1-ol | 237 |
| 222 | (2Z)-2-fluoro-3-(5-pyrazinyl-2-thienyl)-2-propen-1-ol | 237 |
| 223 | (2Z)-2-fluoro-3-[4-(2-pyridinyl)-2-thienyl]-2-propen-1-ol | 236 |
| 224 | (2Z)-2-fluoro-3-[4-(3-pyridinyl)-2-thienyl]-2-propen-1-ol | 236 |
| 225 | (2Z)-2-fluoro-3-[4-(4-pyridinyl)-2-thienyl]-2-propen-1-ol | 236 |
| 226 | (2Z)-2-fluoro-3-[4-(2-pyrimidinyl)-2-thienyl]-2-propen-1-ol | 237 |
| 227 | (2Z)-2-fluoro-3-(4-pyrazinyl-2-thienyl)-2-propen-1-ol | 237 |
| 228 | (2Z)-2-fluoro-3-[5-(2-pyridinyl)-3-thienyl]-2-propen-1-ol | 236 |
| 229 | (2Z)-2-fluoro-3-[5-(2-pyrimidinyl)-3-thienyl]-2-propen-1-ol | 237 |
| 230 | (2Z)-2-fluoro-3-(5-pyrazinyl-3-thienyl)-2-propen-1-ol | 237 |
| 231 | (2Z)-2-fluoro-3-(2-phenyl-5-pyrimidinyl)-2-propen-1-ol | 231 |
| 232 | (2Z)-2-fluoro-3-[2,2'-bithiophen]-5-yl-2-propen-1-ol | 241 |
| 233 | (2Z)-2-fluoro-3-[4-(2-pyrimidinyloxy)phenyl]-2-propen-1-ol | 247 |
| 234 | (2Z)-2-fluoro-3-[2-fluoro-4-(2-pyrimidinyl)phenyl]-2-propen-1-ol | 249 |

REFERENCE EXAMPLE 235

[4-(3-hydroxy-1-propynyl)phenyl]boronic Acid

Pyrrolidine (100 mL) was added to a mixture of 4-iodophenylboronic acid (19.83 g, 80.01 mol) and Pd(Ph$_3$P)$_4$ (0.93 g, 0.80 mmol) and the mixture was stirred for 5 min to give a solution. The solution was cooled to 0° C. and propargyl alcohol (9.4 mL, 161.5 mol) was added. The resulting solution was stirred for 1 h at 0° C. and 18 h at room temperature and then concentrated in vacuo. The residue was diluted with 2 N NaOH (200 ml), washed with dichloromethane (2×100 mL), cooled to 0° C., and acidified with 10% HCl. The precipitated solids were isolated by filtration, washed with water and dried in vacuo to provided 12.76 g (91%) of the title compound as a tan solid. MS 175 (M–H)−.

REFERENCE EXAMPLE 236

[4-(4-hydroxy-1-butynyl)phenyl]boronic Acid

The title compound was prepared by a procedure analogous to Reference Example 235 by substituting 3-butyn-1-ol for the propargyl alcohol of Reference Example 235. MS 189 (M–H)−.

REFERENCE EXAMPLE 237

[4-(5-hydroxy-1-pentynyl)phenyl]boronic Acid

The title compound was prepared by a procedure analogous to Reference Example 235 by substituting 4-pentyn-1-ol for the propargyl alcohol of Reference Example 235. MS 203 (M–H)−.

REFERENCE EXAMPLE 238

[4-[(1E)-3-hydroxy-1-propenyl]phenyl]boronic Acid

Lithium aluminum hydride (1.0 M solution in THF, 19.0 mL, 19.0 mmol) was added dropwise over 10 min to a solution of [4-(3-hydroxy-1-propynyl)phenyl]boronic acid (1.06 mg, 6.02 mmol, prepared as described in Reference Example 235) in THF (50 mL) with vigorous stirring. The resulting suspension was heated to reflux for 3 h, cooled to 0° C., cautiously quenched with water (2 mL), stirred for 10 min, and concentrated to dryness in vacuo. Water (20 mL) was added to the residue, the mixture was cooled to 0° C., acidified with 20% H$_2$SO$_4$ (10 mL), and stirred for 10 min at 0° C. The solids were removed by filtration, washed with water, and allowed to air-dry. Recrystallization from water provided 0.70 g (69%) of the title compound as colorless crystals. MS 177 (M–H)−.

REFERENCE EXAMPLE 239

3-[4-(2-pyrimidinyl)phenyl]-2-propyn-1-ol

A mixture of 2-bromopyrimidine (1.00 g, 6.29 mmol) and Pd(Ph$_3$P)$_4$ (220 mg, 0.19 mmol) in ethylene glycol dimethyl ether (25 mL) was stirred for 10 min, a slurry of sodium bicarbonate (1.58 g, 18.81 mmol) and [4-(3-hydroxy-1-propynyl)phenyl]boronic acid (1.32 g, 7.50 mmol, prepared as described in Reference Example 235) in water (25 mL) was added, and the mixture was heated to reflux for 4 h. The cooled reaction mixture was diluted with methylene chloride (100 mL) and washed with water (100 mL). The aqueous layer was extracted with dichloromethane (25 mL) and the combined organic layers were dried (MgSO$_4$) and concentrated. Purification by chromatography (SiO$_2$, 3:2 hexane/ethyl acetate) provided 1.04 g (79%) of the title compound as a yellow solid. MS 211 (M+H)$^+$.

REFERENCE EXAMPLE 240

4-[4-(2-pyrimidinyl)phenyl]-3-butyn-1-ol

The title compound is prepared by a procedure analogous to Reference Example 239 by substituting [4-(4-hydroxy-1-butynyl)phenyl]boronic acid (prepared as described in Reference Example 236) for the [4-(3-hydroxy-1-propynyl) phenyl]boronic acid of Reference Example 239. MS 225 (M+H)$^+$.

REFERENCE EXAMPLE 241

5-[4-(2-pyrimidinyl)phenyl]-4-pentyn-1-ol

The title compound is prepared by a procedure analogous to Reference Example 239 by substituting [4-(5-hydroxy-1-pentynyl)phenyl]boronic acid (prepared as described in Reference Example 237) for the [4-(3-hydroxy-1-propynyl) phenyl]boronic acid of Reference Example 239. MS 239 (M+H)$^+$.

REFERENCE EXAMPLES 242–247

The compounds of Reference Examples 242–247, listed in the table below, are prepared by the method of Reference Example 239 by substituting the appropriate brominated or iodinated heterocycle for the 2-bromopyrimidine of Reference Example 239.

| Ref. Ex. | Compound | MS [(M + H)$^+$] |
|---|---|---|
| 242 | 3-[4-(5-pyrimidinyl)phenyl]-2-propyn-1-ol | 211 |
| 243 | 3-[4-(2-Pyridinyl)phenyl]-2-propyn-1-ol | 210 |
| 244 | 3-[4-(3-Pyridinyl)phenyl]-2-propyn-1-ol | 210 |
| 245 | 3-[4-(4-Pyridinyl)phenyl]-2-propyn-1-ol | 210 |
| 246 | 3-[4-(4-Methyl-2-pyrimidinyl)phenyl]-2-propyn-1-ol | 225 |
| 247 | 3-[4-(5-Bromo-2-pyrimidinyl)phenyl]-2-propyn-1-ol | 289,291 |

REFERENCE EXAMPLE 248

3-(4-pyrazinylphenyl)-2-propyn-1-ol

Chloropyrazine (0.78 mL, 8.73 mmol), 1 M aq. Na2CO3 (10 mL), and ethanol (5 mL) were successively added to a mixture of [1,4-bis(diphenylphosphino)butane]palladium (II) dichloride (0.30 g, 0.50 mmol) and [4-(3-hydroxy-1-propynyl)phenyl]boronic acid (1.85 g, 10.51 mmol, prepared as described in Reference Example 235) in toluene (20 mL) and the resulting mixture was heated to reflux for 3 h. The cooled reaction mixture was diluted with ethyl acetate (50 mL) and the organic layer was separated, washed with brine (50 mL), dried (MgSO$_4$) and concentrated. Purification by chromatography (SiO$_2$, 97:3 dichloromethane/methanol) followed by a second chromatography (SiO$_2$, 1:1 hexane/ethyl acetate) provided 1.22 g (66%) of the title compound as a colorless solid. MS 211 (M+H)$^+$.

REFERENCE EXAMPLES 249–255

The compounds of Reference Examples 249–255, listed in the table below, are prepared by the method of Reference Example 248 by substituting the appropriate chlorinated heterocycle for the chloropyrazine of Reference Example 248.

| Ref. Ex. | Compound | MS [(M + H)$^+$] |
|---|---|---|
| 249 | 3-[4-(3-Pyridazinyl)phenyl]-2-propyn-1-ol | 211 |
| 250 | 3-[4-(4-Methoxy-2-pyrimidinyl)phenyl]-2-propyn-1-ol | 241 |
| 251 | 3-[4-(5-Fluoro-2-pyrimidinyl)phenyl]-2-propyn-1-ol | 229 |
| 252 | 3-[4-(5-Ethyl-2-pyrimidinyl)phenyl]-2-propyn-1-ol | 239 |
| 253 | 3-[4-(6-methyl-3-pyridazinyl)phenyl]-2-propyn-1-ol | 225 |
| 254 | 3-[4-(6-methoxy-3-pyridazinyl)phenyl]-2-propyn-1-ol | 241 |
| 255 | 3-[4-(4-pyrimidinyl)phenyl]-2-propyn-1-ol | 211 |

REFERENCE EXAMPLES 256–293

The compounds of Reference Examples 256–293, listed in the table below, are prepared by the method of Step A of Reference Example 20 by substituting the appropriate brominated or iodinated compound for the 1-(4-bromophenyl)-1H-pyrazole of Step A of Reference Example 20.

| Ref. Ex. | Compound | MS [(M + H)$^+$] |
|---|---|---|
| 256 | 3-[4-(1H-pyrazol-1-yl)phenyl]-2-propyn-1-ol | 199 |
| 257 | 3-[4-(1H-1,2,4-triazol-1-yl)phenyl]-2-propyn-1-ol | 200 |
| 258 | 3-[4-(4H-1,2,4-triazol-4-yl)phenyl]-2-propyn-1-ol | 200 |
| 259 | 3-[4-(1H-1,2,3-triazol-1-yl)phenyl]-2-propyn-1-ol | 200 |
| 260 | 3-[4-(1H-imidazol-1-yl)phenyl]-2-propyn-1-ol | 199 |
| 261 | 3-[4-(1-methyl-1H-pyrazol-3-yl)phenyl]-2-propyn-1-ol | 213 |
| 262 | 3-[4-(1-methyl-1H-pyrazol-5-yl)phenyl]-2-propyn-1-ol | 213 |
| 263 | 3-(1-phenyl-1H-pyrazol-4-yl)-2-propyn-1-ol | 199 |
| 264 | 3-(5-quinolinyl)-2-propyn-1-ol | 184 |
| 265 | 3-(6-quinolinyl)-2-propyn-1-ol | 184 |
| 266 | 3-(7-quinolinyl)-2-propyn-1-ol | 184 |
| 267 | 3-(6-quinoxalinyl)-2-propyn-1-ol | 185 |
| 268 | 3-[4-(2-oxazolyl)phenyl]-2-propyn-1-ol | 200 |
| 269 | 3-[4-(5-oxazolyl)phenyl]-2-propyn-1-ol | 200 |
| 270 | 3-[4-(2-thiazolyl)phenyl]-2-propyn-1-ol | 216 |
| 271 | 3-[4-(2-thienyl)phenyl]-2-propyn-1-ol | 215 |
| 272 | 3-[4-(3-isoxazolyl)phenyl]-2-propyn-1-ol | 200 |
| 273 | 3-[4-(1,3,4-oxadiazol-2-yl)phenyl]-2-propyn-1-ol | 201 |
| 274 | 3-[4-(1,2,4-oxadiazol-3-yl)phenyl]-2-propyn-1-ol | 201 |
| 275 | 3-[4-(1,2,4-oxadiazol-5-yl)phenyl]-2-propyn-1-ol | 201 |
| 276 | 3-(1-methyl-1H-benzimidazol-2-yl)-2-propyn-1-ol | 187 |
| 277 | 3-[5-(2-pyridinyl)-2-thienyl]-2-propyn-1-ol | 216 |
| 278 | 3-[5-(3-pyridinyl)-2-thienyl]-2-propyn-1-ol | 216 |
| 279 | 3-[5-(4-pyridinyl)-2-thienyl]-2-propyn-1-ol | 216 |
| 280 | 3-[5-(2-pyrimidinyl)-2-thienyl]-2-propyn-1-ol | 217 |
| 281 | 3-[5-(4-pyrimidinyl)-2-thienyl]-2-propyn-1-ol | 217 |
| 282 | 3-[5-(5-pyrimidinyl)-2-thienyl]-2-propyn-1-ol | 217 |
| 283 | 3-(5-pyrazinyl-2-thienyl)-2-propyn-1-ol | 217 |
| 284 | 3-[4-(2-pyridinyl)-2-thienyl]-2-propyn-1-ol | 216 |
| 285 | 3-[4-(3-pyridinyl)-2-thienyl]-2-propyn-1-ol | 216 |
| 286 | 3-[4-(4-pyridinyl)-2-thienyl]-2-propyn-1-ol | 216 |
| 287 | 3-[4-(2-pyrimidinyl)-2-thienyl]-2-propyn-1-ol | 217 |
| 288 | 3-[4-(4-pyrimidinyl)-2-thienyl]-2-propyn-1-ol | 217 |
| 289 | 3-[4-(5-pyrimidinyl)-2-thienyl]-2-propyn-1-ol | 217 |
| 290 | 3-[5-(2-pyridinyl)-3-thienyl]-2-propyn-1-ol | 216 |

-continued

| Ref. Ex. | Compound | MS [(M + H)+] |
|---|---|---|
| 291 | 3-[5-(3-pyridinyl)-3-thienyl]-2-propyn-1-ol | 216 |
| 292 | 3-(2-phenyl-5-pyrimidinyl)-2-propyn-1-ol | 211 |
| 293 | 3-[4-(2-pyrimidinyloxy)phenyl]-2-propyn-1-ol | 227 |

REFERENCE EXAMPLE 294

3-[3-(2-pyridinyl)-5-isoxazolyl]-2-propyn-1-ol

A solution of 2-(5-iodo-3-isoxazolyl)pyridine (prepared as described in WO0232919, 1.38 g, 5 mmol) and dichlorobis(triphenylphosphine)palladium(II) (35 mg, 0.05 mmol) in 8 mL triethylamine was degassed with nitrogen. Propargyl alcohol (560 mg, 10 mmol) was added and the mixture was heated at 65° C. for 16 h. The reaction mixture was cooled to room temperature, concentrated to remove the solvent. The residue was diluted with ethyl acetate (100 mL), washed with saturated NaHCO$_3$, water and brine. The organic layer was dried and concentrated. Purification by chromatography (SiO$_2$, 1:1 hexane/ethyl acetate) yielded 220 mg (22%) of the title compound. MS 201 (M+H)$^+$.

REFERENCE EXAMPLE 295

(2E)-3-[4-(5-bromo-2-pyrimidinyl)phenyl]-2-propen-1-ol

2 M aq. Na$_2$CO$_3$ (2 mL) was added to a mixture of 5-bromo-2-iodopyrimidine (0.57 g, 2.00 mmol), Pd(Ph$_3$P)$_4$ (23 mg, 0.020 mmol), and [4-[(1E)-3-hydroxy-1-propenyl]phenyl]boronic acid (360 mg, 2.02 mmol, prepared as described in Reference Example 238) in toluene (5 mL) and the resulting mixture was heated to reflux for 24 h. The cooled reaction mixture was diluted with ethyl acetate (20 mL) and the organic layer was separated, washed with brine (10 mL), dried (MgSO$_4$) and concentrated. Purification by chromatography (SiO$_2$, 3:1 hexane/ethyl acetate) provided 104 mg (18%) of the title compound as a yellow solid. MS 291, 293 (M+H)$^+$.

REFERENCE EXAMPLE 296

(2E)-3-[4-(5-ethyl-2-pyrimidinyl)phenyl]-2-propen-1-ol

1 M aq. Na$_2$CO$_3$ (2 mL), and ethanol (1 mL) were successively added to a mixture of 2-chloro-5-ethylpyrimidine (0.30 mL, 2.47 mmol), [1,4-bis(diphenylphosphino)butane]palladium(II) dichloride (61 mg, 0.10 mmol) and [4-[(1E)-3-hydroxy-1-propenyl]phenyl]boronic acid (360 mg, 2.02 mmol, prepared as described in Reference Example 238) in toluene (4 mL) and the resulting mixture was heated to reflux for 18 h. The cooled reaction mixture was diluted with ethyl acetate (10 mL) and the organic layer was separated, washed with brine (10 mL), dried (MgSO$_4$) and concentrated. Purification by chromatography (SiO$_2$, 3:2 hexane/ethyl acetate) provided 220 mg (45%) of the title compound as a yellow solid. MS 241 (M+H)$^+$.

REFERENCE EXAMPLES 297–299

The compounds of Reference Examples 297–299, listed in the table below, are prepared by the method of Reference Example 296 by substituting the appropriate chlorinated heterocycle for the 2-chloro-5-ethylpyrimidine of Reference Example 296.

| Ref. Ex. | Compound | MS [(M + H)+] |
|---|---|---|
| 297 | (2E)-3-[4-(6-methyl-3-pyridazinyl)phenyl]-2-propen-1-ol | 227 |
| 298 | (2E)-3-[4-(6-methoxy-3-pyridazinyl)phenyl]-2-propen-1-ol | 243 |
| 299 | (2E)-3-[4-(5-Fluoro-2-pyrimidinyl)phenyl]-2-propen-1-ol | 231 |

REFERENCE EXAMPLE 300

[4-(2-pyrimidinyl)phenyl]-2-propynal

A mixture of the Dess-Martin reagent (1.59 g, 3.75 mmol) and 3-[4-(2-pyrimidinyl)phenyl]-2-propyn-1-ol (525 mg, 2.50 mmol, prepared as described in Reference Example 239) in dichloromethane (15 mL) was stirred at room temperature for 30 min. Aqueous 10% Na$_2$S$_2$O$_3$ (25 mL) and aq. sat. NaHCO$_3$ (15 mL) were added, the mixture was stirred for 5 min, the layers were separated, and the aqueous layer was extracted with dichloromethane (10 mL). The combined organic layers were dried (MgSO$_4$) and concentrated to provide 465 mg (89%) of the title compound as a yellow solid. MS 209 (M+H)$^+$.

REFERENCE EXAMPLES 301–356

The compounds of Reference Examples 301–356, listed in the table below, are prepared by the method of Reference Example 300 by substituting the appropriate alcohol for the [4-(2-pyrmidinyl)phenyl]-2-propyn-1-ol of Reference Example 300.

| Ref. Ex. | Compound | MS [(M + H)+] |
|---|---|---|
| 301 | 3-[4-(4-pyrimidinyl)phenyl]-2-propynal | 209 |
| 302 | 3-[4-(5-pyrimidinyl)phenyl]-2-propynal | 209 |
| 303 | 3-[4-(2-pyridinyl)phenyl]-2-propynal | 208 |
| 304 | 3-[4-(3-pyridinyl)phenyl]-2-propynal | 208 |
| 305 | 3-[4-(4-pyridinyl)phenyl]-2-propynal | 208 |
| 306 | 3-(4-pyrazinylphenyl)-2-propynal | 209 |
| 307 | 3-[4-(3-pyridazinyl)phenyl]-2-propynal | 209 |
| 308 | 3-[4_(1H-1,2,4-triazol-1-yl)phenyl]-2-propynal | 198 |
| 309 | 3-[4-(4H-1,2,4-triazol-4-yl)phenyl]-2-propynal | 198 |
| 310 | 3-[4-(1H-1,2,3-triazol-1-yl)phenyl]-2-propynal | 198 |
| 311 | 3-[4-(1H-imidazol-1-yl)phenyl]-2-propynal | 197 |
| 312 | 3-[4-(1-methyl-1H-pyrazol-3-yl)phenyl]-2-propynal | 211 |
| 313 | 3-[4-(1-methyl-1H-pyrazol-5-yl)phenyl]-2-propynal | 211 |
| 314 | 3-(1-phenyl-1H-pyrazol-4-yl)-2-propynal | 197 |
| 315 | 3-(2-quinolinyl)-2-propynal | 182 |
| 316 | 3-(4-quinolinyl)-2-propynal | 182 |
| 317 | 3-(5-quinolinyl)-2-propynal | 182 |
| 318 | 3-(6-quinolinyl)-2-propynal | 182 |
| 319 | 3-(7-quinolinyl)-2-propynal | 182 |
| 320 | 3-(8-quinolinyl)-2-propynal | 182 |
| 321 | 3-(2-quinoxalinyl)-2-propynal | 183 |
| 322 | 3-(6-quinoxalinyl)-2-propynal | 183 |
| 323 | 3-(4-isoquinolinyl)-2-propynal | 182 |
| 324 | 3-[4-(2-oxazolyl)phenyl]-2-propynal | 198 |
| 325 | 3-[4-(5-oxazolyl)phenyl]-2-propynal | 198 |
| 326 | 3-[4-(2-thiazolyl)phenyl]-2-propynal | 214 |
| 327 | 3-[4-(2-thienyl)phenyl]-2-propynal | 213 |
| 328 | 3-[4-(3-isoxazolyl)phenyl]-2-propynal | 198 |
| 329 | 3-[4-(1,3,4-oxadiazol-2-yl)phenyl]-2-propynal | 199 |
| 330 | 3-[4-(1,2,4-oxadiazol-3-yl)phenyl]-2-propynal | 199 |

-continued

| Ref. Ex. | Compound | MS [(M + H)+] |
|---|---|---|
| 331 | 3-[4-(1,2,4-oxadiazol-5-yl)phenyl]-2-propynal | 199 |
| 332 | 3-(1-methyl-1H-benzimidazol-2-yl)-2-propynal | 185 |
| 333 | 3-[4-(5-bromo-2-pyrimidinyl)phenyl]-2-propynal | 287,289 |
| 334 | 3-[4-(5-fluoro-2-pyrimidinyl)phenyl]-2-propynal | 227 |
| 335 | 3-[4-(5-ethyl-2-pyrimidinyl)phenyl]-2-propynal | 237 |
| 336 | 3-[4-(4-methyl-2-pyrimidinyl)phenyl]-2-propynal | 223 |
| 337 | 3-[4-(4-methoxy-2-pyrimidinyl)phenyl]-2-propynal | 239 |
| 338 | 3-[4-(6-methyl-3-pyridazinyl)phenyl]-2-propynal | 223 |
| 339 | 3-[4-(6-methoxy-3-pyridazinyl)phenyl]-2-propynal | 239 |
| 340 | 3-[5-(2-pyridinyl)-2-thienyl]-2-propynal | 214 |
| 341 | 3-[5-(3-pyridinyl)-2-thienyl]-2-propynal | 214 |
| 342 | 3-[5-(4-pyridinyl)-2-thienyl]-2-propynal | 214 |
| 343 | 3-[5-(2-pyrimidinyl)-2-thienyl]-2-propynal | 215 |
| 344 | 3-[5-(4-pyrimidinyl)-2-thienyl]-2-propynal | 215 |
| 345 | 3-[5-(5-pyrimidinyl)-2-thienyl]-2-propynal | 215 |
| 346 | 3-(5-pyrazinyl-2-thienyl)-2-propynal | 215 |
| 347 | 3-[4-(2-pyridinyl)-2-thienyl]-2-propynal | 214 |
| 348 | 3-[4-(3-pyridinyl)-2-thienyl]-2-propynal | 214 |
| 349 | 3-[4-(4-pyridinyl)-2-thienyl]-2-propynal | 214 |
| 350 | 3-[4-(2-pyrimidinyl)-2-thienyl]-2-propynal | 215 |
| 351 | 3-[4-(4-pyrimidinyl)-2-thienyl]-2-propynal | 215 |
| 352 | 3-[4-(5-pyrimidinyl)-2-thienyl]-2-propynal | 215 |
| 353 | 3-[5-(2-pyridinyl)-3-thienyl]-2-propynal | 214 |
| 354 | 3-[5-(3-pyridinyl)-3-thienyl]-2-propynal | 214 |
| 355 | 3-(2-phenyl-5-pyrimidinyl)-2-propynal | 209 |
| 356 | 3-[4-(2-pyrimidinyloxy)phenyl]-2-propynal | 225 |

REFERENCE EXAMPLE 357

(2Z)-3-Fluoro-3-[4-(2-pyrimidinyl)phenyl]-2-propen-1-ol

Step A: (2Z)-3-Fluoro-3-[4-(2-pyrimidinyl)phenyl]-2-propenal

A mixture of 3-[4-(2-pyrimidinyl)phenyl]-2-propynal (210 mg, 1.01 mmol, prepared as described in Reference Example 300) and tetrabutylamonium dihydrogentrifluoride (50 wt % in 1,2-dichloroethane, 1.8 g, 3.0 mmol) was heated to 110° C. for 4 h. The cooled reaction mixture was diluted with ethyl acetate (30 mL), washed with aq. sat. NaHCO$_3$ (30 mL) and brine (30 mL), and filtered through a plug of SiO$_2$ (5 g). The SiO$_2$ plug was rinsed with additional ethyl acetate (30 mL) and the combined filtrates were concentrated. Purification by chromatography (SiO$_2$, 97:3 dichloromethane/ethyl acetate) provided 116 mg (51%) of the title compound as a colorless solid. MS 229 (M+H)$^+$. Also isolated were (2Z)-3-chloro-3-[4-(2-pyrmidinyl)phenyl]-2-propenal (10 mg, 4%, MS 245, 247 (M+H)$^+$) and recovered starting material (15 mg, 7%).

Step B: (2Z)-3-Fluoro-3-[4-(2-pyrimidinyl)phenyl]-2-propen-1ol

Diisobutylaluminum hydride (1.0 M solution in THF, 0.7 mL, 0.70 mmol) was added dropwise to a 0° C. suspension of the product from step A (108 mg, 0.47 mmol) in methylene chloride (5 mL). The resulting solution was stirred for 10 min at 0° C., quenched with methanol (0.2 mL) followed by 15% aq. Rochelle salt (10 mL), and allowed to stir at room temperature for 2 h. The layers were separated and the aqueous layer was extracted with methylene chloride (10 mL). The combined organic layers were dried (MgSO$_4$) and concentrated to provide 106 mg (97%) of the title compound as a colorless solid. MS 231 (M+H)$^+$.

REFERENCE EXAMPLES 358–417

The compounds of Reference Examples 358–417, listed in the table below, are prepared by the method of Reference Example 357 by substituting the appropriate alkynal for the [4-(2-pyrmidinyl)phenyl]-2-propynal of Reference Example 357.

| Ref. Ex. | Compound | MS [(M + H)+] |
|---|---|---|
| 358 | (2Z)-3-fluoro-3-[4-(2-pyrimidinyl)phenyl]-2-propen-1-ol | 231 |
| 359 | (2Z)-3-fluoro-3-[4-(4-pyrimidinyl)phenyl]-2-propen-1-ol | 231 |
| 360 | (2Z)-3-fluoro-3-[4-(5-pyrimidinyl)phenyl]-2-propen-1-ol | 231 |
| 361 | (2Z)-3-fluoro-3-[4-(2-pyridinyl)phenyl]-2-propen-1-ol | 230 |
| 362 | (2Z)-3-fluoro-3-[4-(3-pyridinyl)phenyl]-2-propen-1-ol | 230 |
| 363 | (2Z)-3-fluoro-3-[4-(4-pyridinyl)phenyl]-2-propen-1-ol | 230 |
| 364 | (2Z)-3-fluoro-3-(4-pyrazinylphenyl)-2-propen-1-ol | 231 |
| 365 | (2Z)-3-fluoro-3-[4-(3-pyridazinyl)phenyl]-2-propen-1-ol | 231 |
| 366 | (2Z)-3-fluoro-3-[4-(1H-pyrazol-1-yl)phenyl]-2-propen-1-ol | 219 |
| 367 | (2Z)-3-fluoro-3-[4-(1H-1,2,4-triazol-1-yl)phenyl]-2-propen-1-ol | 220 |
| 368 | (2Z)-3-fluoro-3-[4-(4H-1,2,4-triazol-4-yl)phenyl]-2-propen-1-ol | 220 |
| 369 | (2Z)-3-fluoro-3-[4-(1H-1,2,3-triazol-1-yl)phenyl]-2-propen-1-ol | 220 |
| 370 | (2Z)-3-fluoro-3-[4-(1H-imidazol-1-yl)phenyl]-2-propen-1-ol | 219 |
| 371 | (2Z)-3-fluoro-3-[4-(1-methyl-1H-pyrazol-3-yl)phenyl]-2-propen-1-ol | 233 |
| 372 | (2Z)-3-fluoro-3-[4-(1-methyl-1H-pyrazol-5-yl)phenyl]-2-propen-1-ol | 233 |
| 373 | (2Z)-3-fluoro-3-(1-phenyl-1H-pyrazol-4-yl)-2-propen-1-ol | 219 |
| 374 | (2Z)-3-fluoro-3-(2-quinolinyl)-2-propen-1-ol | 204 |
| 375 | (2Z)-3-fluoro-3-(3-quinolinyl)-2-propen-1-ol | 204 |
| 376 | (2Z)-3-fluoro-3-(4-quinolinyl)-2-propen-1-ol | 204 |
| 377 | (2Z)-3-fluoro-3-(5-quinolinyl)-2-propen-1-ol | 204 |
| 378 | (2Z)-3-fluoro-3-(6-quinolinyl)-2-propen-1-ol | 204 |
| 379 | (2Z)-3-fluoro-3-(7-quinolinyl)-2-propen-1-ol | 204 |
| 380 | (2Z)-3-fluoro-3-(8-quinolinyl)-2-propen-1-ol | 204 |
| 381 | (2Z)-3-fluoro-3-(2-quinoxalinyl)-2-propen-1-ol | 205 |
| 382 | (2Z)-3-fluoro-3-(6-quinoxalinyl)-2-propen-1-ol | 205 |
| 383 | (2Z)-3-fluoro-3-(4-isoquinolinyl)-2-propen-1-ol | 209 |
| 384 | (2Z)-3-fluoro-3-[4-(2-oxazolyl)phenyl]-2-propen-1-ol | 220 |
| 385 | (2Z)-3-fluoro-3-[4-(5-oxazolyl)phenyl]-2-propen-1-ol | 220 |
| 386 | (2Z)-3-fluoro-3-[4-(2-thiazolyl)phenyl]-2-propen-1-ol | 236 |
| 387 | (2Z)-3-fluoro-3-[4-(2-thienyl)phenyl]-2-propen-1-ol | 235 |
| 388 | (2Z)-3-fluoro-3-[4-(3-isoxazolyl)phenyl]-2-propen-1-ol | 220 |
| 389 | (2Z)-3-fluoro-3-[4-(1,3,4-oxadiazol-2-yl)phenyl]-2-propen-1-ol | 221 |
| 390 | (2Z)-3-fluoro-3-[4-(1,2,4-oxadiazol-3-yl)phenyl]-2-propen-1-ol | 221 |
| 391 | (2Z)-3-fluoro-3-[4-(1,2,4-oxadiazol-5-yl)phenyl]-2-propen-1-ol | 221 |
| 392 | (2Z)-3-fluoro-3-(1-methyl-1H-benzimidazol-2-yl)-2-propen-1-ol | 207 |
| 393 | (2Z)-3-fluoro-3-[4-(5-bromo-2-pyrimidinyl)phenyl]-2-propen-1-ol | 309, 311 |
| 394 | (2Z)-3-fluoro-3-[4-(5-fluoro-2-pyrimidinyl)phenyl]-2-propen-1-ol | 249 |
| 395 | (2Z)-3-fluoro-3-[4-(5-ethyl-2-pyrimidinyl)phenyl]-2-propen-1-ol | 259 |
| 396 | (2Z)-3-fluoro-3-[4-(4-methyl-2-pyrimidinyl)phenyl]-2-propen-1-ol | 245 |
| 397 | (2Z)-3-fluoro-3-[4-(4-methoxy-2-pyrimidinyl)phenyl]-2-propen-1-ol | 261 |
| 398 | (2Z)-3-fluoro-3-[4-(6-methyl-3-pyridazinyl)phenyl]-2-propen-1-ol | 245 |
| 399 | (2Z)-3-fluoro-3-[4-(6-methoxy-3-pyridazinyl)phenyl]-2-propen-1-ol | 261 |
| 400 | (2Z)-3-fluoro-3-[5-(2-pyridinyl)-2-thienyl]-2-propen-1-ol | 236 |
| 401 | (2Z)-3-fluoro-3-[5-(3-pyridinyl)-2-thienyl]-2-propen-1-ol | 236 |
| 402 | (2Z)-3-fluoro-3-[5-(4-pyridinyl)-2-thienyl]-2-propen-1-ol | 236 |
| 403 | (2Z)-3-fluoro-3-[5-(2-pyrimidinyl)-2-thienyl]-2-propen-1-ol | 237 |
| 404 | (2Z)-3-fluoro-3-[5-(4-pyrimidinyl)-2-thienyl]-2-propen-1-ol | 237 |
| 405 | (2Z)-3-fluoro-3-[5-(5-pyrimidinyl)-2-thienyl]-2-propen-1-ol | 237 |
| 406 | (2Z)-3-fluoro-3-(5-pyrazinyl-2-thienyl)-2-propen-1-ol | 237 |
| 407 | (2Z)-3-fluoro-3-[4-(2-pyridinyl)-2-thienyl]-2-propen-1-ol | 236 |
| 408 | (2Z)-3-fluoro-3-[4-(3-pyridinyl)-2-thienyl]-2-propen-1-ol | 236 |
| 409 | (2Z)-3-fluoro-3-[4-(4-pyridinyl)-2-thienyl]-2-propen-1-ol | 236 |
| 410 | (2Z)-3-fluoro-3-[4-(2-pyrimidinyl)-2-thienyl]-2-propen-1-ol | 237 |
| 411 | (2Z)-3-fluoro-3-[4-(4-pyrimidinyl)-2-thienyl]-2-propen-1-ol | 237 |
| 412 | (2Z)-3-fluoro-3-[4-(5-pyrimidinyl)-2-thienyl]-2-propen-1-ol | 237 |
| 413 | (2Z)-3-fluoro-3-[5-(2-pyridinyl)-3-thienyl]-2-propen-1-ol | 236 |

-continued

| Ref. Ex. | Compound | MS [(M + H)+] |
|---|---|---|
| 414 | (2Z)-3-fluoro-3-[5-(3-pyridinyl)-3-thienyl]-2-propen-1-ol | 236 |
| 415 | (2Z)-3-fluoro-3-(2-phenyl-5-pyrimidinyl)-2-propen-1-ol | 231 |
| 416 | (2Z)-3-fluoro-3-[2,2'-bithiophen]-5-yl-2-propen-1-ol | 241 |
| 417 | (2Z)-3-fluoro-3-[4-(2-pyrimidinyloxy)phenyl]-2-propen-1-ol | 247 |

REFERENCE EXAMPLE 418

(2E)-3-[4-(2-Pyrimidinyl)phenyl]-2-buten-1-ol

Step A: (2E)-3-[4-(2-Pyrimidinyl)phenyl]-2-butenoic Acid Ethyl Ester

Dioxane (2 mL) was added to a mixture of 2-(4-bromophenyl)pyrimidine (0.59 g, 2.51 mmol, prepared as described in U.S. Pat. No. 5,780,473), tri-t-butylphosphonium tetrafluoroborate (36 mg, 0.12 mmol), and tris(dibenzylideneacetone)dipalladium(0) (57 mg, 0.062 mmol). N-Methyldicyclohexylamine (0.64 mL, 2.99 mmol) and ethyl crotonate (0.62 mL, 4.99 mmol) were added and the mixture was stirred for 18 h at room temperature. The mixture was diluted with ethyl acetate, filtered through a small plug of silica gel which was washed with additional ethyl acetate, and the combined filtrates were concentrated. Purification by chromatography (SiO$_2$, 5:1 hexane/ethyl acetate) provided 0.47 g (70%) of the title compound as an off-white solid. MS 269 (M+H)+.

Step B: (2E)-3-[4-(2-Pyrimidinyl)phenyl]-2-buten-1-ol

Diisobutylaluminum hydride (1.0 M solution in THF, 3.4 mL, 3.40 mmol) was added dropwise to a 0° C. solution of the product from step A (300 mg, 1.12 mmol) in methylene chloride (10 mL). The resulting solution was stirred for 20 min at 0° C., quenched with methanol (0.2 mL) followed by 15% aq. Rochelle salt (20 mL) and dichloromethane (10 mL), and allowed to stir at room temperature for 18 h. The layers were separated and the aqueous layer was extracted with methylene chloride (10 mL). The combined organic layers were washed with brine (20 mL), dried (MgSO$_4$), and concentrated. Purification by chromatography (SiO$_2$, 3:2 hexane/ethyl acetate) provided 221 mg (87%) of the title compound as an off-white solid. MS 227 (M+H)+.

REFERENCE EXAMPLE 419

(2E)-3-(2-Phenyl-5-pyrimidinyl)-2-propen-1-ol

Step A: (2E)-3-(2-Phenyl-5-pyrimidinyl)-2-propenoic Acid Methyl Ester

Dioxane (1.3 mL) was added to a mixture of 5-bromo-2-phenylpyrimidine (310 mg, 1.32 mmol, prepared as described in Org. Lett. 2002, 4, 513), tri-t-butylphosphonium tetrafluoroborate (11 mg, 0.038 mmol), and tris(dibenzylideneacetone)dipalladium(0) (18 mg, 0.020 mmol). N-Methyldicyclohexylamine (0.31 mL, 1.45 mmol) and methyl acrylate (0.24 mL, 2.67 mmol) were added and the mixture was stirred for 72 h at room temperature. The mixture was diluted with ethyl acetate, filtered through a small plug of silica gel which was washed with additional ethyl acetate, and the combined filtrates were concentrated. The residue was triturated with 5:1 hexane/ethyl acetate and the solid was filtered and dried in vacuo to provide 178 mg (56%) of the title compound as an off-white solid. MS 241 (M+H)+.

Step B: (2E)-3-(2-Phenyl-5-pyrimidinyl)-2-propen-1-ol

Diisobutylaluminum hydride (1.0 M solution in THF, 2.1 mL, 2.10 mmol) was added dropwise to a 0° C. solution of the product from step A (165 mg, 0.69 mmol) in methylene chloride (5 mL). The resulting solution was stirred for 15 min at 0° C., quenched with methanol (0.5 mL) followed by 15% aq. Rochelle salt (15 mL) and dichloromethane (5 mL), and allowed to stir at room temperature for 18 h. The layers were separated and the aqueous layer was extracted with methylene chloride (5 mL). The combined organic layers were dried (MgSO$_4$) and concentrated to provide 140 mg (96%) of the title compound as a colorless solid. MS 213 (M+H)+.

REFERENCE EXAMPLE 420

4-Pyrazinyl benzeneacetaldehyde

Step A: 2-[4-[(E)-2-methoxyethenyl]phenyl]-pyrazine

Sodium hexamethyldisilazide (10.80 mL, 10.80 mmol, 1.0M in THF) was added to a suspension of methoxymethyltriphenylphosphonium chloride (3.72 g, 10.80 mmol) in THF (20 mL) at -10° C., and the red-orange mixture was stirred for 15 min at -10° C. A solution of 4-pyrazinylbenzaldehyde (1.00 g, 5.43 mmol) prepared as described in reference example 17) in THF (3 mL) was added dropwise, and stirring was continued at -10° C. for 1 h. The reaction mixture was quenched with sat. aq. NH$_4$Cl, extracted with ethyl acetate, the organic layer dried with Na$_2$SO$_4$, and concentrated in vacuo. Purification by medium pressure liquid chromatography (SiO$_2$, 3:1 hexane/ethyl acetate) yielded 820 mg (71%) of the title compound (E:Z= 1:1). MS 213 (M+H)+.

Step B: 4-Pyrazinylbenzeneacetaldehyde

Iodotrimethylsilane (0.46 mL, 3.30 mmol) was added dropwise to a suspension of the product from step A (175 mg, 0.82 mmol) and solid NaHCO$_3$ (100 mg, 1.18 mmol) in dichloromethane (5 mL) at rt. The reaction mixture was stirred at rt for 18 h, carefully quenched with sat. aq. NaHCO$_3$, extracted with dichloromethane, dried with Na$_2$SO$_4$, and concentrated in vacuo to give 110 mg (68%) of the title compound. The product was >95% pure as judged by its $^1$H NMR spectrum, and was used immediately in the next step without further purification. MS 199 (M+H)+.

REFERENCE EXAMPLES 421–440

The following compounds of Reference Examples 421–440, listed in the table below, were prepared by the method of Reference Example 420 by substituting the appropriate aldehyde for the 4-pyrazinylbenzaldehyde of Reference Example 420.

| Ref. Ex. | Compound | MS [(M + H)+] |
|---|---|---|
| 421 | 3-(2-pyrimidinyl)benzeneacetaldehyde | 199 |
| 422 | 2-fluoro-4-(2-pyrimidinyl)benzeneacetaldehyde | 217 |
| 423 | 4-(5-fluoro-2-pyrimidinyl)benzeneacetaldehyde | 217 |
| 424 | 4-(5-ethyl-2-pyrimidinyl)benzeneacetaldehyde | 227 |
| 425 | 2-phenyl-5-pyrimidineacetaldehyde | 199 |
| 426 | 4-methyl-2-phenyl-5-pyrimidineacetaldehyde | 213 |
| 427 | 4-(2-pyridinyl)benzeneacetaldehyde | 198 |
| 428 | 4-(1H-pyrazol-1-yl)benzeneacetaldehyde | 187 |
| 429 | 4-(1H-1,2,4-triazol-1-yl)benzeneacetaldehyde | 188 |
| 430 | 4-(1-methyl-1H-pyrazol-3-yl)benzeneacetaldehyde | 201 |
| 431 | 4-(1-methyl-1H-pyrazol-5-yl)benzeneacetaldehyde | 201 |
| 432 | 3-quinolineacetaldehyde | 172 |
| 433 | 6-quinolineacetaldehyde | 172 |
| 434 | 6-quinoxalineacetaldehyde | 173 |
| 435 | 4-(3-pyridazinyl)benzeneacetaldehyde | 199 |
| 436 | 4-(2-oxazolyl)benzeneacetaldehyde | 188 |

-continued

| Ref. Ex. | Compound | MS [(M + H)+] |
|---|---|---|
| 437 | 4-(2-thiazolyl)benzeneacetaldehyde | 204 |
| 438 | 4-(1,3,4-oxadiazol-2-yl)benzeneacetaldehyde | 189 |
| 439 | 5-methyl-3-phenyl-4-isoxazoleacetaldehyde | 202 |
| 440 | 4-(4-morpholinyl)benzeneacetaldehyde | 206 |

REFERENCE EXAMPLE 441

2-[4-(Tetrahydro-2,5-dimethoxy-3-furanyl)phenyl]
pyrimidine

Step A: 2-[4-(3-furanyl)phenyl]pyrimidine

A suspension of 3-furanboronic acid (672 mg, 6 mmol) in 2M aq. $Na_3CO_3$ (10 mL, 20 mmol) and ethanol (8 mL) was added to a solution of 2-(4-bromo-phenyl)pyrimidine (1.30 g, 5.55 mmol, prepared as described in U.S. Pat. No. 5,780,473) and tetrakis(triphenylphosphine)palladium (693 mg, 0.60 mmol) in DME (30 mL). The reaction mixture was refluxed for 18 h, cooled to rt, diluted with ethyl acetate, washed with sat. aq. $NaHCO_3$ and brine, dried with $Na_2SO_4$, and concentrated in vacuo. Purification by medium pressure liquid chromatography ($SiO_2$, 3:1 hexanes/ethyl acetate) gave 793 mg (65%) of the title compound. MS 223 (M+H)+.

Step B: 2-[4-(2,5-Dihydro-2,5-dimethoxy-3-furanyl)phenyl]
pyrimidine

To a slurry of 3-[4-(pyrimidin-2-yl)phenyl]furan and $Na_2CO_3$ (46 mg, 0.44 mmol) in methanol (0.8 mL) and benzene (0.8 mL) at −10° C. was added bromine (22 μL, 0.41 mmol) dropwise. The reaction mixture was stirred at −10° C. for 1 h, diluted with ethyl acetate, filtered, and concentrated in vacuo. Purification by medium pressure liquid chromatography ($SiO_2$, 2:1 hexanes/ethyl acetate) gave 95 mg (75%) of the title compound. MS 285 (M+H)+.

Step C: 2-[4-(Tetrahydro-2,5-dimethoxy-3-furanyl)phenyl]
pyrimidine

A mixture of 2,5-dihydro-2,5-dimethoxy-3-[4-(pyrimidin-2-yl)phenyl]furan (70 mg, 0.25 mmol), 10% Pd/C (20 mg), and ammonium formate (46 mg, 0.75 mmol) in methanol (1 mL) was stirred overnight. The reaction mixture was filtered through a fritted funnel, and concentrated in vacuo. The crude product was partitioned between ethyl acetate and sat. aq. $NaHCO_3$, the organic layer dried with $Na_2SO_4$, and concentrated in vacuo to give 60 mg (85%) of the title compound, which was used without further purification. MS 287 (M+H)+.

REFERENCE EXAMPLES 442–447

The compounds of Reference Examples 442–447, listed in the table below, are prepared by the method of Reference Example 104 by substituting the appropriate aldehyde for the (2E)-3-[4-(2-pyridinyl)phenyl]-2-propenal of Reference Example 104.

| Ref. Ex. | Compound | MS [(M + H)+] |
|---|---|---|
| 442 | 4-(2-pyrimidinyl)benzeneethanol | 201 |
| 443 | 4-pyrazinylbenzeneethanol | 201 |
| 444 | 5-(2-pyridinyl)-2-thiophenemethanol | 192 |
| 445 | 4-(1H-1,2,4-triazol-1-yl)benzeneethanol | 190 |

| Ref. Ex. | Compound | MS [(M + H)+] |
|---|---|---|
| 446 | 4-(1H-1,2,4-triazol-1-yl)benzenemethanol | 176 |
| 447 | 1-(2-pyrimidinyl)-1H-imidazole-4-methanol | 177 |

REFERENCE EXAMPLE 448

2-[4-[(1E)-3-(aminooxy)-1-propenyl]phenyl]
pyrimidine

Step A:

DEAD (0.95 mL, 6 mmol) was added dropwise at 0° C. to a stirred suspension of (2E)-3-[(4-(2-pyrimidinyl)phenyl)]-2-propen-1-ol (1.06 g, 5 mmol, prepared as described in Reference Example 65), triphenylphosphine (1.6 g, 6 mmol) and N-hydroxyphthalimide (1.0 g, 6 mmol) in THF (50 mL). The reaction mixture was stirred at room temperature for 16 h. The precipitate was collected and directly used in the next reaction without further purification.

Step B

The crude product from Step A was dissolved in 10 mL dichloromethane and one equivalent of methyl hydrazine was added dropwise. The reaction progress was followed by TLC. After the reaction, the precipitate was filtered and the filtrate was concentrated. Purification by chromatography ($SiO_2$, ethyl acetate/hexanes=3/1) yielded 500 mg (45%) of the title compound. MS 228 (M+H)+.

REFERENCE EXAMPLE 449

O-(2-phenylethyl)hydroxylamine

The title compound was prepared by a procedure analogous to Reference Example 448 by substituting phenyl ethyl alcohol for (2E)-3-[(4-(2-pyrimidinyl)phenyl)]-2-propen-1-ol of Reference Example 448. MS 138 (M+H)+.

REFERENCE EXAMPLE 450

O-(3-phenylpropyl)-hydroxylamine

The title compound was prepared by a procedure analogous to Reference Example 448 by substituting 3-phenyl-1-propanol for (2E)-3-[(4-(2-pyrimidinyl)phenyl)]-2-propen-1-ol of Reference Example 448. MS 152 (M+H)+.

REFERENCE EXAMPLE 451

2-[4-[2-(aminooxy)ethyl]phenyl]pyrimidine

The title compound was prepared by a procedure analogous to Reference Example 448 by substituting 4-(2-pyrimidinyl)benzeneethanol (prepared as described in Reference Example 442) for (2E)-3-[4-(2-pyrimidinyl)phenyl]-2-propen-1-ol of Reference Example 448. MS 216 (M+H)+.

REFERENCE EXAMPLE 452

2-[4-[(aminooxy)methyl]phenyl]pyrimdine

The title compound was prepared by a procedure analogous to Reference Example 448 by substituting 4-(2-pyrimidinyl)benzenemethanol (prepared as described in Step A of Reference Example 63) for (2E)-3-[4-(2-pyrimidinyl)phenyl]-2-propen-1-ol of Reference Example 448. MS 202 (M+H)+.

REFERENCE EXAMPLE 453

2-[4-[2-(aminooxy)ethyl]phenyl]pyrazine

The title compound was prepared by a procedure analogous to Reference Example 448 by substituting 4-pyrazinylbenzeneethanol (prepared as described in Reference Example 443) for (2E)-3-[4-(2-pyrimidinyl)phenyl]-2-propen-1-ol of Reference Example 448. MS 216 (M+H)+.

REFERENCE EXAMPLE 454

2-[4-[(1E)-3-(aminooxy)-1-propenyl]phenyl]pyrazine

The title compound was prepared by a procedure analogous to Reference Example 448 by substituting (2E)-3-(4-pyrazinylphenyl)-2-propen-1-ol (prepared as described in Reference Example 132) for (2E)-3-[4-(2-pyrimidinyl)phenyl]-2-propen-1-ol of Reference Example 448. MS 228 (M+H)+.

REFERENCE EXAMPLE 455

3-[(1E)-3-(aminooxy)-1-propenyl]pyridine

The title compound was prepared by a procedure analogous to Reference Example 448 by substituting (2E)-(3-pyridinyl)-2-propen-1-ol (prepared as described in J. Med. Chem. 1997, 40, 1845) for (2E)-3-[4-(2-pyrimidinyl)phenyl]-2-propen-1-ol of Reference Example 448. MS 151 (M+H)+.

REFERENCE EXAMPLE 456

2-[3-[(1E)-3-(aminooxy)-1-propenyl]phenyl]pyrimidine

The title compound was prepared by a procedure analogous to Reference Example 448 by substituting (2E)-3-[3-(2-pyrimidinyl)phenyl]-2-propen-1-ol (prepared as described in Reference Example 129) for (2E)-3-[4-(2-pyrimidinyl)phenyl]-2-propen-1-ol of Reference Example 448. MS 228 (M+H)+.

REFERENCE EXAMPLE 457

2-[4-[(1E)-3-(aminooxy)-1-propenyl]phenyl]pyridine

The title compound was prepared by a procedure analogous to Reference Example 448 by substituting (2E)-3-[4-(2-pyridinyl)phenyl]-2-propen-1-ol (prepared as described in Reference Example 104) for (2E)-3-[4-(2-pyrimidinyl)phenyl]-2-propen-1-ol of Reference Example 448. MS 227 (M+H)+.

REFERENCE EXAMPLE 458

3-[3-(aminooxy)-1-propynyl]quinoline

The title compound was prepared by a procedure analogous to Reference Example 448 by substituting 3-(3-quinolinyl)-2-propyn-1-ol (prepared as described in J. Med Chem. 1996, 39, 3179) for (2E)-3-[4-(2-pyrimidinyl)phenyl]-2-propen-1-ol of Reference Example 448. MS 199 (M+H)+.

REFERENCE EXAMPLE 459

3-[4-[(1E)-3-(aminooxy)-1-propenyl]phenyl]pyridazine

The title compound was prepared by a procedure analogous to Reference Example 448 by substituting (2E)-3-[4-(3-pyridazinyl)phenyl]-2-propen-1-ol (prepared as described in Reference Example 66) for (2E)-3-[4-(2-pyrimidinyl)phenyl]-2-propen-1-ol of Reference Example 448. MS 228 (M+H)+.

REFERENCE EXAMPLE 460

1-[4-[(1E)-3-(aminooxy)-1-propenyl]phenyl]-1H-pyrazole

The title compound was prepared by a procedure analogous to Reference Example 448 by substituting (2E)-3-[4-(1H-pyrazol-1-yl)phenyl]-2-propen-1-ol (prepared as described in Reference Example 133) for (2E)-3-[4-(2-pyrimidinyl)phenyl]-2-propen-1-ol of Reference Example 448. MS 216 (M+H)+.

REFERENCE EXAMPLE 461

2-[4-[3-(aminooxy)-1-propynyl]phenyl]pyrimidine

The title compound was prepared by a procedure analogous to Reference Example 448 by substituting 3-[4-(2-pyrimidinyl)phenyl]-2-propyn-1-ol (prepared as described in Reference Example 239) for (2E)-3-[4-(2-pyrimidinyl)phenyl]-2-propen-1-ol of Reference Example 448. MS 226 (M+H)+.

REFERENCE EXAMPLE 462

2-[4-[(aminooxy)methyl]phenyl]pyrazine

The title compound was prepared by a procedure analogous to Reference Example 448 by substituting 4-pyrazinylbenzenemethanol (prepared as described in Reference Example 126) for (2E)-3-[4-(2-pyrimidinyl)phenyl]-2-propen-1-ol of Reference Example 448. MS 202 (M+H)+.

REFERENCE EXAMPLE 463

2-[4-[3-(aminooxy)-1-propynyl]phenyl]pyrazine

The title compound was prepared by a procedure analogous to Reference Example 448 by substituting 3-(4-pyrazinylphenyl)-2-propyn-1-ol (prepared as described in Reference Example 248) for (2E)-3-[4-(2-pyrimidinyl)phenyl]-2-propen-1-ol of Reference Example 448. MS 226 (M+H)+.

REFERENCE EXAMPLE 464

4-(2-pyrimidinyl)benzenemethanethiol

Step A:

4-(2-pyrimidinyl)benzenemethanol (400 mg, 2.15 mmol, prepared as described in Step A of Reference Example 63) dissolved in dichloromethane (8 mL) at 0° C. To this solution was added PBr$_3$ (580 mg, 2.15 mmol) dropwise. The reaction mixture was stirred at room temperature for 2 h. Methanol (0.5 mL) was added and the mixture was stirred for 5 min. Solvent was removed under reduced pressure. The residue was dissolved in ethyl acetate (30 mL) and washed with cold 5% aqueous NaHCO$_3$. The organic layer was dried and concentrated. The crude product (450 mg) was directly used in the next step without further purification.

Step B:

The product from Step A (450 mg, 1.8 mmol) was dissolved in 3 mL N,N-dimethylacetamide. Potassium thioacetate (250 mg, 2.2 mmol) was added and the reaction mixture was stirred at room temperature for 4 h. Water (10 mL) was added and the mixture was extracted with dichloromethane (2×20 mL). The organic layer was combined, dried, and concentrated. Purification by chromatography (SiO$_2$, ethyl acetate/hexanes=1/2) yielded 300 mg (68%) of the title compound. MS 245 (M+H)$^+$.

Step C:

The product from Step B (130 mg, 0.53 mmol) was dissolved in 10 mL methanol. The solution was degassed with N$_2$. Aqueous potassium carbonate (0.45 g in 6 mL water) was added and the mixture was stirred at room temperature fro 3 h. Evaporation of methanol followed by extraction with methylene chloride (3×10 mL) gave the product (100 mg, 93%). MS 203 (M+H)$^+$.

REFERENCE EXAMPLE 465

4-(2-pyrimidinyl)benzenemethanethiol

The title compound was prepared by a procedure analogous to Reference Example 464 by substituting 4-(2-pyrimidinyl)benzeneethanol (prepared as described in Reference Example 442) for the 4-(2-pyrimidinyl)benzenemethanol of Reference Example 464. MS 217 (M+H)$^+$.

REFERENCE EXAMPLE 466

4-(1H-1,2,4-triazol-1-yl)benzenemethanethiol

The title compound was prepared by a procedure analogous to Reference Example 464 by substituting 4-(1H-1,2,4-triazol-1-yl)benzeneethanol (prepared as described in Reference Example 445) for the 4-(2-pyrimidinyl)benzenemethanol of Reference Example 464. MS 206 (M+H)$^+$.

REFERENCE EXAMPLE 467

(2E)-3-(3-guinolinyl)-2-propene-1-thiol

The title compound was prepared by a procedure analogous to Reference Example 464 by substituting (2E)-3-(3-quinolinyl)-2-propen-1-ol (prepared as described in Reference Example 138) for the 4-(2-pyrimidinyl)benzenemethanol of Reference Example 464. MS 202 (M+H)$^+$.

REFERENCE EXAMPLE 468

3-quinolinemethanethiol

The title compound was prepared by a procedure analogous to Reference Example 464 by substituting 3-quinolinemethanol (prepared as described in *Tetrahedron* 2000, 56, 2239) for the 4-(2-pyrimidinyl)benzenemethanol of Reference Example 464. MS 176 (M+H)$^+$.

REFERENCE EXAMPLE 469

5-(2-pyridinyl)-2-thiophenemethanethiol

The title compound was prepared by a procedure analogous to Reference Example 464 by substituting 5-(2-pyridinyl)-2-thiophenemethanol (prepared as described in Reference Example 444) for the 4-(2-pyrimidinyl)benzenemethanol of Reference Example 464. MS 208 (M+H)$^+$.

REFERENCE EXAMPLE 470

4-(1H-1,2,4-triazol-1-yl)benzenemethanethiol

The title compound was prepared by a procedure analogous to Reference Example 464 by substituting 4-(1H-1,2,4-triazol-1-yl)benzenemethanol (prepared as described in Reference Example 446) for the 4-(2-pyrimidinyl)benzenemethanol of Reference Example 464. MS 192 (M+H)$^+$.

REFERENCE EXAMPLE 471

1-(2-pyrimidinyl)-1H-imidazole-4-methanethiol

The title compound was prepared by a procedure analogous to Reference Example 464 by substituting 1-(2-pyrimidinyl)-1H-imidazole-4-methanol (prepared as described in Reference Example 447) for the 4-(2-pyrimidinyl)benzenemethanol of Reference Example 464. MS 193 (M+H)$^+$.

REFERENCE EXAMPLE 472

(2E)-3-[4-(2-pyrimidinyl)phenyl]-2-propene-1-thiol

The title compound was prepared by a procedure analogous to Reference Example 464 by substituting (2E)-3-[4-(2-pyrimidinyl)phenyl]-2-propen-1-ol (prepared as described in Reference Example 65) for the 4-(2-pyrimidinyl)benzenemethanol of Reference Example 464. MS 229 (M+H)$^+$.

REFERENCE EXAMPLE 473

(2E)-3-phenyl-2-propene-1-thiol

The title compound was prepared by a procedure analogous to Reference Example 464 by substituting (2E)-3-phenyl-2-propen-1-ol for the 4-(2-pyrimidinyl)benzenemethanol of Reference Example 464. MS 151 (M+H)$^+$.

REFERENCE EXAMPLE 474

3-(2-pyridinyl)-5-isoxazolecarboxaldehyde

The title compound is prepared by a procedure analogous to Reference Example 300 by substituting 3-(2-pyridinyl)-5-isoxazolemethanol (prepared as described in *J. Org. Chem.* 2000, 65, 2225) for the 3-[4-(2-pyrimidinyl)phenyl]-2-propyn-1-ol of Reference Example 300. MS 175 (M+H)$^+$.

REFERENCE EXAMPLE 475

(2Z)-3-fluoro-3-[3-(2-pyridinyl)-5-isoxazolyl]-2-propene-1-ol

The title compound is prepared by a procedure analogous to Reference Example 171 by substituting 3-(2-pyridinyl)-5-isoxazolecarboxaldehyde (prepared as described in Reference Example 474) for the 4-(2-pyrimidinyl)benzaldehyde of Reference Example 171. MS 221 (M+H)$^+$.

REFERENCE EXAMPLE 476

3-[3-(2-pyridinyl)-5-isoxazolyl]-2-propynal

The title compound is prepared by a procedure analogous to Reference Example 300 by substituting 3-[3-(2-pyridinyl)-5-isoxazolyl]-2-propyn-1-ol (prepared as described in Reference Example 294) for the 3-[4-(2-pyrimidinyl)phenyl]-2-propyn-1-ol of Reference Example 300. MS 199 (M+H)$^+$.

REFERENCE EXAMPLE 477

(2Z)-2-fluoro-3-[3-(2-pyridinyl)-5-isoxazolyl]-2-propene-1-ol

The title compound is prepared by a procedure analogous to Reference Example 357 by substituting 3-[3-(2- pyridinyl)-5-isoxazolyl]-2-propyn-1-ol (prepared as described in Reference Example 294) for the 3-[4-(2-pyrimidinyl)phenyl]-2-propynal of Reference Example 357. MS 221 (M+H)$^+$.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula 1

Formula 1

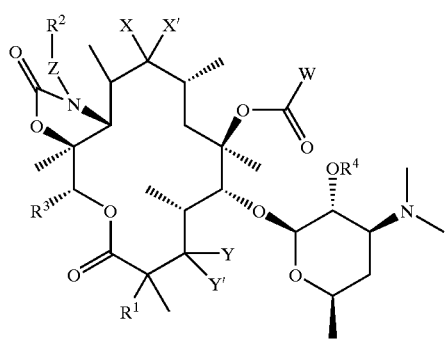

wherein
R$^1$ is selected from the group consisting of hydrogen, halogen, and hydroxy;
Z is selected from the group consisting of —NH—(CH$_2$)$_n$—, —(CH$_2$)$_n$—, —O—(CH$_2$)$_n$—, —NH—C$_1$–C$_6$alkenyl-, —C$_1$–C$_6$alkenyl-, —O—C$_1$–C$_6$alkenyl-, NH—C$_1$–C$_6$alkynyl-, —C$_1$–C$_6$alkynyl-, and —O—C$_1$–C$_6$alkynyl-, wherein n is an integer from 0 to 5;
R$^2$ is selected from the group consisting of hydrogen, aryl, and heteroaryl;
R$^3$ is selected from the group consisting of hydrogen, C$_1$–C$_{10}$alkyl, C$_2$–C$_{10}$-alkenyl, C$_2$–C$_{10}$-alkynyl, aryl, heteroaryl, heterocyclo, aryl(C$_1$–C$_{10}$)alkyl, aryl(C$_2$–C$_{10}$)alkenyl, aryl(C$_2$–C$_{10}$)alkynyl, heterocyclo(C$_1$–C$_{10}$)alkyl, heterocyclo(C$_2$–C$_{10}$)alkenyl, and heterocyclo(C$_2$–C$_{10}$)alkynyl, C$_3$–C$_6$-cycloalkyl, C$_5$–C$_8$-cycloalkenyl, alkoxyalkyl containing 1–6 carbon atoms in each alkyl or alkoxy group, and alkylthioalkyl containing 1–6 carbon atoms in each alkyl or thioalkyl group;
R$^4$ is hydrogen or a hydroxy protecting group;
W is selected from the group consisting of
  (1) a substituted pyrrole of the formula

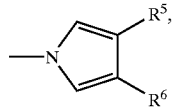

wherein
R$^5$ and R$^6$ are independently selected from the group consisting of hydrogen, CN, —C(NH)CHR$^{10}$R$^{11}$, nitro, —C(O)R$^7$, —C(O)OR$^7$, —C(O)NR$^7$R$^8$, —SO$_2$R$^7$, C$_1$–C$_8$-alkyl, C$_2$–C$_8$-alkenyl, C$_2$–C$_8$-alkynyl, C$_3$–C$_8$-cycloalkyl, C$_5$–C$_8$-cycloalkenyl, aryl, and heteroaryl, wherein
  R$^7$ and R$^8$ are independently selected from the group consisting of hydrogen, alkyl, alkenyl, alkynyl, cycloalkyl, aryl, heteroaryl, heterocyclo, aralkyl, heteroaralkyl, and heterocycloalkyl; and
  R$^{10}$ and R$^{11}$ are independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl, or R$^{10}$ and R$^{11}$, taken together with the atoms to which they are attached, form an optionally substituted 4–8 membered carbocyclic ring wherein the substituents are selected from the group consisting of C$_1$–C$_8$-alkyl, C$_2$–C$_8$-alkenyl, C$_2$–C$_8$-alkynyl, aryl, and heteroaryl;
(2) —OR$^9$, wherein
  R$^9$ is independently selected from the group consisting of C$_1$–C$_8$-alkyl, C$_3$–C$_8$-alkenyl, C$_3$–C$_8$-alkynyl, C$_3$–C$_8$-cycloalkyl, and C$_5$–C$_8$-cycloalkenyl;
(3) —NR$^{10}$OR$^{11}$, wherein
  R$^{10}$ and R$^{11}$ are independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl, or R$^{10}$ and R$^{11}$, taken together with the atoms to which they are attached, form an optionally substituted 5–8 membered heterocyclic ring wherein the substituents are selected from the group consisting of C$_1$–C$_8$-alkyl, C$_2$–C$_8$-alkenyl, C$_2$–C$_8$-alkynyl, aryl, and heteroaryl;
(4) —NR$^{12}$NR$^{13}$R$^{14}$, wherein
  R$^{12}$, R$^{13}$, and R$^{14}$ are independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl,
  or R$^{12}$ and R$^{13}$, taken together with the nitrogens to which they are attached, form an optionally substituted 5–8 membered heterocyclic ring, wherein the substituents are selected from the group consisting of C$_1$–C$_8$-alkyl, C$_2$–C$_8$-alkenyl, C$_2$–C$_8$-alkynyl, aryl, and heteroaryl;
  or R$^{13}$ and R$^{14}$, taken together with the nitrogen to which they are attached, form an optionally substituted 3–8 membered heterocyclic ring or an optionally substituted 5–10 membered heteroaryl ring, wherein the substituents are selected from the group consisting of C$_1$–C$_8$-alkyl, C$_2$–C$_8$-alkenyl, C$_2$–C$_8$-alkynyl, aryl, and heteroaryl;
(5) —NR$^{15}$N=CHR$^{13a}$, wherein
  R$^{15}$ is independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl; and
  R$^{13a}$ is independently selected from the group consisting of C$_1$–C$_8$-alkyl, C$_2$–C$_8$-alkenyl, C$_2$–C$_8$-alkynyl, C$_3$–C$_8$-cycloalkyl, C$_5$–C$_8$-cycloalkenyl, aryl, and heteroaryl;

(6) —NR$^{10}$NR$^{11}$C(O)R$^{16}$, wherein
R$^{16}$ is independently selected from the group consisting of hydrogen, C$_1$–C$_8$-alkyl, C$_2$–C$_8$-alkenyl, C$_2$–C$_8$-alkynyl, C$_3$–C$_8$-cycloalkyl, C$_5$–C$_8$-cycloalkenyl, aryl, and heteroaryl;

(7) —NR$^{10}$NR$^{11}$C(O)OR$^{17}$, wherein
R$^{17}$ is independently selected from the group consisting of C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl;

(8) —NR$^{10}$NR$^{11}$C(O)NR$^{18}$R$^{19}$, wherein
R$^{18}$ and R$^{19}$ are independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl, or R$^{18}$ and R$^{19}$, taken together with the nitrogen to which they are attached, form an optionally substituted 3–8 membered heterocyclic ring or an optionally substituted 5–10 membered heteroaryl ring, wherein the substituents are selected from the group consisting of C$_1$–C$_8$-alkyl, C$_2$–C$_8$-alkenyl, C$_2$–C$_8$-alkynyl, aryl, and heteroaryl;

(9) —NR$^{10}$NR SO$_2$$_1$R$^{20}$, wherein
R$^{20}$ is independently selected from the group consisting of C$_1$–C$_8$-alkyl, C$_2$–C$_8$-alkenyl, C$_2$–C$_8$-alkynyl, C$_3$–C$_8$-cycloalkyl, C$_5$–C$_8$-cycloalkenyl, aryl, and heteroaryl; and
R$^{21}$ is independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, C$_2$–C$_6$ acyl, aryl, and heteroaryl;

(10) —SR$^9$, wherein
R$^9$ is independently selected from the group consisting of C$_1$–C$_8$-alkyl, C$_3$–C$_8$-alkenyl, C$_3$–C$_8$-alkynyl, C$_3$–C$_8$-cycloalkyl, and C$_5$–C$_8$-cycloalkenyl;

(11) —CHR$^{10}$R$^{11}$, wherein
R$^{10}$ and R$^{11}$ are independently selected from the group consisting of hydrogen, C$_1$–C$_8$-alkyl, C$_3$–C$_8$-alkenyl, C$_3$–C$_8$-alkynyl, C$_3$–C$_8$-cycloalkyl, C$_5$–C$_8$-cycloalkenyl, aryl, and heteroaryl, or R$^{10}$ and R$^{11}$, taken together with the atoms to which they are attached, form an optionally substituted 4–8 membered carbocyclic ring wherein the substituents are selected from the group consisting of C$_1$–C$_8$-alkyl, C$_2$–C$_8$-alkenyl, C$_2$–C$_8$-alkynyl, aryl, and heteroaryl; and

(12) a substituted pyrazole of the formula

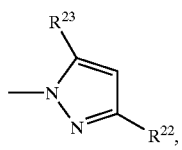

wherein
R$^{22}$ and R$^{23}$ are independently selected from the group consisting of hydrogen, —C(O)OR$^7$, —C(O)NR$^7$R$^8$, C$_1$–C$_8$-alkyl, C$_2$–C$_8$-alkenyl, C$_2$–C$_8$-alkynyl, C$_3$–C$_8$-cycloalkyl, C$_5$–C$_8$-cycloalkenyl, aryl, and heteroaryl, wherein
R$^7$ and R$^8$ are independently selected from the group consisting of hydrogen, alkyl, alkenyl, alkynyl, cycloalkyl, aryl, heteroaryl, heterocyclo, aralkyl, heteroaralkyl, and heterocycloalkyl;

X and X', together with the carbon atom to which they are attached, form C=O, C=NR$_c$, or C=NOR$_c$, wherein R$_c$ is independently selected from hydrogen, alkyl, alkenyl and alkynyl; and Y and Y', together with the carbon atom to which they are attached, form C=O, —CHOH, C=NR$_c$, or C=NOR$_c$, wherein R$_c$ is independently selected from hydrogen, alkyl, alkenyl and alkynyl;

or an optical isomer, enantiomer, diastereomer, racemate or racemic mixture thereof, or a pharmaceutically acceptable salt, esters or pro-drugs thereof.

2. A pharmaceutical composition comprising a compound of claim 1 and a pharmaceutically acceptable carrier.

3. A method of treating a subject having a condition caused by or contributed to by bacterial infection, which comprises administering to said subject a therapeutically effective amount of the compound of Formula I as defined in claim 1.

4. The method of claim 3 wherein said condition is selected from community-acquired pneumonia, upper and lower respiratory tract infections, skin and soft tissue infections, meningitis, hospital-acquired lung infections, and bone and joint infections.

5. The method of claim 3 wherein said bacterium is selected from *S. aureus, S. epidermidis, S. pneumoniae, Enterococcus* spp., *Moraxella catarrhalis* and *H. influenzae*.

6. The method of claim 3 wherein said bacterium is a Gram-positive coccus.

7. The method of claim 3 wherein said Gram-positive coccus is antibiotic-resistant.

8. The method of claim 7 wherein said Gram-positive coccus is erythromycin-resistant.

9. A process for preparation of a compound having the formula,

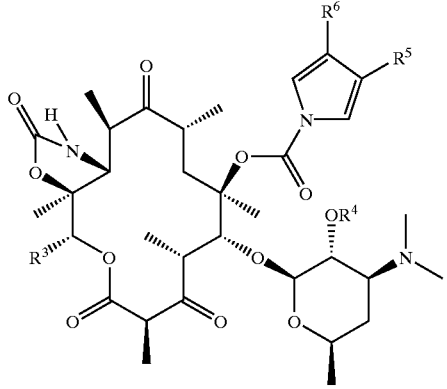

wherein R$^3$, R$^4$, R$^5$, and R$^6$ are as defined in claim 1, comprising:

a) treating a compound having the formula

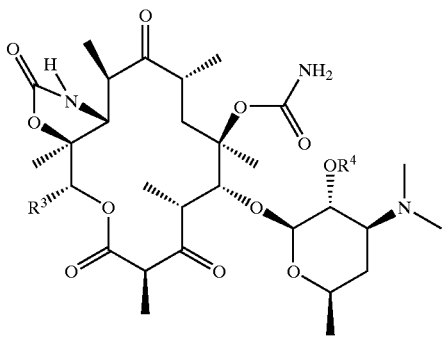

with a suitably substituted 1,4-dialdehyde or 1,4-dialdehyde equivalent and an acid; and b) when $R^4$ is a hydroxy protecting group, optionally deprotecting the 2'-hydroxy group.

10. A process for preparation of a compound having the formula,

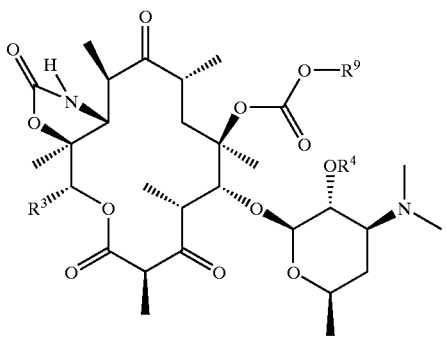

wherein $R^3$, $R^4$, and $R^9$ are as defined in claim 1, comprising:

a) treating a compound having the formula,

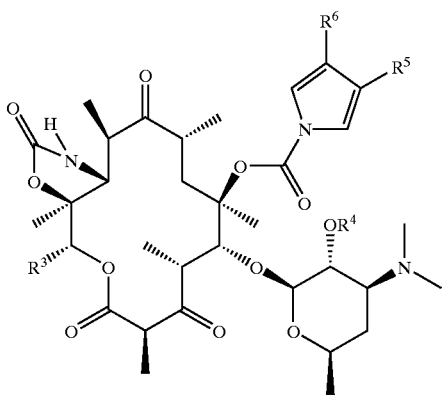

wherein $R^5$ and $R^6$ are as previously defined, with an alcohol of formula $R^9OH$ in the presence of a base; and b) when $R^4$ is a hydroxy protecting group, optionally deprotecting the 2'-hydroxy group.

11. A process for the preparation of a compound having the formula

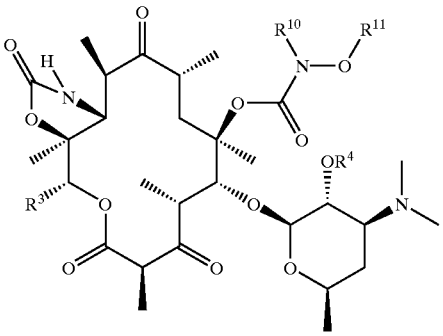

wherein $R^3$, $R^4$, $R^{10}$, and $R^{11}$ are as defined in claim 1, comprising:

a) treating a compound having the formula

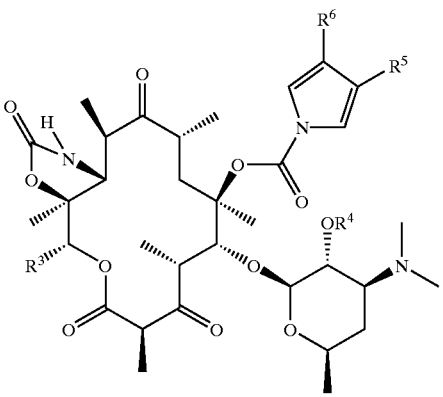

wherein $R^5$ and $R^6$ are as previously defined, with a compound having the formula

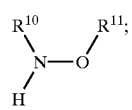

and b) when $R^4$ is a hydroxy protecting group, optionally deprotecting the 2'-hydroxy group.

12. A process for preparation of a compound having the formula

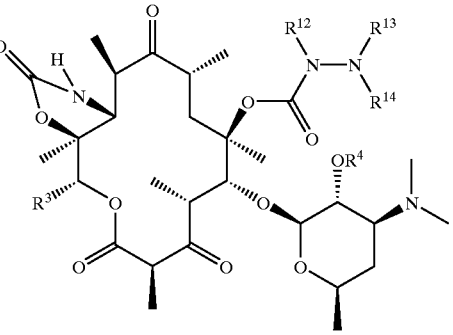

wherein $R^3$, $R^4$, $R^{12}$, $R^{13}$ and $R^{14}$ are as defined in claim 1, comprising:

a) treating a compound having the formula

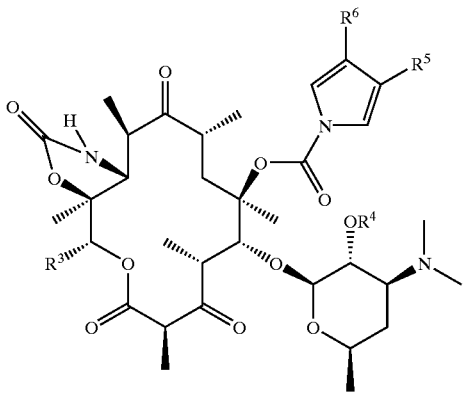

wherein $R^5$ and $R^6$ are as previously defined, with hydrazine or a mono-, di-, or tri-substituted hydrazine;

b) optionally treating the product of step (a) wherein at least one of $R^{13}$ or $R^{14}$ is hydrogen with an aldehyde, an acid catalyst, and a reducing agent;

c) optionally treating the product of step (b) wherein either $R^{13}$ or $R^{14}$ is hydrogen with an aldehyde, an acid catalyst, and a reducing agent;

d) when $R^4$ is a hydroxy protecting group, optionally deprotecting the 2'-hydroxy group.

13. A process for preparation of a compound having the formula

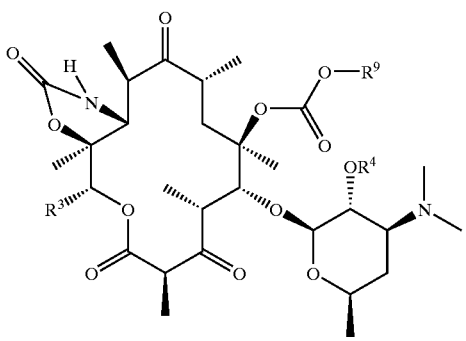

wherein $R^3$, $R^4$, and $R^9$ are as defined in claim 1, comprising:

a) treating a compound having the formula

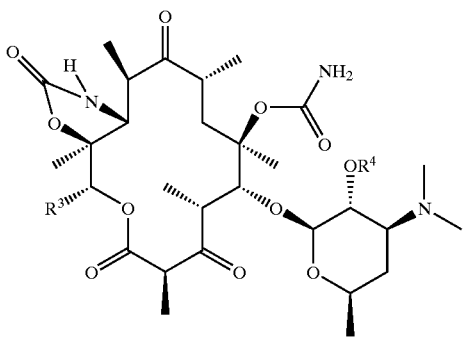

with a suitably substituted 1,4-dialdehyde or 1,4-dialdehyde equivalent and an acid;

b) treating the compound obtained in step (a) with an alcohol of formula $R^9OH$, wherein $R^9$ is as previously defined, in the presence of a base; and c) when $R^4$ is a hydroxy protecting group, optionally deprotecting the 2'-hydroxy group.

14. A process for preparation of a compound having the formula

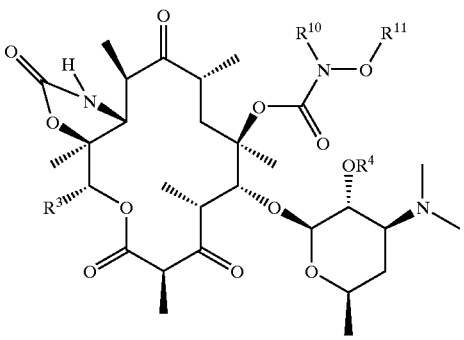

wherein $R^3$, $R^4$, $R^{10}$, and $R^{10}$ are as defined in claim 1, comprising:

a) treating a compound having the formula

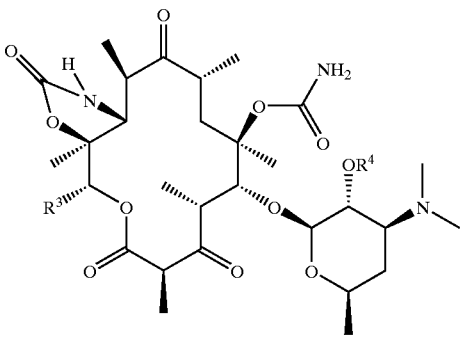

with a suitably substituted 1,4-dialdehyde or 1,4-dialdehyde equivalent and an acid;

b) treating the compound obtained in step (a) with a compound having the formula

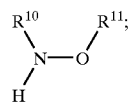

and c) when $R^4$ is a hydroxy protecting group, optionally deprotecting the 2'-hydroxy group.

15. A process for preparation of a compound having the formula

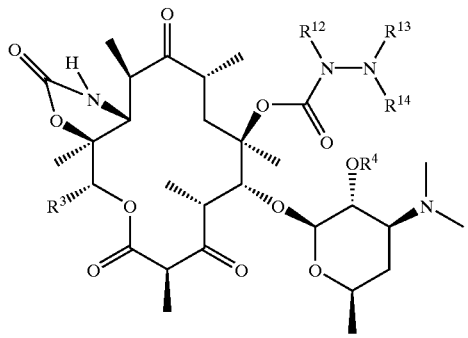

wherein $R^3$, $R^4$, $R^{12}$, $R^{13}$, and $R^{14}$ are as defined in claim 1, comprising:

a) treating a compound having the formula

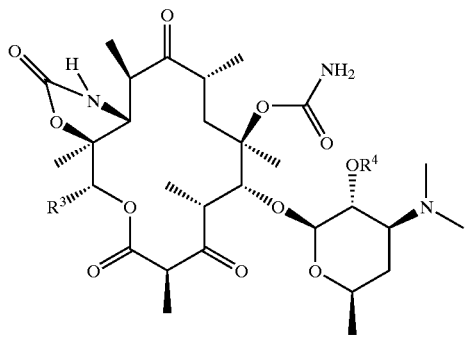

with a suitably substituted 1,4-dialdehyde or 1,4-dialdehyde equivalent and an acid;

b) treating the product of step (a) with hydrazine or a mono-, di-, or tri-substituted hydrazine;

c) optionally treating the product of step (b) wherein at least one of $R^{13}$ or $R^{14}$ is hydrogen with an aldehyde, an acid catalyst, and a reducing agent;

d) optionally treating the product of step (c) wherein either $R^{13}$ or $R^{14}$ is hydrogen with an aldehyde, an acid catalyst, and a reducing agent;

e) when $R^4$ is a hydroxy protecting group, optionally deprotecting the 2'-hydroxy group.

16. The compound of claim 1, wherein R 2 is hydrogen, Z is —$(CH_2)_n$— and n is 0.

17. The compound of claim 1, wherein W is selected from the group consisting of groups (1), (2), (3), and (4) as defined in claim 1.

18. The compound of claim 1, wherein $R^3$ is ethyl.

19. The compound of claim 1, wherein $R^4$ is hydrogen, acyl or aroyl.

20. The compound of claim 1, wherein $R^2$ is hydrogen, Z is —$(CH_2)_n$—, n is 0, W is selected from the group consisting of groups (1), (2), (3), and (4) as defined in claim 1, $R^3$ is ethyl, and $R^4$ is hydrogen.

21. The compound of claim 1 having Formula 1':

Formual 1'

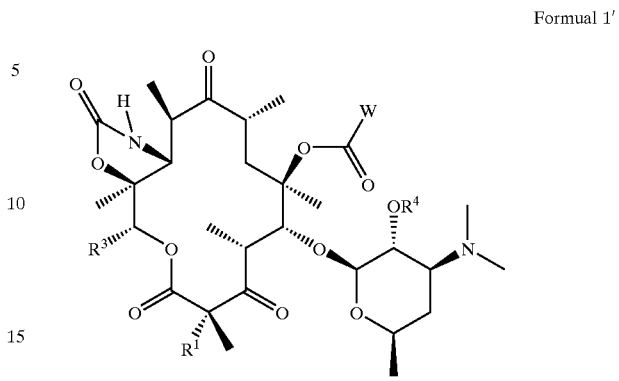

wherein, $R^1$, $R^3$, $R^4$ and W are as defined in claim 1.

22. The compound of claim 21, wherein $R_1$ is selected from the group consisting of H and F.

23. The compound of claim 21, wherein $R^3$ is ethyl.

24. The compound of claim 21, wherein $R^4$ is selected from the group consisting of H and acyl.

25. The compound of claim 21, wherein W is selected from the group consisting of groups (1), (2), (3), (4), (10), (11) and (12) as defined in claim 1.

26. The compound of claim 21, wherein $R^1$ is H and $R^3$ is ethyl.

27. The compound of claim 21, wherein $R^1$ is F and $R^3$ is ethyl.

28. The compound of claim 21, wherein $R^1$ is selected from the group consisting of H and F, $R^3$ is ethyl and $R^4$ is H.

29. The compound of claim 28, wherein W is selected from group consisting of groups (1), (2), (3), (4), (10), (11) and (12) as defined in claim 1.

30. The compound of claim 29, wherein W is group (2) and $R^9$ is independently selected from the group consisting of $C_3$–$C_8$-alkenyl and $C_3$–$C_8$-alkynyl.

31. The compound of claim 30, wherein the $C_3$–$C_8$-alkenyl or $C_3$–$C_8$-alkynyl is substituted with aryl or heteroaryl.

32. The compound of claim 31, wherein the aryl or heteroaryl is substituted with heteroaryl.

33. The compound of claim 30, wherein $R^9$ is $C_3$–$C_8$-alkenyl substituted with fluoro and a substituent selected from the group consisting of aryl or heteroaryl.

34. The compound of claim 33, wherein the aryl or heteroaryl is substituted with heteroaryl.

35. The compound of claim 1 having the formula

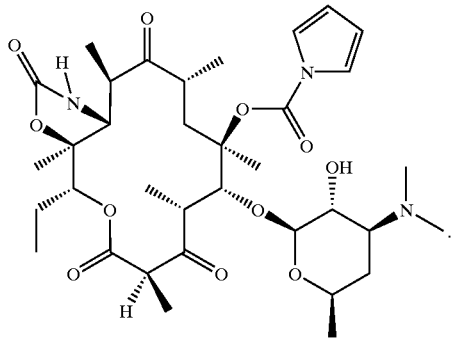

36. The compound of claim 1 having the formula
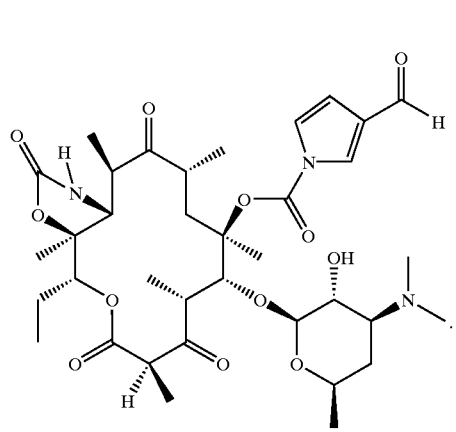
37. The compound of claim 1 having the formula
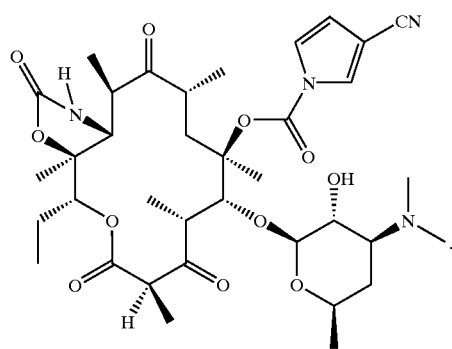
38. The compound of claim 1 having the formula
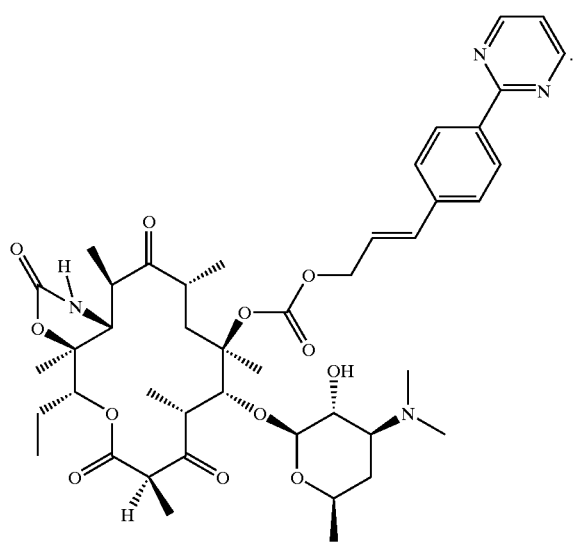
39. The compound of claim 1 having the formula
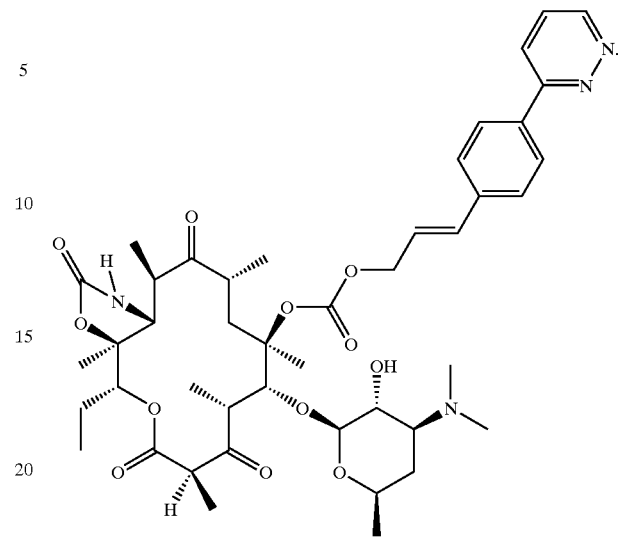
40. The compound of claim 1 having the formula
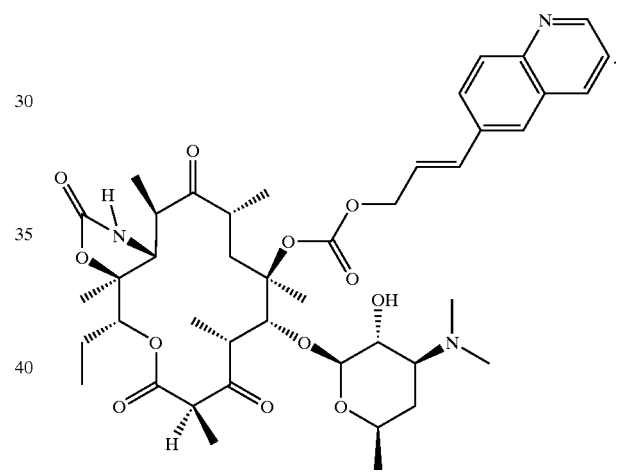
41. The compound of claim 1 having the formula
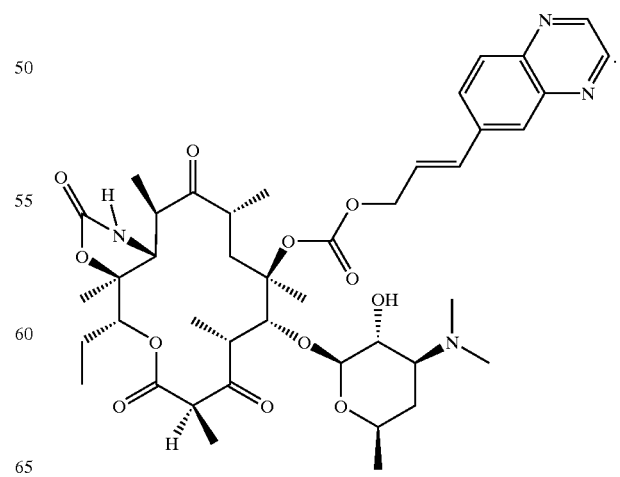

42. The compound of claim 1 having the formula
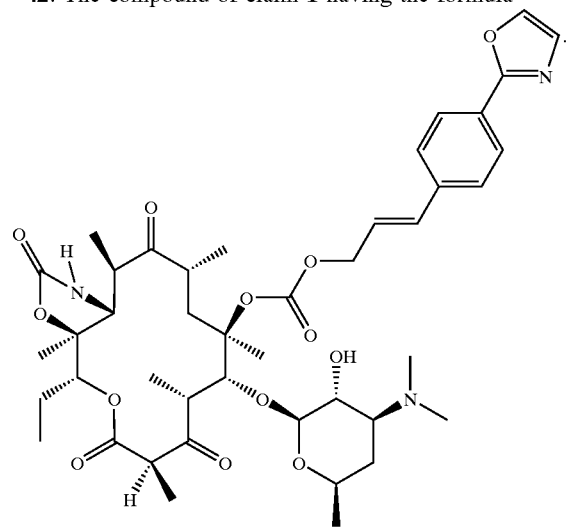
43. The compound of claim 1 having the formula
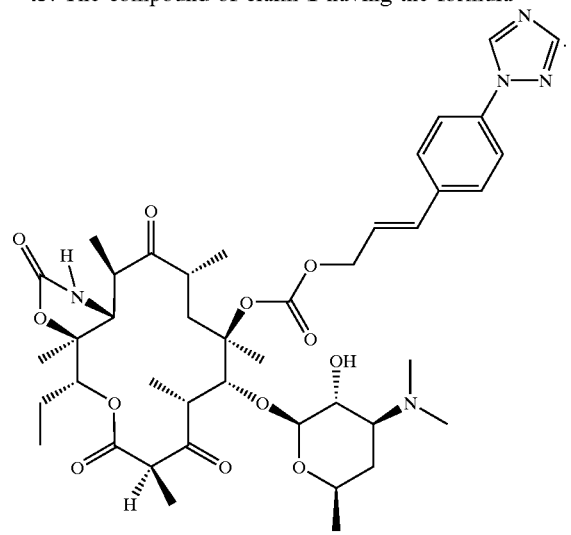
44. The compound of claim 1 having the formula
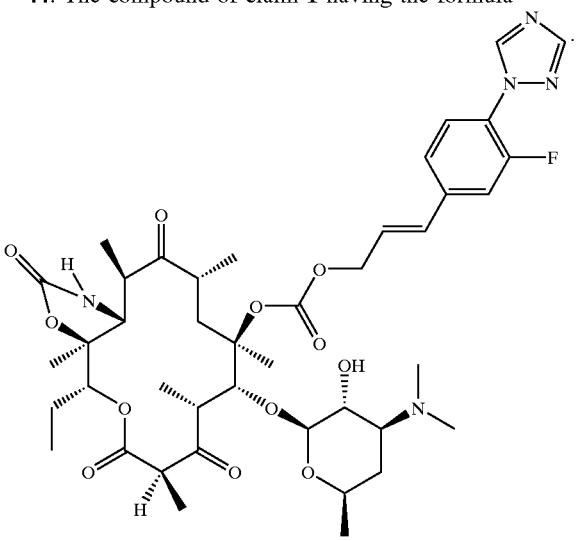
45. The compound of claim 1 having the formula
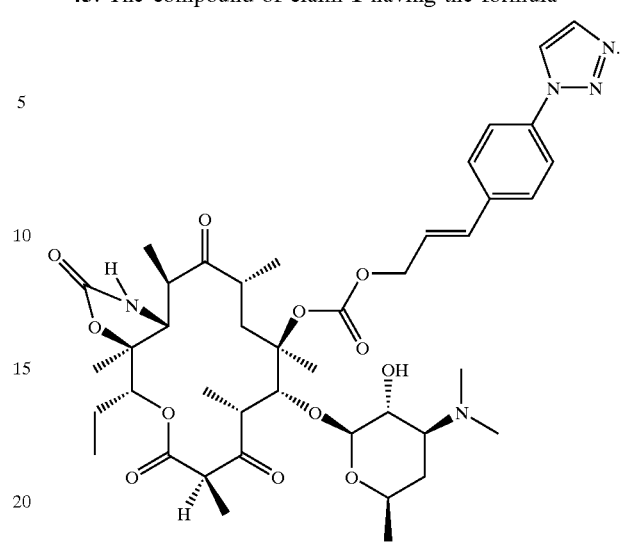
46. The compound of claim 1 having the formula
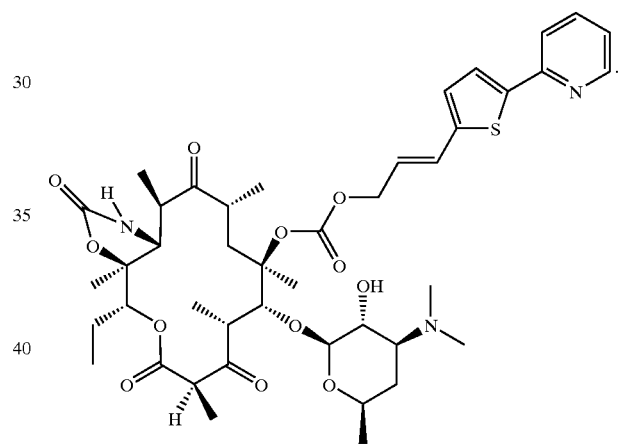
47. The compound of claim 1 having the formula
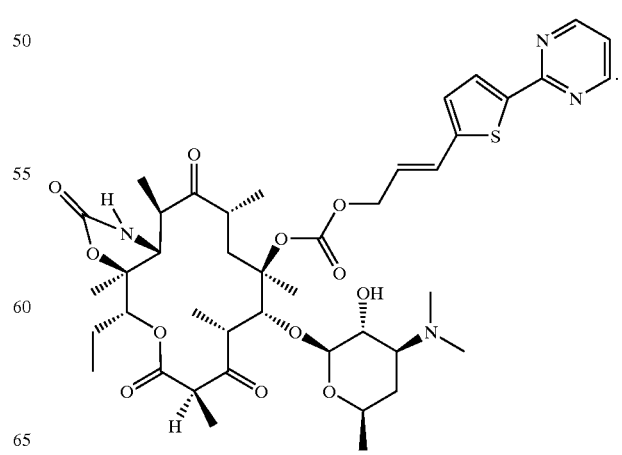

48. The compound of claim 1 having the formula
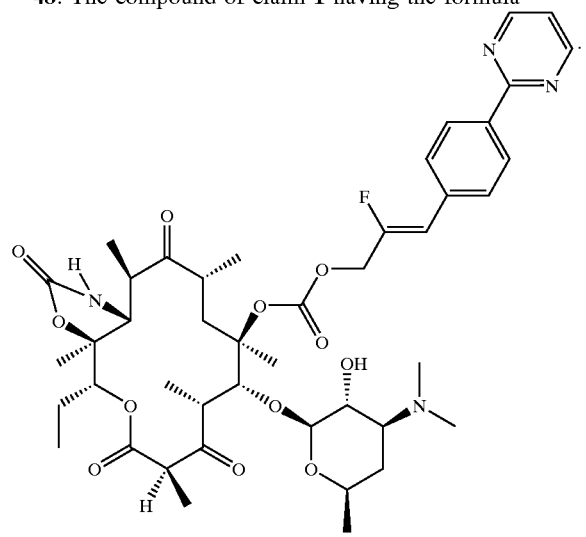
49. The compound of claim 1 having the formula
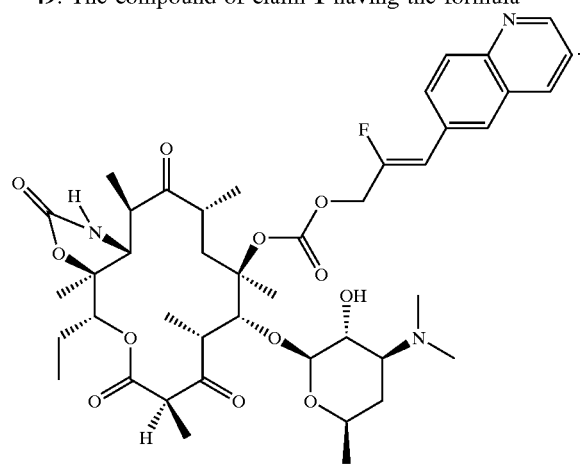
50. The compound of claim 1 having the formula
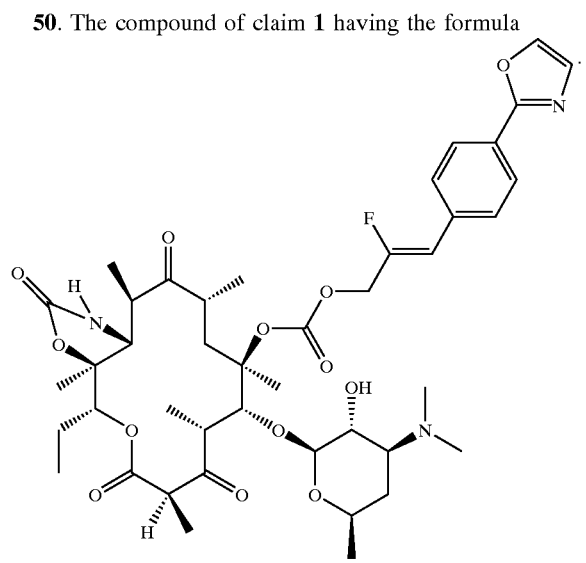
51. The compound of claim 1 having the formula
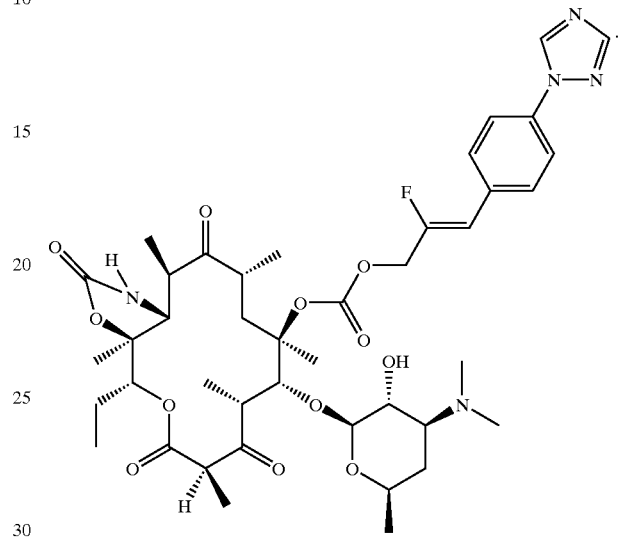
52. The compound of claim 1 having the formula
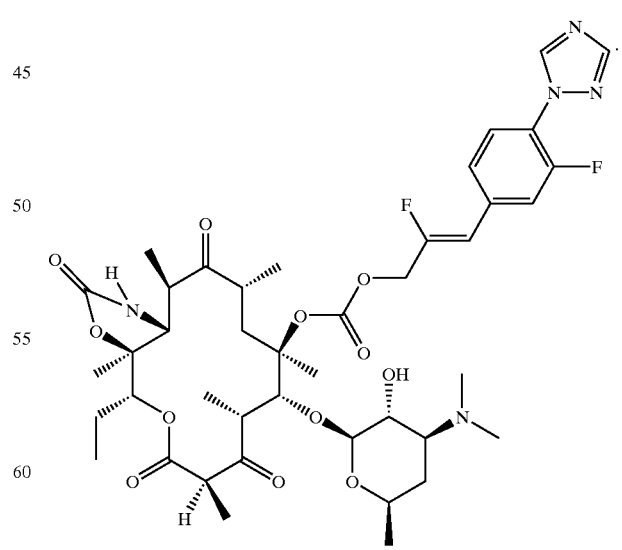

53. The compound of claim 1 having the formula
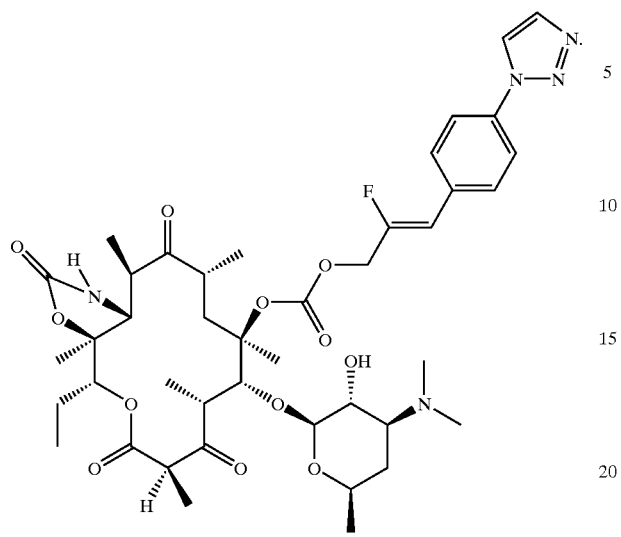
54. The compound of claim 1 having the formula
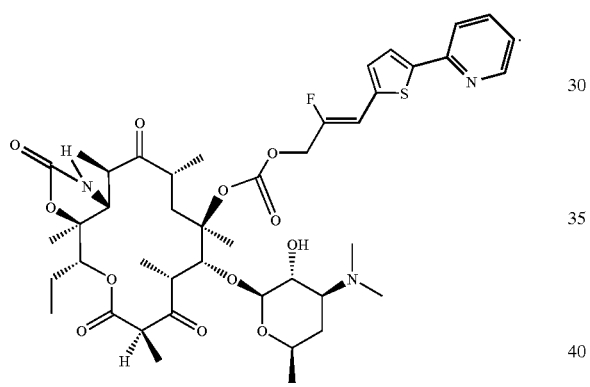
55. The compound of claim 1 having the formula
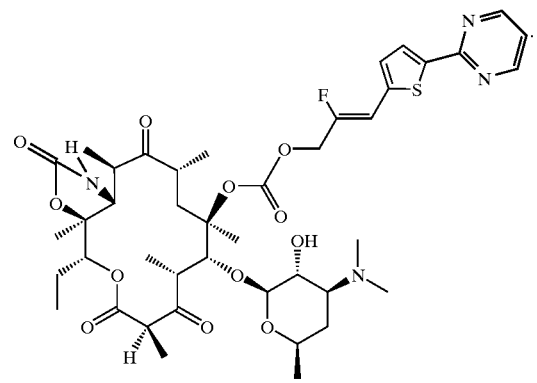
56. The compound of claim 1 having the formula
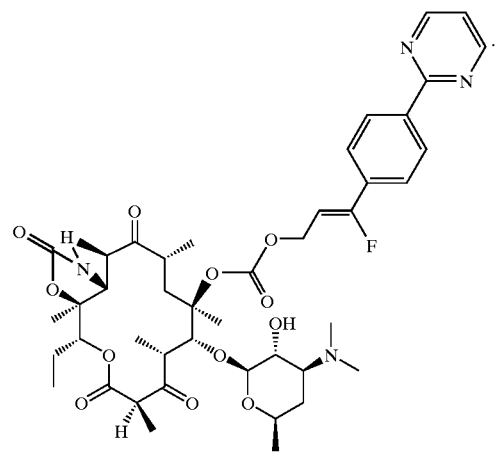
* * * * *

UNITED STATES PATENT AND TRADEMARK OFFICE
CERTIFICATE OF CORRECTION

PATENT NO. : 6,825,170 B2 Page 1 of 1
APPLICATION NO. : 10/301412
DATED : November 30, 2004
INVENTOR(S) : Henninger et al.

It is certified that error appears in the above-identified patent and that said Letters Patent is hereby corrected as shown below:

Column 139, Line 54, "R 2" should be -- $R^2$ --

Column 140, Line 22, "$R_1$" should be -- $R^1$ --

Column 136, Line 46, "R 4" should be -- $R^4$ --

Signed and Sealed this

Tenth Day of October, 2006

JON W. DUDAS
*Director of the United States Patent and Trademark Office*